United States Patent
DiMarchi et al.

(10) Patent No.: US 11,351,268 B2
(45) Date of Patent: Jun. 7, 2022

(54) FGF21 C-TERMINAL PEPTIDE OPTIMIZATION

(71) Applicant: INDIANA UNIVERSITY RESEARCH AND TECHNOLOGY CORPORATION, Indianapolis, IN (US)

(72) Inventors: Richard D. DiMarchi, Carmel, IN (US); Alexei Kharitonenkov, Zionsville, IN (US); Pengyun Li, Bloomington, IN (US); Archita S. Agrawal, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/983,726

(22) Filed: Aug. 3, 2020

(65) Prior Publication Data
US 2020/0360530 A1    Nov. 19, 2020

Related U.S. Application Data

(63) Continuation of application No. 16/092,298, filed as application No. PCT/US2017/027600 on Apr. 14, 2017, now abandoned.

(60) Provisional application No. 63/323,003, filed on Apr. 15, 2016.

(51) Int. Cl.
| | |
|---|---|
| A61K 47/66 | (2017.01) |
| C07K 14/50 | (2006.01) |
| A61K 47/65 | (2017.01) |
| A61P 3/04 | (2006.01) |
| A61P 3/10 | (2006.01) |
| A61K 38/03 | (2006.01) |
| A61K 38/17 | (2006.01) |
| A61K 38/26 | (2006.01) |
| A61K 38/28 | (2006.01) |

(52) U.S. Cl.
CPC ............ *A61K 47/66* (2017.08); *A61K 38/03* (2013.01); *A61K 38/1796* (2013.01); *A61K 38/26* (2013.01); *A61K 38/28* (2013.01); *A61K 47/65* (2017.08); *A61P 3/04* (2018.01); *A61P 3/10* (2018.01); *C07K 14/50* (2013.01)

(58) Field of Classification Search
CPC ... A61P 3/04; A61P 3/10; A61K 47/66; A61K 38/26; A61K 38/1796; A61K 38/03; A61K 47/65; A61K 38/28; C07K 14/50
See application file for complete search history.

(56) References Cited

U.S. PATENT DOCUMENTS

| | | |
|---|---|---|
| 2009/0305986 A1 | 12/2009 | Belouski |
| 2010/0216715 A1 | 8/2010 | Tagmose |
| 2014/0213512 A1 | 7/2014 | Ellison |

FOREIGN PATENT DOCUMENTS

| | | |
|---|---|---|
| WO | WO2011/140086 | 11/2011 |
| WO | WO2011/154349 | 12/2011 |
| WO | WO2013/184958 | 12/2013 |

OTHER PUBLICATIONS

Database Geneseq; Fibroblast Growth Factor 21-SABA fusion polypeptide SEQ 172; XP002794408; Database accession No. AZP63181.
Yasuko Onuma et al., A stable Chimeric Fibroblast Growth Factor (FGF) Can Successfully Replace Basic FGF in Human Pluripotent Stem Cell Culture, PLOS One, vol. 10 No. 4, Apr. 7, 2015.
Chaofeng Yang, et al., Differential Specificity of Endocrine FGF19 and FGF21 to FGFR1 and FGFR4 in Complex with Klb, PLOS One, vol. 7, No. 3 Mar. 19, 2012.
PCT International Search Report and Written Opinion completed by the ISA/EP on Sep. 22, 2017 and issued in connection with PCT/US2017/027600.
Wu, X., et al. "C-terminal Tail of FGF19 Determines Its Specificiaty toward Klotho Co-receptors" Journal of Biological Chemistry, American Society for Biochemistry and Molecular Biology, US vol. 283, No. 48, Nov. 28, 2008, pp. 33304-33309.
Ge, H., et al. "Characterization of a FGF19 Variant with Altered Receptor Specificity Revealed a Central Role for FGFR1c in the Regulation of Glucose Metabolism", POLOS One, vol. 7, No. 3, Mar. 23, 2012, pp. 1-9.
Goetz, R., et al. "Conversation of a Paracrine Fibroblast Growth Factor into an Endocrine Fibroblast Growth Factor" Journal of Bilogical Chemistry, vol. 287, No. 34, Jun. 25, 2012, pp. 29134-29146.

*Primary Examiner* — Li N Komatsu
(74) *Attorney, Agent, or Firm* — Barnes & Thornburg LLP

(57) ABSTRACT

Disclosed herein are modified C-terminal fragments of FGF21 optimized for binding to Klotho β or antagonizing FGF21 activity. FGF21 peptides modified to comprise modifications to the C-terminal amino acid sequence are disclosed that have enhanced activity at the FGF21 receptor. Additionally, conjugates formed between the optimized FGF21 peptide fragments and insulin like peptides or nuclear hormone receptor ligands are provided.

7 Claims, 22 Drawing Sheets
Specification includes a Sequence Listing.

| | FGF21 | FGF19 | | Similarity |
|---|---|---|---|---|
| 157 | P | P | 169 | • |
| 158 | P | L | 170 | x |
| 159 | D | E | 171 | • |
| 160 | V | T | 172 | • |
| 161 | G | D | 173 | x |
| 162 | S | S | 174 | • |
| 163 | S | M | 175 | x |
| 164 | D | D | 176 | • |
| 165 | P | P | 177 | • |
| 166 | L | F | 178 | • |
| 167 | S | G | 179 | x |
| 168 | M | L | 180 | • |
| 169 | V | V | 181 | • |
|  | - | T | 182 | x |
| 170 | G | G | 183 | • |
| 171 | P | L | 184 | x |
| 172 | S | E | 185 | x |
| 173 | Q | A | 186 | x |
| 174 | G | V | 187 | x |
| 175 | R | R | 188 | • |
| 176 | S | S | 189 | • |
| 177 | P | P | 190 | • |
| 178 | S | S | 191 | • |
| 179 | Y | F | 192 | • |
| 180 | A | E | 193 | x |
| 181 | S | K | 194 | x |

Fig. 6

SEQUENCE LISTING

```
<160> NUMBER OF SEQ ID NOS: 253

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30
```

```
Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
 50                  55                  60

Lys Pro Ala Lys Ser Ala
 65                  70

<210> SEQ ID NO 4
<211> LENGTH: 67
<212> TYPE: PRT
<213> ORGANISM: Homo sapiens

<400> SEQUENCE: 4

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
                 20                  25                  30

Ser Arg Val Ser Arg Arg Ser Gly Ile Val Glu Cys Cys Phe
        35                  40                  45

Arg Ser Cys Asp Leu Ala Leu Leu Glu Thr Tyr Cys Ala Thr Pro Ala
 50                  55                  60

Lys Ser Glu
 65

<210> SEQ ID NO 5
<211> LENGTH: 21
<212> TYPE: PRT
<213> ORGANISM: Homo sapiens

<400> SEQUENCE: 5

Gly Ile Val Asp Glu Cys Cys Phe Arg Ser Cys Asp Leu Arg Arg Leu
 1               5                  10                  15

Glu Met Tyr Cys Ala
                 20

<210> SEQ ID NO 6
<211> LENGTH: 30
<212> TYPE: PRT
<213> ORGANISM: Homo sapiens

<400> SEQUENCE: 6

Phe Gly Pro Glu Thr Leu Cys Gly Ala Glu Leu Val Asp Ala Leu Tyr
 1               5                  10                  15

Leu Val Cys Gly Asp Arg Gly Phe Tyr Phe Asn Lys Pro Thr
                 20                  25                  30

<210> SEQ ID NO 7
<211> LENGTH: 21
<212> TYPE: PRT
<213> ORGANISM: Homo sapiens

<400> SEQUENCE: 7

Gly Ile Val Glu Glu Cys Cys Phe Arg Ser Cys Asp Leu Ala Leu Leu
 1               5                  10                  15

Glu Thr Tyr Cys Ala
                 20

<210> SEQ ID NO 8
<211> LENGTH: 32
<212> TYPE: PRT
```

<213> ORGANISM: Homo sapiens

<400> SEQUENCE: 8

```
Ala Tyr Arg Pro Ser Glu Thr Leu Cys Gly Gly Glu Leu Val Asp Thr
1               5                   10                  15
Leu Gln Phe Val Cys Gly Asp Arg Gly Phe Tyr Phe Ser Arg Pro Ala
            20                  25                  30
```

<210> SEQ ID NO 9
<211> LENGTH: 8
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(1)
<223> OTHER INFORMATION: The Xaa at position 1 represents an amino acid
      selected from glycine, alanine, valine, leucine, isoleucine,
      proline, phenylalanine and methionine
<220> FEATURE:
<221> NAME/KEY: MISC_FEATURE
<222> LOCATION: (2)..(2)
<223> OTHER INFORMATION: The Xaa at position 2 represents any amino acid
      other than tyrosine
<220> FEATURE:
<221> NAME/KEY: MISC_FEATURE
<222> LOCATION: (3)..(6)
<223> OTHER INFORMATION: The Xaas at positions 3-6 are independently any
      amino acid
<220> FEATURE:
<221> NAME/KEY: MISC_FEATURE
<222> LOCATION: (7)..(8)
<223> OTHER INFORMATION: The Xaas at positions 7 and 8 are independently
      selected from arginine, lysine or ornithine

<400> SEQUENCE: 9

```
Xaa Xaa Xaa Xaa Xaa Xaa Xaa Xaa
1               5
```

<210> SEQ ID NO 10
<211> LENGTH: 8
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(1)
<223> OTHER INFORMATION: The Xaa at position 1 represents an amino acid
      selected from glycine, alanine, valine, leucine, isoleucine,
      proline, phenylalanine and methionine
<220> FEATURE:
<221> NAME/KEY: MISC_FEATURE
<222> LOCATION: (2)..(2)
<223> OTHER INFORMATION: The Xaa at position 2 represents any amino acid
      other than tyrosine
<220> FEATURE:
<221> NAME/KEY: MISC_FEATURE
<222> LOCATION: (3)..(6)
<223> OTHER INFORMATION: The Xaas at positions 3-6 are independently any
      amino acid

<400> SEQUENCE: 10

```
Xaa Xaa Xaa Xaa Xaa Xaa Arg Arg
1               5
```

<210> SEQ ID NO 11
<211> LENGTH: 4
<212> TYPE: PRT
<213> ORGANISM: Artificial Sequence
<220> FEATURE:

```
<223> OTHER INFORMATION: spacer sequence

<400> SEQUENCE: 11

Pro Gly Pro Glu
1

<210> SEQ ID NO 12
<211> LENGTH: 4
<212> TYPE: PRT
<213> ORGANISM: Artificial Sequence
<220> FEATURE:
<223> OTHER INFORMATION: spacer sequence

<400> SEQUENCE: 12

Phe Val Asn Gln
1

<210> SEQ ID NO 13
<211> LENGTH: 5
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(5)
<223> OTHER INFORMATION: The Xaas at positions 1-5 are independently any
      amino acid

<400> SEQUENCE: 13

Xaa Xaa Xaa Xaa Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: spacer sequence

<400> SEQUENCE: 14

Ala Tyr Arg Pro Ser Glu
1               5

<210> SEQ ID NO 15
<211> LENGTH: 4
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(4)
<223> OTHER INFORMATION: The Xaas at positions 1-4 are independently any
      amino acid

<400> SEQUENCE: 15

Xaa Xaa Xaa Xaa
1

<210> SEQ ID NO 16
<211> LENGTH: 5
<212> TYPE: PRT
<213> ORGANISM: Artificial Sequence
<220> FEATURE:
<223> OTHER INFORMATION: spacer sequence

<400> SEQUENCE: 16
```

```
Tyr Thr Pro Lys Thr
1               5
```

<210> SEQ ID NO 17
<211> LENGTH: 12
<212> TYPE: PRT
<213> ORGANISM: Homo sapiens

<400> SEQUENCE: 17

```
Gly Tyr Gly Ser Ser Ser Arg Arg Ala Pro Gln Thr
1               5                   10
```

<210> SEQ ID NO 18
<211> LENGTH: 8
<212> TYPE: PRT
<213> ORGANISM: Homo sapiens

<400> SEQUENCE: 18

```
Gly Tyr Gly Ser Ser Ser Arg Arg
1               5
```

<210> SEQ ID NO 19
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine

```
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 19

Gly Ile Val Xaa Xaa Cys Cys Xaa Xaa Xaa Cys Xaa Leu Xaa Xaa Leu
1               5                   10                  15

Xaa Xaa Tyr Cys Xaa
            20

<210> SEQ ID NO 20
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 12 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or 4-amino-
      phenylalanine

<400> SEQUENCE: 20

Xaa Leu Cys Gly Xaa Xaa Leu Val Xaa Xaa Leu Tyr Leu Val Cys Gly
1               5                   10                  15

Xaa Xaa Gly Phe Xaa
            20

<210> SEQ ID NO 21
<211> LENGTH: 8
<212> TYPE: PRT
<213> ORGANISM: Artificial Sequence
<220> FEATURE:
<223> OTHER INFORMATION: analog of IGF-1 C peptide
<220> FEATURE:
<221> NAME/KEY: MISC_FEATURE
<222> LOCATION: (7)..(8)
```

```
<223> OTHER INFORMATION: The Xaas at positions 7 and 8 are independently
      arginine, lysine or ornithine

<400> SEQUENCE: 21

Gly Tyr Gly Ser Ser Ser Xaa Xaa
1               5

<210> SEQ ID NO 22
<211> LENGTH: 8
<212> TYPE: PRT
<213> ORGANISM: Artificial Sequence
<220> FEATURE:
<223> OTHER INFORMATION: Analog of IGF-1 C peptide

<400> SEQUENCE: 22

Gly Ala Gly Ser Ser Ser Arg Arg
1               5

<210> SEQ ID NO 23
<211> LENGTH: 12
<212> TYPE: PRT
<213> ORGANISM: Artificial Sequence
<220> FEATURE:
<223> OTHER INFORMATION: linker sequence

<400> SEQUENCE: 23

Gly Ala Gly Ser Ser Ser Arg Arg Ala Pro Gln Thr
1               5                   10

<210> SEQ ID NO 24
<211> LENGTH: 8
<212> TYPE: PRT
<213> ORGANISM: Homo sapiens

<400> SEQUENCE: 24

Ser Arg Val Ser Arg Arg Ser Arg
1               5

<210> SEQ ID NO 25
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid or glutamic
      acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
```

```
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 25

Xaa Leu Cys Gly Xaa Xaa Leu Val Xaa Xaa Leu Tyr Leu Val Cys Gly
1               5                   10                  15

Asp Xaa Gly Phe Xaa
            20

<210> SEQ ID NO 26
<211> LENGTH: 7
<212> TYPE: PRT
<213> ORGANISM: Artificial Sequence
<220> FEATURE:
<223> OTHER INFORMATION: amino acid terminal extension for insulin
<220> FEATURE:
<221> NAME/KEY: MISC_FEATURE
<222> LOCATION: (2)..(6)
<223> OTHER INFORMATION: the Xaas at positions 2-6 are independently
      glutamic acid or aspartic acid

<400> SEQUENCE: 26

Gly Xaa Xaa Xaa Xaa Xaa Lys
1               5

<210> SEQ ID NO 27
<211> LENGTH: 7
<212> TYPE: PRT
<213> ORGANISM: Artificial Sequence
<220> FEATURE:
<223> OTHER INFORMATION: amio acid terminal extension for insulin
<220> FEATURE:
<221> NAME/KEY: MISC_FEATURE
<222> LOCATION: (1)..(5)
<223> OTHER INFORMATION: the Xaas at positions 1-5 are independently
      glutamic acid or aspartic acid

<400> SEQUENCE: 27

Xaa Xaa Xaa Xaa Xaa Arg Lys
1               5

<210> SEQ ID NO 28
<211> LENGTH: 31
<212> TYPE: PRT
<213> ORGANISM: Artificial Sequence
<220> FEATURE:
<223> OTHER INFORMATION: Analog of IGF-1 B chain
<220> FEATURE:
<221> NAME/KEY: MISC_FEATURE
<222> LOCATION: (28)..(28)
<223> OTHER INFORMATION: The Xaa at position 28 is alanine lysine,
      ornithine or arginine

<400> SEQUENCE: 28

Gly Glu Glu Glu Glu Glu Lys Gly Pro Glu His Leu Cys Gly Ala His
1               5                   10                  15

Leu Val Asp Ala Leu Tyr Leu Val Cys Gly Asp Xaa Gly Phe Tyr
            20                  25                  30

<210> SEQ ID NO 29
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
```

```
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 29

Gly Ile Val Xaa Xaa Cys Cys Xaa Xaa Xaa Cys Xaa Leu Xaa Xaa Leu
1               5                   10                  15

Xaa Xaa Xaa Cys Xaa
            20

<210> SEQ ID NO 30
<211> LENGTH: 21
<212> TYPE: PRT
<213> ORGANISM: Artificial Sequence
<220> FEATURE:
<223> OTHER INFORMATION: Analog of insulin A chain
<220> FEATURE:
<221> NAME/KEY: MISC_FEATURE
<222> LOCATION: (8)..(8)
<223> OTHER INFORMATION: Xaa at position 8 is  threonine or histidine
<220> FEATURE:
<221> NAME/KEY: MISC_FEATURE
```

```
<222> LOCATION: (19)..(19)
<223> OTHER INFORMATION: Xaa at position 19 is tyrosine, 4-methoxy-
      phenylalanine or 4-amino phenylalanine
<220> FEATURE:
<221> NAME/KEY: MISC_FEATURE
<222> LOCATION: (21)..(21)
<223> OTHER INFORMATION: Xaa at position 21 is asparagine or glycine

<400> SEQUENCE: 30

Gly Ile Val Glu Gln Cys Cys Xaa Ser Ile Cys Ser Leu Tyr Gln Leu
1               5                   10                  15

Glu Asn Xaa Cys Xaa
            20

<210> SEQ ID NO 31
<211> LENGTH: 21
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is  histidine, aspartic acid,
      glutamic acid, homocysteic acid or cysteic acid

<400> SEQUENCE: 31

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 32
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or threonine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (21)..(21)
<223> OTHER INFORMATION: Xaa at position 21 is asparagine or glycine

<400> SEQUENCE: 32

Gly Ile Val Glu Gln Cys Cys Xaa Ser Ile Cys Ser Leu Tyr Gln Leu
1               5                   10                  15

Xaa Asn Tyr Cys Xaa
            20

<210> SEQ ID NO 33
<211> LENGTH: 21
<212> TYPE: PRT
<213> ORGANISM: Artificial Sequence
```

```
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 33

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 34
<211> LENGTH: 27
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine and
      desamino-phenylalanine
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 34

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr
            20                  25

<210> SEQ ID NO 35
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (14)..(14)
<223> OTHER INFORMATION: Xaa at position 14 is arginine, lysine,
      ornithine or alanine
```

```
<220> FEATURE:
<221> NAME/KEY: MISC_FEATURE
<222> LOCATION: (15)..(15)
<223> OTHER INFORMATION: Xaa at position 15 is arginine, lysine,
      ornithine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine or
      threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 35

Gly Ile Val Asp Glu Cys Cys Xaa Xaa Ser Cys Asp Leu Xaa Xaa Leu
1               5                   10                  15

Xaa Xaa Xaa Cys Xaa
            20

<210> SEQ ID NO 36
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid or glutamic
      acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 36

Xaa Leu Cys Gly Xaa Xaa Leu Val Xaa Xaa Leu Tyr Leu Val Cys Gly
1               5                   10                  15

Asp Xaa Gly Phe Xaa
```

```
<210> SEQ ID NO 37
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
<220> FEATURE:
<221> NAME/KEY: MISC_FEATURE
<222> LOCATION: (15)..(15)
<223> OTHER INFORMATION: Xaa at position 15 is arginine, ornithine, or
      lysine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 37

Gly Ile Val Asp Glu Cys Cys His Xaa Ser Cys Asp Leu Xaa Xaa Leu
1               5                   10                  15

Xaa Met Xaa Cys Xaa
            20

<210> SEQ ID NO 38
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      or glutamic acid
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 38

Xaa Leu Cys Gly Ala Xaa Leu Val Asp Ala Leu Tyr Leu Val Cys Gly
1               5                   10                  15
```

```
Asp Xaa Gly Phe Xaa
         20

<210> SEQ ID NO 39
<211> LENGTH: 21
<212> TYPE: PRT
<213> ORGANISM: Artificial Sequence
<220> FEATURE:
<223> OTHER INFORMATION: analog of insulin B chain
<220> FEATURE:
<221> NAME/KEY: MISC_FEATURE
<222> LOCATION: (18)..(18)
<223> OTHER INFORMATION: The Xaa at position 18 is ornithine, lysine or
      arginine

<400> SEQUENCE: 39

His Leu Cys Gly Ala Glu Leu Val Asp Ala Leu Tyr Leu Val Cys Gly
1               5                   10                  15

Asp Xaa Gly Phe Tyr
         20

<210> SEQ ID NO 40
<211> LENGTH: 24
<212> TYPE: PRT
<213> ORGANISM: Artificial Sequence
<220> FEATURE:
<223> OTHER INFORMATION: analog of IGF-1 B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 40

Gly Pro Glu His Leu Cys Gly Ala Glu Leu Val Asp Ala Leu Tyr Leu
1               5                   10                  15

Val Cys Gly Asp Xaa Gly Phe Tyr
             20

<210> SEQ ID NO 41
<211> LENGTH: 29
<212> TYPE: PRT
<213> ORGANISM: Artificial Sequence
<220> FEATURE:
<223> OTHER INFORMATION: Analog of IGF-1 B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 41

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
             20                  25

<210> SEQ ID NO 42
<211> LENGTH: 29
<212> TYPE: PRT
<213> ORGANISM: Artificial Sequence
<220> FEATURE:
<223> OTHER INFORMATION: Analog of IGF-1 B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine
```

```
<400> SEQUENCE: 42

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
                20                  25

<210> SEQ ID NO 43
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
<220> FEATURE:
<221> NAME/KEY: MISC_FEATURE
<222> LOCATION: (15)..(15)
<223> OTHER INFORMATION: Xaa at position 15 is arginine, ornithine, or
      lysine

<400> SEQUENCE: 43

Gly Ile Val Asp Glu Cys Cys His Xaa Ser Cys Asp Leu Xaa Xaa Leu
1               5                   10                  15

Gln Met Tyr Cys Asn
                20

<210> SEQ ID NO 44
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine, histidine or
      phenylalnine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine

<400> SEQUENCE: 44

Gly Ile Val Asp Glu Cys Cys Xaa Arg Ser Cys Asp Leu Tyr Gln Leu
1               5                   10                  15

Glu Asn Xaa Cys Asn
                20

<210> SEQ ID NO 45
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (18)..(18)
```

```
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine, histidine,
      asparagine or phenylalanine

<400> SEQUENCE: 45

Xaa Leu Cys Gly Ser His Leu Val Asp Ala Leu Tyr Leu Val Cys Gly
1               5                   10                  15

Asp Xaa Gly Phe Xaa
            20

<210> SEQ ID NO 46
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 46

Gly Ile Val Glu Gln Cys Cys His Ser Ile Cys Ser Leu Tyr Gln Leu
1               5                   10                  15

Glu Asn Xaa Cys Xaa
            20

<210> SEQ ID NO 47
<211> LENGTH: 21
<212> TYPE: PRT
<213> ORGANISM: Homo sapiens
<220> FEATURE:
<221> NAME/KEY: MISC_FEATURE
<222> LOCATION: (19)..(19)
<223> OTHER INFORMATION: The Xaa at position 19 is tyrosine, 4-methoxy-
      phenylalanine or 4-amino phenylalanine
<220> FEATURE:
<221> NAME/KEY: MISC_FEATURE
<222> LOCATION: (21)..(21)
<223> OTHER INFORMATION: The Xaa at position 21 is alanine, glycine or
      asparagine

<400> SEQUENCE: 47

Gly Ile Val Asp Glu Cys Cys His Arg Ser Cys Asp Leu Arg Arg Leu
1               5                   10                  15

Glu Met Xaa Cys Xaa
            20

<210> SEQ ID NO 48
<211> LENGTH: 29
<212> TYPE: PRT
<213> ORGANISM: Homo sapiens

<400> SEQUENCE: 48

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Pro Lys Thr
            20                  25
```

```
<210> SEQ ID NO 49
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (7)..(8)
<223> OTHER INFORMATION: Xaas at positions 7 and 8 are independently
      arginine, lysine or ornithine

<400> SEQUENCE: 49

Xaa Xaa Gly Ser Ser Ser Xaa Xaa
1               5

<210> SEQ ID NO 50
<211> LENGTH: 12
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (7)..(8)
<223> OTHER INFORMATION: Xaas at positions 7 and 8 are independently
      arginine, lysine or ornithine

<400> SEQUENCE: 50

Xaa Xaa Gly Ser Ser Ser Xaa Xaa Ala Pro Gln Thr
1               5                   10

<210> SEQ ID NO 51
<211> LENGTH: 29
<212> TYPE: PRT
<213> ORGANISM: Homo sapiens

<400> SEQUENCE: 51

Ser Ser Ser Ser Arg Ala Pro Pro Ser Leu Pro Ser Pro Ser Arg
1               5                   10                  15

Leu Pro Gly Pro Ser Asp Thr Pro Ile Leu Pro Gln Lys
            20                  25

<210> SEQ ID NO 52
<211> LENGTH: 29
<212> TYPE: PRT
<213> ORGANISM: Homo sapiens

<400> SEQUENCE: 52
```

```
Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Arg
            20                  25
```

```
<210> SEQ ID NO 53
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position 1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid

<400> SEQUENCE: 53

Xaa Xaa Gly Ser Ser Ser Arg Arg
1               5
```

```
<210> SEQ ID NO 54
<211> LENGTH: 12
<212> TYPE: PRT
<213> ORGANISM: Artificial Sequence
<220> FEATURE:
<223> OTHER INFORMATION: Analog of IGF-1 C peptide
<220> FEATURE:
<221> NAME/KEY: MISC_FEATURE
<222> LOCATION: (8)..(8)
<223> OTHER INFORMATION: The Xaa at positions 8 is arginine, lysine or
      ornithine

<400> SEQUENCE: 54

Gly Ala Gly Ser Ser Ser Arg Xaa Ala Pro Gln Thr
1               5                   10
```

```
<210> SEQ ID NO 55
<211> LENGTH: 12
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (8)..(8)
<223> OTHER INFORMATION: Xaa at position 8 is arginine, lysine or
      ornithine

<400> SEQUENCE: 55

Gly Xaa Gly Ser Ser Ser Arg Xaa Ala Pro Gln Thr
1               5                   10
```

```
<210> SEQ ID NO 56
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
```

```
<222> LOCATION: (2)..(2)
<223> OTHER INFORMATION: Xaa at position 2 is any non-aromatic amino
      acid

<400> SEQUENCE: 56

Gly Xaa Gly Ser Ser Ser Arg Arg
1               5

<210> SEQ ID NO 57
<211> LENGTH: 9
<212> TYPE: PRT
<213> ORGANISM: Artificial Sequence
<220> FEATURE:
<223> OTHER INFORMATION: linker sequence

<400> SEQUENCE: 57

Gly Ala Gly Ser Ser Ser Arg Arg Ala
1               5

<210> SEQ ID NO 58
<211> LENGTH: 10
<212> TYPE: PRT
<213> ORGANISM: Artificial Sequence
<220> FEATURE:
<223> OTHER INFORMATION: linker sequence

<400> SEQUENCE: 58

Gly Ala Gly Ser Ser Ser Arg Arg Ala Pro
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Analog of IGF-1 C peptide

<400> SEQUENCE: 59

Gly Ala Gly Ser Ser Ser Arg Arg Ala Pro Gln
1               5                   10

<210> SEQ ID NO 60
<211> LENGTH: 12
<212> TYPE: PRT
<213> ORGANISM: Artificial Sequence
<220> FEATURE:
<223> OTHER INFORMATION: linker sequence

<400> SEQUENCE: 60

Gly Ala Gly Ser Ser Ser Arg Arg Ala Pro Gln Thr
1               5                   10

<210> SEQ ID NO 61
<211> LENGTH: 8
<212> TYPE: PRT
<213> ORGANISM: Artificial Sequence
<220> FEATURE:
<223> OTHER INFORMATION: linker sequence

<400> SEQUENCE: 61

Pro Tyr Gly Ser Ser Ser Arg Arg
1               5

<210> SEQ ID NO 62
<211> LENGTH: 8
<212> TYPE: PRT
<213> ORGANISM: Artificial Sequence
```

```
<220> FEATURE:
<223> OTHER INFORMATION: linker sequence

<400> SEQUENCE: 62

Pro Ala Gly Ser Ser Ser Arg Arg
1               5

<210> SEQ ID NO 63
<211> LENGTH: 9
<212> TYPE: PRT
<213> ORGANISM: Artificial Sequence
<220> FEATURE:
<223> OTHER INFORMATION: linker sequence

<400> SEQUENCE: 63

Pro Ala Gly Ser Ser Ser Arg Arg Ala
1               5

<210> SEQ ID NO 64
<211> LENGTH: 10
<212> TYPE: PRT
<213> ORGANISM: Artificial Sequence
<220> FEATURE:
<223> OTHER INFORMATION: linker sequence

<400> SEQUENCE: 64

Pro Ala Gly Ser Ser Ser Arg Arg Ala Pro
1               5                   10

<210> SEQ ID NO 65
<211> LENGTH: 11
<212> TYPE: PRT
<213> ORGANISM: Artificial Sequence
<220> FEATURE:
<223> OTHER INFORMATION: linker sequence

<400> SEQUENCE: 65

Pro Ala Gly Ser Ser Ser Arg Arg Ala Pro Gln
1               5                   10

<210> SEQ ID NO 66
<211> LENGTH: 12
<212> TYPE: PRT
<213> ORGANISM: Artificial Sequence
<220> FEATURE:
<223> OTHER INFORMATION: linker sequence

<400> SEQUENCE: 66

Pro Ala Gly Ser Ser Ser Arg Arg Ala Pro Gln Thr
1               5                   10

<210> SEQ ID NO 67
<211> LENGTH: 28
<212> TYPE: PRT
<213> ORGANISM: Homo sapiens

<400> SEQUENCE: 67

Ser Ser Ser Ser Arg Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 68
<211> LENGTH: 29
<212> TYPE: PRT
<213> ORGANISM: Homo sapiens
```

```
<220> FEATURE:
<221> NAME/KEY: MISC_FEATURE
<222> LOCATION: (5)..(5)
<223> OTHER INFORMATION: Xaa at position 5 is lysine or Arginine
<220> FEATURE:
<221> NAME/KEY: MISC_FEATURE
<222> LOCATION: (29)..(29)
<223> OTHER INFORMATION: Xaa at position 29 is lysine or Arginine

<400> SEQUENCE: 68

Ser Ser Ser Ser Xaa Ala Pro Pro Ser Leu Pro Ser Pro Ser Arg
1               5                   10                  15

Leu Pro Gly Pro Ser Asp Thr Pro Ile Leu Pro Gln Xaa
            20                  25

<210> SEQ ID NO 69
<211> LENGTH: 12
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (7)..(8)
<223> OTHER INFORMATION: Xaas at positions 7 and 8 are independently
      arginine, lysine or ornithine

<400> SEQUENCE: 69

Gly Tyr Gly Ser Ser Ser Xaa Xaa Ala Pro Gln Thr
1               5                   10

<210> SEQ ID NO 70
<211> LENGTH: 4
<212> TYPE: PRT
<213> ORGANISM: Homo sapiens

<400> SEQUENCE: 70

Tyr Thr Pro Lys
1

<210> SEQ ID NO 71
<211> LENGTH: 4
<212> TYPE: PRT
<213> ORGANISM: Homo sapiens

<400> SEQUENCE: 71

Phe Asn Lys Pro
1

<210> SEQ ID NO 72
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (1)..(1)
<223> OTHER INFORMATION: Xaa at position 1 = His, D-histidine,
      desaminohistidine, hydroxyl-histidine, acetyl-histidine,
      homo-histidine or alpha, alpha-dimethyl imidiazole acetic acid
      (DMIA), N-methyl histidine, alpha-methyl histidine, or imidazole
      acetic acid
<220> FEATURE:
<221> NAME/KEY: MISC_FEATURE
<222> LOCATION: (2)..(2)
<223> OTHER INFORMATION: Xaa at position 2 = Ser, D-serine, Ala,
      D-alanine, Val, glycine, n-methyl serine, aminoisobutyric acid
      (AIB) or N-methyl alanine
<220> FEATURE:
```

```
<221> NAME/KEY: MISC_FEATURE
<222> LOCATION: (3)..(3)
<223> OTHER INFORMATION: Xaa at position 3 is Gln, Glu, Orn or Nle
<220> FEATURE:
<221> NAME/KEY: MISC_FEATURE
<222> LOCATION: (10)..(10)
<223> OTHER INFORMATION: Xaa at position 10 = Tyr, Val or Trp
<220> FEATURE:
<221> NAME/KEY: MISC_FEATURE
<222> LOCATION: (12)..(12)
<223> OTHER INFORMATION: Xaa at position 12 = Ser, Lys or Arg
<220> FEATURE:
<221> NAME/KEY: MISC_FEATURE
<222> LOCATION: (15)..(15)
<223> OTHER INFORMATION: Xaa at position 15 = Asp, Glu, cysteic acid,
     homoglutamic acid and homocysteic acid
<220> FEATURE:
<221> NAME/KEY: MISC_FEATURE
<222> LOCATION: (16)..(16)
<223> OTHER INFORMATION: Xaa at position 16 = Ser, Gly, Glu, Gln,
     homoglutamic acid or homocysteic acid
<220> FEATURE:
<221> NAME/KEY: MISC_FEATURE
<222> LOCATION: (17)..(17)
<223> OTHER INFORMATION: Xaa at position 17 = Arg, Gln, Lys, Cys, Orn,
     homocycstein or acetyl phenylalanine
<220> FEATURE:
<221> NAME/KEY: MISC_FEATURE
<222> LOCATION: (18)..(18)
<223> OTHER INFORMATION: Xaa at position 18 = Arg, Ala,Lys, Cys, Orn,
     homocycstein or acetyl phenylalanine
<220> FEATURE:
<221> NAME/KEY: MISC_FEATURE
<222> LOCATION: (20)..(20)
<223> OTHER INFORMATION: Xaa at position 20 = Gln, Lys, arginine,
     ornithine or citrulline
<220> FEATURE:
<221> NAME/KEY: MISC_FEATURE
<222> LOCATION: (21)..(21)
<223> OTHER INFORMATION: Xaa at position 21 = Gln, Glu, Asp, Lys, Cys,
     Orn, homocycstein or acetyl phenylalanine
<220> FEATURE:
<221> NAME/KEY: MISC_FEATURE
<222> LOCATION: (23)..(23)
<223> OTHER INFORMATION: Xaa at position 23 is Val or Ile
<220> FEATURE:
<221> NAME/KEY: MISC_FEATURE
<222> LOCATION: (24)..(24)
<223> OTHER INFORMATION: Xaa at position 24 = Ala, Gln, Glu, Lys, Cys,
     Orn, homocycstein or acetyl phenylalanine
<220> FEATURE:
<221> NAME/KEY: MISC_FEATURE
<222> LOCATION: (27)..(27)
<223> OTHER INFORMATION: Xaa at position 27 = Met, Leu, Val or Nle
<220> FEATURE:
<221> NAME/KEY: MISC_FEATURE
<222> LOCATION: (28)..(28)
<223> OTHER INFORMATION: Xaa at position 28 = Asn, Lys or Asp
<220> FEATURE:
<221> NAME/KEY: MISC_FEATURE
<222> LOCATION: (29)..(29)
<223> OTHER INFORMATION: Xaa at position 29 is Thr, Gly, Lys, Cys, Orn,
     homocycstein or acetyl phenylalanine

<400> SEQUENCE: 72

Xaa Xaa Xaa Gly Thr Phe Thr Ser Asp Xaa Ser Xaa Tyr Leu Xaa Xaa
1               5                   10                  15

Xaa Xaa Ala Xaa Xaa Phe Xaa Xaa Trp Leu Xaa Xaa Xaa
            20                  25

<210> SEQ ID NO 73
<211> LENGTH: 21
<212> TYPE: PRT
<213> ORGANISM: Artificial Sequence
<220> FEATURE:
<223> OTHER INFORMATION: Analog of Insulin A chain
```

```
<220> FEATURE:
<221> NAME/KEY: MISC_FEATURE
<222> LOCATION: (8)..(8)
<223> OTHER INFORMATION: Xaa at position 8 is  threonine or histidine
<220> FEATURE:
<221> NAME/KEY: MISC_FEATURE
<222> LOCATION: (9)..(9)
<223> OTHER INFORMATION: Xaa at position 9 is  valine or tyrosine
<220> FEATURE:
<221> NAME/KEY: MISC_FEATURE
<222> LOCATION: (21)..(21)
<223> OTHER INFORMATION: Xaa at position 21 is asparagine or glycine

<400> SEQUENCE: 73

Gly Ile Val Glu Gln Cys Cys Xaa Xaa Ile Cys Ser Leu Tyr Gln Leu
1               5                   10                  15

Glu Asn Tyr Cys Xaa
            20

<210> SEQ ID NO 74
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 74

Gly Ile Val Asp Glu Cys Cys Xaa Xaa Ser Cys Asp Leu Arg Arg Leu
1               5                   10                  15

Glu Met Xaa Cys Xaa
            20

<210> SEQ ID NO 75
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine

<400> SEQUENCE: 75
```

```
Xaa Leu Cys Gly Ala Xaa Leu Val Asp Ala Leu Tyr Leu Val Cys Gly
1               5                   10                  15

Asp Xaa Gly Phe Tyr
            20

<210> SEQ ID NO 76
<211> LENGTH: 8
<212> TYPE: PRT
<213> ORGANISM: Artificial Sequence
<220> FEATURE:
<223> OTHER INFORMATION: Analog of IGF-1 C peptide
<220> FEATURE:
<221> NAME/KEY: MISC_FEATURE
<222> LOCATION: (7)..(8)
<223> OTHER INFORMATION: The Xaas at positions 7 and 8 are independently
      arginine, lysine or ornithine

<400> SEQUENCE: 76

Gly Ala Gly Ser Ser Ser Xaa Xaa
1               5

<210> SEQ ID NO 77
<211> LENGTH: 12
<212> TYPE: PRT
<213> ORGANISM: Artificial Sequence
<220> FEATURE:
<223> OTHER INFORMATION: Analog of IGF-1 C peptide
<220> FEATURE:
<221> NAME/KEY: MISC_FEATURE
<222> LOCATION: (7)..(8)
<223> OTHER INFORMATION: The Xaas at positions 7 and 8 are independently
      arginine, lysine or ornithine

<400> SEQUENCE: 77

Gly Tyr Gly Ser Ser Ser Xaa Xaa Ala Pro Gln Thr
1               5                   10

<210> SEQ ID NO 78
<211> LENGTH: 10
<212> TYPE: PRT
<213> ORGANISM: Artificial Sequence
<220> FEATURE:
<223> OTHER INFORMATION: peptide fragment representing the carboxy
      terminal 10 amino acids of Exendin-4

<400> SEQUENCE: 78

Gly Pro Ser Ser Gly Ala Pro Pro Pro Ser
1               5                   10

<210> SEQ ID NO 79
<211> LENGTH: 10
<212> TYPE: PRT
<213> ORGANISM: Artificial Sequence
<220> FEATURE:
<223> OTHER INFORMATION: peptide fragment representing the carboxy
      terminal 10 amino acids of Exendin-4
<220> FEATURE:
<221> NAME/KEY: MOD_RES
<222> LOCATION: (10)..(10)
<223> OTHER INFORMATION: AMIDATION

<400> SEQUENCE: 79

Gly Pro Ser Ser Gly Ala Pro Pro Pro Ser
1               5                   10

<210> SEQ ID NO 80
<211> LENGTH: 11
<212> TYPE: PRT
```

```
<213> ORGANISM: Artificial Sequence
<220> FEATURE:
<223> OTHER INFORMATION: peptide fragment representing the carboxy
      terminal 10 amino acids of Exendin-4
<220> FEATURE:
<221> NAME/KEY: MISC_FEATURE
<222> LOCATION: (11)..(11)
<223> OTHER INFORMATION: pegylated

<400> SEQUENCE: 80

Gly Pro Ser Ser Gly Ala Pro Pro Pro Ser Cys
1               5                   10

<210> SEQ ID NO 81
<211> LENGTH: 29
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Xaa at position 15 = Asp, Glu, homoglutamic
      acid, cysteic acid or homocysteic acid
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln or Lys
<220> FEATURE:
<221> NAME/KEY: MISC_FEATURE
<222> LOCATION: (24)..(24)
<223> OTHER INFORMATION: Xaa at position 24 = Gln or Glu
<220> FEATURE:
<221> NAME/KEY: MISC_FEATURE
<222> LOCATION: (28)..(28)
<223> OTHER INFORMATION: Xaa at position 28 = Asn, Lys or an acidic
      amino acid
<220> FEATURE:
<221> NAME/KEY: MISC_FEATURE
<222> LOCATION: (29)..(29)
<223> OTHER INFORMATION: Xaa at position 29 = Thr, Gly or an acidic
      amino acid

<400> SEQUENCE: 81

His Ser Gln Gly Thr Phe Thr Ser Asp Tyr Ser Lys Tyr Leu Xaa Xaa
1               5                   10                  15

Arg Arg Ala Xaa Asp Phe Val Xaa Trp Leu Met Xaa Xaa
            20                  25

<210> SEQ ID NO 82
<211> LENGTH: 29
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Xaa at position 15 = Asp, Glu, cysteic acid,
      homoglutamic acid or homocysteic acid
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln or Lys
<220> FEATURE:
<221> NAME/KEY: MISC_FEATURE
<222> LOCATION: (24)..(24)
<223> OTHER INFORMATION: Xaa at position 24 = Gln or Glu
```

```
<220> FEATURE:
<221> NAME/KEY: MISC_FEATURE
<222> LOCATION: (28)..(28)
<223> OTHER INFORMATION: Xaa at position 28 = Asn, Asp or Lys
<220> FEATURE:
<221> NAME/KEY: MISC_FEATURE
<222> LOCATION: (29)..(29)
<223> OTHER INFORMATION: Xaa at position 29 is Thr or Gly

<400> SEQUENCE: 82

His Ser Gln Gly Thr Phe Thr Ser Asp Tyr Ser Lys Tyr Leu Asp Xaa
1               5                   10                  15

Arg Arg Ala Xaa Asp Phe Val Xaa Trp Leu Met Xaa Xaa
            20                  25

<210> SEQ ID NO 83
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (3)..(3)
<223> OTHER INFORMATION: Xaa at position 3= Glu, Orn or Nle
<220> FEATURE:
<221> NAME/KEY: MISC_FEATURE
<222> LOCATION: (15)..(15)
<223> OTHER INFORMATION: Xaa at position 15 = Asp, Glu, homoglutamic
      acid, cysteic acid or homocysteic acid
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln or Lys
<220> FEATURE:
<221> NAME/KEY: MISC_FEATURE
<222> LOCATION: (24)..(24)
<223> OTHER INFORMATION: Xaa at position 24 = Gln or Glu
<220> FEATURE:
<221> NAME/KEY: MISC_FEATURE
<222> LOCATION: (28)..(28)
<223> OTHER INFORMATION: Xaa at position 28 = Asn, Lys or an acidic
      amino acid
<220> FEATURE:
<221> NAME/KEY: MISC_FEATURE
<222> LOCATION: (29)..(29)
<223> OTHER INFORMATION: Xaa at position 29 = Thr or an acidic amino
      acid

<400> SEQUENCE: 83

His Ser Xaa Gly Thr Phe Thr Ser Asp Tyr Ser Lys Tyr Leu Xaa Xaa
1               5                   10                  15

Arg Arg Ala Xaa Asp Phe Val Xaa Trp Leu Met Xaa Xaa
            20                  25

<210> SEQ ID NO 84
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (15)..(15)
<223> OTHER INFORMATION: Xaa at position 15 is Glu or Asp
<220> FEATURE:
<221> NAME/KEY: MISC_FEATURE
<222> LOCATION: (28)..(28)
```

```
<223> OTHER INFORMATION: Xaa at position 28 is Glu or Asp
<220> FEATURE:
<221> NAME/KEY: MOD_RES
<222> LOCATION: (29)..(29)
<223> OTHER INFORMATION: AMIDATION

<400> SEQUENCE: 84

His Ser Gln Gly Thr Phe Thr Ser Asp Tyr Ser Lys Tyr Leu Xaa Glu
1               5                   10                  15

Arg Arg Ala Gln Asp Phe Val Gln Trp Leu Met Xaa Thr
            20                  25

<210> SEQ ID NO 85
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (12)..(16)
<223> OTHER INFORMATION: lactam ring formed between side chain of Lys 12
      and Glu 16
<220> FEATURE:
<221> NAME/KEY: MISC_FEATURE
<222> LOCATION: (15)..(15)
<223> OTHER INFORMATION: Xaa at position 15 is Glu or Asp
<220> FEATURE:
<221> NAME/KEY: MISC_FEATURE
<222> LOCATION: (28)..(28)
<223> OTHER INFORMATION: Xaa at position 28 is Glu or Asp
<220> FEATURE:
<221> NAME/KEY: MOD_RES
<222> LOCATION: (29)..(29)
<223> OTHER INFORMATION: AMIDATION

<400> SEQUENCE: 85

His Ser Gln Gly Thr Phe Thr Ser Asp Tyr Ser Lys Tyr Leu Xaa Glu
1               5                   10                  15

Arg Arg Ala Gln Asp Phe Val Gln Trp Leu Met Xaa Thr
            20                  25

<210> SEQ ID NO 86
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (15)..(15)
<223> OTHER INFORMATION: Xaa at position 15 is Glu or Asp
<220> FEATURE:
<221> NAME/KEY: MISC_FEATURE
<222> LOCATION: (16)..(20)
<223> OTHER INFORMATION: lactam ring formed between side chain of Glu 16
      and Lys 20
<220> FEATURE:
<221> NAME/KEY: MISC_FEATURE
<222> LOCATION: (28)..(28)
<223> OTHER INFORMATION: Xaa at position 28 is Glu or Asp
<220> FEATURE:
<221> NAME/KEY: MOD_RES
<222> LOCATION: (29)..(29)
<223> OTHER INFORMATION: AMIDATION

<400> SEQUENCE: 86

His Ser Gln Gly Thr Phe Thr Ser Asp Tyr Ser Lys Tyr Leu Xaa Glu
1               5                   10                  15

Arg Arg Ala Lys Asp Phe Val Gln Trp Leu Met Xaa Thr
            20                  25
```

```
<210> SEQ ID NO 87
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (15)..(15)
<223> OTHER INFORMATION: Xaa at position 15 is Glu or Asp
<220> FEATURE:
<221> NAME/KEY: MISC_FEATURE
<222> LOCATION: (20)..(24)
<223> OTHER INFORMATION: lactam ring formed between side chain of Lys 20
      and Glu 24
<220> FEATURE:
<221> NAME/KEY: MISC_FEATURE
<222> LOCATION: (28)..(28)
<223> OTHER INFORMATION: Xaa at position 28 is Glu or Asp
<220> FEATURE:
<221> NAME/KEY: MOD_RES
<222> LOCATION: (29)..(29)
<223> OTHER INFORMATION: AMIDATION

<400> SEQUENCE: 87

His Ser Gln Gly Thr Phe Thr Ser Asp Tyr Ser Lys Tyr Leu Xaa Ser
1               5                   10                  15

Arg Arg Ala Lys Asp Phe Val Glu Trp Leu Met Xaa Thr
            20                  25

<210> SEQ ID NO 88
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (15)..(15)
<223> OTHER INFORMATION: Xaa at position 15 is Glu or Asp
<220> FEATURE:
<221> NAME/KEY: MISC_FEATURE
<222> LOCATION: (24)..(28)
<223> OTHER INFORMATION: lactam ring formed between side chain of Glu 24
      and Lys 28
<220> FEATURE:
<221> NAME/KEY: MISC_FEATURE
<222> LOCATION: (29)..(29)
<223> OTHER INFORMATION: Xaa at position 29 is Glu or Thr
<220> FEATURE:
<221> NAME/KEY: MOD_RES
<222> LOCATION: (29)..(29)
<223> OTHER INFORMATION: AMIDATION

<400> SEQUENCE: 88

His Ser Gln Gly Thr Phe Thr Ser Asp Tyr Ser Lys Tyr Leu Xaa Ser
1               5                   10                  15

Arg Arg Ala Gln Asp Phe Val Glu Trp Leu Met Lys Xaa
            20                  25

<210> SEQ ID NO 89
<211> LENGTH: 29
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa at position 27 is Met, Leu or Nle

<400> SEQUENCE: 89
```

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr
            20                  25
```

<210> SEQ ID NO 90
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (16)..(16)
<223> OTHER INFORMATION: Xaa is Glu, Gln, homoglutamic acid or
      homocysteic acid
<220> FEATURE:
<221> NAME/KEY: MISC_FEATURE
<222> LOCATION: (17)..(17)
<223> OTHER INFORMATION: Xaa is Arg, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa at position 27 is Met, Leu or Nle

<400> SEQUENCE: 90

```
His Ser Gln Gly Thr Phe Thr Ser Asp Tyr Ser Lys Tyr Leu Asp Xaa
1               5                   10                  15

Xaa Arg Ala Gln Asp Phe Val Gln Trp Leu Xaa Asn Thr
            20                  25
```

<210> SEQ ID NO 91
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (16)..(16)
<223> OTHER INFORMATION: Xaa is Glu, Gln, homoglutamic acid or
      homocysteic acid
<220> FEATURE:
<221> NAME/KEY: MISC_FEATURE
<222> LOCATION: (21)..(21)
<223> OTHER INFORMATION: Xaa is Asp, Cys, Orn, homocysteine or acetyl
      phenyalanine
<220> FEATURE:
<221> NAME/KEY: MISC_FEATURE
<222> LOCATION: (27)..(27)
<223> OTHER INFORMATION: Xaa at position 27 is Met, Leu or Nle

<400> SEQUENCE: 91

```
His Ser Gln Gly Thr Phe Thr Ser Asp Tyr Ser Lys Tyr Leu Asp Xaa
1               5                   10                  15

Arg Arg Ala Gln Xaa Phe Val Gln Trp Leu Xaa Asn Thr
            20                  25
```

<210> SEQ ID NO 92
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<222> LOCATION: (16)..(16)
<223> OTHER INFORMATION: Xaa is Glu, Gln, homoglutamic acid or
      homocysteic acid
<220> FEATURE:

```
<221> NAME/KEY: MISC_FEATURE
<222> LOCATION: (24)..(24)
<223> OTHER INFORMATION: Xaa is Gln, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa at postion 27 is Met, Leu or Nle

<400> SEQUENCE: 92

His Ser Gln Gly Thr Phe Thr Ser Asp Tyr Ser Lys Tyr Leu Asp Xaa
1               5                   10                  15

Arg Arg Ala Gln Asp Phe Val Xaa Trp Leu Xaa Asn Thr
            20                  25

<210> SEQ ID NO 93
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (16)..(16)
<223> OTHER INFORMATION: Xaa is Glu, Gln, homoglutamic acid or
      homocysteic acid
<220> FEATURE:
<221> NAME/KEY: MISC_FEATURE
<222> LOCATION: (21)..(21)
<223> OTHER INFORMATION: Xaa is Asp, Cys, Orn, homocysteine or acetyl
      phenylalanine
<220> FEATURE:
<221> NAME/KEY: MISC_FEATURE
<222> LOCATION: (24)..(24)
<223> OTHER INFORMATION: Xaa is Gln, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa at position 27 is Met, Leu or Nle

<400> SEQUENCE: 93

His Ser Gln Gly Thr Phe Thr Ser Asp Tyr Ser Lys Tyr Leu Asp Xaa
1               5                   10                  15

Arg Arg Ala Gln Xaa Phe Val Xaa Trp Leu Xaa Asn Thr
            20                  25

<210> SEQ ID NO 94
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (21)..(21)
<223> OTHER INFORMATION: Xaa is Asp, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 94

His Ser Gln Gly Thr Phe Thr Ser Asp Tyr Ser Lys Tyr Leu Asp Glu
1               5                   10                  15

Arg Arg Ala Gln Xaa Phe Val Gln Trp Leu Xaa Asn Thr
            20                  25

<210> SEQ ID NO 95
```

```
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (24)..(24)
<223> OTHER INFORMATION: Xaa at position 24 is Gln, Cys, Orn,
      homocysteine or acetyl phenylalanine
<220> FEATURE:
<221> NAME/KEY: MISC_FEATURE
<222> LOCATION: (27)..(27)
<223> OTHER INFORMATION: Xaa at position 27 is Met, Leu or Nle

<400> SEQUENCE: 95

His Ser Gln Gly Thr Phe Thr Ser Asp Tyr Ser Lys Tyr Leu Asp Glu
1               5                   10                  15

Arg Arg Ala Gln Asp Phe Val Xaa Trp Leu Xaa Asn Thr
            20                  25

<210> SEQ ID NO 96
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (16)..(16)
<223> OTHER INFORMATION: Xaa at position 16 is Glu, Gln, homoglutamic
      acid or homocysteic acid

<400> SEQUENCE: 96

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 97
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa at position 27 = Met, Leu or Nle

<400> SEQUENCE: 97

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Xaa Asn Thr
            20                  25

<210> SEQ ID NO 98
<211> LENGTH: 29
<212> TYPE: PRT
<213> ORGANISM: Artificial Sequence
<220> FEATURE:
<223> OTHER INFORMATION: Glucagon analogue

<400> SEQUENCE: 98

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25
```

<210> SEQ ID NO 99
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (29)..(29)
<223> OTHER INFORMATION: AMIDATION

<400> SEQUENCE: 99

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 100
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (12)..(16)
<223> OTHER INFORMATION: lactam ring formed between side chain of Lys 12
      and Glu 16

<400> SEQUENCE: 100

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 101
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (16)..(20)
<223> OTHER INFORMATION: lactam ring formed between side chain of Glu 16
      and Lys 20

<400> SEQUENCE: 101

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 102
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (20)..(24)
<223> OTHER INFORMATION: lactam ring formed between side chain of Lys 20
      and Glu 24

<400> SEQUENCE: 102

His Ser Gln Gly Thr Phe Thr Ser Asp Tyr Ser Lys Tyr Leu Asp Ser

```
                1               5                   10                  15
Arg Arg Ala Lys Asp Phe Val Glu Trp Leu Met Asn Thr
                20                  25

<210> SEQ ID NO 103
<211> LENGTH: 29
<212> TYPE: PRT
<213> ORGANISM: Homo sapiens
<220> FEATURE:
<221> NAME/KEY: MISC_FEATURE
<222> LOCATION: (24)..(28)
<223> OTHER INFORMATION: lactam ring formed between side chain of Glu 24
      and Lys 28

<400> SEQUENCE: 103

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Thr
                20                  25

<210> SEQ ID NO 104
<211> LENGTH: 29
<212> TYPE: PRT
<213> ORGANISM: Homo sapiens
<220> FEATURE:
<221> NAME/KEY: MISC_FEATURE
<222> LOCATION: (12)..(16)
<223> OTHER INFORMATION: lactam ring formed between side chain of Lys 12
      and Glu 16
<220> FEATURE:
<221> NAME/KEY: MISC_FEATURE
<222> LOCATION: (20)..(24)
<223> OTHER INFORMATION: lactam ring formed between side chain of Lys 20
      and Glu 24

<400> SEQUENCE: 104

His Ser Gln Gly Thr Phe Thr Ser Asp Tyr Ser Lys Tyr Leu Asp Glu
1               5                   10                  15

Arg Arg Ala Lys Asp Phe Val Glu Trp Leu Met Asn Thr
                20                  25

<210> SEQ ID NO 105
<211> LENGTH: 29
<212> TYPE: PRT
<213> ORGANISM: Homo sapiens
<220> FEATURE:
<221> NAME/KEY: MISC_FEATURE
<222> LOCATION: (16)..(20)
<223> OTHER INFORMATION: lactam ring formed between side chain of Lys 12
      and Glu 16
<220> FEATURE:
<221> NAME/KEY: MISC_FEATURE
<222> LOCATION: (24)..(28)
<223> OTHER INFORMATION: lactam ring formed between side chain of Glu 24
      and Lys 28

<400> SEQUENCE: 105

His Ser Gln Gly Thr Phe Thr Ser Asp Tyr Ser Lys Tyr Leu Asp Glu
1               5                   10                  15

Arg Arg Ala Asp Asp Phe Val Glu Trp Leu Met Lys Thr
                20                  25

<210> SEQ ID NO 106
<211> LENGTH: 29
<212> TYPE: PRT
<213> ORGANISM: Homo sapiens
<220> FEATURE:
<221> NAME/KEY: MISC_FEATURE
```

<222> LOCATION: (16)..(20)
<223> OTHER INFORMATION: lactam ring formed between side chain of Glu 16
      and Lys 20
<220> FEATURE:
<221> NAME/KEY: MISC_FEATURE
<222> LOCATION: (24)..(28)
<223> OTHER INFORMATION: lactam ring formed between side chain of Glu 24
      and Lys 28

<400> SEQUENCE: 106

His Ser Gln Gly Thr Phe Thr Ser Asp Tyr Ser Lys Tyr Leu Asp Glu
1               5                   10                  15

Arg Arg Ala Lys Asp Phe Val Glu Trp Leu Met Lys Thr
            20                  25

<210> SEQ ID NO 107
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (30)..(30)
<223> OTHER INFORMATION: Xaa = any amino acid
<220> FEATURE:
<221> NAME/KEY: MOD_RES
<222> LOCATION: (30)..(30)
<223> OTHER INFORMATION: AMIDATION

<400> SEQUENCE: 107

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr Xaa
            20                  25                  30

<210> SEQ ID NO 108
<211> LENGTH: 29
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = glutamine, lysine,
      arginine, ornithine or citrulline
<220> FEATURE:
<221> NAME/KEY: MISC_FEATURE
<222> LOCATION: (24)..(24)
<223> OTHER INFORMATION: Xaa at position 24 = Gln or Glu
<220> FEATURE:
<221> NAME/KEY: MISC_FEATURE
<222> LOCATION: (28)..(28)
<223> OTHER INFORMATION: Xaa at position 28 = Asn, Asp or Lys
<220> FEATURE:
<221> NAME/KEY: MISC_FEATURE
<222> LOCATION: (29)..(29)
<223> OTHER INFORMATION: Xaa at position 29 = Thr or Gly

<400> SEQUENCE: 108

His Ser Gln Gly Thr Phe Thr Ser Asp Tyr Ser Lys Tyr Leu Asp Xaa
1               5                   10                  15

Arg Arg Ala Xaa Asp Phe Val Xaa Trp Leu Met Xaa Xaa
            20                  25

<210> SEQ ID NO 109

```
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (12)..(16)
<223> OTHER INFORMATION: lactam ring formed between side chain of Lys 12
      and Glu 16
<220> FEATURE:
<221> NAME/KEY: MISC_FEATURE
<222> LOCATION: (28)..(28)
<223> OTHER INFORMATION: Xaa at position 28 is Asp or Asn
<220> FEATURE:
<221> NAME/KEY: MISC_FEATURE
<222> LOCATION: (29)..(29)
<223> OTHER INFORMATION: Xaa at position 29 is Thr or Gly

<400> SEQUENCE: 109

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Xaa Xaa
            20                  25

<210> SEQ ID NO 110
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (16)..(20)
<223> OTHER INFORMATION: lactam ring formed between side chain of Glu 16
      and Lys 20
<220> FEATURE:
<221> NAME/KEY: MISC_FEATURE
<222> LOCATION: (28)..(28)
<223> OTHER INFORMATION: Xaa at position 28 is Asp or Asn
<220> FEATURE:
<221> NAME/KEY: MISC_FEATURE
<222> LOCATION: (29)..(29)
<223> OTHER INFORMATION: Xaa at position 29 is Thr or Gly

<400> SEQUENCE: 110

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Xaa Xaa
            20                  25

<210> SEQ ID NO 111
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (20)..(24)
<223> OTHER INFORMATION: lactam ring formed between side chain of Lys 20
      and Glu 24
<220> FEATURE:
<221> NAME/KEY: MISC_FEATURE
<222> LOCATION: (28)..(28)
<223> OTHER INFORMATION: Xaa at position 28 is Asp or Asn
<220> FEATURE:
<221> NAME/KEY: MISC_FEATURE
<222> LOCATION: (29)..(29)
<223> OTHER INFORMATION: Xaa at position 29 is Thr or Gly

<400> SEQUENCE: 111
```

```
His Ser Gln Gly Thr Phe Thr Ser Asp Tyr Ser Lys Tyr Leu Asp Ser
1               5                   10                  15

Arg Arg Ala Lys Asp Phe Val Glu Trp Leu Met Xaa Xaa
            20                  25
```

<210> SEQ ID NO 112
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (24)..(28)
<223> OTHER INFORMATION: lactam ring formed between side chain of Glu 24
      and Lys 28
<220> FEATURE:
<221> NAME/KEY: MISC_FEATURE
<222> LOCATION: (29)..(29)
<223> OTHER INFORMATION: Xaa at position 29 is Thr or Gly

<400> SEQUENCE: 112

```
His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Xaa
            20                  25
```

<210> SEQ ID NO 113
<211> LENGTH: 29
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = glutamine, lysine,
      arginine, ornithine or citrulline
<220> FEATURE:
<221> NAME/KEY: MISC_FEATURE
<222> LOCATION: (24)..(24)
<223> OTHER INFORMATION: Xaa at position 24 = Gln or Glu
<220> FEATURE:
<221> NAME/KEY: MISC_FEATURE
<222> LOCATION: (28)..(28)
<223> OTHER INFORMATION: Xaa at position 28 = Asn, Asp or Lys
<220> FEATURE:
<221> NAME/KEY: MISC_FEATURE
<222> LOCATION: (29)..(29)
<223> OTHER INFORMATION: Xaa at position 29 = Thr or Gly

<400> SEQUENCE: 113

```
His Ser Gln Gly Thr Phe Thr Ser Asp Tyr Ser Lys Tyr Leu Asp Xaa
1               5                   10                  15

Arg Arg Ala Xaa Asp Phe Val Xaa Trp Leu Met Xaa Xaa
            20                  25
```

<210> SEQ ID NO 114
<211> LENGTH: 29
<212> TYPE: PRT
<213> ORGANISM: Homo sapiens

<400> SEQUENCE: 114

```
His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
```

```
            20                  25

<210> SEQ ID NO 115
<211> LENGTH: 29
<212> TYPE: PRT
<213> ORGANISM: Artificial Sequence
<220> FEATURE:
<223> OTHER INFORMATION: glucagon analogue

<400> SEQUENCE: 115

His Ser Gln Gly Thr Phe Thr Ser Asp Tyr Ser Lys Tyr Leu Asp Ser
1               5                   10                  15

Arg Arg Ala Lys Asp Phe Val Glu Trp Leu Met Asn Thr
            20                  25

<210> SEQ ID NO 116
<211> LENGTH: 29
<212> TYPE: PRT
<213> ORGANISM: Artificial Sequence
<220> FEATURE:
<223> OTHER INFORMATION: glucagon analogue

<400> SEQUENCE: 116

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Thr
            20                  25

<210> SEQ ID NO 117
<211> LENGTH: 8
<212> TYPE: PRT
<213> ORGANISM: Artificial Sequence
<220> FEATURE:
<223> OTHER INFORMATION: peptide fragment representing the carboxy
      terminal 8 amino acids of oxyntomodulin

<400> SEQUENCE: 117

Lys Arg Asn Arg Asn Asn Ile Ala
1               5

<210> SEQ ID NO 118
<211> LENGTH: 4
<212> TYPE: PRT
<213> ORGANISM: Artificial Sequence
<220> FEATURE:
<223> OTHER INFORMATION: peptide fragment representing the amino 4 amino
      acids of oxyntomodulin carboxy terminus of SEQ ID NO: 27

<400> SEQUENCE: 118

Lys Arg Asn Arg
1

<210> SEQ ID NO 119
<211> LENGTH: 29
<212> TYPE: PRT
<213> ORGANISM: homo sapiens

<400> SEQUENCE: 119

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 120
<211> LENGTH: 29
```

```
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (1)..(1)
<223> OTHER INFORMATION: Xaa at position 1 = His, D-histidine,
      desaminohistidine, hydroxyl-histidine, acetyl-histidine,
      homo-histidine or alpha, alpha-dimethyl imidazole acetic acid
      (DMIA), N-methyl histidine, alpha-methyl histidine, or imidazole
      acetic acid
<220> FEATURE:
<221> NAME/KEY: MISC_FEATURE
<222> LOCATION: (2)..(2)
<223> OTHER INFORMATION: Xaa at position 2 = Ser, D-serine, Ala,
      D-alanine, Val, glycine, n-methyl serine, aminoisobutyric acid
      (AIB) or N-methyl alanine
<220> FEATURE:
<221> NAME/KEY: MISC_FEATURE
<222> LOCATION: (3)..(3)
<223> OTHER INFORMATION: Xaa at position 3 is Gln, Glu, Orn or Nle
<220> FEATURE:
<221> NAME/KEY: MISC_FEATURE
<222> LOCATION: (15)..(15)
<223> OTHER INFORMATION: Xaa at position 15 = Asp, Glu, cysteic acid,
      homoglutamic acid and homocysteic acid
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln, Lys, arginine,
      ornithine or citrulline
<220> FEATURE:
<221> NAME/KEY: MISC_FEATURE
<222> LOCATION: (21)..(21)
<223> OTHER INFORMATION: Xaa at position 21 = Gln, Glu, Asp, Lys, Cys,
      Orn, homocycstein or acetyl phenylalanine
<220> FEATURE:
<221> NAME/KEY: MISC_FEATURE
<222> LOCATION: (23)..(23)
<223> OTHER INFORMATION: Xaa at position 23 is Val or Ile
<220> FEATURE:
<221> NAME/KEY: MISC_FEATURE
<222> LOCATION: (24)..(24)
<223> OTHER INFORMATION: Xaa at position 24 = Ala, Gln, Glu, Lys, Cys,
      Orn, homocycstein or acetyl phenylalanine
<220> FEATURE:
<221> NAME/KEY: MISC_FEATURE
<222> LOCATION: (27)..(27)
<223> OTHER INFORMATION: Xaa at position 27 = Met, Leu or Nle
<220> FEATURE:
<221> NAME/KEY: MISC_FEATURE
<222> LOCATION: (28)..(28)
<223> OTHER INFORMATION: Xaa at position 28 = Asn, Lys or Asp
<220> FEATURE:
<221> NAME/KEY: MISC_FEATURE
<222> LOCATION: (29)..(29)
<223> OTHER INFORMATION: Xaa at position 29 is Thr or Gly, Lys, Cys,
      Orn, homocycstein or acetyl phenylalanine

<400> SEQUENCE: 120

Xaa Xaa Xaa Gly Thr Phe Thr Ser Asp Tyr Ser Lys Tyr Leu Xaa Xaa
1               5                   10                  15

Arg Arg Ala Xaa Xaa Phe Xaa Xaa Trp Leu Xaa Xaa Xaa
            20                  25

<210> SEQ ID NO 121
<211> LENGTH: 38
<212> TYPE: PRT
<213> ORGANISM: Artificial Sequence
<220> FEATURE:
```

```
<223> OTHER INFORMATION: glucagon analogue
<220> FEATURE:
<221> NAME/KEY: MISC_FEATURE
<222> LOCATION: (15)..(15)
<223> OTHER INFORMATION: Xaa at position 15 = Asp, Glu, homoglutamic
      acid, cysteic acid or homocysteic acid
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln or Lys
<220> FEATURE:
<221> NAME/KEY: MISC_FEATURE
<222> LOCATION: (24)..(24)
<223> OTHER INFORMATION: Xaa at position 24 = Gln or Glu
<220> FEATURE:
<221> NAME/KEY: MISC_FEATURE
<222> LOCATION: (28)..(28)
<223> OTHER INFORMATION: Xaa at position 28 = Asn, Lys or Asp

<400> SEQUENCE: 121

His Ser Gln Gly Thr Phe Thr Ser Asp Tyr Ser Lys Tyr Leu Xaa Xaa
1               5                   10                  15

Arg Arg Ala Xaa Asp Phe Val Xaa Trp Leu Met Xaa Gly Gly Pro Ser
            20                  25                  30

Ser Gly Pro Pro Pro Ser
        35

<210> SEQ ID NO 122
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (16)..(16)
<223> OTHER INFORMATION: Xaa at position 16 = Ser, Glu, Gln,
      homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln or Lys
<220> FEATURE:
<221> NAME/KEY: MISC_FEATURE
<222> LOCATION: (21)..(21)
<223> OTHER INFORMATION: Xaa at position 21 = Asp, Lys, Cys, Orn,
      homocycstein or acetyl phenylalanine
<220> FEATURE:
<221> NAME/KEY: MISC_FEATURE
<222> LOCATION: (24)..(24)
<223> OTHER INFORMATION: Xaa at position 24 = Gln, Lys, Cys, Orn,
      homocycstein or acetyl phenylalanine
<220> FEATURE:
<221> NAME/KEY: MISC_FEATURE
<222> LOCATION: (27)..(27)
<223> OTHER INFORMATION: Xaa at position 27 = Met, Leu or Nle

<400> SEQUENCE: 122

His Ser Gln Gly Thr Phe Thr Ser Asp Tyr Ser Lys Tyr Leu Asp Xaa
1               5                   10                  15

Arg Arg Ala Xaa Xaa Phe Val Xaa Trp Leu Xaa Asn Thr
            20                  25

<210> SEQ ID NO 123
<211> LENGTH: 29
<212> TYPE: PRT
<213> ORGANISM: Artificial Sequence
```

<220> FEATURE:
<223> OTHER INFORMATION: glucagon analogue
<220> FEATURE:
<221> NAME/KEY: MISC_FEATURE
<222> LOCATION: (15)..(15)
<223> OTHER INFORMATION: Xaa at position 15 = Asp, Glu, homoglutamic
    acid, cysteic acid or homocysteic acid
<220> FEATURE:
<221> NAME/KEY: MISC_FEATURE
<222> LOCATION: (16)..(16)
<223> OTHER INFORMATION: Xaa at position 16 = Ser, Glu, Gln,
    homoglutamic acid or homocysteic acid
<220> FEATURE:
<221> NAME/KEY: MISC_FEATURE
<222> LOCATION: (20)..(20)
<223> OTHER INFORMATION: Xaa at position 20 = Gln, Lys, Arg, Orn, or
    citrulline
<220> FEATURE:
<221> NAME/KEY: MISC_FEATURE
<222> LOCATION: (21)..(21)
<223> OTHER INFORMATION: Xaa at position 21 = Asp, Glu, homoglutamic
    acid, or homocysteic acid
<220> FEATURE:
<221> NAME/KEY: MISC_FEATURE
<222> LOCATION: (24)..(24)
<223> OTHER INFORMATION: Xaa at position 24 = Gln or Glu
<220> FEATURE:
<221> NAME/KEY: MISC_FEATURE
<222> LOCATION: (28)..(28)
<223> OTHER INFORMATION: Xaa at position 28 = Asn, Lys or an acidic
    amino acid
<220> FEATURE:
<221> NAME/KEY: MISC_FEATURE
<222> LOCATION: (29)..(29)
<223> OTHER INFORMATION: Xaa at position 29 = Thr, Gly or an acidic
    amino acid

<400> SEQUENCE: 123

His Ser Gln Gly Thr Phe Thr Ser Asp Tyr Ser Lys Tyr Leu Xaa Xaa
1               5                   10                  15

Arg Arg Ala Xaa Xaa Phe Val Xaa Trp Leu Met Xaa Xaa
            20                  25

<210> SEQ ID NO 124
<211> LENGTH: 29
<212> TYPE: PRT
<213> ORGANISM: Homo sapiens

<400> SEQUENCE: 124

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 125
<211> LENGTH: 29
<212> TYPE: PRT
<213> ORGANISM: Artificial Sequence
<220> FEATURE:
<223> OTHER INFORMATION: glucagon analogue

<400> SEQUENCE: 125

His Ser Gln Gly Thr Phe Thr Ser Asp Tyr Ser Lys Tyr Leu Asp Ser
1               5                   10                  15

Arg Arg Ala Lys Asp Phe Val Glu Trp Leu Met Asn Thr
            20                  25

<210> SEQ ID NO 126
<211> LENGTH: 29
<212> TYPE: PRT

<213> ORGANISM: Artificial Sequence
<220> FEATURE:
<223> OTHER INFORMATION: glucagon analogue

<400> SEQUENCE: 126

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Thr
            20                  25

<210> SEQ ID NO 127
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (2)..(2)
<223> OTHER INFORMATION: Xaa is d-serine, alanine, glycine, n-methyl
      serine and aminoisobutyric acid
<220> FEATURE:
<221> NAME/KEY: MOD_RES
<222> LOCATION: (29)..(29)
<223> OTHER INFORMATION: AMIDATION

<400> SEQUENCE: 127

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 128
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (2)..(2)
<223> OTHER INFORMATION: Xaa is aminoisobutyric acid
<220> FEATURE:
<221> NAME/KEY: MOD_RES
<222> LOCATION: (29)..(29)
<223> OTHER INFORMATION: AMIDATION

<400> SEQUENCE: 128

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 129
<211> LENGTH: 39
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 129

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Xaa Asn Thr Gly Pro Ser

```
                 20                  25                  30

Ser Gly Ala Pro Pro Ser
        35

<210> SEQ ID NO 130
<211> LENGTH: 37
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 130

His Ser Gln Gly Thr Phe Thr Ser Asp Tyr Ser Lys Tyr Leu Asp Glu
1               5                  10                  15

Arg Arg Ala Gln Asp Phe Val Gln Trp Leu Xaa Asn Thr Lys Arg Asn
            20                  25                  30

Arg Asn Asn Ile Ala
        35

<210> SEQ ID NO 131
<211> LENGTH: 33
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 131

His Ser Gln Gly Thr Phe Thr Ser Asp Tyr Ser Lys Tyr Leu Asp Glu
1               5                  10                  15

Arg Arg Ala Gln Asp Phe Val Gln Trp Leu Xaa Asn Thr Lys Arg Asn
            20                  25                  30

Arg

<210> SEQ ID NO 132
<211> LENGTH: 88
<212> TYPE: PRT
<213> ORGANISM: Artificial Sequence
<220> FEATURE:
<223> OTHER INFORMATION: Insulin conjugate

<400> SEQUENCE: 132

His Ala Glu Gly Thr Phe Thr Ser Asp Val Ser Ser Tyr Leu Glu Glu
1               5                  10                  15

Gln Ala Ala Arg Glu Phe Ile Ala Trp Leu Val Arg Gly Arg Gly Gly
            20                  25                  30

Pro Glu His Leu Cys Gly Ala His Leu Val Asp Ala Leu Tyr Leu Val
        35                  40                  45

Cys Gly Asp Arg Gly Phe Tyr Phe Asn Asp Arg Gly Ala Gly Ser Ser
    50                  55                  60

Ser Arg Arg Gly Ile Val Asp Glu Cys Cys His Arg Ser Cys Asp Leu
65                  70                  75                  80

Arg Arg Leu Glu Asn Tyr Cys Asn
                85
```

<210> SEQ ID NO 133
<211> LENGTH: 88
<212> TYPE: PRT
<213> ORGANISM: Artificial Sequence
<220> FEATURE:
<223> OTHER INFORMATION: Insulin conjugate

<400> SEQUENCE: 133

His Ala Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Gly
            20                  25                  30

Pro Glu His Leu Cys Gly Ala His Leu Val Asp Ala Leu Tyr Leu Val
        35                  40                  45

Cys Gly Asp Arg Gly Phe Tyr Phe Asn Asp Arg Gly Ala Gly Ser Ser
    50                  55                  60

Ser Arg Arg Gly Ile Val Asp Glu Cys Cys His Arg Ser Cys Asp Leu
65                  70                  75                  80

Arg Arg Leu Glu Asn Ala Cys Asn
                85

<210> SEQ ID NO 134
<211> LENGTH: 88
<212> TYPE: PRT
<213> ORGANISM: Artificial Sequence
<220> FEATURE:
<223> OTHER INFORMATION: Insulin conjugate

<400> SEQUENCE: 134

His Ala Glu Gly Thr Phe Thr Ser Asp Val Ser Ser Tyr Leu Glu Glu
1               5                   10                  15

Gln Ala Ala Arg Glu Ala Ile Ala Trp Leu Val Arg Gly Arg Gly Gly
            20                  25                  30

Pro Glu His Leu Cys Gly Ala His Leu Val Asp Ala Leu Tyr Leu Val
        35                  40                  45

Cys Gly Asp Arg Gly Phe Tyr Phe Asn Asp Arg Gly Ala Gly Ser Ser
    50                  55                  60

Ser Arg Arg Gly Ile Val Asp Glu Cys Cys His Arg Ser Cys Asp Leu
65                  70                  75                  80

Arg Arg Leu Glu Asn Tyr Cys Asn
                85

<210> SEQ ID NO 135
<211> LENGTH: 86
<212> TYPE: PRT
<213> ORGANISM: Artificial Sequence
<220> FEATURE:
<223> OTHER INFORMATION: Insulin conjugate

<400> SEQUENCE: 135

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Glu
            20                  25                  30

His Leu Cys Gly Ala His Leu Val Asp Ala Leu Tyr Leu Val Cys Gly
        35                  40                  45

Asp Arg Gly Phe Tyr Phe Asn Asp Arg Gly Ala Gly Ser Ser Ser Arg
    50                  55                  60

Arg Gly Ile Val Asp Glu Cys Cys His Arg Ser Cys Asp Leu Arg Arg
65                  70                  75                  80

Leu Glu Asn Tyr Cys Asn
                85

<210> SEQ ID NO 136
<211> LENGTH: 86
<212> TYPE: PRT
<213> ORGANISM: Artificial Sequence
<220> FEATURE:
<223> OTHER INFORMATION: Insulin conjugate

<400> SEQUENCE: 136

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Glu
            20                  25                  30

His Leu Cys Gly Ala His Leu Val Asp Ala Leu Tyr Leu Val Cys Gly
        35                  40                  45

Asp Arg Gly Phe Tyr Phe Asn Asp Arg Gly Ala Gly Ser Ser Ser Arg
    50                  55                  60

Arg Gly Ile Val Asp Glu Cys Cys His Arg Ser Cys Asp Leu Arg Arg
65                  70                  75                  80

Leu Glu Asn Ala Cys Asn
                85

<210> SEQ ID NO 137
<211> LENGTH: 86
<212> TYPE: PRT
<213> ORGANISM: Artificial Sequence
<220> FEATURE:
<223> OTHER INFORMATION: Insulin conjugate

<400> SEQUENCE: 137

His Ser Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Glu
            20                  25                  30

His Leu Cys Gly Ala His Leu Val Asp Ala Leu Tyr Leu Val Cys Gly
        35                  40                  45

Asp Arg Gly Phe Tyr Phe Asn Asp Arg Gly Ala Gly Ser Ser Ser Arg
    50                  55                  60

Arg Gly Ile Val Asp Glu Cys Cys His Arg Ser Cys Asp Leu Arg Arg
65                  70                  75                  80

Leu Glu Asn Tyr Cys Asn
                85

<210> SEQ ID NO 138
<211> LENGTH: 86
<212> TYPE: PRT
<213> ORGANISM: Artificial Sequence
<220> FEATURE:
<223> OTHER INFORMATION: Insulin conjugate

<400> SEQUENCE: 138

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr Gly Pro Glu
            20                  25                  30

His Leu Cys Gly Ala His Leu Val Asp Ala Leu Tyr Leu Val Cys Gly
        35                  40                  45

```
Asp Arg Gly Phe Tyr Phe Asn Asp Arg Gly Ala Gly Ser Ser Ser Arg
        50                  55                  60
Arg Gly Ile Val Asp Glu Cys Cys His Arg Ser Cys Asp Leu Arg Arg
65                  70                  75                  80
Leu Glu Asn Tyr Cys Asn
                85

<210> SEQ ID NO 139
<211> LENGTH: 90
<212> TYPE: PRT
<213> ORGANISM: Artificial Sequence
<220> FEATURE:
<223> OTHER INFORMATION: Conjugate of GLP-1 and insulin

<400> SEQUENCE: 139

His Ala Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Phe
                20                  25                  30

Val Asn Gln His Leu Cys Gly Ser His Leu Val Glu Ala Leu Tyr Leu
                35                  40                  45

Val Cys Gly Glu Arg Gly Phe Phe Tyr Thr Pro Lys Thr Gly Ala Gly
        50                  55                  60

Ser Ser Ser Arg Arg Gly Ile Val Glu Gln Cys Cys Thr Ser Ile Cys
65                  70                  75                  80

Ser Leu Tyr Gln Leu Glu Asn Tyr Cys Asn
                85                  90

<210> SEQ ID NO 140
<211> LENGTH: 88
<212> TYPE: PRT
<213> ORGANISM: Artificial Sequence
<220> FEATURE:
<223> OTHER INFORMATION: Conjugate of glucagon and insulin

<400> SEQUENCE: 140

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Phe Val Asn
                20                  25                  30

Gln His Leu Cys Gly Ser His Leu Val Glu Ala Leu Tyr Leu Val Cys
                35                  40                  45

Gly Glu Arg Gly Phe Phe Tyr Thr Pro Lys Thr Gly Ala Gly Ser Ser
        50                  55                  60

Ser Arg Arg Gly Ile Val Glu Gln Cys Cys Thr Ser Ile Cys Ser Leu
65                  70                  75                  80

Tyr Gln Leu Glu Asn Tyr Cys Asn
                85

<210> SEQ ID NO 141
<211> LENGTH: 35
<212> TYPE: PRT
<213> ORGANISM: Homo sapiens

<400> SEQUENCE: 141

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
                20                  25                  30
```

Gln Lys Arg
      35

<210> SEQ ID NO 142
<211> LENGTH: 23
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 17 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or 4-amino-
      phenylalanine

<400> SEQUENCE: 142

Xaa Leu Cys Gly Xaa Xaa Leu Val Xaa Xaa Leu Tyr Leu Val Cys Gly
1               5                  10                  15

Xaa Xaa Gly Phe Xaa Tyr Thr
            20

<210> SEQ ID NO 143
<211> LENGTH: 59
<212> TYPE: PRT
<213> ORGANISM: Artificial Sequence
<220> FEATURE:
<223> OTHER INFORMATION: Single chain insulin analog

<400> SEQUENCE: 143

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr Gly Ala
            20                  25                  30

Gly Ser Ser Ser Arg Arg Gly Ile Val Glu Gln Cys Cys Thr Ser Ile
            35                  40                  45

Cys Ser Leu Tyr Gln Leu Glu Asn Tyr Cys Asn
    50                  55

```
<210> SEQ ID NO 144
<211> LENGTH: 57
<212> TYPE: PRT
<213> ORGANISM: Artificial Sequence
<220> FEATURE:
<223> OTHER INFORMATION: Single chain insulin analog
<220> FEATURE:
<221> NAME/KEY: MISC_FEATURE
<222> LOCATION: (4)..(4)
<223> OTHER INFORMATION: Xaa at position 4 is histidine or threonine
<220> FEATURE:
<221> NAME/KEY: MISC_FEATURE
<222> LOCATION: (9)..(9)
<223> OTHER INFORMATION: Xaa at position 9 is ihistidine, aspartic acid,
      glutamic acid, homocysteic acid or cysteic acid
<220> FEATURE:
<221> NAME/KEY: MISC_FEATURE
<222> LOCATION: (21)..(21)
<223> OTHER INFORMATION: Xaa at position 21 is alanine ornithine or
      arginine
<220> FEATURE:
<221> NAME/KEY: MISC_FEATURE
<222> LOCATION: (27)..(27)
<223> OTHER INFORMATION: Xaa at position 27 is lysine or aspartic acid
<220> FEATURE:
<221> NAME/KEY: MISC_FEATURE
<222> LOCATION: (28)..(28)
<223> OTHER INFORMATION: Xaa at position 21 is proline, ornithine or
      arginine
<220> FEATURE:
<221> NAME/KEY: MISC_FEATURE
<222> LOCATION: (44)..(44)
<223> OTHER INFORMATION: Xaa at position 44 is phenylalanine or
      histidine

<400> SEQUENCE: 144

Gly Pro Glu Xaa Leu Cys Gly Ala Xaa Leu Val Asp Ala Leu Tyr Leu
1               5                   10                  15

Val Cys Gly Asp Xaa Gly Phe Tyr Phe Asn Xaa Xaa Gly Ala Gly Ser
            20                  25                  30

Ser Ser Arg Arg Gly Ile Val Asp Glu Cys Cys Xaa Arg Ser Cys Asp
        35                  40                  45

Leu Arg Arg Leu Glu Asn Tyr Cys Asn
    50                  55

<210> SEQ ID NO 145
<211> LENGTH: 57
<212> TYPE: PRT
<213> ORGANISM: Artificial Sequence
<220> FEATURE:
<223> OTHER INFORMATION: Single chain insulin analog

<400> SEQUENCE: 145

Gly Pro Glu His Leu Cys Gly Ala His Leu Val Asp Ala Leu Tyr Leu
1               5                   10                  15

Val Cys Gly Asp Arg Gly Phe Tyr Phe Asn Asp Arg Gly Ala Gly Ser
            20                  25                  30

Ser Ser Arg Arg Gly Ile Val Asp Glu Cys Cys His Arg Ser Cys Asp
        35                  40                  45

Leu Arg Arg Leu Glu Asn Tyr Cys Asn
    50                  55

<210> SEQ ID NO 146
<211> LENGTH: 4
<212> TYPE: PRT
<213> ORGANISM: Artificial Sequence
<220> FEATURE:
<223> OTHER INFORMATION: peptide linker
```

```
<400> SEQUENCE: 146

Gly Gly Gly Lys
1

<210> SEQ ID NO 147
<211> LENGTH: 25
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 147

Phe Val Lys Gln Xaa Leu Cys Gly Ser His Leu Val Glu Ala Leu Tyr
1               5                   10                  15

Leu Val Cys Gly Glu Arg Gly Phe Phe
            20                  25

<210> SEQ ID NO 148
<211> LENGTH: 25
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 148

Phe Val Asn Gln Xaa Leu Cys Gly Ser His Leu Val Glu Ala Leu Tyr
1               5                   10                  15

Leu Val Cys Gly Glu Arg Gly Phe Phe
            20                  25

<210> SEQ ID NO 149
<211> LENGTH: 5
<212> TYPE: PRT
<213> ORGANISM: Artificial Sequence
<220> FEATURE:
<223> OTHER INFORMATION: peptide fragment of insulin
<220> FEATURE:
<221> NAME/KEY: MISC_FEATURE
<222> LOCATION: (3)..(3)
<223> OTHER INFORMATION: Xaa at position 3 is proline, aspartic acid or
      glutamic acid

<400> SEQUENCE: 149

Tyr Thr Xaa Lys Thr
1               5

<210> SEQ ID NO 150
<211> LENGTH: 5
<212> TYPE: PRT
<213> ORGANISM: Artificial Sequence
<220> FEATURE:
<223> OTHER INFORMATION: peptide fragment of insulin

<400> SEQUENCE: 150

Tyr Thr Lys Pro Thr
1               5

<210> SEQ ID NO 151
<211> LENGTH: 5
<212> TYPE: PRT
<213> ORGANISM: Artificial Sequence
<220> FEATURE:
<223> OTHER INFORMATION: peptide fragment of insulin
```

<400> SEQUENCE: 151

Tyr Thr Lys Pro Thr
1               5

<210> SEQ ID NO 152
<211> LENGTH: 4
<212> TYPE: PRT
<213> ORGANISM: Artificial Sequence
<220> FEATURE:
<223> OTHER INFORMATION: peptide fragment of insulin
<220> FEATURE:
<221> NAME/KEY: MISC_FEATURE
<222> LOCATION: (3)..(3)
<223> OTHER INFORMATION: Xaa at position 3 is proline, aspartic acid or
      glutamic acid

<400> SEQUENCE: 152

Tyr Thr Xaa Lys
1

<210> SEQ ID NO 153
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine or histidine
<220> FEATURE:
<221> NAME/KEY: MISC_FEATURE
<222> LOCATION: (21)..(21)
<223> OTHER INFORMATION: Xaa at position 21 is asparagine, glycine,
      alanine, glutamine, glutamate, threonine, or serine

<400> SEQUENCE: 153

Gly Ile Val Glu Gln Cys Cys Xaa Ser Ile Cys Ser Leu Tyr Gln Leu
1               5                   10                  15

Glu Asn Tyr Cys Xaa
            20

<210> SEQ ID NO 154
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 154

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Glu Lys Thr
            20                  25                  30

<210> SEQ ID NO 155
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 155

```
Phe Val Asn Gln Xaa Leu Cys Gly Ser His Leu Val Glu Ala Leu Tyr
1               5                  10                 15

Leu Val Cys Gly Glu Arg Gly Phe Phe Tyr Thr Asp Lys Thr
            20                  25                  30

<210> SEQ ID NO 156
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 156

Phe Val Asn Gln Xaa Leu Cys Gly Ser His Leu Val Glu Ala Leu Tyr
1               5                  10                 15

Leu Val Cys Gly Glu Arg Gly Phe Phe Tyr Thr Lys Pro Thr
            20                  25                  30

<210> SEQ ID NO 157
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 157

Phe Val Asn Gln Xaa Leu Cys Gly Ser His Leu Val Glu Ala Leu Tyr
1               5                  10                 15

Leu Val Cys Gly Glu Arg Gly Phe Phe Tyr Thr Pro Lys Thr
            20                  25                  30

<210> SEQ ID NO 158
<211> LENGTH: 29
<212> TYPE: PRT
<213> ORGANISM: Homo sapiens

<400> SEQUENCE: 158

Ser Ser Ser Ser Lys Ala Pro Pro Ser Leu Pro Ser Pro Ser Arg
1               5                  10                 15

Leu Pro Gly Pro Ser Asp Thr Pro Ile Leu Pro Gln Lys
            20                  25

<210> SEQ ID NO 159
<211> LENGTH: 29
<212> TYPE: PRT
<213> ORGANISM: Homo sapiens

<400> SEQUENCE: 159

Ser Ser Ser Ser Arg Ala Pro Pro Ser Leu Pro Ser Pro Ser Arg
1               5                  10                 15

Leu Pro Gly Pro Ser Asp Thr Pro Ile Leu Pro Gln Lys
            20                  25

<210> SEQ ID NO 160
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
```

```
<222> LOCATION: (21)..(21)
<223> OTHER INFORMATION: Xaa at position 21 is alanine, glycine or
      asparagine

<400> SEQUENCE: 160

Gly Ile Val Glu Gln Cys Cys His Ser Ile Cys Ser Leu Tyr Gln Leu
1               5                   10                  15

Glu Asn Tyr Cys Xaa
            20

<210> SEQ ID NO 161
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 161

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 162
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 162

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Glu Lys Thr
            20                  25                  30

<210> SEQ ID NO 163
<211> LENGTH: 28
<212> TYPE: PRT
<213> ORGANISM: Artificial Sequence
<220> FEATURE:
<223> OTHER INFORMATION: Single chain insulin analog
<220> FEATURE:
<221> NAME/KEY: MISC_FEATURE
<222> LOCATION: (4)..(4)
<223> OTHER INFORMATION: Xaa at position 4 is histidine or threonine
<220> FEATURE:
<221> NAME/KEY: MISC_FEATURE
<222> LOCATION: (9)..(9)
<223> OTHER INFORMATION: Xaa at position 9 is ihistidine, aspartic acid,
      glutamic acid, homocysteic acid or cysteic acid
<220> FEATURE:
<221> NAME/KEY: MISC_FEATURE
<222> LOCATION: (21)..(21)
<223> OTHER INFORMATION: Xaa at position 21 is alanine ornithine or
      arginine
<220> FEATURE:
<221> NAME/KEY: MISC_FEATURE
<222> LOCATION: (27)..(27)
<223> OTHER INFORMATION: Xaa at position 27 is lysine or aspartic acid
<220> FEATURE:
<221> NAME/KEY: MISC_FEATURE
<222> LOCATION: (28)..(28)
<223> OTHER INFORMATION: Xaa at position 28 is proline, ornithine or
      arginine
<220> FEATURE:
```

```
<221> NAME/KEY: MISC_FEATURE
<222> LOCATION: (44)..(44)
<223> OTHER INFORMATION: Xaa at position 44 is phenylalanine or
      histidine

<400> SEQUENCE: 163

Gly Pro Glu His Leu Cys Gly Ala Xaa Leu Val Asp Ala Leu Tyr Leu
1               5                   10                  15

Val Cys Gly Asp Xaa Gly Phe Tyr Phe Asn Xaa Xaa
            20                  25

<210> SEQ ID NO 164
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 164

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 165
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 165

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 166
<211> LENGTH: 25
<212> TYPE: PRT
<213> ORGANISM: Homo sapiens

<400> SEQUENCE: 166

Pro Pro Asp Val Gly Ser Ser Asp Pro Leu Ser Met Val Gly Pro Ser
1               5                   10                  15

Gln Gly Arg Ser Pro Ser Tyr Ala Ser
            20                  25

<210> SEQ ID NO 167
<211> LENGTH: 209
<212> TYPE: PRT
<213> ORGANISM: Homo sapiens

<400> SEQUENCE: 167

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45
```

Leu Tyr Thr Asp Asp Ala Gln Gln Thr Glu Ala His Leu Glu Ile Arg
            50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
            195                 200                 205

Ser

<210> SEQ ID NO 168
<211> LENGTH: 25
<212> TYPE: PRT
<213> ORGANISM: Homo sapiens
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 168

Pro Pro Xaa Xaa Gly Xaa Ser Xaa Xaa Xaa Ser Xaa Xaa Gly Pro Ser
 1               5                  10                  15

Gln Gly Arg Xaa Xaa Ser Xaa Ala Ser
                20                  25

<210> SEQ ID NO 169
<211> LENGTH: 25
<212> TYPE: PRT
<213> ORGANISM: Homo sapiens
<220> FEATURE:
<221> NAME/KEY: misc_feature
<222> LOCATION: (8)..(9)

<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 169

Pro Pro Asp Val Gly Ser Ser Xaa Xaa Leu Ser Xaa Val Gly Pro Ser
1               5                   10                  15

Gln Gly Arg Ser Pro Ser Tyr Ala Ser
            20                  25

<210> SEQ ID NO 170
<211> LENGTH: 216
<212> TYPE: PRT
<213> ORGANISM: Homo sapiens

<400> SEQUENCE: 170

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 171
<211> LENGTH: 209
<212> TYPE: PRT
<213> ORGANISM: Homo sapiens

<400> SEQUENCE: 171

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr

-continued

```
                35                  40                  45
Leu Tyr Thr Asp Asp Ala Gln Gln Thr Glu Ala His Leu Glu Ile Arg
 50                  55                  60

Glu Asp Gly Thr Val Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
                130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser
```

<210> SEQ ID NO 172
<211> LENGTH: 250
<212> TYPE: PRT
<213> ORGANISM: Homo sapiens

<400> SEQUENCE: 172

```
Met Leu Gly Ala Arg Leu Arg Leu Trp Val Cys Ala Leu Cys Ser Val
 1                   5                  10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
                35                  40                  45

Asn Ser Tyr His Leu Gln Ile His Lys Asn Gly His Val Asp Gly Ala
 50                  55                  60

Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
                115                 120                 125

Ser Pro Gln Tyr His Phe Leu Val Ser Leu Gly Arg Ala Lys Arg Ala
                130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
                180                 185                 190

Leu Lys Pro Arg Ala Arg Met Thr Pro Ala Pro Ala Ser Cys Ser Gln
```

```
            195                 200                 205
Glu Leu Pro Ser Ala Glu Asp Asn Ser Pro Met Ala Ser Asp Pro Leu
            210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe
            245                 250

<210> SEQ ID NO 173
<211> LENGTH: 181
<212> TYPE: PRT
<213> ORGANISM: Homo sapiens

<400> SEQUENCE: 173

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 174
<211> LENGTH: 188
<212> TYPE: PRT
<213> ORGANISM: Homo sapiens

<400> SEQUENCE: 174

Asp Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
    50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
```

85                  90                  95

Glu Ile Arg Pro Asp Gly Tyr Asn Val Tyr Arg Ser Glu Lys His Arg
                100                 105                 110

Leu Pro Val Ser Leu Ser Ser Ala Lys Gln Arg Gln Leu Tyr Lys Asn
            115                 120                 125

Arg Gly Phe Leu Pro Leu Ser His Phe Leu Pro Met Leu Pro Met Val
130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 175
<211> LENGTH: 181
<212> TYPE: PRT
<213> ORGANISM: Homo sapiens

<400> SEQUENCE: 175

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Leu Glu Thr Asp
145                 150                 155                 160

Ser Met Asp Pro Phe Gly Leu Val Thr Gly Leu Glu Ala Val Arg Ser
                165                 170                 175

Pro Ser Phe Glu Ala
            180

<210> SEQ ID NO 176
<211> LENGTH: 181
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa at position 31 is Alanine or Cysteine
<220> FEATURE:
<221> NAME/KEY: MISC_FEATURE
<222> LOCATION: (43)..(43)
<223> OTHER INFORMATION: Xaa at position 43 is Glycine or Cysteine
<220> FEATURE:
<221> NAME/KEY: MISC_FEATURE

```
<222> LOCATION: (98)..(98)
<223> OTHER INFORMATION: Xaa at position 98 is Leucine or Aspartic Acid
<220> FEATURE:
<221> NAME/KEY: MISC_FEATURE
<222> LOCATION: (100)..(100)
<223> OTHER INFORMATION: Xaa at position 100 is Leucine or Lysine
<220> FEATURE:
<221> NAME/KEY: MISC_FEATURE
<222> LOCATION: (121)..(121)
<223> OTHER INFORMATION: Xaa at position 121 is Asparagine or Aspartic
      Acid
<220> FEATURE:
<221> NAME/KEY: MISC_FEATURE
<222> LOCATION: (127)..(127)
<223> OTHER INFORMATION: Xaa at position 127 is Aspartic Acid or Lysine

<400> SEQUENCE: 176

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Xaa His
            20                  25                  30

Leu Glu Ile Arg Glu Asp Gly Thr Val Gly Xaa Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Xaa Leu Xaa Glu Asp Gly Tyr Asn Val Tyr Gln Ser Glu Ala His
            100                 105                 110

Gly Leu Pro Leu His Leu Pro Gly Xaa Lys Ser Pro His Arg Xaa Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Leu Glu Thr Asp
145                 150                 155                 160

Ser Met Asp Pro Phe Gly Leu Val Thr Gly Leu Glu Ala Val Arg Ser
                165                 170                 175

Pro Ser Phe Glu Ala
            180

<210> SEQ ID NO 177
<211> LENGTH: 25
<212> TYPE: PRT
<213> ORGANISM: Homo sapiens

<400> SEQUENCE: 177

Pro Pro Asp Val Gly Ser Ser Asp Pro Leu Ser Met Val Gly Pro Ser
1               5                   10                  15

Gln Gly Arg Ser Pro Ser Tyr Ala Ser
            20                  25

<210> SEQ ID NO 178
<211> LENGTH: 26
<212> TYPE: PRT
<213> ORGANISM: Homo sapiens

<400> SEQUENCE: 178

Pro Leu Glu Thr Asp Ser Met Asp Pro Phe Gly Leu Val Thr Gly Leu
1               5                   10                  15
```

Glu Ala Val Arg Ser Pro Ser Phe Glu Ala
            20                  25

<210> SEQ ID NO 179
<211> LENGTH: 25
<212> TYPE: PRT
<213> ORGANISM: Homo sapiens

<400> SEQUENCE: 179

Pro Leu Glu Thr Asp Ser Met Asp Pro Phe Gly Leu Val Gly Pro Ser
1               5                   10                  15

Gln Gly Arg Ser Pro Ser Phe Glu Ala
            20                  25

<210> SEQ ID NO 180
<211> LENGTH: 25
<212> TYPE: PRT
<213> ORGANISM: Homo sapiens

<400> SEQUENCE: 180

Pro Pro Asp Val Gly Ser Met Asp Pro Phe Gly Leu Val Gly Pro Ser
1               5                   10                  15

Gln Gly Arg Ser Pro Ser Phe Glu Ala
            20                  25

<210> SEQ ID NO 181
<211> LENGTH: 25
<212> TYPE: PRT
<213> ORGANISM: Homo sapiens

<400> SEQUENCE: 181

Pro Leu Glu Thr Asp Ser Ser Asp Pro Leu Ser Met Val Gly Pro Ser
1               5                   10                  15

Gln Gly Arg Ser Pro Ser Phe Glu Ala
            20                  25

<210> SEQ ID NO 182
<211> LENGTH: 26
<212> TYPE: PRT
<213> ORGANISM: Homo sapiens

<400> SEQUENCE: 182

Pro Pro Asp Val Gly Ser Met Asp Pro Phe Gly Leu Val Thr Gly Leu
1               5                   10                  15

Glu Ala Val Arg Ser Pro Ser Tyr Ala Ala
            20                  25

<210> SEQ ID NO 183
<211> LENGTH: 26
<212> TYPE: PRT
<213> ORGANISM: Homo sapiens

<400> SEQUENCE: 183

Pro Leu Glu Thr Asp Ser Ser Asp Pro Leu Ser Met Val Thr Gly Leu
1               5                   10                  15

Glu Ala Val Arg Ser Pro Ser Tyr Ala Ala
            20                  25

<210> SEQ ID NO 184
<211> LENGTH: 26
<212> TYPE: PRT
<213> ORGANISM: Homo sapiens

```
<400> SEQUENCE: 184

Pro Pro Asp Val Gly Ser Ser Asp Pro Leu Ser Met Val Thr Gly Leu
1               5                   10                  15

Glu Ala Val Arg Ser Pro Ser Phe Glu Ala
            20                  25

<210> SEQ ID NO 185
<211> LENGTH: 25
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: Xaa at position 11 is D-serine

<400> SEQUENCE: 185

Pro Pro Asp Val Gly Ser Ser Asp Pro Leu Xaa Met Val Gly Pro Ser
1               5                   10                  15

Gln Gly Arg Ser Pro Ser Tyr Ala Ser
            20                  25

<210> SEQ ID NO 186
<211> LENGTH: 25
<212> TYPE: PRT
<213> ORGANISM: Homo sapiens
<220> FEATURE:
<221> NAME/KEY: MISC_FEATURE
<222> LOCATION: (19)..(19)
<223> OTHER INFORMATION: Xaa at position 19 is D-arginine

<400> SEQUENCE: 186

Pro Pro Asp Val Gly Ser Ser Asp Pro Leu Ser Met Val Gly Pro Ser
1               5                   10                  15

Gln Gly Xaa Ser Pro Ser Tyr Ala Ser
            20                  25

<210> SEQ ID NO 187
<211> LENGTH: 25
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: Xaa at position 11 is D-serine
<220> FEATURE:
<221> NAME/KEY: MISC_FEATURE
<222> LOCATION: (19)..(19)
<223> OTHER INFORMATION: Xaa at position 19 is D-arginine

<400> SEQUENCE: 187

Pro Pro Asp Val Gly Ser Ser Asp Pro Leu Xaa Met Val Gly Pro Ser
1               5                   10                  15

Gln Gly Xaa Ser Pro Ser Tyr Ala Ser
            20                  25

<210> SEQ ID NO 188
<211> LENGTH: 25
<212> TYPE: PRT
<213> ORGANISM: Homo sapiens

<400> SEQUENCE: 188

Leu Glu Thr Asp Ser Met Asp Pro Phe Gly Leu Val Thr Gly Leu Glu
1               5                   10                  15

Ala Val Arg Ser Pro Ser Phe Glu Ala
            20                  25
```

<210> SEQ ID NO 189
<211> LENGTH: 25
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa at position 10 is D-serine

<400> SEQUENCE: 189

Leu Glu Thr Asp Ser Met Asp Pro Phe Xaa Leu Val Thr Gly Leu Glu
1               5                   10                  15

Ala Val Arg Ser Pro Ser Phe Glu Ser
            20                  25

<210> SEQ ID NO 190
<211> LENGTH: 25
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa at position 10 is D-serine

<400> SEQUENCE: 190

Leu Glu Thr Asp Ser Met Asp Pro Phe Xaa Leu Val Thr Gly Leu Glu
1               5                   10                  15

Ala Val Arg Ser Pro Ser Phe Glu Ala
            20                  25

<210> SEQ ID NO 191
<211> LENGTH: 25
<212> TYPE: PRT
<213> ORGANISM: Homo sapiens

<400> SEQUENCE: 191

Pro Pro Asp Val Gly Ser Ser Asp Pro Leu Ser Met Val Gly Pro Ser
1               5                   10                  15

Gln Gly Arg Ser Pro Ser Tyr Ala Ala
            20                  25

<210> SEQ ID NO 192
<211> LENGTH: 181
<212> TYPE: PRT
<213> ORGANISM: Homo sapiens

<400> SEQUENCE: 192

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

```
Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Leu Glu Thr Asp
145                 150                 155                 160

Ser Met Asp Pro Phe Gly Leu Val Thr Gly Leu Glu Ala Val Arg Ser
                165                 170                 175

Pro Ser Phe Glu Ala
            180

<210> SEQ ID NO 193
<211> LENGTH: 181
<212> TYPE: PRT
<213> ORGANISM: Homo sapiens

<400> SEQUENCE: 193

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Leu Glu Thr Asp
145                 150                 155                 160

Ser Met Asp Pro Phe Gly Leu Val Thr Gly Leu Glu Ala Val Arg Ser
                165                 170                 175

Pro Ser Phe Glu Ala
            180

<210> SEQ ID NO 194
<211> LENGTH: 156
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa at position 31 is Alanine or Cysteine
<220> FEATURE:
<221> NAME/KEY: MISC_FEATURE
<222> LOCATION: (43)..(43)
<223> OTHER INFORMATION: Xaa at position 43 is Glycine or Cysteine
<220> FEATURE:
<221> NAME/KEY: MISC_FEATURE
<222> LOCATION: (98)..(98)
<223> OTHER INFORMATION: Xaa at position 98 is Leucine or Aspartic Acid
<220> FEATURE:
<221> NAME/KEY: MISC_FEATURE
```

```
<222> LOCATION: (100)..(100)
<223> OTHER INFORMATION: Xaa at position 100 is Leucine or Lysine
<220> FEATURE:
<221> NAME/KEY: MISC_FEATURE
<222> LOCATION: (121)..(121)
<223> OTHER INFORMATION: Xaa at position 121 is Asparagine or Aspartic
      Acid
<220> FEATURE:
<221> NAME/KEY: MISC_FEATURE
<222> LOCATION: (127)..(127)
<223> OTHER INFORMATION: Xaa at position 127 is Aspartic Acid or Lysine

<400> SEQUENCE: 194

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Xaa His
            20                  25                  30

Leu Glu Ile Arg Glu Asp Gly Thr Val Gly Xaa Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Xaa Leu Xaa Glu Asp Gly Tyr Asn Val Tyr Gln Ser Glu Ala His
            100                 105                 110

Gly Leu Pro Leu His Leu Pro Gly Xaa Lys Ser Pro His Arg Xaa Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln
145                 150                 155

<210> SEQ ID NO 195
<211> LENGTH: 156
<212> TYPE: PRT
<213> ORGANISM: Homo sapiens

<400> SEQUENCE: 195

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Leu Pro Glu Pro Pro Gly Ile Leu Ala Pro Gln
145                 150                 155

<210> SEQ ID NO 196
<211> LENGTH: 156
<212> TYPE: PRT
<213> ORGANISM: Homo sapiens

<400> SEQUENCE: 196

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln
145                 150                 155

<210> SEQ ID NO 197
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Acetyl D-Tyr
<220> FEATURE:
<221> NAME/KEY: MISC_FEATURE
<222> LOCATION: (10)..(10)
<223> OTHER INFORMATION: Covalently bound to a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 197

Xaa Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Glu Gly Gly Pro Ser
            20                  25                  30

Ser Gly Ala Pro Pro Pro Ser
        35

<210> SEQ ID NO 198
<211> LENGTH: 39
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Acetyl D-His
<220> FEATURE:
<221> NAME/KEY: MISC_FEATURE
<222> LOCATION: (10)..(10)
<223> OTHER INFORMATION: Covalently bound to a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 198

Xaa Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Glu Gly Gly Pro Ser
            20                  25                  30

Ser Gly Ala Pro Pro Pro Ser
        35

<210> SEQ ID NO 199
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Acetyl D-thio Ala
<220> FEATURE:
<221> NAME/KEY: MISC_FEATURE
<222> LOCATION: (10)..(10)
<223> OTHER INFORMATION: Covalently bound to a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 199

Xaa Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Glu Gly Gly Pro Ser
            20                  25                  30

Ser Gly Ala Pro Pro Pro Ser
        35

<210> SEQ ID NO 200
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is acetyl-D-Tyr
<220> FEATURE:
<221> NAME/KEY: MISC_FEATURE
<222> LOCATION: (10)..(10)
<223> OTHER INFORMATION: Covalently bound to a C16 fatty acyl group via
      a gamma-Glu spacer
<220> FEATURE:
<221> NAME/KEY: MISC_FEATURE
<222> LOCATION: (39)..(39)
<223> OTHER INFORMATION: C-terminal amidation
```

<400> SEQUENCE: 200

Xaa Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Ala Gly Pro Ser
            20                  25                  30

Ser Gly Ala Pro Pro Pro Ser
            35

<210> SEQ ID NO 201
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is acetyl-D-Tyr

<400> SEQUENCE: 201

Xaa Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Glu Ala Gly Pro Ser
            20                  25                  30

Ser Gly Ala Pro Pro Pro Ser
            35

<210> SEQ ID NO 202
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (16)..(16)
<223> OTHER INFORMATION: Xaa at position 16 is Aib

<400> SEQUENCE: 202

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 203
<211> LENGTH: 25
<212> TYPE: PRT
<213> ORGANISM: Homo sapiens

<400> SEQUENCE: 203

Leu Glu Thr Asp Ser Met Asp Pro Phe Gly Leu Val Thr Gly Leu Glu
1               5                   10                  15

Ala Val Arg Ser Pro Ser Phe Glu Lys
            20                  25

<210> SEQ ID NO 204
<211> LENGTH: 181
<212> TYPE: PRT
<213> ORGANISM: Homo sapiens

<400> SEQUENCE: 204

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ala
            180

<210> SEQ ID NO 205
<211> LENGTH: 181
<212> TYPE: PRT
<213> ORGANISM: Homo sapiens

<400> SEQUENCE: 205

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Met Asp Pro Phe Gly Leu Val Gly Pro Ser Gln Val Arg Ser
                165                 170                 175

Pro Ser Phe Glu Ala

<210> SEQ ID NO 206
<211> LENGTH: 181
<212> TYPE: PRT
<213> ORGANISM: Homo sapiens

<400> SEQUENCE: 206

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ala
            180
```

<210> SEQ ID NO 207
<211> LENGTH: 181
<212> TYPE: PRT
<213> ORGANISM: Homo sapiens

<400> SEQUENCE: 207

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
```

```
                130             135              140

Ala Leu Pro Glu Pro Pro Gly Ile Leu Ala Pro Gln Pro Pro Asp Val
145                 150                 155                 160

Gly Ser Met Asp Pro Phe Gly Leu Val Gly Pro Ser Gln Gly Arg Ser
                165                 170                 175

Pro Ser Phe Glu Ala
            180

<210> SEQ ID NO 208
<211> LENGTH: 181
<212> TYPE: PRT
<213> ORGANISM: Homo sapiens

<400> SEQUENCE: 208

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Leu Glu Thr
145                 150                 155                 160

Asp Ser Met Asp Pro Phe Gly Leu Val Gly Pro Ser Gln Gly Arg Ser
                165                 170                 175

Pro Ser Phe Glu Ala
            180

<210> SEQ ID NO 209
<211> LENGTH: 181
<212> TYPE: PRT
<213> ORGANISM: Homo sapiens

<400> SEQUENCE: 209

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
```

```
                    85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Asp Val Gly
145                 150                 155                 160

Ser Met Asp Pro Phe Gly Leu Val Thr Gly Leu Glu Ala Val Arg Ser
                165                 170                 175

Pro Ser Tyr Ala Ala
            180

<210> SEQ ID NO 210
<211> LENGTH: 25
<212> TYPE: PRT
<213> ORGANISM: Homo sapiens

<400> SEQUENCE: 210

Ala Pro Asp Val Gly Ser Ser Asp Pro Leu Ser Met Val Gly Pro Ser
1               5                   10                  15

Gln Gly Arg Ser Pro Ser Tyr Ala Ser
            20                  25

<210> SEQ ID NO 211
<211> LENGTH: 25
<212> TYPE: PRT
<213> ORGANISM: Homo sapiens

<400> SEQUENCE: 211

Pro Ala Asp Val Gly Ser Ser Asp Pro Leu Ser Met Val Gly Pro Ser
1               5                   10                  15

Gln Gly Arg Ser Pro Ser Tyr Ala Ser
            20                  25

<210> SEQ ID NO 212
<211> LENGTH: 25
<212> TYPE: PRT
<213> ORGANISM: Homo sapiens

<400> SEQUENCE: 212

Pro Pro Ala Val Gly Ser Ser Asp Pro Leu Ser Met Val Gly Pro Ser
1               5                   10                  15

Gln Gly Arg Ser Pro Ser Tyr Ala Ser
            20                  25

<210> SEQ ID NO 213
<211> LENGTH: 25
<212> TYPE: PRT
<213> ORGANISM: Homo sapiens

<400> SEQUENCE: 213

Pro Pro Asp Ala Gly Ser Ser Asp Pro Leu Ser Met Val Gly Pro Ser
1               5                   10                  15

Gln Gly Arg Ser Pro Ser Tyr Ala Ser
            20                  25

<210> SEQ ID NO 214
<211> LENGTH: 25
```

```
<212> TYPE: PRT
<213> ORGANISM: Homo sapiens

<400> SEQUENCE: 214

Pro Pro Asp Val Ala Ser Ser Asp Pro Leu Ser Met Val Gly Pro Ser
1               5                   10                  15

Gln Gly Arg Ser Pro Ser Tyr Ala Ser
            20                  25

<210> SEQ ID NO 215
<211> LENGTH: 25
<212> TYPE: PRT
<213> ORGANISM: Homo sapiens

<400> SEQUENCE: 215

Pro Pro Asp Val Gly Ala Ser Asp Pro Leu Ser Met Val Gly Pro Ser
1               5                   10                  15

Gln Gly Arg Ser Pro Ser Tyr Ala Ser
            20                  25

<210> SEQ ID NO 216
<211> LENGTH: 25
<212> TYPE: PRT
<213> ORGANISM: Homo sapiens

<400> SEQUENCE: 216

Pro Pro Asp Val Gly Ser Ala Asp Pro Leu Ser Met Val Gly Pro Ser
1               5                   10                  15

Gln Gly Arg Ser Pro Ser Tyr Ala Ser
            20                  25

<210> SEQ ID NO 217
<211> LENGTH: 25
<212> TYPE: PRT
<213> ORGANISM: Homo sapiens

<400> SEQUENCE: 217

Pro Pro Asp Val Gly Ser Ser Ala Pro Leu Ser Met Val Gly Pro Ser
1               5                   10                  15

Gln Gly Arg Ser Pro Ser Tyr Ala Ser
            20                  25

<210> SEQ ID NO 218
<211> LENGTH: 25
<212> TYPE: PRT
<213> ORGANISM: Homo sapiens

<400> SEQUENCE: 218

Pro Pro Asp Val Gly Ser Ser Asp Ala Leu Ser Met Val Gly Pro Ser
1               5                   10                  15

Gln Gly Arg Ser Pro Ser Tyr Ala Ser
            20                  25

<210> SEQ ID NO 219
<211> LENGTH: 25
<212> TYPE: PRT
<213> ORGANISM: Homo sapiens

<400> SEQUENCE: 219

Pro Pro Asp Val Gly Ser Ser Asp Pro Ala Ser Met Val Gly Pro Ser
1               5                   10                  15

Gln Gly Arg Ser Pro Ser Tyr Ala Ser
```

20                  25

<210> SEQ ID NO 220
<211> LENGTH: 25
<212> TYPE: PRT
<213> ORGANISM: Homo sapiens

<400> SEQUENCE: 220

Pro Pro Asp Val Gly Ser Ser Asp Pro Leu Ala Met Val Gly Pro Ser
1               5                   10                  15

Gln Gly Arg Ser Pro Ser Tyr Ala Ser
            20                  25

<210> SEQ ID NO 221
<211> LENGTH: 25
<212> TYPE: PRT
<213> ORGANISM: Homo sapiens

<400> SEQUENCE: 221

Pro Pro Asp Val Gly Ser Ser Asp Pro Leu Ser Ala Val Gly Pro Ser
1               5                   10                  15

Gln Gly Arg Ser Pro Ser Tyr Ala Ser
            20                  25

<210> SEQ ID NO 222
<211> LENGTH: 25
<212> TYPE: PRT
<213> ORGANISM: Homo sapiens

<400> SEQUENCE: 222

Pro Pro Asp Val Gly Ser Ser Asp Pro Leu Ser Met Ala Gly Pro Ser
1               5                   10                  15

Gln Gly Arg Ser Pro Ser Tyr Ala Ser
            20                  25

<210> SEQ ID NO 223
<211> LENGTH: 25
<212> TYPE: PRT
<213> ORGANISM: Homo sapiens

<400> SEQUENCE: 223

Pro Pro Asp Val Gly Ser Ser Asp Pro Leu Ser Met Val Ala Pro Ser
1               5                   10                  15

Gln Gly Arg Ser Pro Ser Tyr Ala Ser
            20                  25

<210> SEQ ID NO 224
<211> LENGTH: 25
<212> TYPE: PRT
<213> ORGANISM: Homo sapiens

<400> SEQUENCE: 224

Pro Pro Asp Val Gly Ser Ser Asp Pro Leu Ser Met Val Gly Ala Ser
1               5                   10                  15

Gln Gly Arg Ser Pro Ser Tyr Ala Ser
            20                  25

<210> SEQ ID NO 225
<211> LENGTH: 25
<212> TYPE: PRT
<213> ORGANISM: Homo sapiens

<400> SEQUENCE: 225

```
Pro Pro Asp Val Gly Ser Ser Asp Pro Leu Ser Met Val Gly Pro Ala
1               5                   10                  15

Gln Gly Arg Ser Pro Ser Tyr Ala Ser
            20                  25

<210> SEQ ID NO 226
<211> LENGTH: 25
<212> TYPE: PRT
<213> ORGANISM: Homo sapiens

<400> SEQUENCE: 226

Pro Pro Asp Val Gly Ser Ser Asp Pro Leu Ser Met Val Gly Pro Ser
1               5                   10                  15

Ala Gly Arg Ser Pro Ser Tyr Ala Ser
            20                  25

<210> SEQ ID NO 227
<211> LENGTH: 25
<212> TYPE: PRT
<213> ORGANISM: Homo sapiens

<400> SEQUENCE: 227

Pro Pro Asp Val Gly Ser Ser Asp Pro Leu Ser Met Val Gly Pro Ser
1               5                   10                  15

Gln Ala Arg Ser Pro Ser Tyr Ala Ser
            20                  25

<210> SEQ ID NO 228
<211> LENGTH: 25
<212> TYPE: PRT
<213> ORGANISM: Homo sapiens

<400> SEQUENCE: 228

Pro Pro Asp Val Gly Ser Ser Asp Pro Leu Ser Met Val Gly Pro Ser
1               5                   10                  15

Gln Gly Ala Ser Pro Ser Tyr Ala Ser
            20                  25

<210> SEQ ID NO 229
<211> LENGTH: 25
<212> TYPE: PRT
<213> ORGANISM: Homo sapiens

<400> SEQUENCE: 229

Pro Pro Asp Val Gly Ser Ser Asp Pro Leu Ser Met Val Gly Pro Ser
1               5                   10                  15

Gln Gly Arg Ala Pro Ser Tyr Ala Ser
            20                  25

<210> SEQ ID NO 230
<211> LENGTH: 25
<212> TYPE: PRT
<213> ORGANISM: Homo sapiens

<400> SEQUENCE: 230

Pro Pro Asp Val Gly Ser Ser Asp Pro Leu Ser Met Val Gly Pro Ser
1               5                   10                  15

Gln Gly Arg Ser Ala Ser Tyr Ala Ser
            20                  25

<210> SEQ ID NO 231
```

```
<211> LENGTH: 25
<212> TYPE: PRT
<213> ORGANISM: Homo sapiens

<400> SEQUENCE: 231

Pro Pro Asp Val Gly Ser Ser Asp Pro Leu Ser Met Val Gly Pro Ser
1               5                   10                  15

Gln Gly Arg Ser Pro Ala Tyr Ala Ser
            20                  25

<210> SEQ ID NO 232
<211> LENGTH: 25
<212> TYPE: PRT
<213> ORGANISM: Homo sapiens

<400> SEQUENCE: 232

Pro Pro Asp Val Gly Ser Ser Asp Pro Leu Ser Met Val Gly Pro Ser
1               5                   10                  15

Gln Gly Arg Ser Pro Ser Ala Ala Ser
            20                  25

<210> SEQ ID NO 233
<211> LENGTH: 25
<212> TYPE: PRT
<213> ORGANISM: Homo sapiens

<400> SEQUENCE: 233

Pro Pro Asp Val Gly Ser Ser Asp Pro Leu Ser Met Val Gly Pro Ser
1               5                   10                  15

Gln Gly Arg Ser Pro Ser Tyr Ala Ala
            20                  25

<210> SEQ ID NO 234
<211> LENGTH: 25
<212> TYPE: PRT
<213> ORGANISM: Homo sapiens

<400> SEQUENCE: 234

Pro Asp Val Gly Ser Met Asp Pro Phe Gly Leu Val Thr Gly Leu Glu
1               5                   10                  15

Ala Val Arg Ser Pro Ser Tyr Ala Ala
            20                  25

<210> SEQ ID NO 235
<211> LENGTH: 26
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is Pro or absent
<220> FEATURE:
<221> NAME/KEY: MISC_FEATURE
<222> LOCATION: (2)..(2)
<223> OTHER INFORMATION: Xaa at position 2 is Pro or Leu
<220> FEATURE:
<221> NAME/KEY: MISC_FEATURE
<222> LOCATION: (3)..(3)
<223> OTHER INFORMATION: Xaa at position 3 is Asp or Glu
<220> FEATURE:
<221> NAME/KEY: MISC_FEATURE
<222> LOCATION: (4)..(4)
<223> OTHER INFORMATION: Xaa at position 4 is Val or Thr
<220> FEATURE:
<221> NAME/KEY: MISC_FEATURE
<222> LOCATION: (5)..(5)
<223> OTHER INFORMATION: Xaa at position 5 is Gly, Asp, Phe, Leu or Ser
```

```
<220> FEATURE:
<221> NAME/KEY: MISC_FEATURE
<222> LOCATION: (7)..(7)
<223> OTHER INFORMATION: Xaa at position 7 is Ser or Met
<220> FEATURE:
<221> NAME/KEY: MISC_FEATURE
<222> LOCATION: (10)..(10)
<223> OTHER INFORMATION: Xaa at position 10 is Leu or Phe
<220> FEATURE:
<221> NAME/KEY: MISC_FEATURE
<222> LOCATION: (11)..(11)
<223> OTHER INFORMATION: Xaa at position 11 is Ser or Gly
<220> FEATURE:
<221> NAME/KEY: MISC_FEATURE
<222> LOCATION: (12)..(12)
<223> OTHER INFORMATION: Xaa at position 12 is Met or Leu
<220> FEATURE:
<221> NAME/KEY: MISC_FEATURE
<222> LOCATION: (14)..(14)
<223> OTHER INFORMATION: Xaa at position 14 is absent or Thr
<220> FEATURE:
<221> NAME/KEY: MISC_FEATURE
<222> LOCATION: (16)..(16)
<223> OTHER INFORMATION: Xaa at position 16 is Pro, Leu, Arg, Glu, or
      Gly
<220> FEATURE:
<221> NAME/KEY: MISC_FEATURE
<222> LOCATION: (17)..(17)
<223> OTHER INFORMATION: Xaa at position 17 is Ser or  Glu
<220> FEATURE:
<221> NAME/KEY: MISC_FEATURE
<222> LOCATION: (18)..(18)
<223> OTHER INFORMATION: Xaa at position 18 is Gln or  Ala
<220> FEATURE:
<221> NAME/KEY: MISC_FEATURE
<222> LOCATION: (19)..(19)
<223> OTHER INFORMATION: Xaa at position 19 is Gly or  Val
<220> FEATURE:
<221> NAME/KEY: MISC_FEATURE
<222> LOCATION: (24)..(24)
<223> OTHER INFORMATION: Xaa at position 24 is Tyr or  Phe
<220> FEATURE:
<221> NAME/KEY: MISC_FEATURE
<222> LOCATION: (25)..(25)
<223> OTHER INFORMATION: Xaa at position 25 is Ala or  Glu
<220> FEATURE:
<221> NAME/KEY: MISC_FEATURE
<222> LOCATION: (26)..(26)
<223> OTHER INFORMATION: Xaa at position 26 is an aliphatic amino acid
      selected from Gly, Ala, Val, Leu, Ser, or Ile

<400> SEQUENCE: 235

Xaa Xaa Xaa Xaa Xaa Ser Xaa Asp Pro Xaa Xaa Xaa Val Xaa Gly Xaa
1               5                   10                  15

Xaa Xaa Xaa Arg Ser Pro Ser Xaa Xaa Xaa
            20                  25

<210> SEQ ID NO 236
<211> LENGTH: 26
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is Pro or absent
<220> FEATURE:
<221> NAME/KEY: MISC_FEATURE
<222> LOCATION: (2)..(2)
<223> OTHER INFORMATION: Xaa at position 2 is Pro or Leu
<220> FEATURE:
<221> NAME/KEY: MISC_FEATURE
<222> LOCATION: (3)..(3)
<223> OTHER INFORMATION: Xaa at position 3 is Asp or Glu
<220> FEATURE:
<221> NAME/KEY: MISC_FEATURE
<222> LOCATION: (4)..(4)
```

```
<223> OTHER INFORMATION: Xaa at position 4 is Val or Thr
<220> FEATURE:
<221> NAME/KEY: MISC_FEATURE
<222> LOCATION: (5)..(5)
<223> OTHER INFORMATION: Xaa at position 5 is Gly, Asp, Phe, Leu or Ser
<220> FEATURE:
<221> NAME/KEY: MISC_FEATURE
<222> LOCATION: (7)..(7)
<223> OTHER INFORMATION: Xaa at position 7 is Ser or Met
<220> FEATURE:
<221> NAME/KEY: MISC_FEATURE
<222> LOCATION: (10)..(10)
<223> OTHER INFORMATION: Xaa at position 10 is Leu or Phe
<220> FEATURE:
<221> NAME/KEY: MISC_FEATURE
<222> LOCATION: (11)..(11)
<223> OTHER INFORMATION: Xaa at position 11 is Ser or Gly
<220> FEATURE:
<221> NAME/KEY: MISC_FEATURE
<222> LOCATION: (12)..(12)
<223> OTHER INFORMATION: Xaa at position 12 is Met or Leu
<220> FEATURE:
<221> NAME/KEY: MISC_FEATURE
<222> LOCATION: (14)..(14)
<223> OTHER INFORMATION: Xaa at position 14 is absent or Thr
<220> FEATURE:
<221> NAME/KEY: MISC_FEATURE
<222> LOCATION: (16)..(16)
<223> OTHER INFORMATION: Xaa at position 16 is Pro, Leu, Arg, Glu, or
      Gly
<220> FEATURE:
<221> NAME/KEY: MISC_FEATURE
<222> LOCATION: (17)..(17)
<223> OTHER INFORMATION: Xaa at position 17 is Ser or Glu
<220> FEATURE:
<221> NAME/KEY: MISC_FEATURE
<222> LOCATION: (18)..(18)
<223> OTHER INFORMATION: Xaa at position 18 is Gln or Ala
<220> FEATURE:
<221> NAME/KEY: MISC_FEATURE
<222> LOCATION: (19)..(19)
<223> OTHER INFORMATION: Xaa at position 19 is Gly or Val
<220> FEATURE:
<221> NAME/KEY: MISC_FEATURE
<222> LOCATION: (24)..(24)
<223> OTHER INFORMATION: Xaa at position 24 is Tyr or Phe
<220> FEATURE:
<221> NAME/KEY: MISC_FEATURE
<222> LOCATION: (25)..(25)
<223> OTHER INFORMATION: Xaa at position 25 is Ala or Glu

<400> SEQUENCE: 236

Xaa Xaa Xaa Xaa Xaa Ser Xaa Asp Pro Xaa Xaa Xaa Val Xaa Gly Xaa
1               5                   10                  15

Xaa Xaa Xaa Arg Ser Pro Ser Xaa Xaa Ala
            20                  25

<210> SEQ ID NO 237
<211> LENGTH: 25
<212> TYPE: PRT
<213> ORGANISM: Homo sapiens

<400> SEQUENCE: 237

Pro Pro Asp Val Gly Ser Met Asp Pro Phe Gly Leu Val Gly Arg Ser
1               5                   10                  15

Gln Gly Arg Ser Pro Ser Phe Glu Ala
            20                  25

<210> SEQ ID NO 238
<211> LENGTH: 25
<212> TYPE: PRT
<213> ORGANISM: Homo sapiens
```

-continued

```
<400> SEQUENCE: 238

Pro Pro Asp Val Phe Ser Met Asp Pro Phe Gly Leu Val Gly Pro Ser
1               5                   10                  15

Gln Gly Arg Ser Pro Ser Phe Glu Ala
            20                  25

<210> SEQ ID NO 239
<211> LENGTH: 25
<212> TYPE: PRT
<213> ORGANISM: Homo sapiens

<400> SEQUENCE: 239

Pro Pro Asp Val Leu Ser Met Asp Pro Phe Gly Leu Val Gly Pro Ser
1               5                   10                  15

Gln Gly Arg Ser Pro Ser Phe Glu Ala
            20                  25

<210> SEQ ID NO 240
<211> LENGTH: 25
<212> TYPE: PRT
<213> ORGANISM: Homo sapiens

<400> SEQUENCE: 240

Pro Pro Asp Val Ser Ser Met Asp Pro Phe Gly Leu Val Gly Pro Ser
1               5                   10                  15

Gln Gly Arg Ser Pro Ser Phe Glu Ala
            20                  25

<210> SEQ ID NO 241
<211> LENGTH: 25
<212> TYPE: PRT
<213> ORGANISM: Homo sapiens

<400> SEQUENCE: 241

Pro Pro Asp Val Gly Ser Ser Asp Pro Phe Gly Leu Val Gly Pro Ser
1               5                   10                  15

Gln Gly Arg Ser Pro Ser Phe Glu Ala
            20                  25

<210> SEQ ID NO 242
<211> LENGTH: 181
<212> TYPE: PRT
<213> ORGANISM: Homo sapiens

<400> SEQUENCE: 242

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110
```

```
Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Met Asp Pro Phe Gly Leu Val Gly Arg Ser Gln Val Arg Ser
                165                 170                 175

Pro Ser Phe Glu Ala
            180

<210> SEQ ID NO 243
<211> LENGTH: 181
<212> TYPE: PRT
<213> ORGANISM: Homo sapiens

<400> SEQUENCE: 243

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Phe Ser Met Asp Pro Phe Gly Leu Val Gly Pro Ser Gln Val Arg Ser
                165                 170                 175

Pro Ser Phe Glu Ala
            180

<210> SEQ ID NO 244
<211> LENGTH: 181
<212> TYPE: PRT
<213> ORGANISM: Homo sapiens

<400> SEQUENCE: 244

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
50                  55                  60
```

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Leu Ser Met Asp Pro Phe Gly Leu Val Gly Pro Ser Gln Val Arg Ser
                165                 170                 175

Pro Ser Phe Glu Ala
            180

<210> SEQ ID NO 245
<211> LENGTH: 181
<212> TYPE: PRT
<213> ORGANISM: Homo sapiens

<400> SEQUENCE: 245

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Cys His
             20                  25                  30

Leu Glu Ile Arg Glu Asp Gly Thr Val Gly Cys Ala Ala Asp Gln Ser
         35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Ser Ser Met Asp Pro Phe Gly Leu Val Gly Pro Ser Gln Val Arg Ser
                165                 170                 175

Pro Ser Phe Glu Ala
            180

<210> SEQ ID NO 246
<211> LENGTH: 181
<212> TYPE: PRT
<213> ORGANISM: Homo sapiens

<400> SEQUENCE: 246

His Pro Ile Pro Asp Ser Ser Pro Leu Leu Gln Phe Gly Gly Gln Val
 1               5                  10                  15
```

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Phe Gly Leu Val Gly Pro Ser Gln Val Arg Ser
            165                 170                 175

Pro Ser Phe Glu Ala
            180

<210> SEQ ID NO 247
<211> LENGTH: 181
<212> TYPE: PRT
<213> ORGANISM: Homo sapiens

<400> SEQUENCE: 247

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Met Asp Pro Phe Gly Leu Val Gly Pro Ser Gln Gly Arg Ser
            165                 170                 175

Pro Ser Phe Glu Ala
            180

<210> SEQ ID NO 248

```
<211> LENGTH: 181
<212> TYPE: PRT
<213> ORGANISM: Homo sapiens

<400> SEQUENCE: 248

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Met Asp Pro Phe Gly Leu Val Gly Arg Ser Gln Gly Arg Ser
                165                 170                 175

Pro Ser Phe Glu Ala
            180

<210> SEQ ID NO 249
<211> LENGTH: 181
<212> TYPE: PRT
<213> ORGANISM: Homo sapiens

<400> SEQUENCE: 249

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160
```

```
Phe Ser Met Asp Pro Phe Gly Leu Val Gly Pro Ser Gln Gly Arg Ser
                165                 170                 175
Pro Ser Phe Glu Ala
            180

<210> SEQ ID NO 250
<211> LENGTH: 181
<212> TYPE: PRT
<213> ORGANISM: Homo sapiens

<400> SEQUENCE: 250

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Cys His
            20                  25                  30
Leu Glu Ile Arg Glu Asp Gly Thr Val Gly Cys Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Asp Leu Lys Glu Asp Gly Tyr Asn Val Tyr Gln Ser Glu Ala His
            100                 105                 110
Gly Leu Pro Leu His Leu Pro Gly Asp Lys Ser Pro His Arg Lys Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Leu Ser Met Asp Pro Phe Gly Leu Val Gly Pro Ser Gln Gly Arg Ser
                165                 170                 175
Pro Ser Phe Glu Ala
            180

<210> SEQ ID NO 251
<211> LENGTH: 181
<212> TYPE: PRT
<213> ORGANISM: Homo sapiens

<400> SEQUENCE: 251

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Cys His
            20                  25                  30
Leu Glu Ile Arg Glu Asp Gly Thr Val Gly Cys Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Asp Leu Lys Glu Asp Gly Tyr Asn Val Tyr Gln Ser Glu Ala His
            100                 105                 110
```

```
Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Ser Ser Met Asp Pro Phe Gly Leu Val Gly Pro Ser Gln Gly Arg Ser
                165                 170                 175

Pro Ser Phe Glu Ala
            180

<210> SEQ ID NO 252
<211> LENGTH: 181
<212> TYPE: PRT
<213> ORGANISM: Homo sapiens

<400> SEQUENCE: 252

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Phe Gly Leu Val Gly Pro Ser Gln Gly Arg Ser
                165                 170                 175

Pro Ser Phe Glu Ala
            180

<210> SEQ ID NO 253
<211> LENGTH: 26
<212> TYPE: PRT
<213> ORGANISM: Homo sapiens

<400> SEQUENCE: 253

Pro Leu Glu Thr Asp Ser Met Asp Pro Phe Gly Leu Val Thr Gly Leu
1               5                   10                  15

Glu Ala Val Arg Ser Pro Ser Phe Glu Lys
            20                  25
```

FGF21 C-TERMINAL PEPTIDE OPTIMIZATION

CROSS REFERENCE TO RELATED APPLICATIONS

This application claims priority to U.S. application Ser. No. 16/092,298, filed Oct. 9, 2018, now abandoned, which is a U.S. national counterpart application of PCT/US2017/027600, filed Apr. 14, 2017, which claims priority to U.S. Provisional Patent Application No. 62/323,003 filed on Apr. 15, 2016, the disclosures of which are hereby expressly incorporated by reference in their entirety.

INCORPORATION BY REFERENCES OF MATERIAL SUBMITTED ELECTRONICALLY

Incorporated by reference in its entirety is a computer-readable nucleotide/amino acid sequence listing submitted concurrently herewith and identified as follows: 165 kilobytes ACII (Text) file named "PCTKlotho_ST25REV2.txt" created on Jun. 23, 2020.

BACKGROUND

Fibroblast growth factor 21 (FGF21) is a recently identified circulating protein that regulates insulin sensitivity along with lipid and energy metabolism. FGF21 belongs to a subfamily of Fibroblast Growth Factors (FGFs) that includes FGF19 (SEQ ID NO: 170), FGF21 (SEQ ID NO: 171), and FGF23 (SEQ ID NO: 172). FGF is expressed with a 28 amino acid signal peptide that is subsequently cleaved to produce the mature protein (SEQ ID NO: 173) FGF21 is an atypical FGF in that it is heparin independent and functions as a hormone in the regulation of glucose, lipid, and energy metabolism.

FGF21 is highly expressed in liver and pancreas and is the only member of the FGF family to be primarily expressed in liver. Transgenic mice overexpressing FGF21 exhibit metabolic phenotypes of slow growth rate, low plasma glucose and triglyceride levels, and an absence of age-associated type 2 diabetes, islet hyperplasia, and obesity.

Pharmacological administration of recombinant FGF21 protein in obese diabetic rodents markedly improved hyperglycemia, lowered elevated triglycerides (TGs), and reduced body weight. Similarly, administration to obese diabetic rhesus monkeys results in normalized levels of plasma glucose, reduced triglyceride and cholesterol levels, and improved glucose tolerance and insulin sensitivity. FGF21 functions to reduce body weight and body fat by increasing energy expenditure, physical activity, and metabolic rate. Experimental research (see Gaich et al., Cell Metab. Vol. 18(3):333-40 (September 2013)) provides support for the pharmacological administration of FGF21 for the treatment of type 2 diabetes, obesity, dyslipidemia, and other metabolic conditions or disorders in humans.

At a molecular level, FGF21 interacts with the FGF receptor only in tissues expressing the cofactor Klotho β. The Klotho β-dependent tissue specificity is consistent with the predominant effects of FGF21 occurring in liver and adipose tissue. The terminal residues of FGF21 are vital for effective biochemical signaling and their truncation dramatically affects the biochemical activity of the molecule. While it is evident that the C-termini of the hormonal FGFs are important for facilitating the interaction with their respective co-receptor partners for the formation of an active receptor complex, the detailed molecular requirements for the association are unknown.

The beneficial pharmacology observed in preclinical models indicated that FGF21 and its analogs or mimetics hold promise as innovative therapeutics for treating metabolic disorders. However, analogs of FGF21 having greater potency at the FGF receptor is desirable to enhance the efficacy of FGF21 mediated therapies

SUMMARY

In accordance with one embodiment of the present disclosure a method of identifying an optimized FGF21 analog is provided. In one embodiment the method of identifying an optimized FGF21 analog is based on analyzing the C-terminal 25 amino acid peptide fragment of FGF21 (SEQ ID NO: 166) for determining the structure-activity relationship for protein FGF21. Applicants have found that in terms of its ability to antagonize FGF21 activity, the peptide of SEQ ID NO: 166, and derivatives thereof, are also predictive of FGF receptor activity of the whole FGF protein comprising a derivative peptide of SEQ ID NO: 166. Accordingly, in one embodiment the method of identifying an optimized FGF21 analog comprises the steps of modifying a peptide comprising the sequence PPDVGSSDPLSMVGPSQGRSPSYAS (SEQ ID NO: 166), analyzing the modified peptide's ability to bind to Klotho β or antagonize FGF21 activity in an in vitro assay (e.g., the assay of Example 1) and identifying modified peptides that have an enhanced activity relative to the native peptide (SEQ ID NO: 166). The identified modified peptides can then be incorporated into a full length protein, such as the FGF21 protein or other bioactive proteins, using standard means such as biosynthesis or semi-synthesis.

In accordance with one embodiment peptides based on the C-terminal 25 amino acids of native FGF21 and FGF19 are provided that have an enhanced ability to bind Klotho β and function as antagonist of FGF21 activity relative to the native sequence. In accordance with one embodiment a 25 amino acid peptide selected from the group consisting of

```
                                    (SEQ ID NO: 188)
LETDSMDPFGLVTGLEAVRSPSFEA, (SEQ ID NO: 191)
PPDVGSSDPLSMVGPSQGRSPSYAA, (SEQ ID NO: 180)
PPDVGSMDPFGLVGPSQGRSPSFEA, (SEQ ID NO: 179)
PLETDSMDPFGLVGPSQGRSPSFEA, (SEQ ID NO: 234)
PDVGSMDPFGLVTGLEAVRSPSYAA, (SEQ ID NO: 237)
PPDVGSMDPFGLVGRSQGRSPSFEA, (SEQ ID NO: 238)
PPDVFSMDPFGLVGPSQGRSPSFEA, (SEQ ID NO: 239)
PPDVLSMDPFGLVGPSQGRSPSFEA, (SEQ ID NO: 240)
PPDVSSMDPFGLVGPSQGRSPSFEA,
and (SEQ ID NO: 241)
PPDVGSSDPFGLVGPSQGRSPSFEA
``` is provided. Each of these peptides have been found to be more potent in antagonizing the native FGF21's in vitro signaling than the corresponding native FGF21 C-terminal 25 amino acid fragment.

Substituting any of the novel sequences of SEQ ID NOs: 179, 180, 188, 191, 234, 237, 238, 239, 240 or 241 for the native C-terminal 25 amino acids of FGF21 produces an FGF analog that has higher potency at the FGF receptor than native FGF21. Furthermore, applicants have discovered additional modifications to the native FGF21 sequence that also enhance the peptide's activity at its receptor. In accordance with one embodiment an agonist analog of FGF21 is provided having enhanced potency at the FGF receptor, where said analog comprises at least one amino acid modification selected from the group consisting of amino acids positions 159, 160, 162, 164, 165, 166, 168, 169, 176, 177, and 179, relative to SEQ ID NO: 173. In one embodiment the amino acid modification comprises an amino acid substitution with a non-natural amino acid. In one embodiment the non-natural amino acid substitution is a substitution of an amino acid with an amino acid in the D-stereo configuration, and optionally the corresponding D-stereoisomer of the native amino acid at that position. In one embodiment an analog of FGF21 is provided having enhanced potency relative to the native FGF21 sequence of SEQ ID NO: 167, where said analog comprises 1-6, 1-4, or 1-2 amino acid modifications at amino acid positions selected from positions 159, 160, 162, 164, 165, 166, 168, 169, 176, 177, and 179, relative to SEQ ID NO: 167. In one embodiment an analog of FGF21 is provided having enhanced potency, where said analog comprises 1-2 amino acid modifications selected from the group consisting of amino acids positions 164, 165 and 168, relative to SEQ ID NO: 167.

In accordance with one embodiment an FGF21 analog is provided having enhanced potency at the FGF receptor, wherein the C-terminal amino acid is substituted with a small aliphatic amino acid, optionally wherein said small aliphatic amino acid has a $C_1$-$C_4$ side chain. In accordance with one embodiment the C-terminal amino acid is substituted with an amino acid selected from the group consisting of glycine, alanine, valine, isoleucine and leucine. In one embodiment the C-terminal amino acid is substituted with alanine. In a further embodiment an FGF21 analog is provided having enhanced potency at the FGF receptor wherein the C-terminal 25 amino acids of FGF21 are substituted with the native C-terminal 25 amino acids of FGF19, further modified by substituting the C-terminal amino acid of the FGF21 analog with alanine.

In a further embodiment novel conjugates comprising a modified C-terminal 25 amino acid peptide of FGF21 are provided. In one embodiment the conjugate comprises an insulin agonist peptide or an FGF1 peptide covalently linked to a modified peptide of SEQ ID NO: 166, wherein the modified peptide differs from SEQ ID NO: 166 by one or more amino acid modifications at positions selected from the group consisting of 3, 4, 6, 8, 9, 10, 12, 13, 20, 21 and 23 of SEQ ID NO: 166. In one embodiment the conjugate comprises a modified peptide of SEQ ID NO: 166 wherein the modified peptide differs from SEQ ID NO: 166 by 1, 2, 3, 4 or 5 amino acid substitution at amino acid positions selected from the group consisting of 3, 4, 6, 8, 9, 10, 12, 13, 20, 21 and 23. In one embodiment the conjugate comprises a modified peptide of SEQ ID NO: 166 wherein the modified peptide differs from SEQ ID NO: 166 by 1 or 2 amino acid substitution at amino acid positions selected from the group consisting of 8, 9 and 12. In accordance with one embodiment the conjugate comprises a 25 amino acid peptide selected from the group consisting of (SEQ ID NO: 188), (SEQ ID NO: 191), (SEQ ID NO: 180), (SEQ ID NO: 179), (SEQ ID NO: 234), (SEQ ID NO: 237), (SEQ ID NO: 238), (SEQ ID NO: 239), (SEQ ID NO: 240), and (SEQ ID NO: 241).

In accordance with one embodiment conjugates of the present disclosure can be represented by the following formula:

Q-L-Y wherein Q is an insulin peptide, a glucagon peptide, FGF1, FGF2, or nuclear hormone, Y is a peptide comprising the sequence of SEQ ID NO: 166 or a modified peptide that differs from SEQ ID NO: 166 by 1, 2, 3, 4 or 5 amino acid substitution at amino acid positions selected from the group consisting of 3, 4, 6, 8, 9, 10, 12, 13, 20, 21 and 23 of SEQ ID NO: 166, and L is a linking group or a bond. In accordance with one embodiment Y is a 25 amino acid peptide selected from the group consisting of (SEQ ID NO: 188), (SEQ ID NO: 191), (SEQ ID NO: 180), (SEQ ID NO: 179), (SEQ ID NO: 234), (SEQ ID NO: 237), (SEQ ID NO: 238), (SEQ ID NO: 239), (SEQ ID NO: 240), and (SEQ ID NO: 241). In one embodiment Q is an insulin peptide, or nuclear hormone. The insulin peptide component of the conjugate can be native insulin or any known insulin analog that has activity at the insulin receptor including, for example, any insulin peptide disclosed in published international applications WO96/34882, WO 2010/080607, WO 2010/080609, WO 2011/159882, WO/2011/159895 and U.S. Pat. No. 6,630,348, the disclosures of which are incorporated herein by reference. In embodiments where Q is an NHR ligand, the ligand is wholly or partly non-peptidic and acts at a nuclear hormone receptor with an activity in accordance with any of the teachings set forth herein. In some embodiments the NHR ligand is an agonist that, in its unbound state, has an EC50 or IC50 of about 1 mM or less, or 100 µM or less, or 10 µM or less, or 1 µM or less. In accordance with one embodiment the NHR ligand component of the conjugate can be a ligand that activates the thyroid hormone receptor or activates the peroxisome proliferator-activated receptors (PPAR) when in an unbound state.

In other aspects of the present disclosure, methods are provided for administering a therapeutically effective amount of a Q-L-Y conjugate or FGF21-based analog described herein for treating a disease or medical condition in a patient. In some embodiments, the disease or medical condition is selected from the group consisting of metabolic syndrome, diabetes, obesity, liver steatosis, and chronic cardiovascular disease. In one embodiment the FGF21-based analogs are administered to a patient to treat metabolic syndrome and lipid abnormalities of the liver, including for example non-alcoholic steatohepatitis (NASH).

Also encompassed by the present disclosure are pharmaceutical compositions comprising the conjugates or FGF21-based analogs disclosed herein and a pharmaceutically acceptable carrier. In accordance with one embodiment a pharmaceutical composition is provided comprising any of the conjugates or FGF21-based analogs disclosed herein preferably at a purity level of at least 90%, 91%, 92%, 93%, 94%, 95%, 96%, 97%, 98% or 99%, and a pharmaceutically acceptable diluent, carrier or excipient. Such compositions may contain a conjugate or FGF21-based analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood glucose levels in insulin dependent patients is provided. The method comprises the steps of administering to a patient an FGF21-based peptide analog or conjugate as disclosed herein in an amount therapeutically effective for the control of diabetes. In accordance with one embodiment a method of reducing weight or preventing weight gain is provided wherein the method comprises administering a conjugate or FGF21-based analog as disclosed herein to a patient in need of such therapy.

BRIEF DESCRIPTION OF THE DRAWINGS

FIG. 6 shows the sequence alignment of the C-termini of FGF21 (SEQ ID NO: 177) and FGF19 (SEQ ID NO: 253).

FIGS. 7A & 7B present bar graphs plotting the respective bioactivity of the FGF21 157-181 or FGF19 169-194 alanine mutation analogs. The residue positions are denoted with regard to the FGF19 sequence. FIG. 7A presents the fold change in the potencies of the set of analogs achieving complete antagonistic response in comparison to its respective native FGF21 or FGF19 peptide. FIG. 7B presents % maximal activities of the set of analogs with less than 95% maximal activity with respect to their native FGF21 or FGF19 peptide. The vertical dotted line represents the activities of the native peptides. Surprisingly, a significant difference in bioactivity was achieved in FGF21 and FGF19 analogs having Ala in the C-terminal position. FIG. 7C is a graph demonstrating the superior bioactivity of FGF19 169-194 K194A peptide to antagonize FGF21 activity in Hep3B cells relative to the native FGF21 18-181, FGF21 157-181 and FGF19 169-194 sequences, thus confirming the unexpected activity associated with the K194A substitution.

FIG. 8A graphs the data produced from a mutational analysis at the terminal position of FGF19 169-194 peptide and its effect on the antagonistic activity, IC-50 values provided in [nM]. K194A [10.5] (squares); K194S [22.3] (circles); K194L [17.3] (triangles); K194E [87.9] (inverted triangles). FIG. 8B graphs the data produced from an analysis of the presence or absence of a lysine substitution at terminal position in FGF21 and FGF19 C-terminal peptides. FGF21 157-181 [0.04] (squares); FGF21 157-181 S181K (circles); FGF19 169-194 [0.05] (triangles); FGF19 169-194 K194A [0.0005] (inverted triangles), IC-50 values in [µM].

FIG. 9A shows the activity for FGF21 [4.5, 100] (squares); FGF21 D164A [inactive, 6] (circles); FGF21 P171A [4.5, 100] (triangles). FIG. 9B shows the activity for FGF21 [3.3, 100] (squares); FGF19 [147.9, 27] (circles); FGF19 K194A [8.1, 31] (triangles); FGF21-19 K194A [0.5, 84](inverted triangles). EC-50 and % maximal activity values are provided in [nM, %].

FIGS. 13A and 13B demonstrate the superior change in body weight obtained with the FGF21 analog relative to the control and administered native FGF21, as measured by total body weight (FIG. 13A) or by percent change in body weight (FIG. 13B). FIG. 13C demonstrates those mice receiving the FGF21 analog had a greater reduction in total food intake.

DETAILED DESCRIPTION

Definitions

Figure 1:
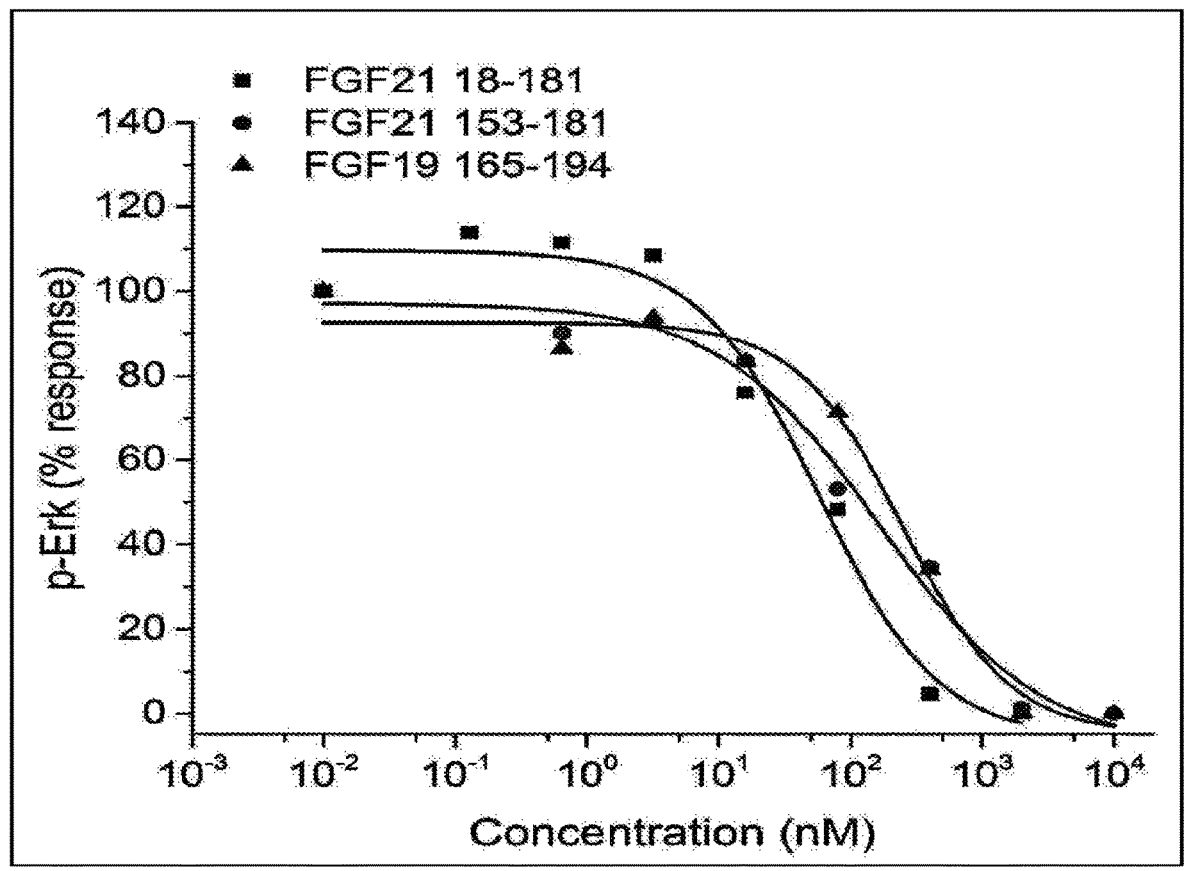
FIG. 1. is a graph demonstrating C-terminal peptides of FGF21 (amino acids 153-181) and FGF19 (amino acids 165-194) exhibit antagonism to FGF21 activity (10 nM stimulation) in 293 HEK hKLB cells equivalent to a much larger fragment of FGF21 (amino acids 18-181).

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture.

As used herein the term "hydroxyl acid" refers to amino acids that have been modified to replace the alpha carbon amino group with a hydroxyl group.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

As used herein a general reference to a peptide is intended to encompass peptides that have modified amino and carboxy termini. For example, an amino acid sequence designating the standard amino acids is intended to encompass standard amino acids at the N- and C-terminus as well as a corresponding hydroxyl acid or acetylated amino acid at the N-terminus and/or a corresponding C-terminal amino acid modified to comprise an amide group in place of the terminal carboxylic acid.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, (iv) an improved resistance to proteases, such as DPP-IV, and (v) increased potency at the IGF and/or insulin peptide receptors.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases, such as DPP-IV, and increased potency at the IGF and/or insulin receptors.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "hydrophilic moiety" refers to any compound that is readily water-soluble or readily absorbs water, and which are tolerated in vivo by mammalian species without toxic effects (i.e. are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of a compound or conjugate refers to a nontoxic but sufficient amount of the compound or conjugate to provide the desired effect. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

Throughout the application, all references to a particular amino acid position in an insulin analog by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted. Similarly, amino acids added to the N-terminus of the native B chain are numbered starting with B0, followed by numbers of increasing negative value (e.g., B-1, B-2 . . . ) as amino acids are added to the N-terminus. Alternatively, any reference to an amino acid position in the linking moiety of a single chain analog, is made in reference to the native C chain of IGF 1 (SEQ ID NO: 17). For example, position 9 of the native C chain (or the "position C9") has an alanine residue.

As used herein the term "native insulin peptide" is intended to designate the 51 amino acid heteroduplex comprising the A chain of SEQ ID NO: 1 and the B chain of SEQ ID NO: 2, as well as single-chain insulin analogs that comprise SEQ ID NOS: 1 and 2. The term "insulin peptide" as used herein, absent further descriptive language is intended to encompass the 51 amino acid heteroduplex comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), including heteroduplexes and single-chain analogs that comprise modified analogs of the native A chain and/or B chain and derivatives thereof. Such modified analogs include modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. Insulin peptides as defined herein can also be analogs derived from a naturally occurring insulin by insertion or substitution of a non-peptide moiety, e.g. a retroinverso fragment, or incorporation of non-peptide bonds such as an azapeptide bond (CO substituted by NH) or pseudo-peptide bond (e.g. NH substituted with $CH_2$) or an ester bond (e.g., a depsipeptide, wherein one or more of the amide (—CONHR—) bonds are replaced by ester (COOR) bonds).

As used herein the term "insulin-like peptide" is intended to designate insulin peptides and related peptides that share the common structural element of having six cysteine residues that form the three disulfide cross-links similar to native insulin. Such related peptides include insulin like growth factors (e.g., IGF I and IGF II), insulin like peptides (e.g., insulin like peptides 3, 4, 5 and 6) and relaxins (e.g., relaxin-1, 2 and 3).

As used herein, the term "single-chain insulin analog" encompasses a group of structurally-related proteins wherein insulin or IGF A and B chains, or analogs or derivatives thereof, are covalently linked to one another to form a linear polypeptide chain. As disclosed herein the single-chain insulin analog comprises the covalent linkage of the carboxy terminus of the B chain to the amino terminus of the A chain via a linking moiety.

As used herein the term "insulin A chain", absent further descriptive language is intended to encompass the 21 amino acid sequence of SEQ ID NO: 1 as well as functional analogs and derivatives thereof, including insulin analogs known to those skilled in the art, including modification of the sequence of SEQ ID NO: 1 by one or more amino acid insertions, deletions or substitutions at positions selected from A4, A5, A8, A9, A10, A12, A14, A15, A17, A18, A21.

As used herein the term "insulin B chain", absent further descriptive language is intended to encompass the 30 amino acid sequence of SEQ ID NO: 2, as well as modified functional analogs of the native B chain, including one or more amino acid insertions, deletions or substitutions at positions selected from B1, B2, B3, B4, B5, B9, B10, B13, B14, B17, B20, B21, B22, B23, B25, B26, B27, B28, B29 and B30 or deletions of any or all of positions B1-4 and B26-30.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an $EC_{50}$ of 1 nM at a first receptor and an $EC_{50}$ of 100 nM at a second receptor has 100-fold selectivity for the first receptor relative to the second receptor.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
  Ala, Ser, Thr, Pro, Gly;
II. Polar, negatively charged residues and their amides:
  Asp, Asn, Glu, Gln, cysteic acid and homocysteic acid;
III. Polar, positively charged residues:
  His, Arg, Lys; Ornithine (Orn)
IV. Large, aliphatic, nonpolar residues:
  Met, Leu, Ile, Val, Cys, Norleucine (Nle), homocysteine
V. Large, aromatic residues:
  Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)OH$, wherein n is at least 2. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms refers to a compound that has been modified from its native state by linking a polyethylene glycol chain to the compound. A "pegylated polypeptide" is a polypeptide that has a PEG chain covalently bound to the polypeptide.

As used herein a "linker" is a bond, molecule or group of molecules that binds two separate entities to one another.

Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-Butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH═$CH_2$), 1,3-butadienyl, (—CH═CHCH═$CH_2$), 1-butenyl (—CH═CH$CH_2CH_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_n$ alkyl)($C_5$-$C_6$ heteroaryl)" refers to a 5 or 6 membered heteroaryl that is attached to a parent moiety via a one to "n" membered alkyl chain.

As used herein, the term "halo" refers to one or more members of the group consisting of fluorine, chlorine, bromine, and iodine.

As used herein the term "patient" without further designation is intended to encompass any warm blooded vertebrate domesticated animal (including for example, but not limited to livestock, horses, cats, dogs and other pets) and humans.

The term "isolated" as used herein means having been removed from its natural environment. In some embodiments, the analog is made through recombinant methods and the analog is isolated from the host cell.

The term "purified," as used herein relates to the isolation of a molecule or compound in a form that is substantially free of contaminants normally associated with the molecule or compound in a native or natural environment and means having been increased in purity as a result of being separated from other components of the original composition. The term "purified polypeptide" is used herein to describe a polypeptide which has been separated from other compounds including, but not limited to nucleic acid molecules, lipids and carbohydrates.

A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include a sequence of naturally-occurring amino acids with the insertion or substitution of a non-peptide moiety, e.g. a retroinverso fragment, or incorporation of non-peptide bonds such as an azapeptide bond (CO substituted by NH) or pseudopeptide bond (e.g. NH substituted with CH2), or an ester bond (e.g., depsipeptides, wherein one or more of the amide (—CONHR—) bonds are replaced by ester (COOR) bonds). Alternatively the peptidomimetic may be devoid of any naturally-occurring amino acids.

As used herein the term "FGF21-based analog" or "FGF21 analog" are used interchangeably, and absent further limitation define an FGF peptide of SEQ ID NO: 173 modified to comprise a substitution at position 181 with a non-charged amino acid (i.e., excluding Asp, Glu, Lys, Arg and His) and optionally selected from the group consisting of Ala, Val, Gly, Thr, Cys, Pro, Met, Ile and Leu, and optionally one or more of the following modifications:

i) one or more substitutions at positions selected from the group consisting of positions 157-161, 163, 166-168, 170-174 and 179-180 (based on the numbering of the mature FGF21 peptide of SEQ ID NO: 173); or ii) one or more substitutions selected from the group consisting of A31C, G43C, L98D, L100K, N121D, and D127K (based on the numbering of the mature FGF21 peptide of SEQ ID NO: 173); or iii) a substitution of the native amino acid at position 167 and/or 175 with the corresponding D-isomer of said native amino acid;

iv) substitution of the native C-terminal 25 amino acids of SEQ ID NO: 173 with the sequence of SEQ ID NO: 188 or v) and any combination of i) and ii) or i), ii) and iii) or a combination of ii) with iii).

As used herein the term "FGF21-based peptide conjugate" defines a conjugate comprising a modified peptide of SEQ ID NO: 166 linked to a conjugate moiety, wherein the modified peptide differs from the peptide of SEQ ID NO: 166 by one or more amino acid substitutions at positions selected from positions 1, 2, 3, 4, 5, 7, 10, 11, 12, 14, 15, 16, 17, 18, 23, 24 and 25 of SEQ ID NO: 166.

ABBREVIATIONS

Insulin analogs will be abbreviated as follows:

The insulin A and B chains will be designated generically by a capital A for the A chain and a capital B for the B chain. When present, a superscript 0 (e.g., $A^0$ or $B^0$) will designate the base sequence is an insulin sequence (A chain: SEQ ID NO: 1, B chain SEQ ID NO: 2) and a superscript 1 (e.g., $A^1$ or $B^1$) will designate the base sequence is an IGF-1 sequence (A chain: SEQ ID NO: 5, B chain SEQ ID NO: 6). Modifications that deviate from the native insulin and IGF sequence are indicated in parenthesis following the designation of the A or B chain (e.g., [$B^1$(H5,H10,Y16,L17): $A^1$(H8,N18,N21)]) with the single letter amino acid abbreviation indicating the substitution and the number indicating the position of the substitution in the respective A or B chain, using native insulin numbering. A colon between the A and B chain indicates a two chain insulin whereas a dash will indicate a covalent bond and thus a single chain analog. In single chain analogs a linking moiety will be included between the A and B chains and the designation $C^1$ refers to the native IGF 1 C peptide, SEQ ID NO: 17. The designation "position C8" in reference to the linking moiety designates an amino acid located at the position corresponding to the eighth amino acid of SEQ ID NO: 17.

EMBODIMENTS

The beneficial pharmacology observed in preclinical models indicate that FGF21 and its analogs or mimetics hold promise as innovative therapeutics for treating metabolic disorders. However, analogs of FGF21 having greater potency at the FGF receptor are needed to enhance the efficacy of FGF21 mediated therapies.

At a molecular level, FGF21 interacts with the FGF receptor only in tissues expressing the cofactor Klotho β. The Klotho β-dependent tissue specificity is consistent with the predominant effects of FGF21 occurring in liver and adipose tissue. Accordingly, one approach to enhance the potency of FGF21 analogs at the FGF21 receptor would be to modify FGF21 to enhance its interaction with Klotho β.

The C-terminus of FGF21 is believed to play a key role in binding with Klotho β and applicants have demonstrated that a peptide comprising the C-terminal 25 amino acids of FGF21 (SEQ ID NO: 166) can inhibit activity of the native FGF21 peptide at its receptor. Presumably this antagonism arises from the affinity of the peptide for Klotho β. In one embodiment, the present disclosure is directed to peptides, and conjugates comprising such peptides, that impact the activity of FGF21 at the FGF21 receptor. More particularly, in one embodiment structural optimization of the peptide of SEQ ID NO: 166 is performed to enhance the peptide's interaction with Klotho β.

In one embodiment a derivative of SEQ ID NO: 166 is provided wherein the derivative comprises a peptide that differs from SEQ ID NO: 166 by one or more amino acid modifications, wherein said peptide has enhanced ability to bind to Klotho β and/or enhanced ability to antagonize FGF21 activity, relative to the peptide of SEQ ID NO: 166. In one embodiment a peptide is provided comprising the structure of PPX$_3$X$_4$GX$_6$SX$_8$X$_9$X$_{10}$SX$_{12}$X$_{13}$GPSQGRX$_{20}$X$_{21}$SX$_{23}$AS (SEQ ID NO: 168) wherein X$_3$, X$_4$, X$_6$, X$_8$, X$_9$, X$_{10}$, X$_{12}$, X$_{13}$, X$_{20}$, X$_{21}$, and X$_{23}$ are independently any amino acid, with the proviso that the peptide of SEQ ID NO: 168 differs from SEQ ID NO: 166 by at least one amino acid substitution. In one embodiment one or more of X$_3$, X$_4$, X$_6$, X$_8$, X$_9$, X$_{10}$, X$_{12}$, X$_{13}$, X$_{20}$, X$_{21}$, and X$_{23}$ are amino acids in the D-stereo configuration, optionally the D-stereoisomer of the corresponding native amino acid at that position.

In accordance with one embodiment a peptide derivative of SEQ ID NO: 166 is provided that differs from SEQ ID NO: 166 by 1, 2, 3, 4, 5, 6, 7, 8, 9 or 10 amino acid substitutions at any of amino acid positions 3, 4, 6, 8, 9, 10, 12, 13, 20, 21 and 23 of SEQ ID NO: 166. In accordance with one embodiment a peptide derivative of SEQ ID NO: 166 is provided that differs from SEQ ID NO: 166 by 1, 2, 3, 4, or 5 amino acid substitutions at any of amino acid positions 3, 4, 6, 8, 9, 10, 12, 13, 20, 21 and 23 of SEQ ID NO: 166. In accordance with one embodiment a peptide derivative of SEQ ID NO: 166 is provided that differs from SEQ ID NO: 166 by 1 or 2 amino acid substitutions at any of amino acid positions 3, 4, 6, 8, 9, 10, 12, 13, 20, 21 and 23 of SEQ ID NO: 166. In accordance with one embodiment a peptide derivative of SEQ ID NO: 166 is provided that differs from SEQ ID NO: 166 by 1, 2 or 3 amino acid substitutions at amino acid positions selected from positions 8, 9 and 12 of SEQ ID NO: 166. In accordance with one embodiment a peptide derivative of SEQ ID NO: 166 is provided that differs from SEQ ID NO: 166 by 1 or 2 amino acid substitutions at amino acid positions selected from positions 8, 9 and 12 of SEQ ID NO: 166.

In one embodiment a peptide is provided comprising the structure of PPDVGSSX$_8$X$_9$LSX$_{12}$VGPSQGRSPSYAS (SEQ ID NO: 169) wherein X$_8$, X$_9$, and X$_{12}$ are independently any amino acid, with the proviso that the peptide of SEQ ID NO: 169 differs from SEQ ID NO: 166 by at least one amino acid substitution. In one embodiment one or more of X$_8$, X$_9$, and X$_{12}$ are amino acids in the D-stereo configuration, optionally the D-stereoisomer of the corresponding native amino acid at that position. In one embodiment X$_8$ is selected from the group consisting of Asp and D-Asp; X$_9$ is selected from the group consisting of Phe and D-Phe; and X$_{12}$ is selected from the group consisting of Met and D-Met, with the proviso that the peptide of SEQ ID NO: 169 differs from SEQ ID NO: 166 by at least one amino acid substitution.

In one embodiment a peptide is provided comprising the structure of PPDVGSSX$_8$X$_9$LSX$_{12}$VGPSQGRSPSYAS (SEQ ID NO: 169) wherein X$_8$ is selected from the group consisting of D-Asp, α-methyl-L-aspartic acid, α-methyl-D-aspartic acid;

X$_9$ is selected from the group consisting of D-Phe, D-4-t-Bu-phenylalanine (D-4-tBuPhe), D-alpha-methylphenylalanine (D-alpha-MePhe), D-4-biphenylalanine (D-4-Bip), D-1-naphthylalanine (D-1-Nal), D-2-naphthylalanine (D-2-Nal), 4-FPhe, 4-CPhe, 4-BrPhe, 4-IPhe, 4-NO$_2$Phe, and 3-NO$_2$Phe; and X$_{12}$ is selected from the group consisting of D-Met, and methionine sulfoxide.

In accordance with one embodiment a peptide antagonist of Klotho β binding/FGF21 activity is provided wherein the peptide is a derivative of the C-terminal 25 amino acid sequence of FGF21. In particular, applicants have discovered that the C-terminal 25 amino acids of FGF21 has equivalent antagonist activity for binding to Klotho β as a much larger fragment of FGF21 (amino acids 18-181). Furthermore, applicants have discovered that by substituting the C-terminal amino acid of the 25mer peptide fragment of FGF21, the potency of antagonism of the peptide for FGF21 binding to Klotho β can be significantly enhanced. In accordance with one embodiment, a modified C-terminal 25 amino acid fragment of FGF21 (SEQ ID NO: 177) or a C-terminal 25 amino acid fragment of FGF19 (SEQ ID NO: 203) is provided wherein the C-terminal amino acid is substituted with a non-charged amino acid (e.g., excluding Arg, Lys, Asp, Glu or His). This peptide can be further modified with 1, 2, 3, 4, 5, 6, 7, 8, 9 or 10 additional amino acid modifications. In one embodiment the C-terminal amino acid of the FGF21 modified peptide fragment is an aliphatic amino acid selected from the group consisting of Gly, Ala, Val, Pro, Cys, Thr, Met, Leu and Ile. In one embodiment the C-terminal amino acid of the FGF21 modified peptide fragment is an aliphatic amino acid selected from the group consisting of Gly, Ala, Val, Pro, Met, Leu and Ile. In one embodiment the C-terminal amino acid of the FGF21 modified peptide fragment is an aliphatic amino acid selected from the group consisting of Gly, Ala, Val, Leu and Ile. In one embodiment the C-terminal amino acid of the FGF21 modified peptide fragment is an aliphatic amino acid selected from the group consisting of Gly, Ala and Val. In one embodiment the C-terminal amino acid of the FGF21 modified peptide fragment is Ala.

In accordance with one embodiment peptides based on the C-terminal 25 amino acids of native FGF21 and FGF19 are provided that have an enhanced ability to bind Klotho β and can be used as antagonists of FGF receptor activity. In one embodiment these peptides comprise a C-terminal 25 amino acid fragment of FGF21 (SEQ ID NO: 177) that is modified by a substitution at position 25 with a non-charged amino acid (e.g., excluding Arg, Lys, Asp, Glu or His), optionally substituted with alanine, and optionally one or more modifications selected from:

i) one or more substitutions selected from the group consisting of G5L, G5F, G5S, S7M, L10F, S11G, M12L, P15R, Y23F, and A24E (based on the numbering of the FGF21 peptide fragment of SEQ ID NO: 177); or ii) one or more substitution of the native amino acid at position 11 or 19 (based on the numbering of the FGF21 peptide fragment of SEQ ID NO: 177) with the corresponding D-isomer of that amino acid; or iii) and any combination of i) and ii).

In one embodiment a modified C-terminal 25 amino acid fragment of FGF21 (SEQ ID NO: 177) is provided, wherein the modified peptide comprises a substitution at position 25 with alanine, and i) one or more substitutions selected from the group consisting of G5L, G5F, G5S, S7M, L10F, SIG, M12L, P15R, Y23F, and A24E.

In one embodiment a modified C-terminal 25 amino acid fragment of FGF21 (SEQ ID NO: 177) is provided, wherein the modified peptide comprises a substitution at position 25 with a non-charged amino acid (e.g., excluding Arg, Lys, Asp, Glu or His), optionally substituted with alanine, and i) one or more substitutions selected from the group consisting of G5L, G5F, G5S, S7M, L10F, SIG, M12L, P15R, Y23F, and A24E; and ii) a substitution of the native amino acid at position 11 or 19 (based on the numbering of the FGF21 peptide fragment of SEQ ID NO: 177) with the corresponding D-isomer of that amino acid.

In one embodiment a modified C-terminal 25 amino acid fragment of FGF21 (SEQ ID NO: 177) is provided, wherein the modified peptide comprises a substitution at position 25 with a non-charged amino acid (e.g., excluding Arg, Lys, Asp, Glu or His), optionally substituted with alanine, and one or more substitutions selected from the group consisting of S7M, L10F, SIG, and M12L.

In one embodiment a modified C-terminal 25 amino acid fragment of FGF21 (SEQ ID NO: 177) is provided, wherein the modified peptide comprises a substitution at position 25 with a non-charged amino acid (e.g., excluding Arg, Lys, Asp, Glu or His), optionally substituted with alanine, and 2, 3, 4, 5, 6, 7 or 8 substitutions selected from the group consisting of G5L, G5F, G5S, S7M, L10F, S11G, M12L, P15R, Y23F, and A24E.

In one embodiment a modified C-terminal 25 amino acid fragment of FGF21 (SEQ ID NO: 177) is provided, wherein the modified peptide comprises a substitution at position 25 with a non-charged amino acid (e.g., excluding Arg, Lys, Asp, Glu or His), optionally substituted with alanine, and further substitutions of S7M, L10F, S11G, M12L, P15R, Y23F, and A24E.

In accordance with one embodiment peptides based on the C-terminal 25 amino acids of native FGF21 and FGF19 are provided that have an enhanced ability to bind Klotho β and can function as antagonists of FGF receptor activity. In accordance with one embodiment a 25 amino acid peptide antagonist of FGF21 receptor activity is selected from the group consisting of SEQ ID NOs: 179, 180, 188, 191, 234, 237, 238, 239, 240 or 241. Each of these peptides have been found to be more potent in antagonizing the native FGF21's in vitro signaling than the corresponding native FGF21 C-terminal 25 amino acid fragment.

As demonstrated by the data presented in Examples 1 and 2 certain positions of the 25 amino acid C-terminal peptide are tolerant of amino acid substitutions without substantial impact to the ability of the peptide to bind Klotho β and/or inhibit FGF21 activity at the FGF21 receptor. In particular positions 1, 2, 5, 7, 11, 14, 15, 16, 17, 18 and 19 of the C-terminal FGF21 fragment tolerate amino acid substitutions without substantial loss in their ability to antagonizing the native FGF21's in vitro signaling. In accordance with one embodiment a derivative of a peptide comprising SEQ ID NO: 188, SEQ ID NO: 191, SEQ ID NO: 180, SEQ ID NO: 179 or SEQ ID NO: 234 is provided, wherein the derivative peptide differs from SEQ ID NO: 188, SEQ ID NO: 191, SEQ ID NO: 180, SEQ ID NO: 179 or SEQ ID NO: 234 by 1, 2, 3, 4, 5, 6, 7, 8, 9, 10 or 11 amino acid substitutions selected from positions 1, 2, 5, 7, 11, 14, 15, 16, 17, 18 and 19 relative to those sequences. In one embodiment the derivative peptide differs by 1, 2 or 3 amino acid substitutions selected from positions 1, 2, 5, 7, 11, 14, 15, 16, 17, 18 and 19. In one embodiment the amino acid substitutions at positions 1, 2, 5, 7, 11, 14, 15, 16, 17, 18 and 19 are conservative amino acid substitutions. In one embodiment a derivative of a peptide comprising SEQ ID NO: 188, SEQ ID NO: 191, SEQ ID NO: 180, SEQ ID NO: 179 or SEQ ID NO: 234 is provided, wherein the derivative peptide differs from SEQ ID NO: 188, SEQ ID NO: 191, SEQ ID NO: 180, SEQ ID NO: 179 or SEQ ID NO: 234 by 1, 2 or 3 amino acid substitutions selected from positions 1, 2, 5, 14, 15, 16, 17, 18 and 19, optionally wherein the amino acid substitutions are conservative amino acid substitutions. In one embodiment a derivative of a peptide comprising SEQ ID NO: 188, SEQ ID NO: 191, SEQ ID NO: 180, SEQ ID NO: 179 or SEQ ID NO: 234 is provided, wherein the derivative peptide differs from SEQ ID NO: 188, SEQ ID NO: 191, SEQ ID NO: 180, SEQ ID NO: 179 or SEQ ID NO: 234 by 1, 2 or 3 amino acid substitutions selected from positions 2, 5, 14, 15, 16, 17, 18 and 19, optionally wherein the amino acid substitutions are conservative amino acid substitutions. In one embodiment a peptide with antagonist activity against Klotho β is provided wherein the peptide comprises an amino acid sequence of (SEQ ID NO: 235)
$X_1X_2X_3X_4X_5SX_7DPX_{10}X_{11}X_{12}VX_{14}GX_{16}X_{17}X_{18}X_{19}RSPSX_{24}X_{25}X_{26}$, wherein
$X_1$ is Pro or absent;
$X_2$ is Pro or Leu;
$X_3$ is Asp or Glu;
$X_4$ is Val or Thr;
$X_5$ is Gly, Asp, Phe, Leu or Ser;
$X_7$ is Ser or Met;
$X_{10}$ is Leu or Phe;
$X_{11}$ is Ser or Gly;
$X_{12}$ is Met or Leu;
$X_{14}$ is absent or Thr;
$X_{16}$ is Pro, Leu, Arg, Glu, or Gly;

X$_{17}$ is Ser or Glu;
X$_{18}$ is Gln or Ala;
X$_{19}$ is Gly or Val;
X$_{24}$ is Tyr or Phe;
X$_{25}$ is Ala or Glu; and
X$_{26}$ is an aliphatic amino acid selected from Gly, Ala, Val, Leu, Ser, or Ile, optionally comprising up to 5 (i.e., 1, 2, 3, 4 or 5) further amino acid substitutions. Optionally the up to 5 further modification can include additional amino acid substitutions at any of positions 1-5, 7, 10-12, 14, 16-19 or 24-26 of SEQ ID NO: 235, or at positions 1, 2, 3, 5, 7, 11, 14, 15, 16, 17, 18 and 19 of SEQ ID NO: 235, or optionally the peptide comprises up to 2 further amino acid substitutions at positions selected from positions 15 and 23 of SEQ ID NO: 235. In one embodiment X$_1$ is absent and X$_{14}$ is Thr. In one embodiment X$_1$ is Pro, Leu, or Arg. In one embodiment a peptide with antagonist activity against Klotho β is provided wherein the peptide comprises an amino acid sequence of (SEQ ID NO: 236)
X$_1$X$_2$X$_3$X$_4$X$_5$SX$_7$DPX$_{10}$X$_{11}$X$_{12}$VX$_{14}$GX$_{16}$X$_{17}$X$_{18}$X$_{19}$RSPSX$_{24}$X$_{25}$A, wherein
X$_1$ is Pro or absent;
X$_2$ is Pro or Leu;
X$_3$ is Asp or Glu;
X$_4$ is Val or Thr;
X$_5$ is Gly, Asp, Phe, Leu or Ser;
X$_7$ is Ser or Met;
X$_{10}$ is Leu or Phe;
X$_{11}$ is Ser or Gly;
X$_{12}$ is Met or Leu;
X$_{14}$ is absent or Thr;
X$_{16}$ is Pro, Leu, or Arg;
X$_{17}$ is Ser or Glu;
X$_{18}$ is Gln or Ala;
X$_{19}$ is Gly or Val;
X$_{24}$ is Tyr or Phe;
X$_{25}$ is Ala or Glu; and In accordance with one embodiment a pharmaceutical composition is provided comprising an FGF peptide fragment antagonist as disclosed herein and a pharmaceutically acceptable carrier, diluent, or excipient.

Each of the 25 amino acid FGF21 C-terminal peptide fragments, analogs and derivatives disclosed herein can be linked to the carboxy terminus of a larger peptide to form a contiguous polypeptide sequence. For example each of the 25 amino acid FGF21 peptide fragments, analogs and derivatives disclosed herein can be fused to the carboxy terminus of a N-terminal polypeptide fragment of FGF21 (or analog thereof) including for example a peptide selected from the group consisting of SEQ ID NO: 194, SEQ ID NO: 195 and SEQ ID NO: 196, or a peptide that differs from SEQ ID NO: 194, SEQ ID NO: 195 and SEQ ID NO: 196 by 1, 2, 3, 4, 5, 6, 7, 8, or 9 amino acid substitutions, to form a polypeptide having agonist activity at the FGF21 receptor. In one embodiment the 1, 2, 3, 4, 5, 6, 7, 8, or 9 amino acid substitutions are conservative amino acid substitutions.

Substituting the novel sequences of SEQ ID NOs: 179, 180, 234, 188 or 191 for the native C-terminal 25 amino acids of FGF21 or FGF19 produces an FGF analog that has higher potency at the FGF receptor than native FGF2. Accordingly, one aspect of the present disclosure is directed to an FGF21 analog comprising the sequence of (SEQ ID NO: 192)
HPIPDSSPLLQFGGQVRQRYLYTDDAQQTEAHLEIREDGTVG

GAADQSPESLLQLKALKPGVIQILGVKTSRFLCQRPDGALYGSLHFDPEA

CSFRELLLEDGYNVYQSEAHGLPLHLPGNKSPHRDPAPRGPARFLPLPGL

PPALPEPPGILAPQLETDSMDPFGLVTGLEAVRSPSFEA;
or (SEQ ID NO: 206)
HPIPDSSPLLQFGGQVRQRYLYTDDAQQTEAHLEIREDGTVG

GAADQSPESLLQLKALKPGVIQILGVKTSRFLCQRPDGALYGSLHFDPEA

CSFRELLLEDGYNVYQSEAHGLPLHLPGNKSPHRDPAPRGPARFLPLPGL

PPALPEPPGILAPQPPDVGSSDPLSMVGPSQGRSPSYAA;
or (SEQ ID NO: 207)
HPIPDSSPLLQFGGQVRQRYLYTDDAQQTEAHLEIREDGTVG

GAADQSPESLLQLKALKPGVIQILGVKTSRFLCQRPDGALYGSLHFDPEA

CSFRELLLEDGYNVYQSEAHGLPLHLPGNKSPHRDPAPRGPARFLPLPGL

PPALPEPPGILAPQPPDVGSMDPFGLVGPSQGRSPSPEA;
or (SEQ ID NO: 208)
HPIPDSSPLLQFGGQVRQRYLYTDDAQQTEAHLEIREDGTVG

GAADQSPESLLQLKALKPGVIQILGVKTSRFLCQRPDGALYGSLHFDPEA

CSFRELLLEDGYNVYQSEAHGLPLHLPGNKSPHRDPAPRGPARFLPLPGL

PPALPEPPGILAPQPLETDSMDPFGLVGPSQGRSPSFEA;
or (SEQ ID NO: 209)
HPIPDSSPLLQFGGQVRQRYLYTDDAQQTEAHLEIREDGTVG

GAADQSPESLLQLKALKPGVIQILGVKTSRFLCQRPDGALYGSLHFDPEA

CSFRELLLEDGYNVYQSEAHGLPLHLPGNKSPHRDPAPRGPARFLPLPGL

PPALPEPPGILAPQPDVGSMDPFGLVTGLEAVRSPSYAA.

Each of the peptides of SEQ ID NOs: 192, 206, 207, 208 and 209 can be further modified to enhance the potency of the FGF21 analog as an FGF receptor agonist. In one embodiment the peptides of SEQ ID NOs: 192, 206, 207, 208 and 209 are further modified to comprise i) one or more substitutions selected from the group consisting of A31C, G43C, L98D, L100K, N121D, and D127K (based on the numbering of the mature FGF21 sequence of SEQ ID NO: 173); or ii) a substitution of the native amino acid at position 167 and/or 175 with the corresponding D-isomer of that amino acid (based on the numbering of the mature FGF21 sequence of SEQ ID NO: 173); or iii) any combination of i) or ii).

In accordance with one embodiment an FGF21 analog having enhanced activity at the FGF receptor relative to native FGF (based on the Erk1/2 phosphorylation in 293T HEK hKLB cell assay of Example 1) is provided. In one embodiment the FGF21 analog comprises the sequence of SEQ ID NO: 175 or SEQ ID NO: 176.

In accordance with one embodiment analogs of FGF21 are provided wherein the analog has higher potency at the FGF receptor relative to native FGF (based on the Erk1/2 phosphorylation in 293T HEK hKLB cell assay of Example 1). In accordance with one embodiment an FGF21-based analog is provided that differs from the FGF peptide of SEQ ID NO: 173 by a substitution at position 181 with a non-charged amino acid (i.e., excluding Asp, Glu, Lys, Arg and His), and optionally an amino acid selected from the group consisting of Ala, Val, Gly, Thr, Cys, Pro, Met, Ile and Leu, and optionally one or more of the following modifications:

i) one or more substitutions selected from the group consisting of G161L, G161F, G161S, S163M, L166F, S167G, M168L, P171R, Y179F, and A180E (based on the numbering of the mature FGF21 peptide of SEQ ID NO: 173); or ii) one or more substitutions selected from the group consisting of A31C, G43C, L98D, L100K, N121D, and D127K (based on the numbering of the mature FGF21 peptide of SEQ ID NO: 173); or iii) a substitution of the native amino acid at position 167 and/or 175 with the corresponding D-isomer of that amino acid (based on the numbering of the mature FGF21 peptide of SEQ ID NO: 173);

iv) substitution of the native C-terminal 25 amino acids of SEQ ID NO: 173 with the sequence of SEQ ID NO: 188 or v) any combination of i) and ii), any combination of i), ii) and iii) or any combination of ii) with iv). Optionally the amino acid at position 181 is selected from the group consisting of Ala, Val, Gly, Ile and Leu, or is selected from the group consisting of Ala, Val, Ile and Leu, or is selected from the group consisting of Ala and Val.

In one embodiment the FGF21-based analog peptides comprise a modified peptide of SEQ ID NO: 204, wherein the modified peptide comprises one or more modifications selected from:

i) one or more substitutions selected from the group consisting of G161L, G161F, G161S, S163M, L166F, S167G, M168L, P171R, Y179F, and A180E (based on the numbering of the mature FGF21 peptide of SEQ ID NO: 173); or ii) one or more substitutions selected from the group consisting of A31C, G43C, L98D, L100K, N121D, and D127K (based on the numbering of the mature FGF21 peptide of SEQ ID NO: 173); or iii) a substitution of the native amino acid at position 167 and/or 175 (based on the numbering of the mature FGF21 peptide of SEQ ID NO: 173) with the corresponding D-isomer of that amino acid; or iv) any combination of i) ii), and iii).

In one embodiment a modified analog of FGF21 comprising the sequence of SEQ ID NO: 204 is provided, wherein the modified peptide differs from SEQ ID NO: 204 by comprising i) one or more substitutions selected from the group consisting of G161L, G161F, G161S, S163M, L166F, S167G, M168L, P171R, Y179F, and A180E (based on the numbering of the mature FGF21 peptide of SEQ ID NO: 173); and ii) one or more substitutions selected from the group consisting of A31C, G43C, L98D, L100K, N121D, and D127K (based on the numbering of the mature FGF21 peptide of SEQ ID NO: 173).

In one embodiment a modified analog of FGF21 comprising the sequence of SEQ ID NO: 204 is provided, wherein the modified peptide differs from SEQ ID NO: 204 by comprising i) one or more substitutions selected from the group consisting of G161L, G161F, G161S, S163M, L166F, S167G, M168L, P171R, Y179F, and A180E (based on the numbering of the mature FGF21 peptide of SEQ ID NO: 173); and ii) one or more substitutions selected from the group consisting of A31C, G43C, L98D, L100K, N121D, and D127K (based on the numbering of the mature FGF21 peptide of SEQ ID NO: 173); and iii) a substitution of the native amino acid at position 167 and/or 175 (based on the numbering of the mature FGF21 peptide of SEQ ID NO: 173) with the corresponding D-isomer of that amino acid.

In one embodiment a modified analog of FGF21 comprising the sequence of SEQ ID NO: 204 is provided, wherein the modified peptide differs from SEQ ID NO: 204 by comprising i) one or more substitutions selected from the group consisting of S163M, L166F, S167G, M168L (based on the numbering of the mature FGF21 peptide of SEQ ID NO: 173); and ii) a substitution of the native amino acid at position 167 and/or 175 (based on the numbering of the mature FGF21 peptide of SEQ ID NO: 173) with the corresponding D-isomer of that amino acid.

In one embodiment a modified analog of FGF21 comprising the sequence of SEQ ID NO: 204 is provided, wherein the modified peptide differs from SEQ ID NO: 204 by comprising i) one or more substitutions selected from the group consisting of G161L, G161F, G161S, S163M, L166F, S167G, M168L, P171R, Y179F, and A180E (based on the numbering of the mature FGF21 peptide of SEQ ID NO: 173).

In one embodiment a modified analog of FGF21 comprising the sequence of SEQ ID NO: 204 is provided, wherein the modified peptide differs from SEQ ID NO: 204 by comprising i) 2, 3, 4, 5, 6 or 7 substitutions selected from the group consisting of G161L, G161F, G161S, S163M, L166F, S167G, M168L, P171R, Y179F, and A180E (based on the numbering of the mature FGF21 peptide of SEQ ID NO: 173); and ii) one or more substitutions selected from the group consisting of A31C, G43C, L98D, L100K, N121D, and D127K (based on the numbering of the mature FGF21 peptide of SEQ ID NO: 173).

In one embodiment a modified analog of FGF21 comprising the sequence of SEQ ID NO: 204 is provided, wherein the modified peptide differs from SEQ ID NO: 204 by comprising i) substitutions of S163M, L166F, S167G, M168L, P171R, Y179F, and A180E (based on the numbering of the mature FGF21 peptide of SEQ ID NO: 173); and ii) one or more substitutions selected from the group consisting of A31C, G43C, L98D, L100K, N121D, and D127K (based on the numbering of the mature FGF21 peptide of SEQ ID NO: 173).

In one embodiment a modified analog of FGF21 comprising the sequence of SEQ ID NO: 204 is provided, wherein the modified peptide differs from SEQ ID NO: 204 by comprising i) substitutions of S163M, L166F, S167G, M168L, P171R, Y179F, and A180E and one of G161L, G161F and G161S (based on the numbering of the mature FGF21 peptide of SEQ ID NO: 173); and ii) one or more substitutions selected from the group consisting of A31C, G43C, L98D, L100K, N121D, and D127K (based on the numbering of the mature FGF21 peptide of SEQ ID NO: 173).

In one embodiment a modified analog of FGF21 comprising the sequence of SEQ ID NO: 204 is provided, wherein the modified peptide differs from SEQ ID NO: 204 by comprising
  i) substitutions of S163M, L166F, S167G, M168L, P171R, Y179F, and A180E and one of G161L, G161F and G161S (based on the numbering of the mature FGF21 peptide of SEQ ID NO: 173); and
  ii) substitutions of A31C, G43C, L98D, L100K, N121D, and D127K (based on the numbering of the mature FGF21 peptide of SEQ ID NO: 173). In accordance with one embodiment an FGF21-based analog is provided wherein the analog comprises a sequence selected from the group consisting of SEQ ID NO: 192, SEQ ID NO: 193, SEQ ID NO: 204, SEQ ID NO: 205, SEQ ID NO: 247, SEQ ID NO: 248, SEQ ID NO: 249, SEQ ID NO: 250, SEQ ID NO: 251 and SEQ ID NO: 252. In accordance with one embodiment an analog of FGF21 is provided wherein the analog comprises a peptide sequence selected from the group consisting of SEQ ID NO: 247, SEQ ID NO: 248, SEQ ID NO: 249, SEQ ID NO: 250, SEQ ID NO: 251 and SEQ ID NO: 252. In accordance with one embodiment an analog of FGF21 is provided wherein the analog comprises the sequence of SEQ ID NO: 193 or SEQ ID NO: 205. In accordance with one embodiment an analog of FGF21 is provided wherein the analog consists of the sequence of SEQ ID NO: 193. In accordance with one embodiment an analog of FGF21 is provided wherein the analog consists of the sequence of SEQ ID NO: 205. In accordance with one embodiment an analog of FGF21 is provided wherein the analog consists of the sequence of SEQ ID NO: 248.

The FGF21 analogs disclosed herein as having high potency at the FGF receptor can be used for any previous use identified for native FGF21. This includes but is not limited to the treatment of a disease or medical condition selected from the group consisting of metabolic syndrome, diabetes, obesity, liver steatosis, dyslipidemia, and chronic cardiovascular disease.

In accordance with one embodiment a pharmaceutical composition is provided comprising an FGF21 agonist analog as disclosed herein and a pharmaceutically acceptable carrier, diluent, or excipient. In accordance with one embodiment the pharmaceutical composition can be used for reducing weight gain or inducing weight loss in a patient in need thereof or for reducing elevated triglycerides, improving hyperglycemia and treating diabetes.

In some aspects, the invention provides a pharmaceutical composition comprising any of the novel FGF21 analogs disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain an FGF21 analog peptide at a concentration of at least A, wherein A is 0.001 mg/ml, 0.01 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In other embodiments, such compositions may contain an FGF21 analog at a concentration of at most B, wherein B is 30 mg/ml, 25 mg/ml, 24 mg/ml, 23, mg/ml, 22 mg/ml, 21 mg/ml, 20 mg/ml, 19 mg/ml, 18 mg/ml, 17 mg/ml, 16 mg/ml, 15 mg/ml, 14 mg/ml, 13 mg/ml, 12 mg/ml, 11 mg/ml, 10 mg/ml, 9 mg/ml, 8 mg/ml, 7 mg/ml, 6 mg/ml, 5 mg/ml, 4 mg/ml, 3 mg/ml, 2 mg/ml, 1 mg/ml, or 0.1 mg/ml. In some embodiments, the compositions may contain an FGF21 analog at a concentration range of A to B mg/ml, for example, 0.001 to 30.0 mg/ml. In one embodiment the pharmaceutical compositions comprise aqueous solutions that are sterilized and optionally stored within various containers. The compounds of the present invention can be used in some embodiments to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The FGF21 analog peptides can be administered to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly.

In one embodiment the kit is provided with a device for administering the FGF21 analog composition to a patient, e.g. syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the FGF21 analog in a lyophilized form or in an aqueous solution. Preferably, the kits will also include instructions for use. In some embodiments the device of the kit is an aerosol dispensing device, wherein the composition is prepackaged within the aerosol device. In another embodiment the kit comprises a syringe and a needle, and in one embodiment the sterile composition comprising the FGF21 analog is prepackaged within the syringe.

In accordance with one embodiment a pharmaceutical composition is provided wherein the composition comprises an FGF21 analog of the present disclosure, or pharmaceutically acceptable salt thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. The instant compositions may further comprise, for example, micelles or liposomes, or some other encapsulated form, or may be administered in an extended release form to provide a prolonged storage and/or delivery effect. In certain embodiments, the pharmaceutical compositions may comprise buffering agents to achieve a physiological compatible pH.

The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

In some embodiments, a method of treating hyperglycemia, or a method of reducing weight gain or inducing weight loss in a patient is provided, which involves administering to the patient an effective amount of an aqueous solution comprising an FGF21 analog as disclosed herein. In further embodiments, methods of treating diabetes involving co-administering a conventional dose or a reduced dose of insulin and an FGF21 analog as disclosed herein are provided. Methods of treating diabetes with an FGF21 analog of the present disclosure, without co-administering insulin are also provided.

Methods for treating hyperglycemia are expected to be useful for a variety of types of hyperglycemia, including diabetes, diabetes mellitus type I, diabetes mellitus type II, or gestational diabetes, either insulin-dependent or non-insulin-dependent, and reducing complications of diabetes including nephropathy, retinopathy and vascular disease.

Methods for reducing appetite or promoting loss of body weight are expected to be useful in reducing body weight, preventing weight gain, or treating obesity of various causes, including drug-induced obesity, and reducing complications associated with obesity including vascular disease (coronary artery disease, stroke, peripheral vascular disease, ischemia reperfusion, etc.), hypertension, onset of diabetes type II, hyperlipidemia and musculoskeletal diseases.

Metabolic Syndrome, also known as metabolic syndrome X, insulin resistance syndrome or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g. high fibrinogen or plasminogen activator inhibitor-1 in blood), and (6) pro-inflammatory state (e.g. elevated C-reactive protein in blood). Other risk factors may include aging, hormonal imbalance and genetic predisposition.

In accordance with one embodiment, a method of preventing or treating Metabolic Syndrome, or reducing one, two, three or more risk factors thereof, in a subject, is provided wherein the method comprises administering to the subject an FGF21 analog described herein in an amount effective to prevent or treat Metabolic Syndrome, or one or more risk factors thereof.

Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. Accordingly, the present disclosure also provides a method of preventing or treating Alcoholic Liver Disease, NAFLD, or any stage thereof, in a subject comprising administering to a subject an FGF21 analog described herein in an amount effective to prevent or treat Alcoholic Liver Disease, NAFLD, or any stage thereof. Such treatment methods include reduction in one, two, three or more of the following: liver fat content, incidence or progression of cirrhosis, incidence of hepatocellular carcinoma, signs of inflammation, e.g. abnormal hepatic enzyme levels (e.g., aspartate aminotransferase AST and/or alanine aminotransferase ALT, or LDH), elevated serum ferritin, elevated serum bilirubin, and/or signs of fibrosis, e.g. elevated TGF-beta levels.

The FGF21 analogs disclosed herein may be administered alone or in combination with other anti-diabetic or anti-obesity agents. Anti-diabetic agents known in the art or under investigation include insulin, sulfonylureas, such as tolbutamide (Orinase), acetohexamide (DYMELOR®), tolazamide (Tolinase), chlorpropamide (DIABINESE®), glipizide (GLUCOTROL®), glyburide (DIABETA®, MICRONASE®, GLYNASE®), glimepiride (AMARYL), or gliclazide (Diamicron); meglitinides, such as repaglinide (PRANDIN®) or nateglinide (STARLIX®); biguanides such as metformin (GLUCOPHAGE®) or phenformin; thiazolidinediones such as rosiglitazone (AVANDIA®), pioglitazone (ACTOS®), or troglitazone (Rezulin), or other PPARγ inhibitors; alpha glucosidase inhibitors that inhibit carbohydrate digestion, such as miglitol (GLYSET®), acarbose (PRECOSE®/GLUCOBAY®); exenatide (BYETTA®) or pramlintide; Dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors.

Anti-obesity agents known in the art or under investigation include, Leptin and Fibroblast Growth Factor 21 (FGF-21), appetite suppressants, such as phenethylamine type stimulants, phentermine (optionally with fenfluramine or dexfenfluramine), diethylpropion (TENUATE®), phendimetrazine (PRELU-2®, BONTRIL®), benzphetamine (DIDREX®), sibutramine (MERIDIA®, REDUCTIL®); rimonabant (ACOMPLIA®), other cannabinoid receptor antagonists; oxyntomodulin; fluoxetine hydrochloride (PROZAC®); Qnexa (topiramate and phentermine), EXCALIA® (bupropion and zonisamide) or Contrave® (bupropion and naltrexone); or lipase inhibitors, similar to xenical (Orlistat) or Cetilistat (also known as ATL-962), or GT 389-255.

Additional conjugates can be formed between the FGF21 analogs disclosed herein (and peptide fragments thereof) and other bioactive peptides such as insulin or nuclear hormones to mediated selective delivery of the conjugates to the liver.

In accordance with one embodiment a peptide conjugate is provided comprising the C-terminal 25 amino acids of FGF21 (SEQ ID NO: 166) or a derivative of that sequence linked to a bioactive agent. In one embodiment the conjugate comprises a compound of the general formula: Q-L-Y, wherein Q is a bioactive peptide, including for example a peptide selected from the group consisting of insulin, FGF1, FGF2, and a nuclear hormone; Y is a peptide comprising the sequence of SEQ ID NO: 166 or a modified peptide that differs from SEQ ID NO: 166 by 1, 2, 3, 4 or 5 amino acid substitution at amino acid positions selected from any of positions 3, 4, 6, 8, 9, 10, 12, 13, 20, 21 and 23 of SEQ ID NO: 166; and L is a linking group or a bond. In accordance with one embodiment Y is a peptide comprising a sequence selected from the group consisting of

```
                                    (SEQ ID NO: 188)
LETDSMDPFGLVTGLEAVRSPSFEA, (SEQ ID NO: 191)
PPDVGSSDPLSMVGPSQGRSPSYAA, (SEQ ID NO: 180)
PPDVGSMDPFGLVGPSQGRSPSFEA, (SEQ ID NO: 179)
PLETDSMDPFGLVGPSQGRSPSFEA, (SEQ ID NO: 234)
PDVGSMDPFGLVTGLEAVRSPSYAA, (SEQ ID NO: 237)
PPDVGSMDPFGLVGRSQGRSPSFEA, (SEQ ID NO: 238)
PPDVFSMDPFGLVGPSQGRSPSFEA, (SEQ ID NO: 239)
PPDVLSMDPFGLVGPSQGRSPSFEA, (SEQ ID NO: 240)
PPDVSSMDPFGLVGPSQGRSPSFEA,
and (SEQ ID NO: 241)
PPDVGSSDPFGLVGPSQGRSPSFEA.
```

In accordance with one embodiment an FGF21 analog is provided comprising the sequence of SEQ ID NO: 167 modified by one or more amino acid substitutions at positions selected from the group consisting of positions 159, 160, 162, 164, 165, 166, 168, 169, 176, 177, and 179 relative to SEQ ID NO: 167. In one embodiment the substitutions are replacement of the native amino acid with its corresponding D-stereoisomer. In an alternative embodiment the substitutions are replacement of the native amino acid with a corresponding amino acid mimetic of the native amino acid at that position.

In one embodiment conjugates of the FGF21 C-terminal peptide (SEQ ID NO: 166 and derivative disclosed herein) and other bioactive peptides (e.g., FGF1, FGF2 and insulin) are prepared as a means of directing the activity of those bioactive peptides to adipose and liver. Conjugates of the FGF21 based peptide can also be used to restrict the pharmacology of nuclear hormones as a means to enhance their safety without lessening their proven pharmacology, thus rendering them suitable for chronic use.

Disclosed herein are FGF21 based peptides conjugated comprising an insulin-like peptide, insulin peptide or a NHR ligand. In one embodiment the NHR ligand is an NHR agonist. In one embodiment the NHR ligand is selected from the group consisting of a steroid that exhibits an $EC_{50}$ of about 1 µM or less when unconjugated to Q-L, and has a molecular weight of up to about 1000 daltons. In one embodiment the NHR ligand is a ligand that activates the thyroid hormone receptor or a ligand that activates the peroxisome proliferator-activated receptors (PPAR).

In one embodiment Q is a glucagon peptide comprising a sequence from the group consisting of

```
                                         (SEQ ID NO: 202)
HX₁QGTFTSDKSKYLDX₂RAAQDFVQWLMDT, (SEQ ID NO: 197)
X₃AQGTFTSDKSKYLDERAAQDFVQWLLEGGPSSGAPPPS, (SEQ ID NO: 198)
X₄AQGTFTSDKSKYLDERAAQDFVQWLLEGGPSSGAPPPS, (SEQ ID NO: 199)
X₅AQGTFTSDKSKYLDERAAQDFVQWLLEGGPSSGAPPPS, (SEQ ID NO: 200)
X₆AQGTFTSDKSKYLDERAAQDFVQWLLDAGPSSGAPPPS
and (SEQ ID NO: 201)
X₇AQGTFTSDKSKYLDERAAQDFVQWLLEAGPSSGAPPPS
``` wherein $X_1$ and $X_2$ are both Aib;

$X_3$ is Acetyl D-Tyr;

$X_4$ is Acetyl D-His;

$X_5$ is Acetyl D-thio Ala, and $X_6$ and $X_7$ are both acetyl-D-Tyr.

In some embodiments the NHR ligand is an NHR agonist. In one embodiment the NHR agonist has activity at a Type I NHR when bound to Q-L. In one embodiment the NHR agonist has activity at a Type II NHR when bound to Q-L. In one embodiment the NHR ligand is i) a steroid that exhibits an $EC_{50}$ of about 1 µM or less when unconjugated to Q-L, and further has a molecular weight of up to about 1000 daltons; or ii) a ligand that activates the thyroid hormone receptor; or iii) a ligand that activates the peroxisome proliferator-activated receptors (PPAR).

In one embodiment the NHR ligand of the conjugate is selected from the group consisting of estradiol and derivatives thereof, estrone and derivatives thereof, testosterone and derivatives thereof, and cortisol and derivatives thereof. In one embodiment the NHR ligand is dexamethasone.

In accordance with one embodiment the NHR ligand of the FGF21 based conjugate is a thyroid hormone receptor agonist having the general structure

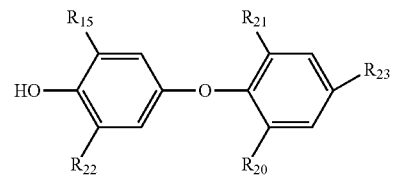

wherein $R_{15}$ is $C_1$-$C_4$ alkyl, —CH₂(pyridazinone), —CH₂(OH)(phenyl)F, —CH(OH)CH₃, halo or H;

$R_{20}$ is halo, CH₃ or H;

$R_{21}$ is halo, CH₃ or H;

$R_{22}$ is H, OH, halo, —CH₂(OH)(C₆ aryl)F, or $C_1$-$C_4$ alkyl; and $R_{23}$ is —CH₂CH(NH₂)COOH, —OCH₂COOH, —NHC(O)COOH, —CH₂COOH, —NHC(O)CH$_2$COOH, —CH$_2$CH$_2$COOH, or —OCH$_2$PO$_3^{2-}$. In one embodiment the thyroid hormone receptor agonist has the general structure of Formula I:

wherein

R$_{20}$, R$_{21}$, and R$_{22}$ are independently selected from the group consisting of H, OH, halo and C$_1$-C$_4$ alkyl; and R$_{15}$ is halo or H. In one embodiment the thyroid hormone receptor agonist is selected from the group consisting of thyroxine T4 (3,5,3',5'-tetra-iodothyronine), and 3,5,3'-triiodo L-thyronine.

In one embodiment the NHR ligand is an agonist of a PPAR. In one embodiment the PPAR agonist is selected from the group consisting of Tesaglitazar, Aleglitazar and thiazolidinediones. In one embodiment the PPAR agonist is Tesaglitazar or Aleglitazar.

In one embodiment the insulin-like peptide of the FGF21 based conjugate Q-L-Y is a peptide selected from IGF I, IGF II, an insulin like peptide 3, 4, 5 or 6, or a Relaxin-1, 2 or 3. In one embodiment the insulin-like peptide of the FGF21 based conjugate Q-L-Y is an insulin like peptide or a Relaxin peptide.

In one embodiment the insulin peptide of the FGF21 based conjugate Q-L-Y is a native insulin peptide or any insulin receptor agonist known to those skilled in the art. In one embodiment the insulin peptide (Q) comprises an A chain and a B chain wherein said A chain comprises a sequence GIVX$_4$X$_5$CCX$_8$X$_9$X$_{10}$CX$_{12}$LX$_{14}$X$_5$LX$_{17}$X$_{18}$YCX$_{21}$-R$_{53}$ (SEQ ID NO: 19), and said B chain comprises a sequence R$_{62}$-X$_{25}$LCGX$_{29}$X$_{30}$LVX$_{33}$X$_{34}$LYLVCGX$_{41}$X$_{42}$GFX$_{45}$ (SEQ ID NO: 20), wherein X$_4$ is glutamic acid or aspartic acid;
X$_5$ is glutamine or glutamic acid
X$_8$ is histidine, threonine or phenylalanine;
X$_9$ is serine, arginine, lysine, ornithine or alanine;
X$_{10}$ is isoleucine or serine;
X$_{12}$ is serine or aspartic acid;
X$_{14}$ is tyrosine, arginine, lysine, ornithine or alanine;
X$_{15}$ is glutamine, glutamic acid, arginine, alanine, lysine, ornithine or leucine;
X$_{17}$ is glutamic acid, aspartic acid, asparagine, lysine, ornithine or glutamine;
X$_{18}$ is methionine, asparagine, glutamine, aspartic acid, glutamic acid or threonine;
X$_{21}$ is selected from the group consisting of alanine, glycine, serine, valine, threonine, isoleucine, leucine, glutamine, glutamic acid, asparagine, aspartic acid, histidine, tryptophan, tyrosine, and methionine;
X$_{25}$ is histidine or threonine;
X$_{29}$ is selected from the group consisting of alanine, glycine and serine;
X$_{30}$ is selected from the group consisting of histidine, aspartic acid, glutamic acid, homocysteic acid and cysteic acid;
X$_{33}$ is selected from the group consisting of aspartic acid and glutamic acid;
X$_{34}$ is selected from the group consisting of alanine and threonine;
X$_{41}$ is selected from the group consisting of glutamic acid, aspartic acid or asparagine;
X$_{42}$ is selected from the group consisting of alanine, ornithine, lysine and arginine;
X$_{45}$ is tyrosine or phenylalanine;
R$_{62}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and
R$_{53}$ is COOH or CONH$_2$. In one embodiment the insulin peptide is a two chain insulin analog. In another embodiment the insulin peptide is a single chain insulin analog wherein the carboxy terminus of the B chain is linked to the amino terminus of the A chain via a peptide linker. Any of the previous disclosed single chain insulin analogs having activity at the insulin receptor and known to those skilled in the art are encompassed by the present disclosure.

In one embodiment the insulin peptide of the conjugate is a two chain insulin wherein the A and B chains are linked by interchain disulfide bonds, wherein the A chain comprises the sequence GIVEQCCX$_8$X$_9$ICSLYQLENYCX$_{21}$-R$_{53}$ (SEQ ID NO: 73) and the B chain comprises a sequence R$_{62}$-X$_{25}$LCGAX$_{30}$LVDALYLVCGDX$_{42}$GFY (SEQ ID NO: 75), wherein X$_8$ is histidine or threonine;
X$_9$ is serine, lysine, or alanine;
X$_{21}$ is alanine, glycine or asparagine;
X$_{25}$ is histidine or threonine;
X$_{30}$ is selected from the group consisting of histidine, aspartic acid, glutamic acid, homocysteic acid and cysteic acid;
X$_{42}$ is selected from the group consisting of alanine ornithine and arginine; and R$_{53}$ is COOH or CONH$_2$;
R$_{62}$ is selected from the group consisting of FVNQ (SEQ ID NO: 12), a tripeptide valine-asparagine-glutamine, a dipeptide asparagine-glutamine, glutamine, and an N-terminal amine; and
R$_{53}$ is COOH or CONH$_2$. In one embodiment the A chain comprises the sequence GIVEQCCX$_8$X$_9$ ICSLYQLENYCX$_{21}$-R$_{53}$ (SEQ ID NO: 73) and the B chain comprises the B chain sequence comprises the sequence FVKQX$_{25}$LCGSHLVEALYLVCGERGFF-R$_{63}$ (SEQ ID NO: 147), or FVNQX$_{25}$LCGSHLVEALYLVCGERGFF-R$_{63}$ (SEQ ID NO: 148), wherein X$_8$ is histidine or threonine;
X$_9$ is serine, lysine, or alanine;
X$_{21}$ is alanine, glycine or asparagine;
X$_{25}$ is selected from the group consisting of histidine and threonine; and
R$_{63}$ is selected from the group consisting of YTX$_{28}$KT (SEQ ID NO: 149), YTKPT (SEQ ID NO: 150), YTX$_{28}$K (SEQ ID NO: 152), YTKP (SEQ ID NO: 151), YTPK (SEQ ID NO: 70), YTX$_{28}$, YT, Y and a bond.

In one embodiment the A chain comprises the sequence GIVEQCCX$_8$SICSLYQLENYCX$_{21}$-R$_{53}$ (SEQ ID NO: 153) or GIVEQCCTSICSLYQLENYCN-R$_{53}$ (SEQ ID NO: 1) and the B chain comprises the sequence FVKQX$_{25}$L-CGSHLVEALYLVCGERGFFYTEKT (SEQ ID NO: 154), FVNQX$_{25}$LCGSHLVEALYLVCGERGFFYTDKT(SEQ ID NO: 155), FVNQX$_{25}$LCGSHLVEALYLVCGERGFFYT- KPT (SEQ ID NO: 156) or FVNQX$_{25}$LCGSHL VEALYL-VCGERGFFYTPKT (SEQ ID NO: 157) wherein
X$_8$ is histidine or threonine;
X$_{21}$ is alanine, glycine or asparagine; X$_{25}$ is selected from the group consisting of histidine and threonine and R$_{53}$ is COOH or CONH$_2$. In one embodiment the A chain comprises a sequence GIVEQCCTSICSLYQLENY CN-R$_{53}$ (SEQ ID NO: 1) and said B chain comprises a sequence FVNQHLCGSHLVEALYLVCGERG FFYTPKT (SEQ ID NO: 2) wherein R$_{53}$ is COOH or CONH$_2$.

In one embodiment the insulin peptide is a single chain insulin analog. In one embodiment the peptide linker joining the B and A chains is selected from the group consisting of SSSSKAPPPSLPSPSRLPGPSDTPILPQR (SEQ ID NO: 158), SSSSRAPPPSLPSPSRLPGPSDTPILPQK (SEQ ID NO: 159), GAGSSSX$_{57}$X$_{58}$ (SEQ ID NO: 76), GYGSSS-X$_{57}$X$_{58}$ (SEQ ID NO: 21) and GYGSSSX$_{57}$X$_{58}$APQT; (SEQ ID NO: 77), wherein X$_{57}$ and X$_{58}$ are independently arginine, lysine or ornithine. In one embodiment both X$_{57}$ and X$_{58}$ are independently arginine. In one embodiment the peptide linking moiety joining the insulin A and B chains to form a single chain insulin analog is a peptide sequence
consisting of GYGSSSRR (SEQ ID NO: 18) GAGSSSRR (SEQ ID NO: 22) or GAGSSSRRAPQT (SEQ ID NO: 23).

In accordance with one embodiment, the linker (L in the formula Q-L-Y) is a linking group or a bond that covalently links the insulin peptide to the NHR ligand. In one embodiment the NHR ligand is linked to the side chain of an amino acid at position B28 or B29 of the insulin peptide. In one embodiment the amino acid at position B28 or B29 of the insulin peptide is lysine and the NHR ligand is linked to the side chain of the lysine. In one embodiment the NHR ligand is linked to the insulin peptide via the N-terminal alpha amine of the insulin A or B chain. In one embodiment the NHR ligand is linked to the insulin peptide via an amid bond formed between an amino group of the insulin peptide and a carboxy group of the NHR ligand, optionally through a spacer moiety.

In one embodiment the linker (L in the formula Q-L-Y) is a linking group wherein L is stable in vivo, hydrolyzable in vivo, or metastable in vivo. In one embodiment L comprises an ether moiety, or an amide moiety, an ester moiety, an acid-labile moiety, a reduction-labile moiety, an enzyme-labile moiety, a hydrazone moiety, a disulfide moiety, or a cathepsin-cleavable moiety.

Structure of the NHR Ligand (Q)

The NHR ligand of the FGF21 based conjugates is partly or wholly non-peptidic and is hydrophobic or lipophilic. In some embodiments, the NHR ligand has a molecular weight that is about 5000 daltons or less, or about 4000 daltons or less, or about 3000 daltons or less, or about 2000 daltons or less, or about 1750 daltons or less, or about 1500 daltons or less, or about 1250 daltons or less, or about 1000 daltons or less, or about 750 daltons or less, or about 500 daltons or less, or about 250 daltons or less. The structure of Q can be in accordance with any of the teachings disclosed herein.

In the embodiments described herein, Q is conjugated to L (e.g. when L is a linking group) or Y (e.g. when L is a bond) at any position of Q that is capable of reacting with Y or L. One skilled in the art could readily determine the position and means of conjugation in view of general knowledge and the disclosure provided herein.

In any of the embodiments described herein wherein Q comprises a tetracyclic skeleton having three 6-membered rings joined to one 5-membered ring or a variation thereof (e.g. a Q that acts at the vitamin D receptor), the carbon atoms of the skeleton are referred to by position number, as shown below:

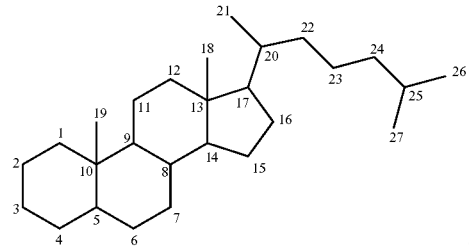

For example, a modification having a ketone at position-6 refers to the following structure:

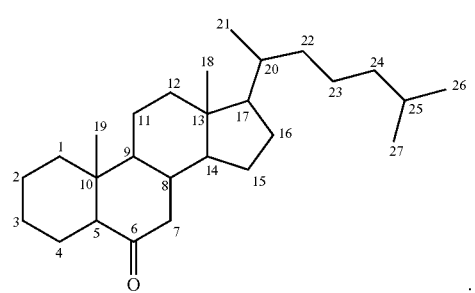 [SMILES: CC(C)CCCC(C)C1CCC2C3CC(=O)C4CCCCC4(C)C3CCC12C]

NHR Ligand that Acts on a Type I Nuclear Hormone Receptor

In some embodiments of the invention, the NHR ligand (Q) acts on a Type I nuclear hormone reactor. In some embodiments, Q can have any structure that permits or promotes agonist activity upon binding of the ligand to a Type I nuclear hormone receptor, while in other embodiments Q is an antagonist of the Type I nuclear hormone receptor.

In exemplary embodiments, Q comprises a structure as shown in Formula A:

Formula A

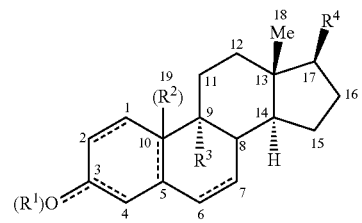

wherein R$^1$ and R$^2$, when present, are independently moieties that permit or promote agonist or antagonist activity upon binding of the compound of Formula A to the Type I nuclear hormone receptor; R$^3$ and R$^4$ are independently moieties that permit or promote agonist or antagonist activity upon binding of the compound of Formula A to the Type I nuclear hormone receptor; and each dashed line represents an optional double bond. Formula A may further comprise one or more substituents at one or more of positions 1, 2, 3, 4, 5, 6, 7, 8, 9, 11, 12, 14, 15, 16, 17, 18, and 19. Contemplated optional substituents include, but are not limited to, OH, $NH_2$, ketone, and $C_1$-$C_{18}$ alkyl groups.

In some embodiments, Q comprises a structure of Formula A wherein $R^1$ is present and is hydrogen, $C_1$-$C_7$ alkyl; ($C_0$-$C_3$ alkyl)C(O)$C_1$-$C_7$ alkyl, ($C_0$-$C_3$ alkyl)C(O)aryl, or $SO_3H$;

$R^2$ is present and is hydrogen, halo, OH, or $C_1$-$C_7$ alkyl;

$R^3$ is hydrogen, halo, OH, or $C_1$-$C_7$ alkyl;

$R^4$ is hydrogen, ($C_0$-$C_8$ alkyl)halo, $C_1$-$C_8$ alkyl, $C_2$-$C_8$ alkenyl, $C_{2-18}$ alkynyl, heteroalkyl, ($C_0$-$C_8$ alkyl)aryl, ($C_0$-$C_8$ alkyl)heteroaryl, ($C_0$-$C_8$ alkyl)O$C_1$-$C_8$ alkyl, ($C_0$-$C_8$ alkyl)O$C_2$-$C_8$ alkenyl, ($C_0$-$C_8$ alkyl)O$C_2$-$C_8$ alkynyl, ($C_0$-$C_8$ alkyl)OH, ($C_0$-$C_8$ alkyl)SH, ($C_0$-$C_8$ alkyl)$NR^{24}$—$C_1$-$C_8$ alkyl, ($C_0$-$C_8$ alkyl)$NR^{24}$—$C_2$-$C_8$ alkenyl, ($C_0$-$C_8$ alkyl)$NR^{24}$—$C_2$-$C_8$ alkynyl, ($C_0$-$C_8$ alkyl)$NR^{24}H_2$, ($C_0$-$C_8$ alkyl)C(O)$C_1$-$C_8$ alkyl, ($C_0$-$C_8$ alkyl)C(O)$C_2$-$C_8$ alkenyl, ($C_0$-$C_8$ alkyl)C(O)$C_2$-$C_8$ alkynyl, ($C_0$-$C_8$ alkyl)C(O)H, ($C_0$-$C_8$ alkyl)C(O)aryl, ($C_0$-$C_8$ alkyl)C(O)heteroaryl, ($C_0$-$C_8$ alkyl)C(O)O$C_1$-$C_8$ alkyl, ($C_0$-$C_8$ alkyl)C(O)O$C_2$-$C_8$ alkenyl, ($C_0$-$C_8$ alkyl)C(O)O$C_2$-$C_8$ alkynyl, ($C_0$-$C_8$ alkyl)C(O)OH, ($C_0$-$C_8$ alkyl)C(O)O aryl, ($C_0$-$C_8$ alkyl)C(O)O heteroaryl, ($C_0$-$C_8$ alkyl)OC(O)$C_1$-$C_8$ alkyl, ($C_0$-$C_8$ alkyl)OC(O)$C_2$-$C_8$ alkenyl, ($C_0$-$C_8$ alkyl)OC(O)$C_2$-$C_{18}$ alkynyl, ($C_0$-$C_8$ alkyl)C(O)$NR^{24}$—$C_1$-$C_8$ alkyl, ($C_0$-$C_8$ alkyl)C(O)$NR^{24}$—$C_2$-$C_8$ alkenyl, ($C_0$-$C_8$ alkyl)C(O)$NR^{24}$—$C_2$-$C_8$ alkynyl, ($C_0$-$C_8$ alkyl)C(O)$NR^{24}H_2$, ($C_0$-$C_8$ alkyl)C(O)$NR^{24}$aryl, ($C_0$-$C_8$ alkyl)C(O)$NR^{24}$heteroaryl, ($C_0$-$C_8$ alkyl)$NR^{24}$C(O)$C_1$-$C_8$ alkyl, ($C_0$-$C_8$ alkyl)$NR^{24}$C(O)$C_2$-$C_8$ alkenyl, or ($C_0$-$C_8$ alkyl)$NR^{24}$C(O)$C_2$-$C_8$ alkynyl, ($C_0$-$C_8$ alkyl)$NR^{24}$C(O)OH, ($C_0$-$C_8$ alkyl)OC(O)O$C_1$-$C_8$ alkyl, ($C_0$-$C_8$ alkyl)OC(O)O$C_2$-$C_8$ alkenyl, ($C_0$-$C_8$ alkyl)OC(O)O$C_2$-$C_8$ alkynyl, ($C_0$-$C_8$ alkyl)OC(O)OH, ($C_0$-$C_8$ alkyl)OC(O)$NR^{24}C_1$-$C_8$ alkyl, ($C_0$-$C_8$ alkyl)OC(O)$NR^{24}$—$C_2$-$C_8$ alkenyl, ($C_0$-$C_8$ alkyl)OC(O)$NR^{24}$—$C_2$-$C_8$ alkynyl, ($C_0$-$C_8$ alkyl)OC(O)$NR^{24}H_2$, ($C_0$-$C_8$ alkyl)$NR^{24}$(O)O$C_1$-$C_8$ alkyl, ($C_0$-$C_8$ alkyl)$NR^{24}$(O)O$C_2$-$C_8$ alkenyl, ($C_0$-$C_8$ alkyl)$NR^{24}$(O)O$C_2$-$C_8$ alkynyl, or ($C_0$-$C_8$ alkyl)$NR^{24}$(O)OH; and, $R^{24}$ is hydrogen or $C_1$-$C_7$ alkyl.

In some embodiments, $R^1$ is hydrogen, propionate, acetate, benzoate, or sulfate; $R^2$ is hydrogen or methyl; $R^3$ is hydrogen or methyl; and $R^4$ is acetate, cypionate, hemisucciniate, enanthate, or propionate.

In embodiments wherein Q comprises a structure of Formula A, Q is conjugated to L (e.g. when L is a linking group) or Y (e.g. when L is a bond) at any position of Formula A that is capable of reacting with Y or L. One skilled in the art could readily determine the position of conjugation on Formula A and means of conjugation of Formula A to Y or L in view of general knowledge and the disclosure provided herein. In some embodiments, Formula A is conjugated to L or Y at any of positions 1, 2, 3, 4, 5, 6, 7, 8, 9, 10, 11, 12, 13, 14, 15, 16, 17, 18, 19, or 20 of Formula A. In some embodiments, Formula A is conjugated to L or Y at position 1, 3, 6, 7, 12, 10, 13, 16, 17, or 19 of Formula A.

In some embodiments, Q acts at an estrogen receptor (e.g. ERα, ERβ). In some embodiments, Q permits or promotes agonist activity at the estrogen receptor, while in other embodiments Q is an antagonist of ER. In exemplary embodiments, Q can have a structure of Formula B:

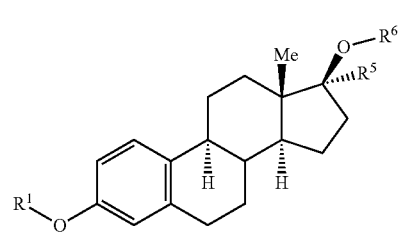

Formula B wherein $R^1$, $R^5$ and $R^6$ are moieties that permit or promote agonist or antagonist activity upon binding of the compound of Formula B to the estrogen receptor. In some embodiments, Formula B further comprises one or more substituents at one or more of positions 1, 2, 4, 6, 7, 8 9 11, 12 14 15, and 16 (e.g. a ketone at position-6).

In some embodiments when Q comprises a structure of Formula B, wherein $R^1$ is hydrogen, $C_1$-$C_7$ alkyl; ($C_0$-$C_3$ alkyl)C(O)$C_1$-$C_7$ alkyl, ($C_0$-$C_3$ alkyl)C(O)aryl, or $SO_3H$;

$R^5$ is hydrogen, ($C_0$-$C_8$ alkyl)halo, $C_1$-$C_8$ alkyl, $C_2$-$C_8$ alkenyl, $C_{2-18}$ alkynyl, heteroalkyl, ($C_0$-$C_8$ alkyl)aryl, ($C_0$-$C_8$ alkyl)heteroaryl, ($C_0$-$C_8$ alkyl)O$C_1$-$C_8$ alkyl, ($C_0$-$C_8$ alkyl)O$C_2$-$C_8$ alkenyl, ($C_0$-$C_8$ alkyl)O$C_2$-$C_8$ alkynyl, ($C_0$-$C_8$ alkyl)OH, ($C_0$-$C_8$ alkyl)SH, ($C_0$-$C_8$alkyl)$NR^{24}$—$C_1$-$C_8$ alkyl, ($C_0$-$C_8$ alkyl)$NR^{24}$—$C_2$-$C_8$ alkenyl, ($C_0$-$C_8$ alkyl)$NR^{24}$—$C_2$-$C_8$ alkynyl, ($C_0$-$C_8$ alkyl)$NR^{24}H_2$, ($C_0$-$C_8$ alkyl)C(O)$C_1$-$C_8$ alkyl, ($C_0$-$C_8$ alkyl)C(O)$C_2$-$C_8$ alkenyl, ($C_0$-$C_8$ alkyl)C(O)$C_2$-$C_8$ alkynyl, ($C_0$-$C_8$ alkyl)C(O)H, ($C_0$-$C_8$ alkyl)C(O)aryl, ($C_0$-$C_8$ alkyl)C(O)heteroaryl, ($C_0$-$C_8$ alkyl)C(O)O$C_1$-$C_8$ alkyl, ($C_0$-$C_8$ alkyl)C(O)O$C_2$-$C_8$ alkenyl, ($C_0$-$C_8$ alkyl)C(O)O$C_2$-$C_8$ alkynyl, ($C_0$-$C_8$ alkyl)C(O)OH, ($C_0$-$C_8$ alkyl)C(O)O aryl, ($C_0$-$C_8$ alkyl)C(O)O heteroaryl, ($C_0$-$C_8$ alkyl)OC(O)$C_1$-$C_8$ alkyl, ($C_0$-$C_8$ alkyl)OC(O)$C_2$-$C_8$ alkenyl, ($C_0$-$C_8$ alkyl)OC(O)$C_2$-$C_{18}$ alkynyl, ($C_0$-$C_8$ alkyl)C(O)$NR^{24}$—$C_1$-$C_8$ alkyl, ($C_0$-$C_8$ alkyl)C(O)$NR^{24}$—$C_2$-$C_8$ alkenyl, ($C_0$-$C_8$ alkyl)C(O)$NR^{24}$—$C_2$-$C_8$ alkynyl, ($C_0$-$C_8$ alkyl)C(O)$NR^{24}H_2$, ($C_0$-$C_8$ alkyl)C(O)$NR^{24}$aryl, ($C_0$-$C_8$ alkyl)C(O)$NR^{24}$heteroaryl, ($C_0$-$C_8$ alkyl)$NR^{24}$C(O)$C_1$-$C_8$ alkyl, ($C_0$-$C_8$ alkyl)$NR^{24}$C(O)$C_2$-$C_8$ alkenyl, or ($C_0$-$C_8$ alkyl)$NR^{24}$C(O)$C_2$-$C_8$ alkynyl, ($C_0$-$C_8$ alkyl)$NR^{24}$C(O)OH, ($C_0$-$C_8$ alkyl)OC(O)O$C_1$-$C_8$ alkyl, ($C_0$-$C_8$ alkyl)OC(O)O$C_2$-$C_8$ alkenyl, ($C_0$-$C_8$ alkyl)OC(O)O$C_2$-$C_8$ alkynyl, ($C_0$-$C_8$ alkyl)OC(O)OH, ($C_0$-$C_8$ alkyl)OC(O)$NR^{24}$—$C_1$-$C_8$ alkyl, ($C_0$-$C_8$ alkyl)OC(O)$NR^{24}$—$C_2$-$C_8$ alkenyl, ($C_0$-$C_8$ alkyl)OC(O)$NR^{24}$—$C_2$-$C_8$ alkynyl, ($C_0$-$C_8$ alkyl)OC(O)$NR^{24}H_2$, ($C_0$-$C_8$ alkyl)$NR^{24}$(O)O$C_1$-$C_8$ alkyl, ($C_0$-$C_8$ alkyl)$NR^{24}$(O)O$C_2$-$C_8$ alkenyl, ($C_0$-$C_8$ alkyl)$NR^{24}$(O)O$C_2$-$C_8$alkynyl, or ($C_0$-$C_8$ alkyl)$NR^{24}$(O)OH;

$R^6$ is hydrogen, $C_1$-$C_8$ alkyl, $C_2$-$C_8$ alkenyl, $C_2$-$C_8$ alkynyl, heteroalkyl, ($C_0$-$C_8$ alkyl)aryl, ($C_0$-$C_8$ alkyl)heteroaryl, ($C_0$-$C_8$ alkyl)C(O)$C_1$-$C_8$ alkyl, ($C_0$-$C_8$ alkyl)C(O)$C_2$-$C_8$ alkenyl, ($C_0$-$C_8$ alkyl)C(O)$C_2$-$C_8$ alkynyl, ($C_0$-$C_8$ alkyl)C(O)H, ($C_0$-$C_8$ alkyl)C(O)aryl, ($C_0$-$C_8$ alkyl)C(O)heteroaryl, ($C_0$-$C_8$ alkyl)C(O)O$C_1$-$C_8$ alkyl, ($C_0$-$C_8$ alkyl)C(O)O$C_2$-$C_8$ alkenyl, ($C_0$-$C_8$alkyl)C(O)O$C_2$-$C_8$ alkynyl, ($C_0$-$C_8$ alkyl)C(O)OH, $C_0$-$C_8$ alkyl)C(O)O aryl, ($C_0$-$C_8$ alkyl)C(O)O heteroaryl, ($C_0$-$C_8$ alkyl)C(O)$NR^{24}$—$C_1$-$C_8$ alkyl, ($C_0$-$C_8$ alkyl)C(O)$NR^{24}$—$C_2$-$C_8$ alkenyl, ($C_0$-$C_8$ alkyl)C(O)$NR^{24}$—$C_2$-$C_8$ alkynyl, ($C_0$-$C_8$ alkyl)C(O)$NR^{24}H_2$, ($C_0$-$C_8$ alkyl)C(O)$NR^{24}$aryl, or ($C_0$-$C_8$ alkyl)C(O)$NR^{24}$heteroaryl; and $R^{24}$ is hydrogen or $C_1$-$C_7$ alkyl.

For example, $R^1$ is hydrogen, propionate, acetate, benzoate, or sulfate; $R^5$ is hydrogen, ethynyl, hydroxyl; and $R^6$ is acetate, cypionate, hemisucciniate, enanthate, or propionate.

Nonlimiting examples of the compound of Formula B include 17β-estradiol, modified forms of estradiol such as β-estradiol 17-acetate, β-estradiol 17-cypionate, β-estradiol 17-enanthate, β-estradiol 17-valerate, β-estradiol 3,17-diacetate, β-estradiol 3,17-dipropionate, β-estradiol 3-benzoate, β-estradiol 3-benzoate 17-n-butyrate, β-estradiol 3-glycidyl ether, β-estradiol 3-methyl ether, β-estradiol 6-one, β-estradiol 3-glycidyl, β-estradiol 6-one 6-(O-carboxymethyloxime), 16-epiestriol, 17-epiestriol, 2-methoxy estradiol, 4-methoxy estradiol, estradiol 17-phenylpropionate, and 17β-estradiol 2-methyl ether, 17α-ethynylestradiol, megestrol acetate, estriol, and derivatives thereof. In some embodiments, carbon 17 has a ketone substitutent and $R^5$ and $R^6$ are absent (e.g. estrone). Some of the aforementioned compounds of Formula B are shown below:

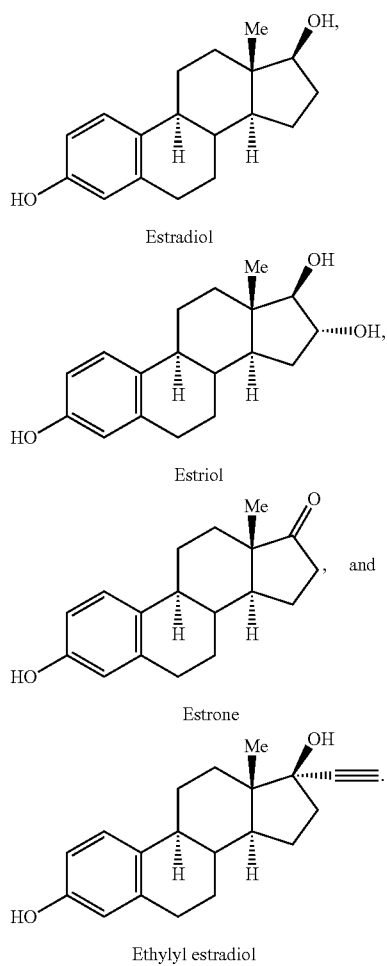

In embodiments wherein Q comprises a structure of Formula B, Q is conjugated to L (e.g. when L is a linking group) or Y (e.g. when L is a bond) at any position of Formula B that is capable of reacting with Y or L. One skilled in the art could readily determine the position of conjugation on Formula B and means of conjugation of Formula B to Y or L in view of general knowledge and the disclosure provided herein. In some embodiments, Formula B is conjugated to L or Y at any of positions 1, 2, 3, 4, 5, 6, 7, 8, 9, 10, 11, 12, 13, 14, 15, 16, 17, 18, 19, or 20 of Formula B. In some embodiments, Formula B is conjugated to L or Y at position 3 or 17 of Formula B.

In other embodiments, Q acts at an estrogen receptor but is not encompassed by Formula B. Nonlimiting examples of ligands that act at an estrogen receptor that are not encompassed by Formula B are shown below:

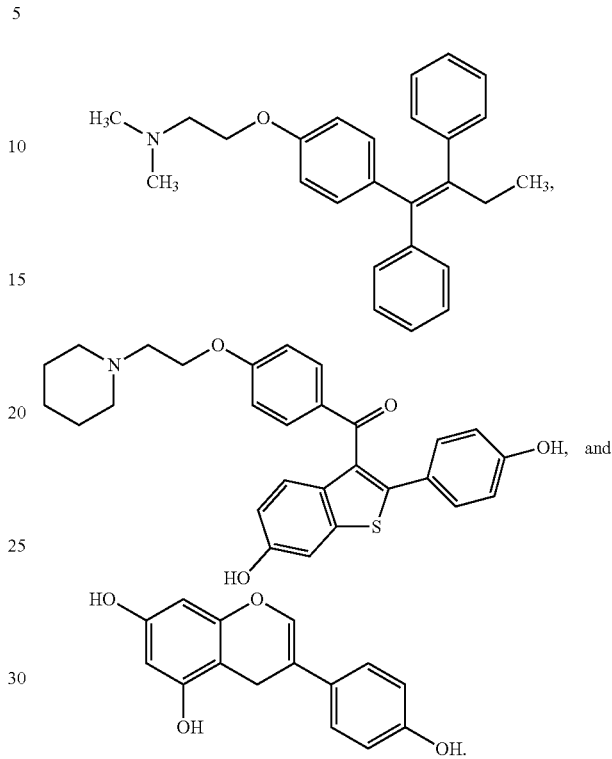

In some embodiments, Q acts at a glucocorticoid receptor (GR). In some embodiments, Q comprises any structure that permits or promotes agonist activity at the GR, while in other embodiments Q is an antagonist of GR. In exemplary embodiments, Q comprises a structure of Formula C:

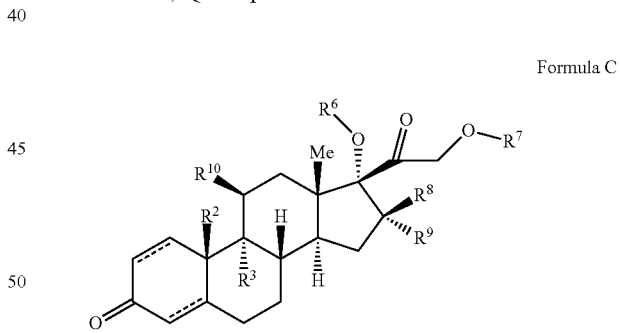

Formula C wherein $R^2$, $R^3$, $R^6$, $R^7$, $R^8$, $R^9$, and $R^{10}$ are each independently moieties that permit or promote agonist or antagonist activity upon the binding of the compound of Formula C to the GR; and each dash represents an optional double bond. In some embodiments, Formula C further comprises one or more substituents at one or more of positions 1, 2, 4, 5, 6, 7, 8, 9, 11, 12, 14, and 15 (e.g. hydroxyl or ketone at position-11).

In some embodiments, Q comprises a structure of Formula C wherein
$R^2$ is hydrogen, halo, OH, or $C_1$-$C_7$ alkyl;
$R^3$ is hydrogen, halo, OH, or $C_1$-$C_7$ alkyl;
$R^6$ is hydrogen, $C_1$-$C_8$ alkyl, $C_2$-$C_8$ alkenyl, $C_2$-$C_8$ alkynyl, heteroalkyl, ($C_0$-$C_8$ alkyl)aryl, ($C_0$-$C_8$ alkyl)heteroaryl, (C₀-C₈ alkyl)C(O)C₁-C₈ alkyl, (C₀-C₈ alkyl)C(O)C₂-C₈ alkenyl, (C₀-C₈ alkyl)C(O)C₂-C₈ alkynyl, (C₀-C₈ alkyl)C(O)H, (C₀-C₈ alkyl)C(O)aryl, (C₀-C₈ alkyl)C(O)heteroaryl, (C₀-C₈ alkyl)C(O)OC₁-C₈ alkyl, (C₀-C₈ alkyl)C(O)OC₂-C₈ alkenyl, (C₀-C₈alkyl)C(O)OC₂-C₈ alkynyl, (C₀-C₈ alkyl)C(O)OH, C₀-C₈ alkyl)C(O)O aryl, (C₀-C₈ alkyl)C(O)O heteroaryl, (C₀-C₈ alkyl)C(O)NR²⁴C₁-C₈ alkyl, (C₀-C₈ alkyl)C(O)NR²⁴—C₂-C₈ alkenyl, (C₀-C₈ alkyl)C(O)NR²⁴—C₂-C₈ alkynyl, (C₀-C₈ alkyl)C(O)NR²⁴H₂, (C₀-C₈ alkyl)C(O)NR²⁴aryl, or (C₀-C₈ alkyl)C(O)NR²⁴heteroaryl;

R⁷ is hydrogen, C₁-C₈ alkyl, C₂-C₈ alkenyl, C₂-C₈ alkynyl, heteroalkyl, (C₀-C₈ alkyl)aryl, (C₀-C₈ alkyl)heteroaryl, (C₀ alkyl)C(O)C₁-C₈ alkyl, (C₀ alkyl)C(O)C₂-C₈ alkenyl, (C₀ alkyl)C(O)C₂-C₈ alkynyl, (C₀)C(O)aryl, (C₀)C(O)heteroaryl, (C₀)C(O)OC₁-C₈ alkyl, (C₀ alkyl)C(O)OC₂-C₈ alkenyl, (C₀ alkyl)C(O)OC₂-C₈ alkynyl, or (C₀ alkyl)C(O)OH;

R⁸ is hydrogen or C₁-C₇ alkyl;

R⁹ is hydrogen or C₁-C₇ alkyl;

R¹⁰ is hydrogen or OH; and

R²⁴ is hydrogen or C₁-C₇ alkyl.

For example, R² is hydrogen or methyl; R³ is hydrogen, fluoro, chloro, or methyl; R⁶ is hydrogen or C(O) C₁-C₇ alkyl; R⁷ is hydrogen, C(O)CH₃, or C(O)CH₂CH₃; R⁸ is hydrogen or methyl; R⁹ is hydrogen or methyl; and R¹⁰ is hydroxyl.

Nonlimiting examples of structures of Formula C include:

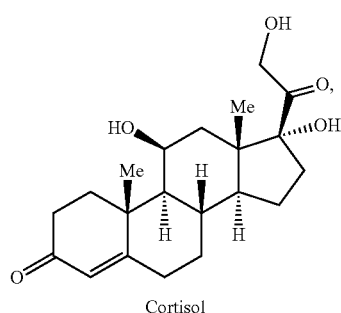

Cortisol

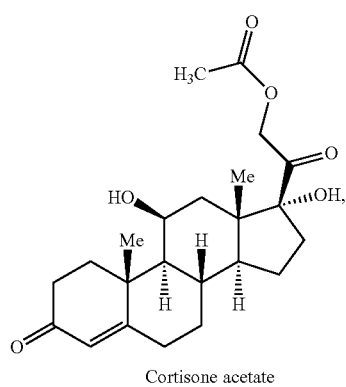

Cortisone acetate

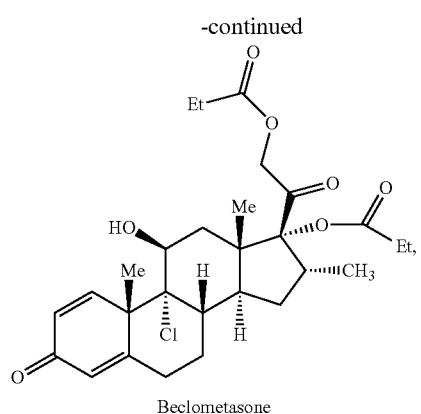

Beclometasone

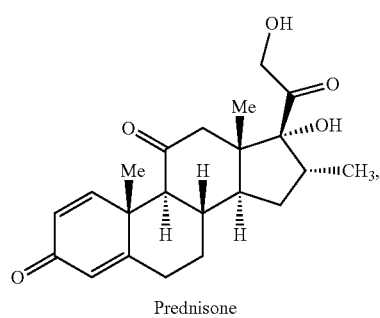

Prednisone

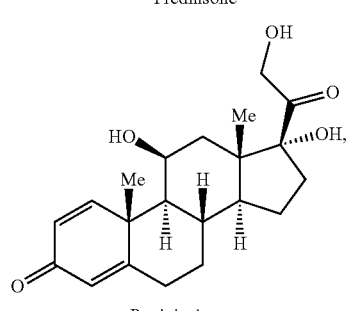

Prednisolone

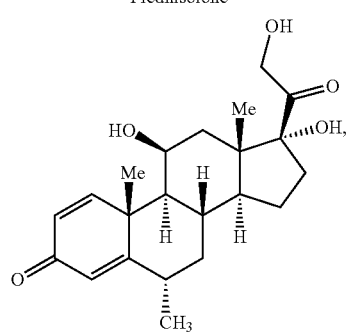

Methylprednisolone

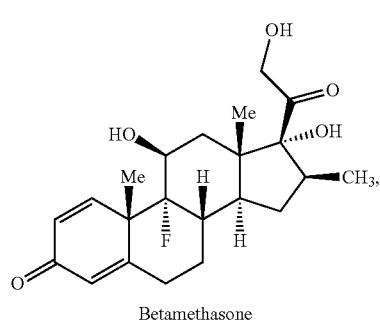

Betamethasone

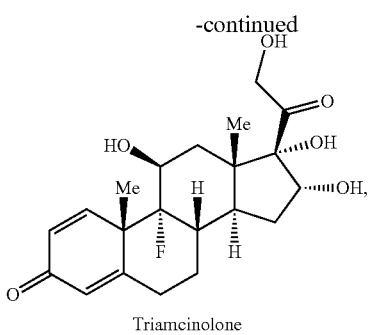

Triamcinolone

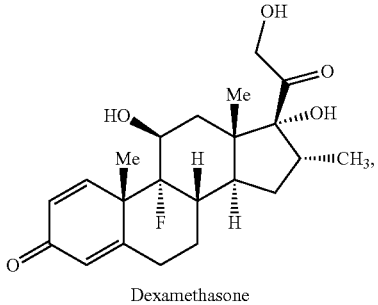

Dexamethasone and derivatives thereof.

In embodiments wherein Q comprises a structure of Formula C, Q is conjugated to L (e.g. when L is a linking group) or Y (e.g. when L is a bond) at any position of Formula C that is capable of reacting with Y or L. One skilled in the art could readily determine the position of conjugation on Formula C and means of conjugation of Formula C to Y or L in view of general knowledge and the disclosure provided herein. In some embodiments, Formula C is conjugated to L or Y at any of positions 1, 2, 3, 4, 5, 6, 7, 8, 9, 10, 11, 12, 13, 14, 15, 16, 17, 18, 19, 20, 21, 22, or 23 of Formula C. In some embodiments, Formula C is conjugated to L or Y at position 3, 10, 16 or 17 of Formula C.

In some embodiments, Q acts at a mineralcorticoid receptor (MR). In some embodiments, Q comprises any structure that permits or promotes agonist activity at the MR, while in other embodiments Q is an antagonist of MR. In exemplary embodiments, Q comprises a structure of Formula D:

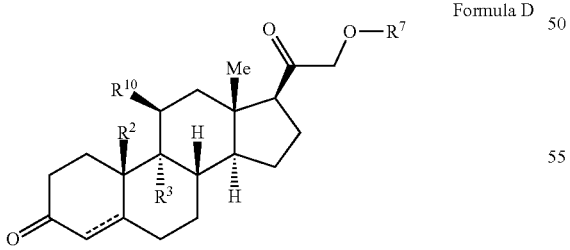

Formula D wherein $R^2$, $R^3$, $R^7$ and $R^{10}$ are each independently a moiety that permits or promotes agonist or antagonist activity upon binding of the compound of Formula D to the MR; and the dashed line indicates an optional double bond. In some embodiments, Formula D further comprises one or more substituents at one or more of positions 1, 2, 4, 5, 6, 7, 8, 11, 12, 14, 15, 16, and 17.

In some embodiments, Q comprises a structure of Formula D wherein $R^2$ is hydrogen, halo, OH, or $C_1$-$C_7$ alkyl;

$R^3$ is hydrogen, halo, OH, or $C_1$-$C_7$ alkyl;

$R^7$ is hydrogen, $C_1$-$C_8$ alkyl, $C_2$-$C_8$ alkenyl, $C_2$-$C_8$ alkynyl, heteroalkyl, ($C_0$-$C_8$ alkyl)aryl, ($C_0$-$C_8$ alkyl)heteroaryl, ($C_0$ alkyl)C(O)$C_1$-$C_8$ alkyl, ($C_0$ alkyl)C(O)$C_2$-$C_8$ alkenyl, ($C_0$ alkyl)C(O)$C_2$-$C_8$ alkynyl, ($C_0$)C(O)aryl, ($C_0$)C(O)heteroaryl, ($C_0$)C(O)O$C_1$-$C_8$ alkyl, ($C_0$ alkyl)C(O)O$C_2$-$C_8$ alkenyl, ($C_0$ alkyl)C(O)O$C_2$-$C_8$ alkynyl, or ($C_0$ alkyl)C(O)OH;

$R^{10}$ is hydrogen or OH; and $R^{24}$ is hydrogen or $C_1$-$C_7$ alkyl.

For example, $R^2$ is hydrogen or methyl; $R^3$ is hydrogen, fluoro, chloro, or methyl; $R^7$ is hydrogen, C(O)CH$_3$, or C(O)CH$_2$CH$_3$; and $R^{10}$ is hydroxyl.

Nonlimiting examples of compounds of Formula D include:

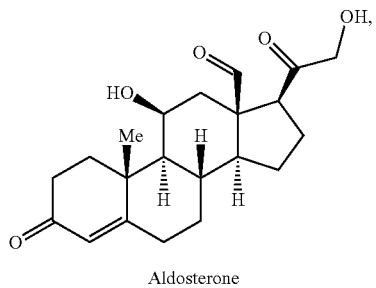

Aldosterone

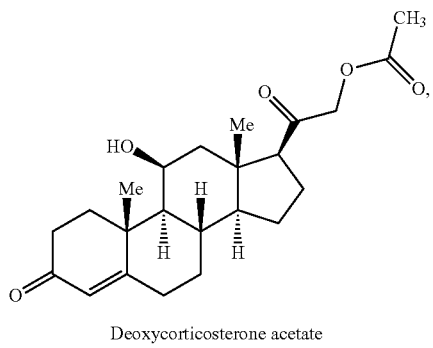

Deoxycorticosterone acetate

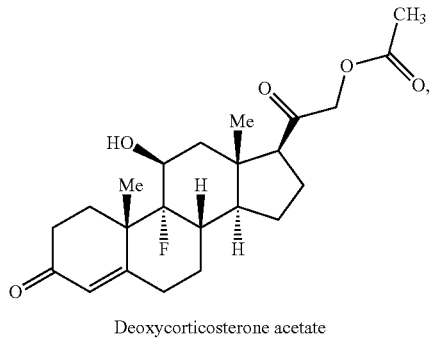

Deoxycorticosterone acetate and derivatives thereof.

In embodiments wherein Q comprises a structure of Formula D, Q is conjugated to L (e.g. when L is a linking group) or Y (e.g. when L is a bond) at any position of Formula D that is capable of reacting with Y or L. One skilled in the art could readily determine the position of conjugation on Formula D and means of conjugation of Formula D to Y or L in view of general knowledge and the disclosure provided herein. In some embodiments, Formula D is conjugated to L or Y at any of positions 1, 2, 3, 4, 5, 6, 7, 8, 9, 10, 11, 12, 13, 14, 15, 16, 17, 18, 19, 20, 21, 22, 23, or 24 of Formula D. In some embodiments, Formula D is conjugated to L or Y at position 3, 10, 13, or 17 of Formula D.

In some embodiments, Q acts at a progesterone receptor (PR). In some embodiments, Q comprises any structure that permits or promotes agonist activity at the PR, while in other embodiments Q is an antagonist of PR. In exemplary embodiments, Q comprises a structure of Formula E:

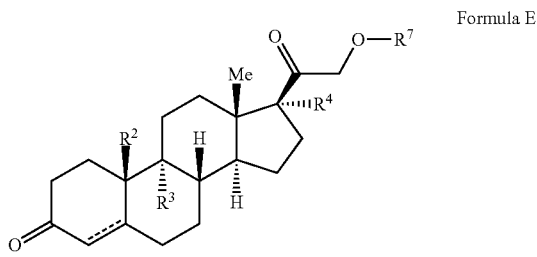

Formula E wherein $R^2$, $R^3$, $R^4$, and $R^7$ are each independently moieties that permit or promote agonist or antagonist activity upon binding of the compound of Formula E to the PR; and the dashed line indicates an optional double bond. In some embodiments, Formula E further comprises one or more substituents at one or more of positions 1, 2, 4, 5, 6, 7, 8, 11, 12, 14, 15, 16, and 17 (e.g. a methyl group at position 6).

In some embodiments, Q comprises a structure of Formula E wherein $R^2$ is hydrogen, halo, OH, or $C_1$-$C_7$ alkyl;

$R^3$ is hydrogen, halo, OH, or $C_1$-$C_7$ alkyl;

$R^4$ is hydrogen, ($C_0$-$C_8$ alkyl)halo, $C_1$-$C_8$ alkyl, $C_2$-$C_8$ alkenyl, $C_{2-18}$ alkynyl, heteroalkyl, ($C_0$-$C_8$ alkyl)aryl, ($C_0$-$C_8$ alkyl)heteroaryl, ($C_0$-$C_8$ alkyl)$OC_1$-$C_8$ alkyl, ($C_0$-$C_8$ alkyl)$OC_2$-$C_8$ alkenyl, ($C_0$-$C_8$ alkyl)$OC_2$-$C_8$ alkynyl, ($C_0$-$C_8$ alkyl)OH, ($C_0$-$C_8$ alkyl)SH, ($C_0$-$C_8$alkyl)$NR^{24}C_1$-$C_8$ alkyl, ($C_0$-$C_8$ alkyl)$NR^{24}$—$C_2$-$C_8$ alkenyl, ($C_0$-$C_8$ alkyl)$NR^{24}$—$C_2$-$C_8$ alkynyl, ($C_0$-$C_8$ alkyl)$NR^{24}H_2$, ($C_0$-$C_8$ alkyl)C(O)$C_1$-$C_8$ alkyl, ($C_0$-$C_8$ alkyl)C(O)$C_2$-$C_8$ alkenyl, ($C_0$-$C_8$ alkyl)C(O)$C_2$-$C_8$ alkynyl, ($C_0$-$C_8$ alkyl)C(O)H, ($C_0$-$C_8$ alkyl)C(O)aryl, ($C_0$-$C_8$ alkyl)C(O)heteroaryl, ($C_0$-$C_8$ alkyl)C(O)$OC_1$-$C_8$ alkyl, ($C_0$-$C_8$ alkyl)C(O)$OC_2$-$C_8$ alkenyl, ($C_0$-$C_8$alkyl)C(O)$OC_2$-$C_8$ alkynyl, ($C_0$-$C_8$ alkyl)C(O)OH, ($C_0$-$C_8$ alkyl)C(O)O aryl, ($C_0$-$C_8$ alkyl)C(O)O heteroaryl, ($C_0$-$C_8$ alkyl)OC(O)$C_1$-$C_8$ alkyl, ($C_0$-$C_8$ alkyl)OC(O)$C_2$-$C_8$ alkenyl, ($C_0$-$C_8$ alkyl)OC(O)$C_2$-$C_{18}$ alkynyl, ($C_0$-$C_8$ alkyl)C(O)$NR^{24}C_1$-$C_8$ alkyl, ($C_0$-$C_8$ alkyl)C(O)$NR^{24}$—$C_2$-$C_8$ alkenyl, ($C_0$-$C_8$ alkyl)C(O)$NR^{24}$—$C_2$-$C_8$ alkynyl, ($C_0$-$C_8$ alkyl)C(O)$NR^{24}H_2$, ($C_0$-$C_8$ alkyl)C(O)$NR^{24}$aryl, ($C_0$-$C_8$ alkyl)C(O)$NR^{24}$heteroaryl, ($C_0$-$C_8$ alkyl)$NR^{24}C(O)C_1$-$C_8$ alkyl, ($C_0$-$C_8$ alkyl)$NR^{24}C(O)C_2$-$C_8$ alkenyl, or ($C_0$-$C_8$ alkyl)$NR^{24}C(O)C_2$-$C_8$ alkynyl, ($C_0$-$C_8$ alkyl)$NR^{24}C(O)OH$, ($C_0$-$C_8$ alkyl)OC(O)$OC_1$-$C_8$ alkyl, ($C_0$-$C_8$ alkyl)OC(O)$OC_2$-$C_8$ alkenyl, ($C_0$-$C_8$ alkyl)OC(O)$OC_2$-$C_8$ alkynyl, ($C_0$-$C_8$ alkyl)OC(O)OH, ($C_0$-$C_8$ alkyl)OC(O)$NR^{24}C_1$-$C_8$ alkyl, ($C_0$-$C_8$ alkyl)OC(O)$NR^{24}$—$C_2$-$C_8$ alkenyl, ($C_0$-$C_8$ alkyl)OC(O)$NR^{24}$—$C_2$-$C_8$ alkynyl, ($C_0$-$C_8$ alkyl)OC(O)$NR^{24}H_2$, ($C_0$-$C_8$ alkyl)$NR^{24}(O)OC_1$-$C_8$ alkyl, ($C_0$-$C_8$ alkyl)$NR^{24}(O)OC_2$-$C_8$ alkenyl, ($C_0$-$C_8$ alkyl)$NR^{24}(O)OC_2$-$C_8$alkynyl, or ($C_0$-$C_8$ alkyl)$NR^{24}(O)OH$;

$R^7$ is hydrogen, $C_1$-$C_8$ alkyl, $C_2$-$C_8$ alkenyl, $C_2$-$C_8$ alkynyl, heteroalkyl, ($C_0$-$C_8$ alkyl)aryl, ($C_0$-$C_8$ alkyl)heteroaryl, ($C_0$ alkyl)C(O)$C_1$-$C_8$ alkyl, ($C_0$ alkyl)C(O)$C_2$-$C_8$ alkenyl, ($C_0$ alkyl)C(O)$C_2$-$C_8$ alkynyl, ($C_0$)C(O)aryl, ($C_0$)C(O)heteroaryl, ($C_0$)C(O)$OC_1$-$C_8$ alkyl, ($C_0$ alkyl)C(O)$OC_2$-$C_8$ alkenyl, ($C_0$ alkyl)C(O)$OC_2$-$C_8$ alkynyl, or ($C_0$ alkyl)C(O)OH; and $R^{24}$ is hydrogen or $C_1$-$C_7$ alkyl.

For example, $R^2$ is hydrogen or methyl; $R^3$ is hydrogen or methyl; $R^4$ is ($C_1$ alkyl)C(O)$C_1$-$C_4$ alkyl, acetate, cypionate, hemisucciniate, enanthate, or propionate; and $R^7$ is hydrogen, C(O)$CH_3$, or C(O)$CH_2CH_3$.

Nonlimiting examples of compounds of Formula E include:

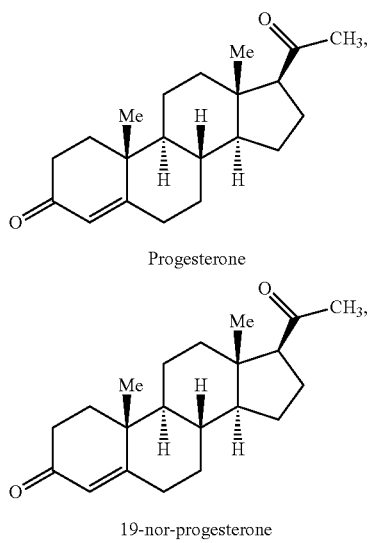

Progesterone 19-nor-progesterone

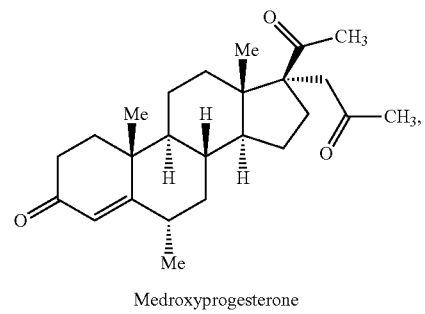

Medroxyprogesterone and derivatives thereof.

In embodiments wherein Q comprises a structure of Formula E, Q is conjugated to L (e.g. when L is a linking group) or Y (e.g. when L is a bond) at any position of Formula E that is capable of reacting with Y or L. One skilled in the art could readily determine the position of conjugation on Formula E and means of conjugation of Formula E to Y or L in view of general knowledge and the disclosure provided herein. In some embodiments, Formula E is conjugated to L or Y at any of positions 1, 2, 3, 4, 5, 6, 7, 8, 9, 10, 11, 12, 13, 14, 15, 16, 17, 18, 19, 20, 21, 22, 23, or 24 of Formula E. In some embodiments, Formula E is conjugated to L or Y through position 3 or 17 of Formula E.

In other embodiments, Q acts at a progesterone receptor but is not encompassed by Formula E. For example, Q can comprise the below structure and analogs thereof:

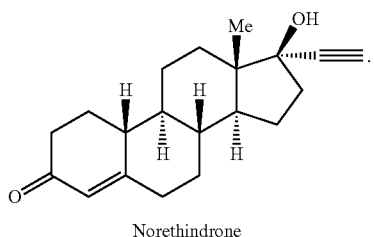

Norethindrone

In some embodiments, Q acts at an androgen receptor (AR). In some embodiments, Q comprises any structure that permits or promotes agonist activity at the AR, while in other embodiments Q is an antagonist of AR. In exemplary embodiments, Q comprises a structure of Formula F:

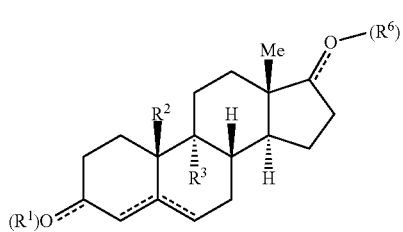

Formula F wherein $R^1$, when present, $R^2$, $R^3$ and $R^6$ are each independently a moiety that permits or promotes agonist or antagonist activity upon binding of the compound of Formula F to the AR; and each dashed line represents an optional double bond, with the proviso that no more than one of the optional carbon-carbon double bond is present at position 5. In some embodiments, Formula F further comprises one or more substituents at one or more of positions 1, 2, 4, 5, 6, 7, 8, 11, 12, 14, 15, 16, and 17.

In some embodiments, Q comprises a structure of Formula F wherein $R^1$ is hydrogen, $C_1$-$C_7$ alkyl; $(C_0$-$C_3$ alkyl)$C(O)C_1$-$C_7$ alkyl, $(C_0$-$C_3$ alkyl)$C(O)$aryl, or $SO_3H$;

$R^2$ is hydrogen, halo, OH, or $C_1$-$C_7$ alkyl;

$R^3$ is hydrogen, halo, OH, or $C_1$-$C_7$ alkyl;

$R^6$ is hydrogen, $C_1$-$C_8$ alkyl, $C_2$-$C_8$ alkenyl, $C_2$-$C_8$ alkynyl, heteroalkyl, $(C_0$-$C_8$ alkyl)aryl, $(C_0$-$C_8$ alkyl)heteroaryl, $(C_0$-$C_8$ alkyl)$C(O)C_1$-$C_8$ alkyl, $(C_0$-$C_8$ alkyl)$C(O)C_2$-$C_8$ alkenyl, $(C_0$-$C_8$ alkyl)$C(O)C_2$-$C_8$ alkynyl, $(C_0$-$C_8$ alkyl)$C(O)H$, $(C_0$-$C_8$ alkyl)$C(O)$aryl, $(C_0$-$C_8$ alkyl)$C(O)$heteroaryl, $(C_0$-$C_8$ alkyl)$C(O)OC_1$-$C_8$ alkyl, $(C_0$-$C_8$ alkyl)$C(O)OC_2$-$C_8$ alkenyl, $(C_0$-$C_8$ alkyl)$C(O)OC_2$-$C_8$ alkynyl, $(C_0$-$C_8$ alkyl)$C(O)OH$, $C_0$-$C_8$ alkyl)$C(O)O$ aryl, $(C_0$-$C_8$ alkyl)$C(O)O$ heteroaryl, $(C_0$-$C_8$ alkyl)$C(O)NR^{24}$—$C_1$-$C_8$ alkyl, $(C_0$-$C_8$ alkyl)$C(O)NR^{24}$—$C_2$-$C_8$ alkenyl, $(C_0$-$C_8$ alkyl)$C(O)NR^{24}$—$C_2$-$C_8$ alkynyl, $(C_0$-$C_8$ alkyl)$C(O)NR^{24}H_2$, $(C_0$-$C_8$ alkyl)$C(O)NR^{24}$aryl, or $(C_0$-$C_8$ alkyl)$C(O)NR^{24}$heteroaryl; and $R^{24}$ is hydrogen or $C_1$-$C_7$ alkyl.

For example, $R^1$ is hydrogen or absent; $R^2$ is hydrogen or methyl; $R^3$ is hydrogen or methyl; and $R^6$ is H or absent.

Nonlimiting examples of compounds of Formula F include:

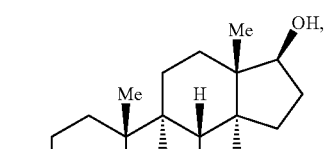

Testoterone

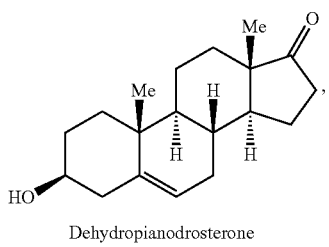

Dehydropianodrosterone

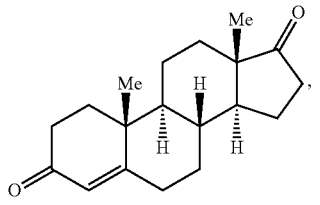

Androstenedione

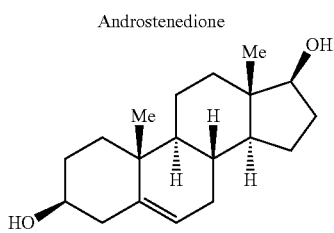

5-Androstenediol

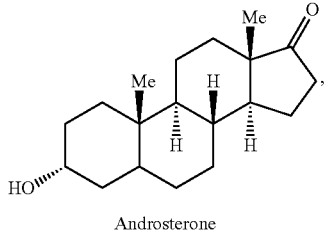

Androsterone

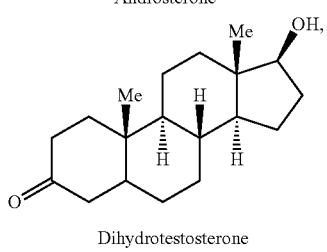

Dihydrotestosterone and derivatives thereof.

In embodiments wherein Q comprises a structure of Formula F, Q is conjugated to L (e.g. when L is a linking group) or Y (e.g. when L is a bond) at any position of Formula F that is capable of reacting with Y or L. One skilled in the art could readily determine the position of conjugation on Formula F and means of conjugation of Formula F to Y or L in view of general knowledge and the disclosure provided herein. In some embodiments, Formula F is conjugated to L or Y at any of positions 1, 2, 3, 4, 5, 6, 7, 8, 9, 10, 11, 12, 13, 14, 15, 16, 17, 18, 19, 20, 21, or 22 of Formula F. In some embodiments, Formula F is conjugated to L or Y at position 3 or 17 of Formula F.

In some embodiments, the binding of the NHR ligand to the Type I nuclear hormone receptor results in agonist activity (or antagonist activity) in some but not all cells or tissues expressing the Type I nuclear hormone receptor.

NHR Ligand that Acts on a Type II Nuclear Hormone Receptor

In some embodiments of the invention, the NHR ligand (Q) acts on a Type II nuclear hormone receptor. In some embodiments, Q can have any structure that permits or promotes agonist activity upon binding of the ligand to a Type II nuclear hormone receptor, while in other embodiments Q is an antagonist of the Type II nuclear hormone receptor. In exemplary embodiments, Q exhibits agonist (or antagonist) activity at a thyroid hormone receptor (TR), retinoic acid receptor (RAR), peroxisome proliferator activated receptor (PPAR), Liver X Receptor (LXR), farnesoid X receptor (FXR), vitamin D receptor (VDR), and/or pregnane X receptor (PXR).

In some embodiments, Q acts at a thyroid hormone receptor (e.g. TRα, TRβ). In some embodiments, Q comprises any structure that permits or promotes agonist activity at the TR, while in other embodiments Q is an antagonist of TR. In one embodiment a thyroid hormone receptor agonist is provided having the general structure of

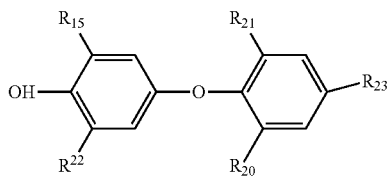

wherein
$R_{15}$ is $C_1$-$C_4$ alkyl, —$CH_2$(pyridazinone), —$CH_2$(OH)(phenyl)F, —CH(OH)CH$_3$, halo or H;
$R_{20}$ is halo, CH$_3$ or H;
$R_{21}$ is halo, CH$_3$ or H;
$R_{22}$ is H, OH, halo, —CH$_2$(OH)(C$_6$ aryl)F, or C$_1$-C$_4$ alkyl; and
$R_{23}$ is —CH$_2$CH(NH$_2$)COOH, —OCH$_2$COOH, —NHC(O)COOH, —CH$_2$COOH,
—NHC(O)CH$_2$COOH, —CH$_2$CH$_2$COOH, or —OCH$_2$PO$_3^{2-}$.

In accordance with one embodiment the thyroid hormone receptor agonist is a compound of the general structure

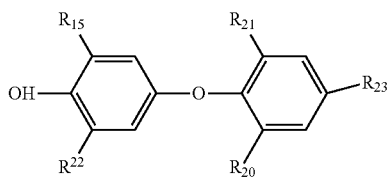

wherein
$R_{15}$ is $C_1$-$C_4$ alkyl, —CH(OH)CH$_3$, I or H
$R_{20}$ is I, Br, CH$_3$ or H;
$R_{21}$ is I, Br, CH$_3$ or H;
$R_{22}$ is H, OH, I, or $C_1$-$C_4$ alkyl; and $R_{23}$ is —CH$_2$CH(NH$_2$)COOH, —OCH$_2$COOH, —NHC(O)COOH, —CH$_2$COOH,
—NHC(O)CH$_2$COOH, —CH$_2$CH$_2$COOH, or —OCH$_2$PO$_3^{2-}$. In one embodiment $R_{23}$ is —CH$_2$CH(NH$_2$)COOH.

In accordance with one embodiment the thyroid hormone receptor agonist is a compound of the general structure

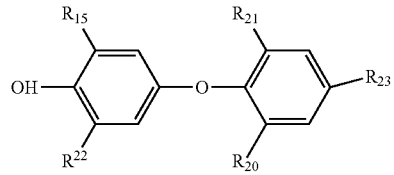

wherein
$R_{15}$ is isopropyl, —CH(OH)CH$_3$, I or H
$R_{20}$ is I, Br, Cl, or CH$_3$;
$R_{21}$ is I, Br, Cl, or CH$_3$;
$R_{22}$ is H; and
$R_{23}$ is —OCH$_2$COOH, —CH$_2$COOH, —NHC(O)CH$_2$COOH, or —CH$_2$CH$_2$COOH.

In accordance with one embodiment the thyroid hormone receptor agonist is a compound of the general structure of Formula I:

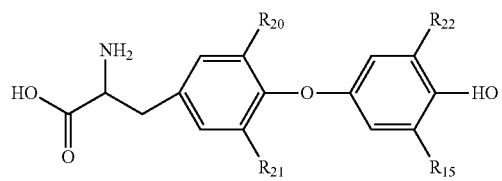

wherein
$R_{20}$, $R_{21}$, and $R_{22}$ are independently selected from the group consisting of H, OH, halo and $C_1$-$C_4$ alkyl; and
$R_{15}$ is halo or H. In one embodiment $R_2$ and $R_{21}$ are each CH$_3$, $R_{15}$ is H and $R_{22}$ are independently selected from the group consisting of H, OH, halo and $C_1$-$C_4$ alkyl. In one embodiment $R_{20}$, $R_{21}$ and $R_{22}$ are each halo and $R_5$ is H or halo. In a further embodiment $R_{20}$, $R_{21}$ and $R_{22}$ are each I, and $R_5$ is H or I. In accordance with one embodiment Q is selected from the group consisting of thyroxine T4 (3,5,3', 5'-tetraiodothyronine) and 3,5,3'-triiodo L-thyronine.

In one embodiment, the thyroid hormone receptor ligand (Y) of the Q-L-Y conjugates, is an indole derivative of thyroxine, including for example, compounds disclosed in U.S. Pat. No. 6,794,406 and US published application no. US 2009/0233979, the disclosures of which are incorporated herein. In one embodiment the indole derivative of thyroxine comprises a compound of the general structure of Formula II:

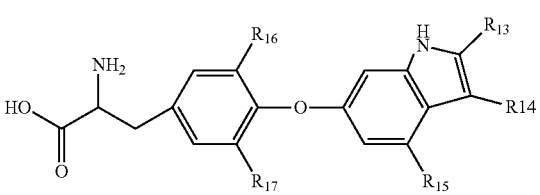

wherein
R$_{13}$ is H or C$_1$-C$_4$ alkyl;
R$_{14}$ is C$_1$-C$_8$ alkyl;
R$_{15}$ is H or C$_1$-C$_4$ alkyl; and
R$_{16}$ and R$_{17}$ are independently halo or C$_1$-C$_4$ alkyl.

In one embodiment, the thyroid receptor ligand (Y) of the Q-L-Y conjugates, is an indole derivative of thyroxine as disclosed in WO97/21993 (U. Cal SF), WO99/00353 (Karo-Bio), GB98/284425 (KaroBio), and U.S. Provisional Application 60/183,223, the disclosures of which are incorporated by reference herein. In one embodiment the thyroid receptor ligand comprises the general structure of Formula III:

wherein X is oxygen, sulfur, carbonyl, methylene, or NH;
Y is (CH$_2$)$_n$, where n is an integer from 1 to 5, or C=C;
R$_1$ is halogen, trifluoromethyl, or C$_1$-C$_6$ alkyl or C$_3$-C$_7$ cycloalkyl;
R$_2$ and R$_3$ are the same or different and are hydrogen, halogen, C$_1$-C$_6$ alkyl or C$_3$-C$_8$ cycloalkyl, with the proviso that at least one of R$_2$ and R$_3$ being other than hydrogen;
R$_4$ is hydrogen or C$_1$-C$_4$ alkyl;
R$_5$ is hydrogen or C$_1$-C$_4$ alkyl;
R$_6$ is carboxylic acid, or ester thereof;
R$_7$ is hydrogen, or an alkanoyl or aroyl group.

Nonlimiting examples of Q include the following compounds:

Thyroxine (T$_4$)

Triiodothyroxine (T$_3$)

derivatives thereof.

In embodiments wherein Q comprises a structure that permits or promotes agonist or antagonist activity at a TR, Q is conjugated to L (e.g. when L is a linking group) or Y (e.g. when L is a bond) at any position of Q that is capable of reacting with Y or L. One skilled in the art could readily determine the position of conjugation on Q and means of conjugation of Q to Y or L in view of general knowledge and the disclosure provided herein. In some embodiments, Q is conjugated to L or Y through any position of Q. In some embodiments, Q is conjugated to L or Y through the carboxylic acid or amine moieties, as indicated below:

In some embodiments, Q acts at a retinoic acid receptor (e.g. RARα, RARβ, RARγ). In some embodiments, Q comprises any structure that permits or promotes agonist activity at the RAR, while in other embodiments Q is an antagonist of RAR. In exemplary embodiments, Q comprises a structure of Formula G:

Formula G wherein R$^{11}$ is a moiety that permits or promotes agonist or antagonist activity upon the binding of the compound of Formula G to a RAR, and represents either E or Z stereochemistry.

In some embodiments, Q comprises a structure of Formula G wherein R$^{11}$ is C(O)OH, CH$_2$OH, or C(O)H. In some embodiments, Q comprises a structure of Formula G wherein R$^{11}$ is a carboxylic acid derivative (e.g. acyl chloride, anhydride, and ester).

Nonlimiting examples of the compound of Formula G include:

All-trans-retinoic acid

Retinol

Retinal

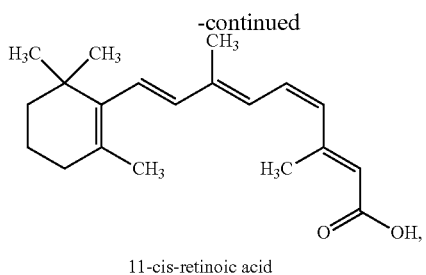
11-cis-retinoic acid

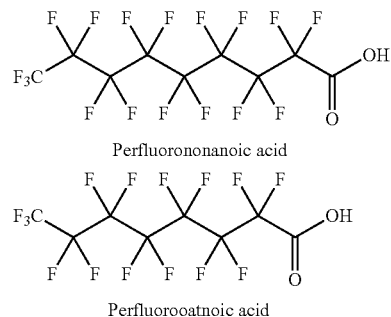
Perfluorononanoic acid

Perfluorooatnoic acid and derivatives thereof.

In embodiments wherein Q comprises a structure of Formula G, Q is conjugated to L (e.g. when L is a linking group) or Y (e.g. when L is a bond) at any position of Formula G that is capable of reacting with Y or L. One skilled in the art could readily determine the position of conjugation on Q and means of conjugation of Q to Y or L in view of general knowledge and the disclosure provided herein. In some embodiments, Q is conjugated to L or Y through any position of Q. In some embodiments, Formula G is conjugated to L or Y at $R^{11}$.

In some embodiments, Q acts at a peroxisome proliferator activated receptor (e.g. PPARα, PPARβ/δ, PPARγ). In some embodiments, Q acts at PPARγ. In some embodiments, Q comprises any structure that permits or promotes agonist activity at the PPAR, while in other embodiments Q is an antagonist of PPAR. In some embodiments, Q is a saturated or unsaturated, halogenated or nonhalogenated free fatty acid (FFA) as described by Formula H:

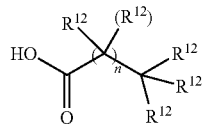

Formula H wherein n is 0-26 and each $R^{12}$, when present, is independently a moiety that permits or promotes agonist or antagonist activity upon binding of the compound of Formula H to a PPAR.

In some embodiments, Q comprises a structure of Formula H, wherein n is 0-26 and each $R^{12}$, when present, is independently hydrogen, $C_1$-$C_7$ alkyl, or halogen. In some embodiments Formula B is saturated such as, for example, formic acid, acetic acid, n-caproic acid, heptanoic acid, caprylic acid, nonanoic acid, capric acid, undecanoic acid, lauric acid, tridecanoic acid, myristic acid, pentadeconoic acid, palmitic acid, heptadecanoic acid, stearic acid, nonadecanoic acid, arachidic acid, heneicosanoic acid, behenic acid, tricosanoic acid, perfluorononanoic acid (see below), perfluorooctanoic acid (see below), and derivatives thereof. In some embodiments Formula H is unsaturated with either cis or trans stereochemistry such as, for example, mead acid, myristoleic acid, palmitoleic acid, sapienic acid, oleic acid, linoleic acid, α-linolenic acid, elaidic acid, petroselinic acid, arachidonic acid, dihydroxyeicosatetraenoic acid (Di-HETE), octadecynoic acid, eicosatriynoic acid, eicosadienoic acid, eicosatrienoic acid, eicosapentaenoic acid, erucic acid, dihomolinolenic acid, docosatrienoic acid, docosapentaenoic acid, docosahexaenoic acid, adrenic acid, and derivatives thereof, including for example:

In embodiments wherein Q comprises a structure of Formula H, Q is conjugated to L (e.g. when L is a linking group) or Y (e.g. when L is a bond) at any position of Formula H that is capable of reacting with Y or L. One skilled in the art could readily determine the position of conjugation on Formula H and means of conjugation of Formula H to Y or L in view of general knowledge and the disclosure provided herein. In some embodiments, Formula H is conjugated to L or Y at any position on Formula H. In some embodiments, Formula H is conjugated to L or Y through the terminal carboxylic acid moiety.

In some of these embodiments, Q is an eiconsanoid. In specific embodiments, Q is a prostaglandin or a leukotriene. In some exemplary embodiments, Q is a prostaglandin having a structure as described by Formula J1-J6:

Formula J1

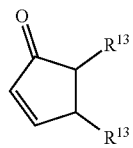

Formula J2

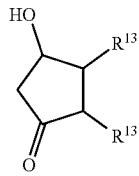

Formula J3

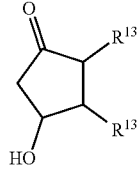

Formula J4

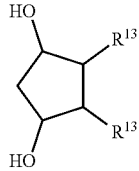

Formula J5

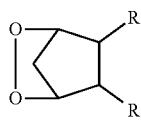

-continued

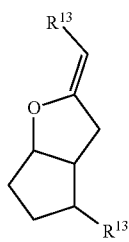

Formula J6 wherein each R[13] is independently a moiety that permits or promotes agonist or antagonist activity upon the binding of the compound of Formula J to a PPAR (e.g. PGJ2 as shown below):

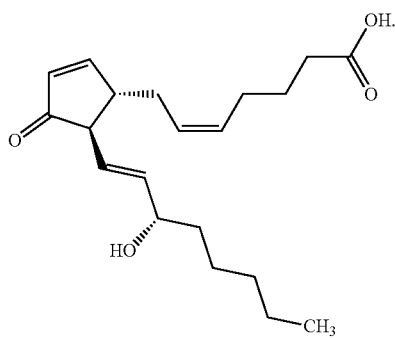 [SMILES: CCCCC[C@H](O)/C=C/[C@H]1C(=O)C=C[C@@H]1C/C=C\CCCC(=O)O]

In some embodiments when Q comprises a structure of any one of Formula J1-J6, each R[13] is independently $C_7$-$C_8$ alkyl, $C_7$-$C_8$ alkenyl, $C_7$-$C_8$ alkynyl, or heteroalkyl.

In embodiments wherein Q is an eicosanoid, Q is conjugated to L (e.g. when L is a linking group) or Y (e.g. when L is a bond) at any position of the eicosanoid that is capable of reacting with Y or L. One skilled in the art could readily determine the position of conjugation on Q and means of conjugation of Q to Y or L in view of general knowledge and the disclosure provided herein. In some embodiments, Q is conjugated to L or Y through any position of Q. In some embodiments, the eicosanoid is conjugated to L or Y through a terminal carboxylic acid moiety or through a pendant alcohol moiety.

In some exemplary embodiments, Q is a leukotriene having a structure as described by Formula K or a derivatized form of Formula K:

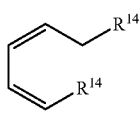

Formula K wherein each R[14] is independently a moiety that permits or promotes agonist or antagonist activity upon the binding of the compound of Formula K to a PPAR (e.g. leukotriene B4 as shown below):

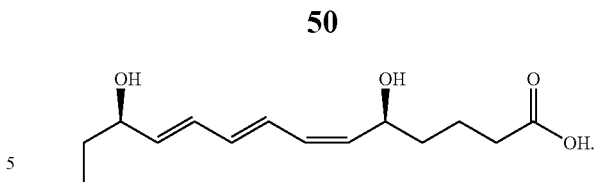

In some embodiments when Q comprises a structure of Formula K, each R[14] is independently $C_3$-$C_{13}$ alkyl, $C_3$-$C_{13}$ alkenyl, $C_3$-$C_{13}$ alkynyl, or heteroalkyl.

In embodiments wherein Q comprises a structure of Formula K, Q is conjugated to L (e.g. when L is a linking group) or Y (e.g. when L is a bond) at any position of Formula K that is capable of reacting with Y or L. One skilled in the art could readily determine the position of conjugation on Formula K and means of conjugation of Formula K to Y or L in view of general knowledge and the disclosure provided herein. In some embodiments, Formula K is conjugated to L or Y at any position on Formula K. In some embodiments, Formula K is conjugated to L or Y through the terminal carboxylic acid moiety or through a pendant alcohol moiety.

In some exemplary embodiments, Q is a thiazolidinedione comprising a structure as described by Formula L:

Formula L

Nonlimiting examples of the compound of Formula L include:

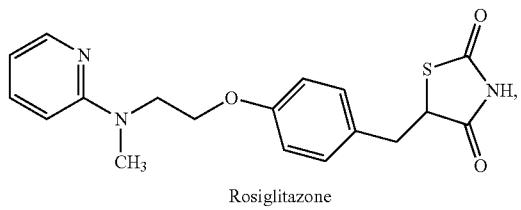

Rosiglitazone

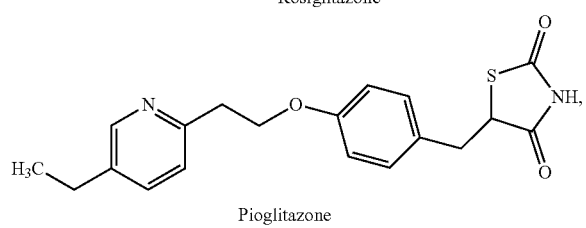

Pioglitazone

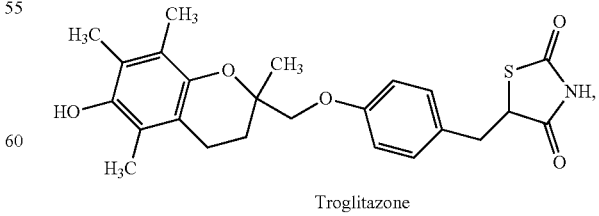

Troglitazone and derivatives thereof.

In embodiments wherein Q comprises a structure of Formula L, Q is conjugated to L (e.g. when L is a linking group) or Y (e.g. when L is a bond) at any position of Formula L that is capable of reacting with Y or L. One skilled in the art could readily determine the position of conjugation on Formula L and means of conjugation of Formula L to Y or L in view of general knowledge and the disclosure provided herein. In some embodiments, Formula L is conjugated to L or Y at any position on Formula L, such as, for example, a pendant alcohol moiety, or through an aromatic substituent.

In one embodiment wherein Y is Tesaglitzar or Aleglitazar:

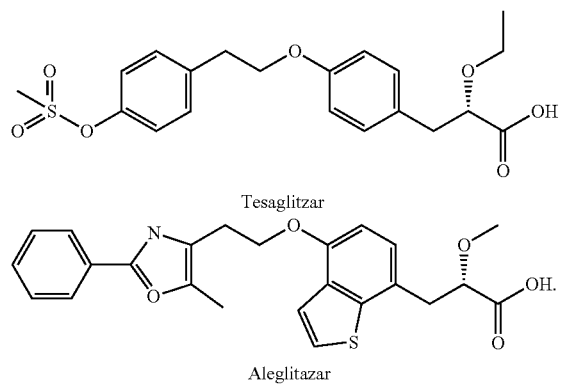

Tesaglitzar

Aleglitazar

In embodiments wherein Q comprises Tesaglitzar or Aleglitazar, Q is conjugated to L (e.g. when L is a linking group) or Y (e.g. when L is a bond) at any position that is capable of reacting with Y or L. In one embodiment, Tesaglitzar or Aleglitazar is conjugated to L or Y through the carboxylic acid moiety of the compound.

In some embodiments, Q acts at a RAR-related orphan receptor (e.g. RORα, RORβ, RORγ). In some embodiments, Q comprises any structure that permits or promotes agonist activity at the ROR, while in other embodiments Q is an antagonist of ROR.

Nonlimiting examples of Q include:

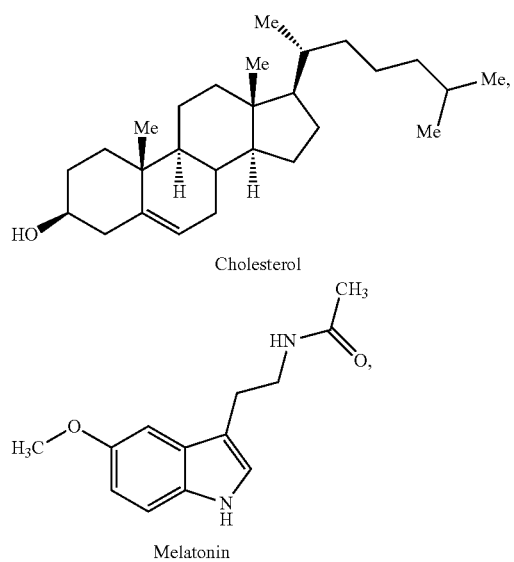

Cholesterol

Melatonin

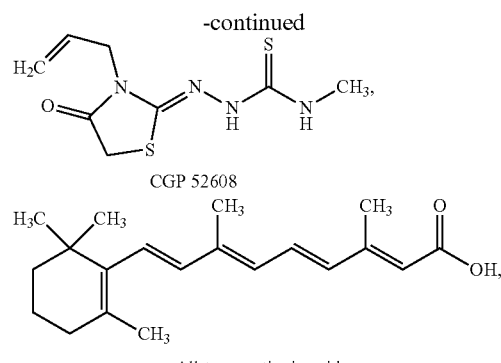

CGP 52608

All-trans-retinoic acid and derivatives thereof.

In embodiments wherein Q acts at a ROR, Q is conjugated to L (e.g. when L is a linking group) or Y (e.g. when L is a bond) at any position of Q that is capable of reacting with Y or L. One skilled in the art could readily determine the position of conjugation on Y and means of conjugation of Q to Y or L in view of general knowledge and the disclosure provided herein. In some embodiments, Q is conjugated to L or Y through any position of Q, such as, for example, any of the positions previously described herein.

In some embodiments, Q acts at a liver X receptor (LXRα, LXRβ). In some embodiments, Q comprises any structure that permits or promotes agonist activity at the LXR, while in other embodiments Q is an antagonist of LXR. In exemplary embodiments, Q is an oxysterol (i.e. oxygenated derivative of cholesterol). Nonlimiting examples of Q in these embodiments include 22(R)-hydroxycholesterol (see below), 24(S)-hydroxycholesterol (see below), 27-hydroxycholesterol, cholestenoic acid, and derivatives thereof.

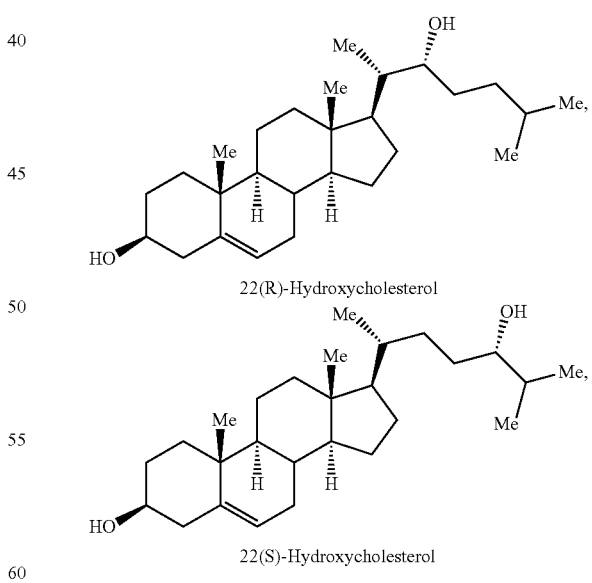

22(R)-Hydroxycholesterol

22(S)-Hydroxycholesterol

In embodiments wherein Q acts at a LXR, Q is conjugated to L (e.g. when L is a linking group) or Y (e.g. when L is a bond) at any position of Y that is capable of reacting with Y or L. One skilled in the art could readily determine the position of conjugation on Y and means of conjugation of Q to Y or L in view of general knowledge and the disclosure provided herein. In some embodiments, Q is conjugated to L or Y at any of positions 1, 2, 3, 4, 5, 6, 7, 8, 9, 10, 11, 12, 13, 14, 15, 16, 17, 18, 19, 20, 21, 22, 23, 24, 25, or 26 of Formula F. In some embodiments, Formula F is conjugated to L or Y at position 3 or 17 of Formula F.

In some embodiments, Q acts at the farnesoid X receptor (FXR). In some embodiments, Q comprises any structure that permits or promotes agonist activity at the FXR, while in other embodiments Q is an antagonist of FXR. In some of these embodiments, Q is a bile acid. In exemplary embodiments, Q has a structure of Formula M:

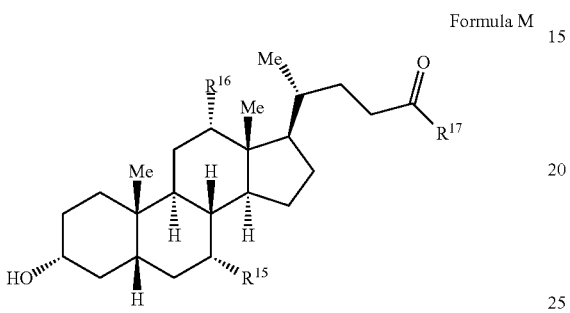

Formula M wherein each of $R^{15}$, $R^{16}$, and $R^{17}$ are independently moieties that permit or promote agonist or antagonist activity upon binding of the compound of Formula M to a FXR.

In some embodiments when Q comprises a structure of Formula M, each of $R^{15}$ and $R^{16}$ are independently hydrogen, ($C_0$-$C_8$ alkyl)halo, $C_1$-$C_{18}$ alkyl, $C_2$-$C_{18}$ alkenyl, $C_2$-$C_{18}$ alkynyl, heteroalkyl, or ($C_0$-$C_8$ alkyl)OH; and $R^{17}$ is OH, ($C_0$-$C_8$ alkyl)NH($C_1$-$C_4$ alkyl)$SO_3H$, or ($C_0$-$C_8$ alkyl)NH ($C_1$-$C_4$ alkyl)COOH.

In some embodiments when Q comprises a structure of Formula M, each of $R^{15}$ and $R^{16}$ are independently hydrogen or OH; and $R^{17}$ is OH, NH($C_1$-$C_2$ alkyl)$SO_3H$, or NH($C_1$-$C_2$ alkyl)COOH.

Nonlimiting examples of the compound of Formula M include:

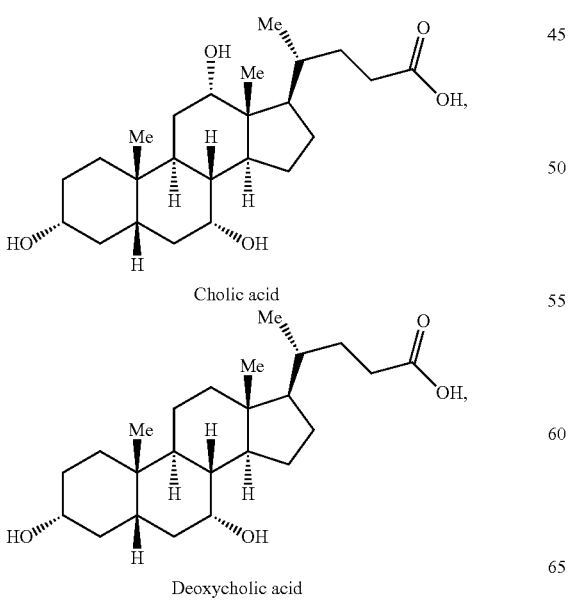

Cholic acid

Deoxycholic acid

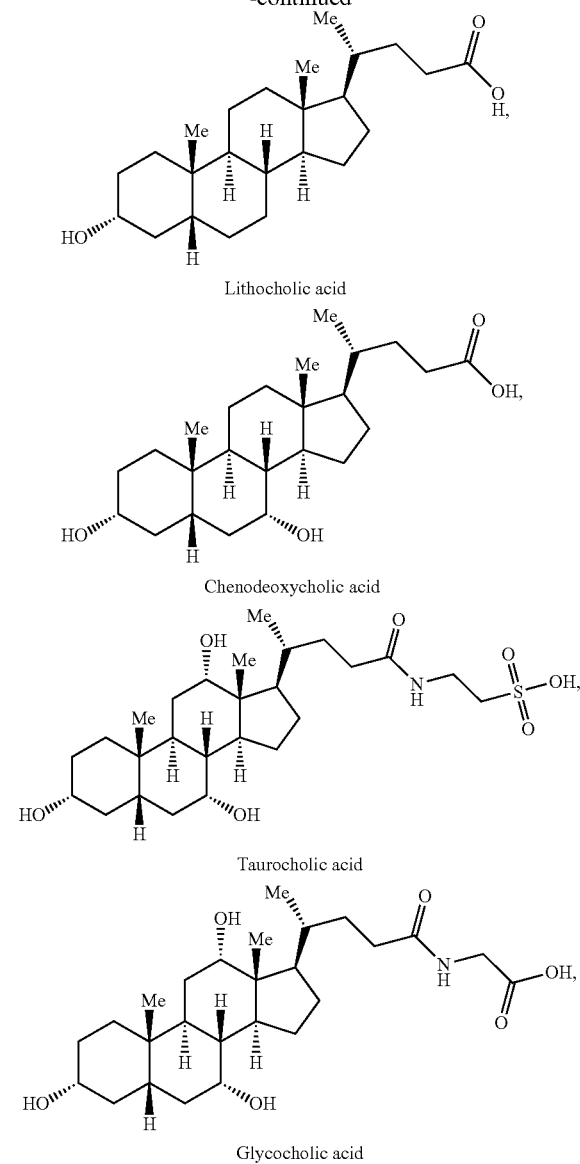

Lithocholic acid

Chenodeoxycholic acid

Taurocholic acid

Glycocholic acid and derivatives thereof.

In embodiments wherein Q comprises a structure of Formula M, Q is conjugated to L (e.g. when L is a linking group) or Y (e.g. when L is a bond) at any position of Formula M that is capable of reacting with Y or L. One skilled in the art could readily determine the position of conjugation on Formula M and means of conjugation of Formula M to Y or L in view of general knowledge and the disclosure provided herein. In some embodiments, Formula M is conjugated to L or Y at any of positions 1, 2, 3, 4, 5, 6, 7, 8, 9, 10, 11, 12, 13, 14, 15, 16, 17, 18, 19, 20, 21, 22, 23, 24, or 25 of Formula M. In some embodiments, Formula M is conjugated to L or Y at position 3, 7, 12 or 17 of Formula M.

In some embodiments, Q acts at the vitamin D receptor (VDR). In some embodiments, Q comprises any structure that permits or promotes agonist activity at the VDR, while in other embodiments Q is an antagonist of VDR. In exemplary embodiments, Q has a structure of Formula N:

Formula N

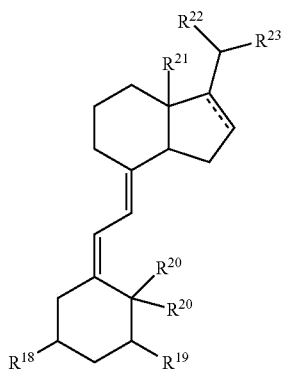

wherein each of $R^{18}$, $R^{19}$, $R^{20}$, $R^{21}$, $R^{22}$, and $R^{23}$ are moieties that permit or promote agonist or antagonist activity upon binding of the compound of Formula N to the VDR such as, for example, any of the vitamin D compounds found in Bouillon et al., *Endocrine Reviews*, 16(2):200-257 (1995).

In some embodiments wherein Q comprises a structure of Formula N, $R^{18}$ and $R^{19}$ are each independently hydrogen, ($C_0$-$C_8$ alkyl)halo, ($C_0$-$C_8$ alkyl)heteroaryl, or ($C_0$-$C_8$ alkyl)OH;

both of $R^{20}$ are hydrogen or both of $R^{20}$ are taken together to form $=CH_2$;

each of $R^{21}$ and $R^{22}$ are independently $C_1$-$C_4$ alkyl; and $R^{23}$ is $C_4$-$C_{18}$ alkyl, $C_4$-$C_{18}$ alkenyl, $C_4$-$C_{18}$ alkynyl, heteroalkyl, ($C_4$-$C_8$ alkyl)aryl, ($C_4$-$C_{18}$ alkyl)heteroaryl, ($C_0$-$C_8$ alkyl)$OC_1$-$C_{18}$ alkyl, ($C_0$-$C_8$ alkenyl)$OC_1$-$C_{18}$ alkyl, ($C_0$-$C_8$ alkynyl)$OC_1$-$C_{18}$ alkyl, ($C_0$-$C_8$ alkyl)$OC_2$-$C_{18}$ alkenyl, ($C_0$-$C_8$ alkyl)$OC_2$-$C_{18}$ alkynyl, ($C_6$-$C_{18}$ alkyl)OH, ($C_6$-$C_{18}$ alkyl) SH, ($C_6$-$C_{18}$ alkenyl)OH, ($C_6$-$C_{18}$ alkynyl)OH, ($C_0$-$C_8$ alkyl)$NR^{24}$—$C_1$-$C_{18}$ alkyl, ($C_0$-$C_8$ alkenyl)$NR^{24}$—$C_1$-$C_{18}$ alkyl, ($C_0$-$C_8$ alkynyl)$NR^{24}$—$C_1$-$C_{18}$ alkyl, ($C_0$-$C_8$ alkyl) $NR^{24}$—$C_2$-$C_{18}$ alkenyl, ($C_0$-$C_8$ alkyl)$NR^{24}$—$C_2$-$C_{18}$ alkynyl, ($C_0$-$C_8$ alkyl)C(O)$C_1$-$C_{18}$ alkyl, ($C_0$-$C_8$ alkyl)C(O)$C_2$-$C_{18}$ alkenyl, ($C_0$-$C_8$ alkyl)C(O)$C_2$-$C_{18}$ alkynyl, ($C_0$-$C_8$ alkyl)C(O)H, ($C_0$-$C_8$alkyl)C(O)aryl, ($C_0$-$C_8$ alkyl)C(O)heteroaryl, ($C_0$-$C_8$ alkyl)C(O)$OC_1$-$C_{18}$ alkyl, ($C_0$-$C_8$ alkyl)C(O)$OC_2$-$C_{18}$ alkenyl, ($C_0$-$C_8$ alkyl)C(O)$OC_2$-$C_{18}$ alkynyl, ($C_0$-$C_8$ alkyl)C(O)OH, ($C_0$-$C_8$ alkyl)C(O)O aryl, ($C_0$-$C_8$ alkyl)C(O)O heteroaryl, ($C_0$-$C_8$ alkyl)OC(O)$C_1$-$C_{18}$ alkyl, ($C_0$-$C_8$ alkyl)OC(O)$C_2$-$C_{18}$ alkenyl, ($C_0$-$C_8$ alkyl)OC(O)$C_2$-$C_{18}$ alkynyl, ($C_0$-$C_8$ alkyl)C(O)$NR^{24}$—$C_1$-$C_{18}$ alkyl, ($C_0$-$C_8$ alkyl)C(O)$NR^{24}$—$C_2$-$C_{18}$ alkenyl, ($C_0$-$C_8$ alkyl)C(O) $NR^{24}$—$C_2$-$C_{18}$ alkynyl, ($C_0$-$C_8$alkyl)C(O)$NR^{24}H_2$, ($C_0$-$C_8$ alkyl)C(O)$NR^{24}$aryl, ($C_0$-$C_8$ alkyl)C(O)$NR^{24}$heteroaryl, ($C_0$-$C_8$ alkyl)$NR^{24}$C(O)$C_1$-$C_{18}$ alkyl, ($C_0$-$C_8$ alkyl)$NR^{24}$C (O)$C_2$-$C_8$ alkenyl, or ($C_0$-$C_8$ alkyl)$NR^{24}$C(O)$C_2$-$C_{18}$ alkynyl, ($C_0$-$C_8$ alkyl)$NR^{24}$C(O)OH, ($C_0$-$C_8$ alkyl)OC(O)$OC_1$-$C_{18}$ alkyl, ($C_0$-$C_8$ alkyl)OC(O)$OC_2$-$C_{18}$ alkenyl, ($C_0$-$C_8$ alkyl)OC(O)$OC_2$-$C_{18}$ alkynyl, ($C_0$-$C_8$ alkyl)OC(O)OH, ($C_0$-$C_8$ alkyl)OC(O)$NR^{24}$—$C_1$-$C_{18}$ alkyl, ($C_0$-$C_8$ alkyl)OC(O)$NR^{24}$—$C_2$-$C_{18}$ alkenyl, ($C_0$-$C_8$ alkyl)OC(O)$NR^{24}$—$C_2$-$C_{18}$ alkynyl, ($C_0$-$C_8$ alkyl)OC(O)$NR^{24}H_2$, ($C_0$-$C_8$ alkyl)$NR^{24}$ (O)$OC_1$-$C_{18}$ alkyl, ($C_0$-$C_8$ alkyl)$NR^{24}$(O)$OC_2$-$C_{18}$ alkenyl, ($C_0$-$C_8$ alkyl)$NR^{24}$(O)$OC_2$-$C_{18}$ alkynyl, or ($C_0$-$C_8$ alkyl) $NR^{24}$(O)OH; and $R^{24}$ is hydrogen or $C_1$-$C_{18}$ alkyl.

Nonlimiting examples of the compound of Formula N include:

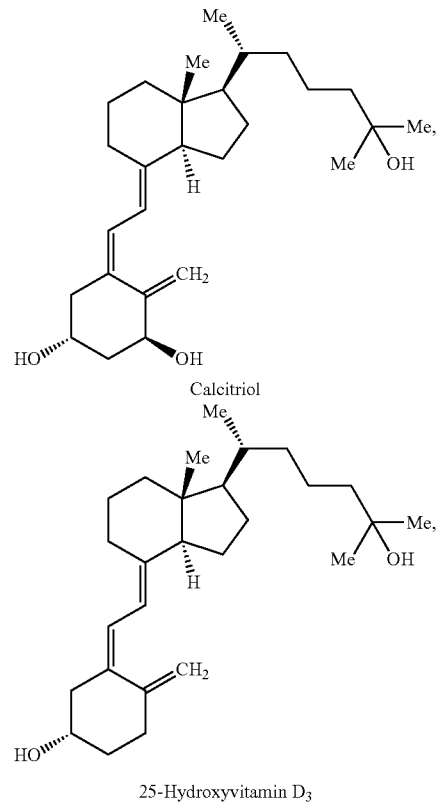

Calcitriol

25-Hydroxyvitamin $D_3$ and derivatives thereof.

In embodiments wherein Q comprises a structure of Formula N, Q is conjugated to L (e.g. when L is a linking group) or Y (e.g. when L is a bond) at any position of Formula N that is capable of reacting with Y or L. One skilled in the art could readily determine the position of conjugation on Formula N and means of conjugation of Formula N to Y or L in view of general knowledge and the disclosure provided herein. In some embodiments, Formula N is conjugated to L or Y at any of positions 1, 2, 3, 4, 5, 6, 7, 8, 9, 10, 11, 12, 13, 14, 15, 16, 17, 18, 19, 20, 21, 22, 23, 24, 25, or 26 of Formula N. In some embodiments, Formula N is conjugated to L or Y at position 1, 3, 19, or 25 of Formula N.

In some embodiments, Q acts at the pregnane X receptor (PXR). In some embodiments, Q comprises any structure that permits or promotes agonist activity at the PXR, while in other embodiments Q is an antagonist of PXR. In some embodiments, Q is a steroid, antibiotic, antimycotic, bile acid, hyperforin, or a herbal compound. In exemplary embodiments, Q is compound that is able to induce CYP3A4, such as dexamethasone and rifampicin. In embodiments wherein Q comprises a structure that acts at the PXR, Q is conjugated to L (e.g. when L is a linking group) or Y (e.g. when L is a bond) at any position of Q that is capable of reacting with Y or L. One skilled in the art could readily determine the position of conjugation on Y and means of conjugation of Q to Y or L in view of general knowledge and the disclosure provided herein. In some embodiments, Q is conjugated to L or Y at any of positions on Q.

Modification of the NHR Ligand (Q)

In some embodiments, the NHR ligand is derivatized or otherwise chemically modified to comprise a reactive moiety that is capable of reacting with the insulin peptide (Y) or the linking group (L). In the embodiments described herein, Q is derivatized at any position of Q that is capable of reacting with Y or L. The position of derivatization on Q is apparent to one skilled in the art and depends on the type of NHR ligand used and the activity that is desired. For example, in embodiments wherein Q has a structure comprising a tetracyclic skeleton having three 6-membered rings joined to one 5-membered ring or a variation thereof, Q can be derivatized at any of positions 1, 2, 3, 4, 5, 6, 7, 8, 9, 10, 11, 12, 13, 14, 15, 16, 17, 18, 19, 20, 21, 22, 23, 24, or 25. Other positions of derivatization can be as previously described herein.

The NHR ligand can be derivatized using any agent known to one skilled in the art or described herein. For example, estradiol can be derivatized with succinic acid, succinic anhydride, benzoic acid, ethyl 2-bromoacetate, or iodoacetic acid to form the below derivatives of estradiol that are capable of conjugating to Q or L.

from the group consisting of thyroxine T4 (3,5,3',5'-tetra-iodothyronine), 3,5,3'-triiodo L-thyronine, Tesaglitazar, Aleglitazar and thiazolidinediones. In one embodiment Q is selected from the group consisting of thyroxine T4 (3,5,3', 5'-tetra-iodothyronine), and 3,5,3'-triiodo L-thyronine. In one embodiment Q is selected from the group consisting of Tesaglitazar and Aleglitazar.

Structure of the Insulin Peptide

In some embodiments, the insulin peptide of the presently disclosed conjugates is native insulin, comprising the A chain of SEQ ID NO: 1 and the B chain of SEQ ID NO: 2, or an analog of native insulin, including for example a single-chain insulin analog comprising SEQ ID NOS: 1 and 2. In accordance with the present disclosure analogs of insulin encompass polypeptides comprising an A chain and a B chain wherein the insulin analogs differ from native insulin by one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30.

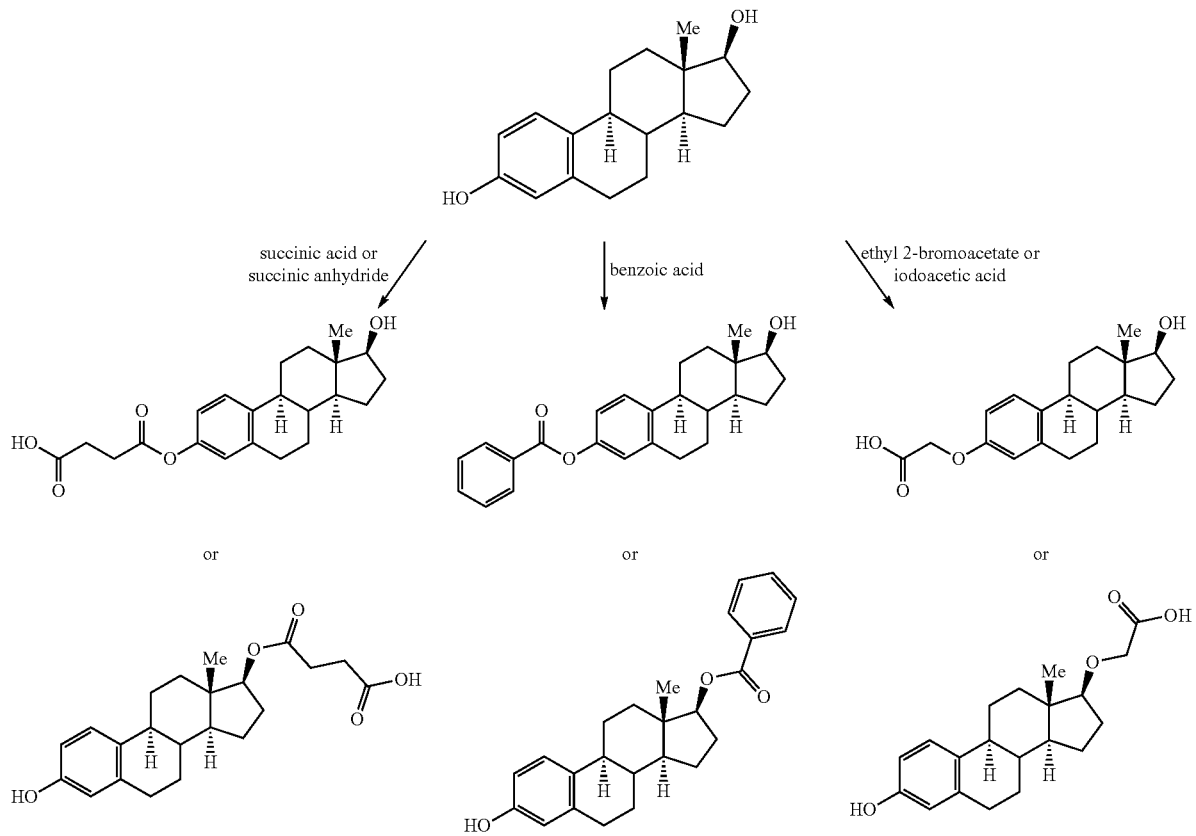

Similarly, any of the aforementioned NHR ligands can be derivatized by methods known in the art. Additionally, certain derivatized ligands are commercially available and can be purchased from chemical companies such as Sigma-Aldrich.

In accordance with one embodiment Q is selected from the group consisting of estradiol and derivatives thereof, estrone and derivatives thereof, testosterone and derivatives thereof, and cortisol and derivatives thereof. In one embodiment Q is dexamethasone. In one embodiment Q is selected In one embodiment the insulin peptide is an insulin analog wherein:
(a) the amino acid residue at position B28 is substituted with Asp, Lys, Leu, Val, or Ala, and the amino acyl residue at position B29 is Lys or Pro;
(b) the amino acid residues at any of positions B27, B28, B29, and B30 are deleted or substituted with a nonnative amino acid. In one embodiment an insulin analog is provided comprising an Asp substituted at position B28 or a Lys substituted at position 28 and a proline substituted at position B29. Additional insulin analogs are disclosed in Chance, et al., U.S. Pat. No. 5,514,646; Chance, et al., U.S. patent application Ser. No. 08/255, 297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). The disclosures of which are expressly incorporated herein by reference.

Insulin analogs may also have replacements of the amidated amino acids with acidic forms. For example, Asn may be replaced with Asp or Glu. Likewise, Gln may be replaced with Asp or Glu. In particular, Asn(A18), Asn(A21), or Asp(B3), or any combination of those residues, may be replaced by Asp or Glu. Also, Gln(A15) or Gln(B4), or both, may be replaced by either Asp or Glu.

As disclosed herein single chain insulin agonists are provided comprising a B chain and an A chain of human insulin, or analogs or derivative thereof, wherein the carboxy terminus of the B chain is linked to the amino terminus of the A chain via a linking moiety. In one embodiment the A chain is an amino acid sequence selected from the group consisting of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises the sequence FVNQHLCG SHLVEALYLVCGERGFFYTPKT (SEQ ID NO: 2), GPETLCGAELVDALYLVCGDRGFYFNKPT (SEQ ID NO: 6) or AYRPSETLCGGELVDTLYLVCGDRGFY FSRPA (SEQ ID NO: 8), or a carboxy shortened sequence thereof having one to five amino acids corresponding to B26, B27, B28, B29 and B30 deleted, and analogs of those sequences wherein each sequence is modified to comprise one to five amino acid substitutions at positions corresponding to native insulin positions (see peptide alignment shown in FIG. 5) selected from A5, A8, A9, A10, A14, A15, A17, A18, A21, B1, B2, B3, B4, B5, B9, B10, B13, B14, B20, B22, B23, B26, B27, B28, B29 and B30. In one embodiment the amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

Additional amino acid sequences can be added to the amino terminus of the B chain or to the carboxy terminus of the A chain of the single chain insulin agonists of the present invention. For example, a series of negatively charged amino acids can be added to the amino terminus of the B chain, including for example a peptide of 1 to 12, 1 to 10, 1 to 8 or 1 to 6 amino acids in length and comprising one or more negatively charged amino acids including for example glutamic acid and aspartic acid. In one embodiment the B chain amino terminal extension comprises 1 to 6 charged amino acids. In one embodiment the B chain amino terminal extension comprises the sequence $GX_{61}X_{62}X_{63}X_{64}X_{65}K$ (SEQ ID NO: 26) or $X_{61}X_{62}X_{63}X_{64}X_{65}RK$ (SEQ ID NO: 27), wherein $X_{61}$, $X_{62}$, $X_{63}$ $X_{64}$ and $X_{65}$ are independently glutamic acid or aspartic acid. In one embodiment the B chain comprises the sequence GEEEEEKGPEHLC GAHLVDALYLVCGDX$_{42}$GFY (SEQ ID NO: 28), wherein $X_{42}$ is selected from the group consisting of alanine lysine, ornithine and arginine.

High potency FGF21 based insulin conjugates can also be prepared based on using a modified IGF I and IGF II sequence described in published International application no. WO 2010/080607, the disclosure of which is expressly incorporated herein by reference, as the insulin peptide component. More particularly, analogs of IGF I and IGF II that comprise a substitution of a tyrosine leucine dipeptide for the native IGF amino acids at positions corresponding to B16 and B17 of native insulin have a tenfold increase in potency at the insulin receptor.

In accordance with one embodiment the insulin peptide for use in the present disclosure comprises a B chain sequence of $R_{62}$-$X_{25}$LCG$X_{29}$$X_{30}$LV$X_{33}$$X_{34}$LYLVCG$X_{41}$ $X_{42}$GF$X_{45}$ (SEQ ID NO: 20) and an A chain sequence of GIV$X_4$XCCX$X_9$$X_{10}$C$X_{12}$L$X_{14}$$X_{15}$L$X_{17}$$X_{18}$$X_{19}$C$X_{21}$-$R_{53}$ (SEQ ID NO: 29) wherein $X_4$ is glutamic acid or aspartic acid;
$X_5$ is glutamine or glutamic acid
$X_8$ is histidine, threonine or phenylalanine;
$X_9$ is serine, arginine, lysine, ornithine or alanine;
$X_{10}$ is isoleucine or serine;
$X_{12}$ is serine or aspartic acid
$X_{14}$ is tyrosine, arginine, lysine, ornithine or alanine;
$X_{15}$ is glutamine, glutamic acid, arginine, alanine, lysine, ornithine or leucine;
$X_{17}$ is glutamine, glutamic acid, arginine, aspartic acid or lysine, ornithine
$X_{18}$ is methionine, asparagine, glutamine, aspartic acid, glutamic acid or threonine;
$X_{19}$ is tyrosine, 4-methoxy-phenylalanine or 4-amino phenylalanine;
$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;
$X_{25}$ is histidine or threonine;
$X_{29}$ is selected from the group consisting of alanine, glycine and serine;
$X_{30}$ is selected from the group consisting of histidine, aspartic acid, glutamic acid, homocysteic acid and cysteic acid;
$X_{33}$ is selected from the group consisting of aspartic acid, glutamine and glutamic acid;
$X_{34}$ is selected from the group consisting of alanine and threonine;
$X_{41}$ is selected from the group consisting of glutamic acid, aspartic acid or asparagine;
$X_{42}$ is selected from the group consisting of alanine, lysine, ornithine and arginine;
$X_{45}$ is tyrosine, histidine, asparagine or phenylalanine;
$R_{62}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and a bond; and $R_{53}$ is COOH or CONH$_2$. In one embodiment the A chain and the B chain are linked to one another by interchain disulfide bonds, including those that form between the A and B chains of native insulin. In an alternative embodiment the A and B chains are linked together as a linear single chain-insulin peptide.

In one embodiment the conjugates comprise an insulin peptide wherein the A chain comprises a sequence of GIVEQCCX$_1$SICSLYQLENX$_2$CX$_3$ (SEQ ID NO: 30) and said B chain sequence comprises a sequence of $X_4$ LCGX$_5$X$_6$LVEALYLVCGERGFF (SEQ ID NO: 31), wherein $X_1$ is selected from the group consisting of threonine and histidine;

$X_2$ is tyrosine, 4-methoxy-phenylalanine or 4-amino phenylalanine;

$X_3$ is selected from the group consisting of asparagine and glycine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid.

In accordance with one embodiment an insulin analog is provided wherein the A chain of the insulin peptide comprises the sequence GIVEQCCXX$_9$ICSLYQLENYCX$_{21}$—R$_{53}$ (SEQ ID NO: 73) or GIVEQCCX$_8$SICSLYQLX$_{17}$NYCX$_{21}$ (SEQ ID NO: 32) and the B chain comprising the sequence R$_{62}$-X$_{25}$LCGX$_{29}$X$_{30}$LVX$_{33}$X$_{34}$LYLVCGX$_{41}$X$_{42}$GFX$_{45}$YT-Z$_1$—B$_1$ (SEQ ID NO: 142), wherein $X_8$ is selected from the group consisting of threonine and histidine;

$X_9$ is valine or tyrosine;

$X_{17}$ is glutamine or glutamic acid;

$X_{21}$ is asparagine or glycine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, ornithine, lysine and arginine;

$X_{45}$ is tyrosine or phenylalanine;

R$_{62}$ is selected from the group consisting of FVNQ (SEQ ID NO: 12), a tripeptide valine-asparagine-glutamine, a dipeptide asparagine-glutamine, glutamine and an N-terminal amine $Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with one embodiment an insulin analog is provided wherein the A chain of the insulin peptide comprises the sequence GIVEQCCXSICSLYQLX$_{17}$NX$_{19}$CX$_{21}$ (SEQ ID NO: 32) and the B chain comprising the sequence X$_{25}$LCGX$_{29}$X$_{30}$LVEALYLVCGERGFF (SEQ ID NO: 33) wherein $X_8$ is selected from the group consisting of threonine and histidine;

$X_{17}$ is glutamic acid or glutamine;

$X_{19}$ is tyrosine, 4-methoxy-phenylalanine or 4-amino phenylalanine;

$X_{21}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid. In a further embodiment the B chain comprises the sequence X$_{22}$VNQX$_{25}$LCGX$_{29}$X$_{30}$LVEALYLVCGERGFFYT-Z$_1$-B$_1$ (SEQ ID NO: 34) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with some embodiments the A chain comprises the sequence GIVEQCCX$_8$SICSLYQLX$_{17}$NX$_{19}$CX$_{23}$ (SEQ ID NO: 32) or GIVDECCX$_8$X$_9$SCDLX$_{14}$X$_{15}$LX$_{17}$X$_{18}$X$_{19}$CX$_{21}$-R$_{53}$ (SEQ ID NO: 35), and the B chain comprises the sequence X$_{25}$LCGX$_{29}$X$_{30}$LVX$_{33}$X$_{34}$ LYLVCGDX$_{42}$GFX$_{45}$ (SEQ ID NO: 36) wherein $X_8$ is histidine or phenylalanine;

$X_9$ and $X_{14}$ are independently selected from arginine, lysine, ornithine or alanine;

$X_{15}$ is arginine, lysine, ornithine or leucine;

$X_{17}$ is glutamic acid or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine; and

R$_{53}$ is COOH or CONH$_2$.

In a further embodiment the A chain comprises the sequence GIVDECCX$_8$X$_9$SCDLX$_{14}$X$_{15}$LX$_{17}$X$_{18}$X$_{19}$CX$_{21}$—R$_3$ (SEQ ID NO: 35), and the B chain comprises the sequence X$_{25}$LCGX$_{29}$X$_{30}$LVX$_{33}$X$_{34}$LYLVCGDX$_{42}$GFX$_{45}$ (SEQ ID NO: 36) wherein $X_8$ is histidine;

$X_9$ and $X_{14}$ are independently selected from arginine, lysine, ornithine or alanine;

$X_{15}$ is arginine, lysine, ornithine or leucine;

$X_{17}$ is glutamic acid, aspartic acid, asparagine, lysine, ornithine or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine or phenylalanine and $R_{53}$ is COOH or CONH$_2$. In a further embodiment the A chain comprises the sequence GIVDECCHX$_9$SCDLX$_{14}$X$_{15}$LX$_{17}$MX$_{19}$CX$_{21}$-R$_{53}$ (SEQ ID NO: 37), and the B chain comprises the sequence X$_{25}$LCGAX$_{30}$LVDALYLVCGDX$_{42}$GFX$_{45}$ (SEQ ID NO: 38) wherein $X_9$, $X_{14}$ and $X_{15}$ are independently ornithine, lysine or arginine;

$X_{17}$ is glutamic acid or glutamine;

$X_{19}$ is tyrosine, 4-methoxy-phenylalanine or 4-amino phenylalanine;

$X_{21}$ is alanine, glycine or asparagine;

$X_{25}$ is selected from the group consisting of histidine and threonine;

$X_{30}$ is selected from the group consisting of histidine, aspartic acid and glutamic acid;

$X_{42}$ is selected from the group consisting of alanine, lysine, ornithine and arginine;

$X_{45}$ is tyrosine or phenylalanine and $R_{53}$ is COOH or CONH$_2$. In one embodiment the B chain is selected from the group consisting of HLCGAELVDALYLVCGDX$_{42}$GFY (SEQ ID NO: 39), GPEHLCGAELVDALYLVCGDX$_{42}$GFY (SEQ ID NO: 40), GPEHLCGAELVDALYLVCGDX$_{42}$GFYFNPKT (SEQ ID NO: 41) and GPEHLCGAELVDALYLVCGDX$_{42}$GFYFNKPT (SEQ ID NO: 42), wherein $X_{42}$ is selected from the group consisting of ornithine, lysine and arginine. In a further embodiment the A chain comprises the sequence GIVDECCHX$_9$SCDLX$_{14}$X$_{15}$LQMYCN-R$_{53}$ (SEQ ID NO: 43), wherein $X_9$, $X_{14}$ and $X_{15}$ are independently ornithine, lysine or arginine.

In another embodiment the A chain comprises the sequence GIVDECCX$_8$RSCDLYQLENX$_{19}$CN-R$_{53}$ (SEQ ID NO: 44) and the B chain comprises the sequence R$_{62}$-X$_{25}$LCGSHLVDALYLVCGDX$_{42}$GFX$_{45}$ (SEQ ID NO: 45) wherein $X_8$ is threonine, histidine or phenylalanine;

$X_{19}$ is tyrosine, 4-methoxy phenylalanine or 4-amino phenylalanine;

$X_{25}$ is histidine or threonine;

$X_{42}$ is alanine, ornithine or arginine;

$X_{45}$ is tyrosine histidine, asparagine or phenylalanine;

$R_{62}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and a bond; and $R_{53}$ is COOH or CONH$_2$. and $R_{53}$ is COOH or CONH$_2$. In a further embodiment $X_{19}$ is Tyr.

In another embodiment the A chain comprises the sequence GIVEQCCHSICSLYQLENX$_{19}$CX$_{21}$-R$_{53}$ (SEQ ID NO: 46) or GIVDECCHRSCDLRRLEMX$_{19}$CX$_{21}$-R$_{53}$ (SEQ ID NO: 47); and the B chain comprises the sequence FVNQHLCGSHLVEALYLVCGERGFFYTPKT (SEQ ID NO: 2), or

GPETLCGAELVDALYLVCGDRGFYFNPKT (SEQ ID NO: 48)

wherein $X_{19}$ is tyrosine, 4-methoxy phenylalanine or 4-aminophenylalanine; and $X_{21}$ is alanine, glycine or asparagine.

In another embodiment, the A chain comprises the sequence GIVEQCCHSICSLYQLENYCX$_{21}$-R$_{53}$ (SEQ ID NO: 160) and the B chain comprises the sequence FVKQX$_{25}$LCGSHLVEALYLVCGERGFF-R$_{63}$ (SEQ ID NO: 147), or FVNQX$_{25}$LCGSHLVEALYLVCGERGFF-R$_{63}$ (SEQ ID NO: 148), wherein $X_{21}$ is alanine, glycine or asparagine; and $X_{25}$ is selected from the group consisting of histidine and threonine;

$X_{28}$ is proline, aspartic acid or glutamic acid; and $R_{63}$ is selected from the group consisting of YTX$_{28}$KT (SEQ ID NO: 149), YTKPT (SEQ ID NO: 150), YTX$_{28}$K (SEQ ID NO: 152), YTKP (SEQ ID NO: 151), YTPK (SEQ ID NO: 70), YTX$_{28}$, YT, Y and a bond. In one embodiment the B chain comprises the sequence FVKQX$_{25}$LCGSHLVEALYLVCGERGFFYTEKT (SEQ ID NO: 162), FVNQX$_{25}$LCGSHLVEALYLVCGERGFFYTDKT (SEQ ID NO: 164), FVNQX$_{25}$LCGSHLVEALYLVCGERGFFYTKPT (SEQ ID NO: 165) or FVNQX$_{25}$ LCGSHLVEALYLVCGERGFFYTPKT (SEQ ID NO: 161) wherein $X_{25}$ is selected from the group consisting of histidine and threonine.

Single Chain Insulin Peptide Agonists

As disclosed herein linking moieties can be used to link human insulin A and B chains, or analogs or derivatives thereof, wherein the carboxy terminus of the B25 amino acid of the B chain is directly linked to a first end of a linking moiety, wherein the second end of the linking moiety is directly linked to the amino terminus of the A1 amino acid of the A chain via the intervening linking moiety.

In accordance with one embodiment the insulin peptide is a single chain insulin agonist that comprises the general structure B-LM-A wherein B represents an insulin B chain, A represents an insulin A chain, and LM represents a linking moiety linking the carboxy terminus of the B chain to the amino terminus of the A chain. Suitable linking moieties for joining the B chain to the A chain are disclosed herein under the header Linking Moieties for Single Chain-Insulin Analogs and the respective subheaders "Peptide linkers". In one embodiment the linking moiety comprises a linking peptide, and more particularly, in one embodiment the peptide represents an analog of the IGF-1 C peptide. Additional exemplary peptide linkers include but are not limited to the sequence X$_{51}$X$_{52}$GSSSX$_{57}$X$_{58}$ (SEQ ID NO: 49) or X$_{51}$X$_{52}$GSSSX$_{57}$X$_{58}$APQT (SEQ ID NO: 50) wherein X$_{51}$ is selected from the group consisting of glycine, alanine, valine, leucine, isoleucine and proline, X$_{52}$ is alanine, valine, leucine, isoleucine or proline and X$_{57}$ or X$_{58}$ are independently arginine, lysine, cysteine, homocysteine, acetyl-phenylalanine or ornithine, optionally with a hydrophilic moiety linked to the side chain of the amino acid at position 7 or 8 of the linking moiety (i.e., at the X$_{57}$ or X$_{58}$ position). Amino acid positions of the linking moiety are designated based on the corresponding position in the native C chain of IGF 1 (SEQ ID NO: 17). In another embodiment the peptide linking moiety comprises a 29 contiguous amino acid sequence having greater than 70%, 80%, 90% sequence identity to SSSSX$_{50}$APPPSLPSPSRLPGPSDTPILPQX$_{51}$ (SEQ ID NO: 68), wherein X$_{50}$ and X$_{51}$ are independently selected from arginine and lysine. In one embodiment the linking moiety is a non-peptide linker comprising a relatively short bifunctional non-peptide polymer linker that approximates the length of an 8-16 amino acid sequence. In one embodiment the non-peptide linker has the structure:

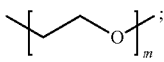

wherein m is an integer ranging from 10 to 14 and the linking moiety is linked directly to the B25 amino acid of the B chain. In accordance with one embodiment the non-peptide linking moiety is a polyethylene glycol linker of approximately 4 to 20, 8 to 18, 8 to 16, 8 to 14, 8 to 12, 10 to 14, 10 to 12 or 11 to 13 monomers.

In one embodiment a FGF21 based insulin conjugate is provided that comprises an insulin peptide having the structure: IB-LM-IA, wherein IB comprises the sequence R$_{62}$—X$_{25}$LCGX$_{29}$X$_{30}$LVX$_{33}$X$_{34}$LYLVCGX$_{41}$X$_{42}$GFX$_{45}$ (SEQ ID NO: 20), LM is a linking moiety as disclosed herein that covalently links IB to IA, and IA comprises the sequence GIVX$_4$X$_5$CCX$_8$X$_9$X$_{10}$CX$_{12}$LX$_{14}$X$_5$LX$_{17}$X$_{18}$X$_{19}$CX$_{21}$-R$_{53}$ (SEQ ID NO: 29), wherein X$_4$ is glutamic acid or aspartic acid;
X$_5$ is glutamine or glutamic acid;
X$_8$ is histidine or phenylalanine;
X$_9$ and X$_{14}$ are independently selected from arginine, lysine, ornithine or alanine;
X$_{10}$ is isoleucine or serine;
X$_{12}$ is serine or aspartic acid;
X$_{14}$ is tyrosine, arginine, lysine, ornithine or alanine;
X$_{15}$ is arginine, lysine, ornithine or leucine;
X$_{17}$ is glutamic acid or glutamine;
X$_{18}$ is methionine, asparagine or threonine;
X$_{19}$ is tyrosine, 4-methoxy-phenylalanine or 4-amino phenylalanine;
X$_{21}$ is alanine, glycine or asparagine;
X$_{25}$ is selected from the group consisting of histidine and threonine;
X$_{29}$ is selected from the group consisting of alanine, glycine and serine;
X$_{30}$ is selected from the group consisting of histidine, aspartic acid, glutamic acid, homocysteic acid and cysteic acid;
X$_{33}$ is selected from the group consisting of aspartic acid and glutamic acid;
X$_{34}$ is selected from the group consisting of alanine and threonine;
X$_{41}$ is selected from the group consisting of glutamic acid, aspartic acid or asparagine;
X$_{42}$ is selected from the group consisting of alanine, lysine, ornithine and arginine;
R$_{62}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and
R$_{53}$ is COOH or CONH$_2$, further wherein the amino acid at the designation X$_{45}$ is directly bound to the linking moiety, LM (i.e., the designation IB-LM-IA as used herein is intended to represent that the B chain carboxyl terminus and the amino terminus of the A chain are directly linked to the linking moiety LM without any further intervening amino acids).

In one embodiment the linking moiety (LM) comprises an amino acid sequence of no more than 17 amino acids in length. In one embodiment the linking moiety comprises the sequence X$_{51}$X$_{52}$GSSSX$_{57}$X$_{58}$ (SEQ ID NO: 49) or X$_{51}$X$_{52}$GSSSX$_{57}$X$_{58}$APQT (SEQ ID NO: 50) wherein X$_{51}$ is selected from the group consisting of glycine, alanine, valine, leucine, isoleucine and proline, X$_{52}$ is alanine, valine, leucine, isoleucine or proline and X$_{57}$ or X$_{58}$ are independently arginine, lysine, cysteine, homocysteine, acetyl-phenylalanine or ornithine, optionally with a hydrophilic moiety linked to the side chain of the amino acid at position 7 or 8 of the linking moiety (i.e., at the X$_{57}$ or X$_{58}$ position). Amino acid positions of the linking moiety are designated based on the corresponding position in the native C chain of IGF 1 (SEQ ID NO: 17). In one embodiment LM is GAGSSSR-RAPQT (SEQ ID NO: 23) or GAGSSSRR (SEQ ID NO: 22).

In another embodiment the linking moiety comprises a 29 contiguous amino acid sequence, directly linked to the carboxy terminal amino acid of the B chain, wherein said 29 contiguous amino acid sequence has greater than 70%, 80%, 90% sequence identity to SSSSX$_{50}$ APPPSLPS-PSRLPGPSDTPILPQX$_{51}$ (SEQ ID NO: 68), wherein X$_{50}$ and X$_{51}$ are independently selected from arginine and lysine. In one embodiment the linking peptide comprises a total of 29 to 158 or 29 to 58 amino acids and comprises the sequence of SEQ ID NO: 68. In another embodiment the linking moiety comprises a 29 contiguous amino acid sequence, directly linked to the carboxy terminal amino acid of the B chain, wherein said 29 contiguous amino acid sequence has greater than 90% sequence identity to SSSSX$_{50}$APPPSLPSPSRLPGPSDTPILPQX$_{51}$ (SEQ ID NO: 68), wherein X$_{50}$ and X$_{51}$ are independently selected from arginine and lysine. In one embodiment the linking moiety comprises the sequence SSSSRAPPPSLPS-PSRLPGPSDTPILPQK (SEQ ID NO: 51) or SSSSKA-PPPSLPSPSRLPGPSDTPILPQR (SEQ ID NO: 52) optionally with one or two amino acid substitutions.

In accordance with one embodiment a single chain insulin agonist polypeptide is provided comprising a B chain and A chain of human insulin, or analogs or derivative thereof, wherein the last five carboxy amino acids of the native B chain are deleted (i.e., B26-B30), and amino acid B25 is linked to amino acid A1 of the A chain via an intervening linking moiety. In one embodiment the linking moiety comprises the structure:

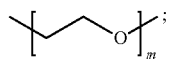

wherein m is an integer ranging from 10 to 14 and the linking moiety is linked directly to the B25 amino acid of the B chain.

In one embodiment an FGF21 based insulin conjugate is provided comprising an insulin peptide having the general formula IB-LM-IA wherein IB comprises the sequence GPEHLCGAX$_{30}$LVDALYLVCGDX$_{42}$GFYFNX$_{48}$X$_{49}$ (SEQ ID NO: 163);

LM comprises the sequence SSSSRAPPPSLPSP-SRLPGPSDTPILPQK (SEQ ID NO: 51), SSSSK APPPSLPSPSRLPGPSDTPILPQR (SEQ ID NO: 52), GYGSSSRR (SEQ ID NO: 18), GAGSSSRRAPQT (SEQ ID NO: 23) or GAGSSSRR (SEQ ID NO: 22); and IA comprises the sequence GIVDECCX$_8$X$_9$SCDLX$_{14}$X$_{15}$LX$_{17}$X$_{18}$X$_{19}$CX$_{21}$—R$_{53}$ (SEQ ID NO: 35) wherein X$_8$ is histidine or phenylalanine;
X$_9$ is arginine, ornithine or alanine;
X$_{14}$ and X$_{15}$ are both arginine;
X$_{17}$ is glutamic acid;
X$_{19}$ is tyrosine, 4-methoxy-phenylalanine or 4-amino phenylalanine;
X$_{21}$ is alanine or asparagine;
X$_{25}$ is histidine or threonine;
X$_{30}$ is selected from the group consisting of histidine, aspartic acid, glutamic acid, homocysteic acid and cysteic acid;
X$_{42}$ is selected from the group consisting of alanine, ornithine and arginine;
R$_{53}$ is COOH.

Linking Moieties for Single Chain Insulin Analogs
Peptide Linkers

In accordance with one embodiment the linking moiety is a peptide or peptidomimetic of 6-18, 8-18, 8-17, 8-12, 8-10, 13-17 or 13-15 amino acids (or amino acid analogs or derivatives thereof). In one embodiment the linking moiety is 8 to 17 amino acids in length and comprises the sequence X$_{51}$X$_{52}$GSSSRR (SEQ ID NO: 53) wherein X$_{51}$ is selected from the group consisting of glycine, alanine, valine, leucine, isoleucine, proline and methionine, and X$_{52}$ is a non-aromatic amino acid, including for example, alanine. In one embodiment the linking moiety is 8 to 17 amino acids in length and comprises a sequence that differs from X$_{51}$X$_{52}$GSSSRR (SEQ ID NO: 53) by a single amino acid substitution wherein the amino acid substitution is an amino acid that is pegylated at its side chain, further wherein X$_{51}$ is selected from the group consisting of glycine, alanine, valine, leucine, isoleucine, proline and methionine, and X$_{52}$ is a non-aromatic amino acid, including for example, alanine.

In accordance with one embodiment the linking moiety is a derivative of the IGF 1 C chain sequence (GYGSSSRRAPQT; SEQ ID NO: 17). In one embodiment the derivative is a peptide that differs from SEQ ID NO: 17 by a single amino acid substitution of a lysine, cysteine ornithine, homocysteine, or acetyl-phenylalanine residue, and in a further embodiment the lysine, cysteine ornithine, homocysteine, or acetyl-phenylalanine amino acid is pegylated. In one further embodiment the linking moiety is a peptide that differs from SEQ ID NO: 17 by a single lysine substitution. In one specific embodiment the substitution is made at position 8 of SEQ ID NO: 17. Applicants have discovered that use of the IGF 1 C chain sequence and analogs thereof as a linking moiety will generate a single chain insulin polypeptide that has near wild type insulin activity. Furthermore, use of a IGF 1 C chain sequence analog as the linking moiety, wherein position 2 of the IGF 1 C chain sequence is modified, or the carboxy terminal four amino acids are deleted from the IGF 1 C chain sequence, produces a single chain insulin polypeptide that is selective for insulin (i.e., has a higher binding and/or activity at the insulin receptor compared to the IGF-1 receptor). In one embodiment the single chain insulin polypeptide has 5×, 10×, 20×, 30×, 40×, or 50× higher affinity or activity at the insulin receptor relative to the IGF-1 receptor.

In accordance with one embodiment the linking moiety is a derivative of the IGF 1 C chain sequence (GYGSSSRRA-PQT; SEQ ID NO: 17) and comprises a non-native sequence that differs from GYGSSSRR (SEQ ID NO: 18) or GAGSSSRRAPQT (SEQ ID NO: 23) by 1 to 3 amino acid substitutions, or 1 to 2 amino acid substitutions. In one embodiment at least one of the amino acid substitutions is a lysine or cysteine substitution, and in one embodiment the amino acid substitutions are conservative amino acid substitutions. In one embodiment the linking moiety is a peptide (or peptidomimetic) of 8 to 17 amino acids comprising a non-native amino acid sequence that differs from GYGSSSRR (SEQ ID NO: 18) or GAGSSSRRAPQT (SEQ ID NO: 23) by 1 amino acid substitution, including for example substitution with a lysine or cysteine. In one embodiment the linking moiety comprises the sequence GYGSSSRR (SEQ ID NO: 18) or GAGSSSRRAPQT (SEQ ID NO: 23). In one embodiment the linking moiety comprises the sequence GAGSSSRX$_{58}$APQT (SEQ ID NO: 54), GYGSSSX$_{57}$X$_{58}$APQT (SEQ ID NO: 69), or an amino acid that differs from SEQ ID NO: 54 by a single amino acid substitution, wherein X$_{57}$ is arginine and X$_{58}$ is arginine, ornithine or lysine, and in a further embodiment a polyethylene glycol chain is linked to the side chain of the amino acid at position 8 of said linking moiety. In another embodiment the linking moiety comprises the sequence GX$_{52}$GSSSRX$_{58}$APQT (SEQ ID NO: 55), wherein X$_{52}$ is any non-aromatic amino acid, including for example, alanine, valine, leucine, isoleucine or proline, and X$_{58}$ represents an amino acid that has a polyethylene chain covalently linked to its side chain. In one embodiment X$_{58}$ is a pegylated lysine.

In another embodiment, the linking moiety is an 8 to 17 amino acid sequence comprising the sequence GX$_{52}$GSSSRR (SEQ ID NO: 56), wherein X$_{52}$ is any amino acid, a peptidomimetic of SEQ ID NO: 31, or an analog thereof that differs from SEQ ID NO: 31 by a single amino acid substitution at any of positions 1, 3, 4, 5, 6, 7 or 8 of SEQ ID NO: 31, with the proviso that when the linking peptide is longer than 8 amino acids X$_{52}$ is other than tyrosine. In accordance with one embodiment the linking moiety comprises an 8-17 amino acid sequence selected from the group consisting of GYGSSSRR (SEQ ID NO: 18), GAGSSSRR (SEQ ID NO: 22), GAGSSSRRA (SEQ ID NO: 57), GAGSSSRRAP (SEQ ID NO: 58), GAGSSSR-RAPQ (SEQ ID NO: 59), GAGSSSRRAPQT (SEQ ID NO: 23), PYGSSSRR (SEQ ID NO: 61), PAGSSSRR (SEQ ID NO: 62), PAGSSSRRA (SEQ ID NO: 63), PAGSSSRRAP (SEQ ID NO: 64), PAGSSSRRAPQ (SEQ ID NO: 65), PAGSSSRRAPQT (SEQ ID NO: 66). In accordance with one embodiment the linking moiety comprises an amino acid sequence that differs from GYGSSSRR (SEQ ID NO: 18), GAGSSSRR (SEQ ID NO: 22), GAGSSSRRA (SEQ ID NO: 57), GAGSSSRRAP (SEQ ID NO: 58), GAGSSSR-RAPQ (SEQ ID NO: 59), GAGSSSRRAPQT (SEQ ID NO: 23), PYGSSSRR (SEQ ID NO: 61), PAGSSSRR (SEQ ID NO: 62), PAGSSSRRA (SEQ ID NO: 63), PAGSSSRRAP (SEQ ID NO: 64), PAGSSSRRAPQ (SEQ ID NO: 65), PAGSSSRRAPQT (SEQ ID NO: 66) by a single pegylated amino acid including for example a pegylated lysine or pegylated cysteine amino acid substitution. In one embodiment the pegylated amino acid is at position 8 of the linking moiety.

In one embodiment a peptide sequence named C-terminal peptide (CTP: SSSSKAPPPSLPSPSRLPGPSDTPILPQR; SEQ ID NO: 52), which is prone to O-linked hyperglycosylation when the protein is expressed in a eukaryotic cellular expression system, can be used as a linker peptide. Surprisingly, applicants have discovered that the CTP peptide can be used to connect the B and A chains of insulin to form a single chain insulin analog while still maintaining high in vitro potency in a manner that the native proinsulin C-peptide cannot. In one embodiment a FGF21 based insulin conjugate is prepared comprising an insulin peptide having the carboxy terminus of the B chain linked to the amino terminus of the A chain via a CTP peptide. In another embodiment an insulin analog is provided as a two-chain construct with the CTP covalently linked to the C-terminus of the B-chain and/or the amino terminus of the B chain. In vitro and in vivo characterization reveals the CTP modified insulin analogs to have high potency in the absence of glycosylation, thus providing a mechanism to extend insulin action that is based on glycosylation, a natural approach to longer duration proteins.

Applicants have discovered that the primary sequence of the CTP peptide does not appear to be critical. Accordingly, in one embodiment the linking moiety comprises a peptide having a length of at least 18 amino acids that shares a similar amino acid content. In one embodiment the linking moiety comprises an analog of (SEQ ID NO: 68), wherein said analog differs from (SEQ ID NO: 68) by 1, 2, 3, 4, 5 or 6 amino acid substitutions. In one embodiment the linking peptide comprises a CTP peptide wherein amino acid substitutions are made at one or more positions selected from positions 1, 2, 3, 4, 10, 13, 15, and 21 of (SEQ ID NO: 68). In one embodiment the linking moiety comprises a 29 contiguous amino acid sequence, directly linked to the carboxy terminal amino acid of the B chain, wherein said 29 contiguous amino acid sequence has greater than 60, 80 or 90% sequence identity to SSSSX$_{50}$APPPSLPSPSRLPGPSDTPILPQX$_{51}$ (SEQ ID NO: 68), with the proviso that the sequence does not comprise a 15 amino acid sequence identical to a 15 amino acid sequence contained within SEQ ID NO 53. In another embodiment the linking moiety comprises a 29 contiguous amino acid sequence, directly linked to the carboxy terminal amino acid of the B chain, wherein at least 58% of the amino acids comprising the 29 contiguous amino acid sequence are selected from the group consisting of serine and proline.

In another embodiment the linking moiety comprises a 29 contiguous amino acid sequence, directly linked to the carboxy terminal amino acid of the B chain, wherein said 29 contiguous amino acid sequence has greater than 70%, 80%, 90% sequence identity to SSSSX$_{50}$APPPSLPSPSRLPGPSDTPILPQX$_{51}$ (SEQ ID NO: 68), wherein X$_{50}$ and X$_{51}$ are independently selected from arginine and lysine, with the proviso that the sequence does not comprise a 15 amino acid sequence identical to a 15 amino acid sequence contained within SEQ ID NO 53. In another embodiment the linking moiety comprises a 29 contiguous amino acid sequence, directly linked to the carboxy terminal amino acid of the B chain, wherein said 29 contiguous amino acid sequence is an analog of (SEQ ID NO: 52), wherein said analog differs from (SEQ ID NO: 52) only by 1, 2, 3, 4, 5 or 6 amino acid modification, and in a further embodiment the amino acid modifications are conservative amino acid substitutions. In another embodiment the linking moiety comprises a 29 contiguous amino acid sequence, directly linked to the carboxy terminal amino acid of the B chain, wherein said 29 contiguous amino acid sequence is an analog of (SEQ ID NO: 52), wherein said analog differs from (SEQ ID NO: 52) only by 1, 2 or 3 amino acid substitutions.

Applicants have also found that multiple copies of the CTP peptide can be used as the linking peptide in single chain analogs and/or linked to the amino terminus of the B chain in single chain or two chain insulin analogs. The multiple copies of the CTP peptide can be identical or can differ in sequence and can be arranged in a head to tail or head to head orientation. In accordance with one embodiment an insulin analog is provided comprising a CTP peptide having the sequence (SSSSX$_{50}$APPPSLPSPSRLPGPSDTPILPQX$_{51}$)$_n$ (SEQ ID NO: 68), wherein n is an integer selected from the group consisting of 1, 2, 3 and 4 and X$_{50}$ and X$_{51}$ are independently selected from arginine and lysine.

In one embodiment the CTP peptide comprises the sequence SSSSX$_{50}$APPPSLPSPSRLPGPSDTPILPQX$_{51}$ (SEQ ID NO: 68), wherein X$_{50}$ and X$_{51}$ are independently selected from arginine and lysine. In another embodiment the CTP peptide comprises a sequence selected from the group consisting of SSSSRAPPPSLPSPSRLPGPSDTPILPQK (SEQ ID NO: 51), SSSSKAPPPSLPSPSRLPGPSDTPILPQR (SEQ ID NO: 52) or SSSSRAPPPSLPSRLPGPSDTPILPQ (SEQ ID NO: 67), and in a further embodiment the CTP peptide comprises the sequence SSSSRAPPPSLPSPSRLPGPSDTPILPQK (SEQ ID NO: 51).

Structure of L

In some embodiments, L is a bond. In these embodiments, Q and Y are conjugated together by reacting a nucleophilic reactive moiety on Q with and electrophilic reactive moiety on Y. In alternative embodiments, Q and Y are conjugated together by reacting an electrophilic reactive moiety on Q with a nucleophilic moiety on Y. In exemplary embodiments, L is an amide bond that forms upon reaction of an amine on Q (e.g. an ε-amine of a lysine residue) with a carboxyl group on Y. In alternative embodiments, Q and or Y are derivatized with a derivatizing agent before conjugation.

In some embodiments, L is a linking group. In some embodiments, L is a bifunctional linker and comprises only two reactive groups before conjugation to Q and Y. In embodiments where both Q and Y have electrophilic reactive groups, L comprises two of the same or two different nucleophilic groups (e.g. amine, hydroxyl, thiol) before conjugation to Q and Y. In embodiments where both Q and Y have nucleophilic reactive groups, L comprises two of the same or two different electrophilic groups (e.g. carboxyl group, activated form of a carboxyl group, compound with a leaving group) before conjugation to Q and Y. In embodiments where one of Q or Y has a nucleophilic reactive group and the other of Q or Y has an electrophilic reactive group, L comprises one nucleophilic reactive group and one electrophilic group before conjugation to Q and Y.

L can be any molecule with at least two reactive groups (before conjugation to Q and Y capable of reacting with each of Q and Y. In some embodiments L has only two reactive groups and is bifunctional. L (before conjugation to the peptides) can be represented by Formula VI:

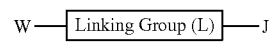

wherein W and J are independently nucleophilic or electrophilic reactive groups. In some embodiments W and J are either both nucleophilic groups or both electrophilic groups. In some embodiments one of W or J is a nucleophilic group and the other of W or J is an electrophilic group.

In some embodiments, L comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, L provides a functional group that is subject to cleavage by an enzyme or other catalyst or hydrolytic conditions found in the target tissue or organ or cell. In some embodiments, the length of L is long enough to reduce the potential for steric hindrance.

In some embodiments, the linking group is hydrophilic such as, for example, polyalkylene glycol. Before conjugation to the peptides of the composition, the hydrophilic linking group comprises at least two reactive groups (W and J), as described herein and as shown below:

In specific embodiments, the linking group is polyethylene glycol (PEG). The PEG in certain embodiments has a molecular weight of about 100 Daltons to about 10,000 Daltons, e.g. about 500 Daltons to about 5000 Daltons. The PEG in some embodiments has a molecular weight of about 10,000 Daltons to about 40,000 Daltons.

In some embodiments, the hydrophilic linking group comprises either a maleimido or an iodoacetyl group and either a carboxylic acid or an activated carboxylic acid (e.g. NHS ester) as the reactive groups. In these embodiments, the maleimido or iodoacetyl group can be coupled to a thiol moiety on Q or Y and the carboxylic acid or activated carboxylic acid can be coupled to an amine on Q or Y with or without the use of a coupling reagent. Any appropriate coupling agent known to one skilled in the art can be used to couple the carboxylic acid with the amine. In some embodiments, the linking group is maleimido-PEG(20 kDa)-COOH, iodoacetyl-PEG(20 kDa)-COOH, maleimido-PEG(20 kDa)-NHS, or iodoacetyl-PEG(20 kDa)-NHS.

In some embodiments, the linking group is comprised of an amino acid, a dipeptide, a tripeptide, or a polypeptide, wherein the amino acid, dipeptide, tripeptide, or polypeptide comprises at least two activating groups, as described herein. In some embodiments, the linking group (L) comprises a moiety selected from the group consisting of: amino, ether, thioether, maleimido, disulfide, amide, ester, thioester, alkene, cycloalkene, alkyne, trizoyl, carbamate, carbonate, cathepsin B-cleavable, and hydrazone. In some embodiments, the linking group is an amino acid selected from the group Asp, Glu, homoglutamic acid, homocysteic acid, cysteic acid, gamma-glutamic acid. In some embodiments, the linking group is a dipeptide selected from the group consisting of: Ala-Ala, β-Ala-β-Ala, Leu-Leu, Pro-Pro, γ-aminobutyric acid-γ-aminobutyric acid, and γ-Glu-γ-Glu. In one embodiment L comprises gamma-glutamic acid.

In embodiments where Q and Y are conjugated together by reacting a carboxylic acid with an amine, an activating agent can be used to form an activated ester of the carboxylic acid. The activated ester of the carboxylic acid can be, for example, N-hydroxysuccinimide (NHS), tosylate (Tos), mesylate, triflate, a carbodiimide, or a hexafluorophosphate. In some embodiments, the carbodiimide is 1,3-dicyclohexylcarbodiimide (DCC), 1,1'-carbonyldiimidazole (CDI), 1-ethyl-3-(3-dimethylaminopropyl)carbodiimide hydrochloride (EDC), or 1,3-diisopropylcarbodiimide (DICD). In some embodiments, the hexafluorophosphate is selected from a group consisting of hexafluorophosphate benzotriazol-1-yl-oxy-tris(dimethylamino)phosphonium hexafluorophosphate (BOP), benzotriazol-1-yl-oxytripyrrolidinophosphonium hexafluorophosphate (PyBOP), 2-(1H-7-azabenzotriazol-1-yl)-1,1,3,3-tetramethyl uronium hexafluorophosphate (HATU), and o-benzotriazole-N,N,N',N'-tetramethyl-uronium-hexafluoro-phosphate (HBTU).

In some embodiments, Q comprises a nucleophilic reactive group (e.g. the amino group, thiol group, or hydroxyl group of the side chain of lysine, cysteine or serine) that is capable of conjugating to an electrophilic reactive group on Y or L. In some embodiments, Q comprises an electrophilic reactive group (e.g. the carboxylate group of the side chain of Asp or Glu) that is capable of conjugating to a nucleophilic reactive group on Y or L. In some embodiments, Q is chemically modified to comprise a reactive group that is capable of conjugating directly to Y or to L. In some embodiments, Q is modified at the C-terminal to comprise a natural or nonnatural amino acid with a nucleophilic side chain, such as an amino acid represented by Formula I, Formula II, or Formula III, as previously described herein (see Acylation and alkylation). In exemplary embodiments, the C-terminal amino acid of Q is selected from the group consisting of lysine, ornithine, serine, cysteine, and homocysteine. For example, the C-terminal amino acid of Q can be modified to comprise a lysine residue. In some embodiments, Q is modified at the C-terminal amino acid to comprise a natural or nonnatural amino acid with an electrophilic side chain such as, for example, Asp and Glu. In some embodiments, an internal amino acid of Q is substituted with a natural or nonnatural amino acid having a nucleophilic side chain, such as an amino acid represented by Formula I, Formula II, or Formula III, as previously described herein (see Acylation and alkylation). In exemplary embodiments, the internal amino acid of Q that is substituted is selected from the group consisting of lysine, ornithine, serine, cysteine, and homocysteine. For example, an internal amino acid of Q can be substituted with a lysine residue. In some embodiments, an internal amino acid of Q is substituted with a natural or nonnatural amino acid with an electrophilic side chain, such as, for example, Asp and Glu.

In some embodiments, Y comprises a reactive group that is capable of conjugating directly to Q or to L. In some embodiments, Y comprises a nucleophilic reactive group (e.g. amine, thiol, hydroxyl) that is capable of conjugating to an electrophilic reactive group on Q or L. In some embodiments, Y comprises electrophilic reactive group (e.g. carboxyl group, activated form of a carboxyl group, compound with a leaving group) that is capable of conjugating to a nucleophilic reactive group on Q or L.

Stability of L In Vivo

In some embodiments, L is stable in vivo. In some embodiments, L is stable in blood serum for at least 5 minutes, e.g. less than 25%, 20%, 15%, 10% or 5% of the conjugate is cleaved when incubated in serum for a period of 5 minutes. In other embodiments, L is stable in blood serum for at least 10, or 20, or 25, or 30, or 60, or 90, or 120 minutes, or 3, 4, 5, 6, 7, 8, 9, 10, 12, 15, 18 or 24 hours. In these embodiments, L does not comprise a functional group that is capable of undergoing hydrolysis in vivo. In some exemplary embodiments, L is stable in blood serum for at least about 72 hours. Nonlimiting examples of functional groups that are not capable of undergoing significant hydrolysis in vivo include amides, ethers, and thioethers. For example, the following compound is not capable of undergoing significant hydrolysis in vivo:

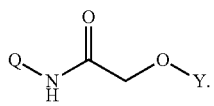

In some embodiments, L is hydrolyzable in vivo. In these embodiments, L comprises a functional group that is capable of undergoing hydrolysis in vivo. Nonlimiting examples of functional groups that are capable of undergoing hydrolysis in vivo include esters, anhydrides, and thioesters. For example the following compound is capable of undergoing hydrolysis in vivo because it comprises an ester group:

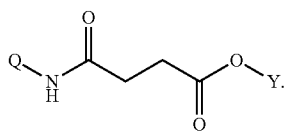

In some exemplary embodiments L is labile and undergoes substantial hydrolysis within 3 hours in blood plasma at 37° C., with complete hydrolysis within 6 hours. In some exemplary embodiments, L is not labile.

In some embodiments, L is metastable in vivo. In these embodiments, L comprises a functional group that is capable of being chemically or enzymatically cleaved in vivo (e.g., an acid-labile, reduction-labile, or enzyme-labile functional group), optionally over a period of time. In these embodiments, L can comprise, for example, a hydrazone moiety, a disulfide moiety, or a cathepsin-cleavable moiety. When L is metastable, and without intending to be bound by any particular theory, the Q-L-Y conjugate is stable in an extracellular environment, e.g., stable in blood serum for the time periods described above, but labile in the intracellular environment or conditions that mimic the intracellular environment, so that it cleaves upon entry into a cell. In some embodiments when L is metastable, L is stable in blood serum for at least about 24, 25, 26, 27, 28, 29, 30, 31, 32, 33, 34, 35, 36, 42, or 48 hours, for example, at least about 48, 54, 60, 66, or 72 hours, or about 24-48, 48-72, 24-60, 36-48, 36-72, or 48-72 hours.

Pegylation of Insulin Peptides

Applicants have discovered that covalent linkage of a hydrophilic moiety to the insulin analogs disclosed herein provide analogs having slower onset, extended duration and exhibit a basal profile of activity. In one embodiment, the insulin peptides disclosed herein are further modified to comprise a hydrophilic moiety covalently linked to the side chain of an amino acid at a position selected from the group consisting of A9, A14 and A15 of the A chain or at the N-terminal alpha amine of the B chain (e.g. at position B1 for insulin based B chain or position B2 for IGF-1 based B chain) or at the side chain of an amino acid at position B1, B2, B10, B22, B28 or B29 of the B chain or at any position of the linking moiety that links the A chain and B chain. In exemplary embodiments, this hydrophilic moiety is covalently linked to a Lys, Cys, Orn, homocysteine, or acetyl-phenylalanine residue at any of these positions. In one embodiment the hydrophilic moiety is covalently linked to the side chain of an amino acid of the linking moiety.

Exemplary hydrophilic moieties include polyethylene glycol (PEG), for example, of a molecular weight of about 1,000 Daltons to about 40,000 Daltons, or about 20,000 Daltons to about 40,000 Daltons. Additional suitable hydrophilic moieties include, polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1, 3-dioxolane, poly-1,3,6-trioxane, ethylene/maleic anhydride copolymer, poly (beta-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

Hydrophilic moieties such as polyethylene glycol can be attached to the FGF21 based conjugates of the present disclosure under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

Acylation

In some embodiments, the FGF21 based conjugate is modified to comprise an acyl group. The acyl group can be covalently linked directly to an amino acid of the bioactive component of the conjugate (ie., the NHR ligand or the insulin component of conjugate), or indirectly to an amino acid of the NHR ligand or insulin peptide via a spacer, wherein the spacer is positioned between the amino acid of the bioactive component of the conjugate and the acyl group. The conjugate may be acylated at the same amino acid position where a hydrophilic moiety is linked, or at a different amino acid position. For example, acylation may occur at any position including any of amino acid of the conjugate, provided that the activity exhibited by the non-acylated conjugate is retained upon acylation.

In one specific aspect of the invention, an FGF21 based insulin conjugate is modified to comprise an acyl group by direct acylation of an amine, hydroxyl, or thiol of a side chain of an amino acid of the FGF21 based insulin conjugate. In some embodiments, the conjugate is directly acylated through the side chain amine, hydroxyl, or thiol of an amino acid. In some embodiments, acylation is at position B28 or B29 of the insulin moiety of the conjugate (according to the amino acid numbering of the native insulin A and B chain sequences). In this regard, an insulin analog can be provided that has been modified by one or more amino acid substitutions in the A or B chain sequence, including for example at positions A14, A15, B1, B2, B10, B22, B28 or B29 (according to the amino acid numbering of the native insulin A and B chain sequences) or at any position of the linking moiety with an amino acid comprising a side chain amine, hydroxyl, or thiol. In some specific embodiments of the invention, the direct acylation of the insulin peptide occurs through the side chain amine, hydroxyl, or thiol of the amino acid at position B28 or B29 (according to the amino acid numbering of the native insulin A and B chain sequences).

In accordance with one embodiment, the acylated conjugates comprise a spacer between the peptide and the acyl group. In some embodiments, the FGF21 based conjugate is covalently bound to the spacer, which is covalently bound to the acyl group. In some exemplary embodiments, the conjugate is modified to comprise an acyl group by acylation of an amine, hydroxyl, or thiol of a spacer, which spacer is attached to a side chain of an amino acid of the conjugate. The amino acid of the FGF21 based conjugate to which the spacer is attached can be any amino acid comprising a moiety which permits linkage to the spacer. For example, an amino acid comprising a side chain —NH$_2$, —OH, or —COOH (e.g., Lys, Orn, Ser, Asp, or Glu) is suitable.

In some embodiments, the spacer between the FGF21 based conjugate and the acyl group is an amino acid comprising a side chain amine, hydroxyl, or thiol (or a dipeptide or tripeptide comprising an amino acid comprising a side chain amine, hydroxyl, or thiol). In some embodiments, the spacer comprises a hydrophilic bifunctional spacer. In a specific embodiment, the spacer comprises an amino poly (alkyloxy)carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.). In one embodiment, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the FGF21 based conjugate and the acyl group is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the FGF21 based insulin conjugate can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), α-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), O-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O2)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO2)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), U-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4,-tetrahydro-isoquinoline-3-carboxylic acid (Tic), tetrahydropyranglycine, thienylalanine (Thi), U-Benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), 1-amino-1-cyclohexane carboxylic acid (Acx), aminovaleric acid, beta-cyclopropyl-alanine (Cpa), propargylglycine (Prg), allylglycine (Alg), 2-amino-2-cyclohexyl-propanoic acid (2-Cha), tertbutylglycine (Tbg), vinylglycine (Vg), 1-amino-1-cyclopropane carboxylic acid (Acp), 1-amino-1-cyclopentane carboxylic acid (Acpe), alkylated 3-mercaptopropionic acid, 1-amino-1-cyclobutane carboxylic acid (Acb). In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

The FGF21 based conjugate can be modified to comprise an acyl group by acylation of a long chain alkane of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

In some embodiments, an amine, hydroxyl, or thiol group of the FGF21 based conjugate is acylated with a cholesterol acid. In a specific embodiment, the peptide is linked to the cholesterol acid through an alkylated des-amino Cys spacer, i.e., an alkylated 3-mercaptopropionic acid spacer. Suitable methods of peptide acylation via amines, hydroxyls, and thiols are known in the art. See, for example, Miller, Biochem Biophys Res Commun 218: 377-382 (1996); Shimohigashi and Stammer, Int J Pept Protein Res 19: 54-62 (1982); and Previero et al., Biochim Biophys Acta 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated peptide the FGF21 based conjugate can be of any size, e.g., any length carbon chain, and can be linear or branched. In some specific embodiments of the invention, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

Alkylation

In some embodiments, the FGF21 based conjugate is modified to comprise an alkyl group. The alkyl group can be covalently linked directly to an amino acid of the conjugate analog, or indirectly to an amino acid of the FGF21 based conjugate via a spacer, wherein the spacer is positioned between the amino acid of the FGF21 based conjugate and the alkyl group. The alkyl group can be attached to the FGF21 based conjugate via an ether, thioether, or amino linkage. For example, the FGF21 based conjugate may be alkylated at the same amino acid position where a hydrophilic moiety is linked, or at a different amino acid position.

Alkylation can be carried out at any position within the FGF21 based conjugate, including for example in the C-terminal region of the B chain or at a position in the linking moiety, provided that FGF activity is retained. In a specific aspect of the invention, the FGF21 based conjugate is modified to comprise an alkyl group by direct alkylation of an amine, hydroxyl, or thiol of a side chain of an amino acid of the FGF21 based conjugate. In some embodiments, the FGF21 based conjugate is directly alkylated through the side chain amine, hydroxyl, or thiol of an amino acid. In some specific embodiments of the invention, the direct alkylation of an FGF21 based insulin conjugate occurs through the side chain amine, hydroxyl, or thiol of the amino acid at position A14, A15, B1 (for insulin based B chains), B2 (for IGF-1 based B chains), B10, B22, B28 or B29 (according to the amino acid numbering of the A and B chain of native insulin).

In some embodiments of the invention, the FGF21 based conjugate comprises a spacer between the peptide and the alkyl group. In some embodiments, the FGF21 based conjugate is covalently bound to the spacer, which is covalently bound to the alkyl group. In some exemplary embodiments, the FGF21 based conjugate is modified to comprise an alkyl group by alkylation of an amine, hydroxyl, or thiol of a spacer, wherein the spacer is attached to a side chain of an amino acid of the conjugate. The amino acid of the FGF21 based conjugate to which the spacer is attached can be any amino acid (e.g., a singly α-substituted amino acid or an α,α-disubstituted amino acid) comprising a moiety which permits linkage to the spacer. An amino acid of the FGF21 based conjugate comprising a side chain —$NH_2$, —OH, or —COOH (e.g., Lys, Orn, Ser, Asp, or Glu) is suitable. In some embodiments, the spacer between the peptide the FGF21 based conjugate and the alkyl group is an amino acid comprising a side chain amine, hydroxyl, or thiol or a dipeptide or tripeptide comprising an amino acid comprising a side chain amine, hydroxyl, or thiol.

In the instance in which the alpha amine is alkylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In exemplary embodiments, the spacer amino acid can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, 8-aminooctanoic acid. Alternatively, the spacer amino acid can be an acidic residue, e.g., Asp and Glu, provided that the alkylation occurs on the alpha amine of the acidic residue. In the instance in which the side chain amine of the spacer amino acid is alkylated, the spacer amino acid is an amino acid comprising a side chain amine, e.g., an amino acid of Formula I (e.g., Lys or Orn). In this instance, it is possible for both the alpha amine and the side chain amine of the spacer amino acid to be alkylated, such that the peptide is dialkylated. Embodiments of the invention include such dialkylated molecules.

In some embodiments, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer between peptide the FGF21 based conjugate and the alkyl group is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

The spacer (e.g., amino acid, dipeptide, tripeptide, hydrophilic bifunctional spacer, or hydrophobic bifunctional spacer) is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a $C_{12}$ to Cis alkyl group, e.g., $C_{14}$ alkyl group, $C_{16}$ alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments the length of the spacer and alkyl is 17 to 28 (e.g., 19 to 26, 19 to 21) atoms.

In accordance with one embodiment the bifunctional spacer is a synthetic or non-naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer attached to the FGF21 based conjugate can be composed of naturally-occurring and/or non-naturally occurring amino acids, including, for example, any of the amino acids taught herein. In some embodiments the spacer comprises an overall negative charge, e.g., comprises one or two negatively charged amino acids. In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu. In one embodiment the dipeptide spacer is γ-Glu-γ-Glu.

Suitable methods of peptide alkylation via amines, hydroxyls, and thiols are known in the art. For example, a Williamson ether synthesis can be used to form an ether linkage between the insulin peptide and the alkyl group. Also, a nucleophilic substitution reaction of the peptide with an alkyl halide can result in any of an ether, thioether, or amino linkage. The alkyl group of the alkylated peptide the FGF21 based conjugate can be of any size, e.g., any length carbon chain, and can be linear or branched. In some embodiments of the invention, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_2$ alkyl, $C_{22}$ alkyl, $C_{24}$ alkyl, $C_{26}$ alkyl, $C_{28}$ alkyl, or a $C_{30}$ alkyl. In some embodiments, the alkyl group is a $C_8$ to $C_{20}$ alkyl, e.g., a $C_{14}$ alkyl or a $C_{16}$ alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

When a long chain alkane is alkylated by the FGF21 based conjugate or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments the long chain alkane comprises a $C_8$ to $C_{20}$ alkane, e.g., a $C_{14}$ alkane, $C_{16}$ alkane, or a $C_{18}$ alkane.

Also, in some embodiments alkylation can occur between the insulin analog and a cholesterol moiety. For example, the hydroxyl group of cholesterol can displace a leaving group on the long chain alkane to form a cholesterol-insulin peptide product.

Self Cleaving Dipeptide Element

In accordance with one embodiment the insulin peptide of the conjugates disclosed herein are further modified to comprise a self cleaving dipeptide element. In one embodiment the dipeptide element comprises the structure U-J, wherein U is an amino acid or a hydroxyl acid and J is an N-alkylated amino acid. In one embodiment one or more dipeptide elements are linked to the FGF21 based insulin conjugate through an amide bond formed through one or more amino groups selected from the N-terminal amino group of the A or B chain of the insulin component, or the side chain amino group of an amino acid present in the conjugate. In accordance with one embodiment one or more dipeptide elements are linked to the FGF21 based insulin conjugate at an amino group selected from the N-terminal amino group of the conjugate, or the side chain amino group of an aromatic amine of a 4-amino-phenylalanine residue present at a position corresponding to position A19, B16 or B25 of native insulin, or a side chain of an amino acid of the linking moiety of a single chain insulin analog.

In one embodiment the dipeptide prodrug element comprises the general structure of Formula X:

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+)NH$_2$, ($C_0$-$C_4$ alkyl)($C_3$-$C_6$ cycloalkyl), ($C_0$-$C_4$ alkyl)($C_2$-$C_8$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_8$ heterocyclic), ($C_0$-$C_4$ alkyl)($C_6$-$C_{10}$ aryl)R$_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH. In one embodiment when the prodrug element is linked to the N-terminal amine of the FGF21 based insulin conjugate and $R_4$ and $R_3$ together with the atoms to which they are attached form a 4, 5 or 6 member heterocyclic ring, then at least one of $R_1$ and $R_2$ are other than H.

In one embodiment a complex is provided comprising the general structure A-B-Y A-B-(Q-L-Y), wherein Y represents any of the FGF21 analogs as described elsewhere in this disclosure, Q-L-Y comprises any of the conjugates as described elsewhere in this disclosure and A-B is a dipeptide that is linked via an amide bond to an amine of Y or the Q-L-Y conjugate. In one embodiment A-B is linked to amine present on the insulin peptide of an FGF21 analog insulin conjugate. In one embodiment A-B is linked to the N-terminal alpha amine of the A or B chain of the insulin peptide of the FGF21 analog conjugate.

In one embodiment the dipeptide A-B (having the structure of Formula IV) is covalently linked to the alpha amine of an FGF21 analog comprising the sequence of SEQ ID NO: 192, SEQ ID NO: 193, SEQ ID NO: 204, SEQ ID NO: 205, SEQ ID NO: 247, SEQ ID NO: 248, SEQ ID NO: 249, SEQ ID NO: 250, SEQ ID NO: 251 and SEQ ID NO: 252.

In one embodiment, a complex of the structure A-B-(Q-L-Y) is provided, wherein Q-L-Y comprises any of the structures as described elsewhere in this disclosure and wherein A is an amino acid or a hydroxy acid;

B is an N-alkylated amino acid linked to Q through an amide bond between a carboxyl moiety of B and an amine of Q; and A-B comprises the structure:

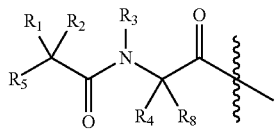

X

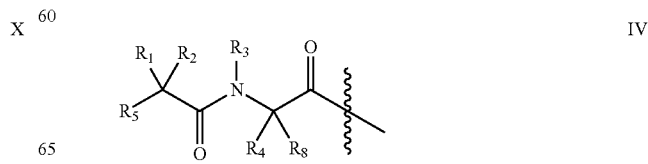

IV wherein
(a) $R^1$, $R^2$, $R^4$ and $R^8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+)NH$_2$, ($C_1$-$C_4$ alkyl)($C_3$-$C_6$ cycloalkyl), ($C_0$-$C_4$ alkyl)($C_2$-$C_8$ heterocyclic), ($C_0$-$C_4$ alkyl)($C_6$-$C_{10}$ aryl)$R^7$, ($C_1$-$C_4$ alkyl)($C_3$-$C_9$ heteroaryl), and $C_1$-$C_{12}$ alkyl(W1)$C_1$-$C_{12}$ alkyl, wherein W1 is a heteroatom selected from the group consisting of N, S and O, or
(ii) $R^1$ and $R^2$ together with the atoms to which they are attached form a $C_3$-$C_{12}$ cycloalkyl or aryl; or
(iii) $R^4$ and $R^8$ together with the atoms to which they are attached form a $C_3$-$C_6$ cycloalkyl;
(b) $R^3$ is selected from the group consisting of C1-C18 alkyl, (C1-C18 alkyl)OH, (C1-C18 alkyl)NH$_2$, (C1-C18 alkyl)SH, (C0-C4 alkyl)(C3-C6)cycloalkyl, (C0-C4 alkyl)(C2-C8 heterocyclic), (C0-C4 alkyl)(C6-C10 aryl)$R^7$, and (C1-C4 alkyl)(C3-C9 heteroaryl) or $R^4$ and $R^3$ together with the atoms to which they are attached form a 4, 5 or 6 member heterocyclic ring;
(c) $R^5$ is NHR$^6$ or OH;
(d) $R^6$ is H, $C_1$-$C_8$ alkyl; and
(e) $R^7$ is selected from the group consisting of H and OH wherein the chemical cleavage half-life ($t_{1/2}$) of A-B from Q or Y is at least about 1 hour to about 1 week in PBS under physiological conditions.

In a further embodiment, A-B comprises the structure:

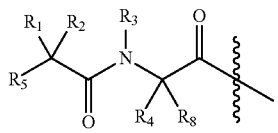

IV wherein
$R_1$ and $R_8$ are independently H or $C_1$-$C_8$ alkyl;
$R_2$ and $R_4$ are independently selected from the group consisting of H, $C_1$—C alkyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, and ($C_1$-$C_4$ alkyl)($C_6$ aryl)$R_7$;
$R_3$ is $C_1$-$C_6$ alkyl;
$R_5$ is NH$_2$; and
$R_7$ is selected from the group consisting of hydrogen, and OH.

In a further embodiment, A-B comprises the structure:

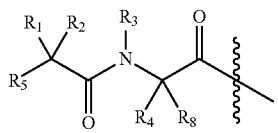

IV wherein
$R_1$ is H;
$R_2$ is H, $C_1$-$C_4$ alkyl, (CH$_2$ alkyl)OH, ($C_1$-$C_4$ alkyl)NH$_2$, or (CH$_2$)($C_6$ aryl)$R_7$;
$R_3$ is $C_1$-$C_6$ alkyl;
$R_4$ is H, $C_1$-$C_4$ alkyl, or (CH$_2$)($C_6$ aryl)$R_7$;
$R_8$ is NH$_2$;
$R_8$ is hydrogen; and
$R_7$ is H or OH.

In a further embodiment, A-B comprises the structure:

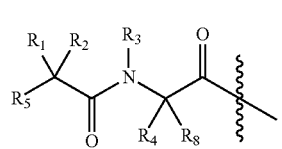

IV wherein
$R_1$ is H or $C_1$-$C_4$ alkyl;
$R_2$ is H, $C_1$-$C_4$ alkyl, or ($C_1$-$C_4$ alkyl)NH$_2$;
$R_3$ is $C_1$-$C_6$ alkyl;
$R_4$ is H, or $C_1$-$C_4$ alkyl;
$R_8$ is NH$_2$; and
$R_8$ is hydrogen.

Pharmaceutical compositions comprising the FGF21 based conjugates disclosed herein can be formulated and administered to patients using standard pharmaceutically acceptable carriers and routes of administration known to those skilled in the art. Accordingly, the present disclosure also encompasses pharmaceutical compositions comprising one or more of the FGF21 based conjugates disclosed herein or a pharmaceutically acceptable salt thereof, in combination with a pharmaceutically acceptable carrier. In one embodiment the pharmaceutical composition comprises a 1 mg/ml concentration of the FGF21 based conjugate at a pH of about 4.0 to about 7.0 in a phosphate buffer system. The pharmaceutical compositions may comprise the FGF21 based conjugate as the sole pharmaceutically active component, or the FGF21 based conjugate peptide can be combined with one or more additional active agents.

All therapeutic methods, pharmaceutical compositions, kits and other similar embodiments described herein contemplate that FGF21 based conjugate peptides include all pharmaceutically acceptable salts thereof.

In one embodiment the kit is provided with a device for administering the FGF21 based conjugate to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the FGF21 based conjugate composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

EXEMPLARY EMBODIMENTS

Embodiment 1

A peptide exhibiting antagonist activity against Klotho β, said peptide comprising an amino acid sequence of $$X_1X_2X_3X_4X_5SX_7DPX_{10}X_{11}X_{12}VX_{14}GX_{16}X_{17}X_{18}X_{19}RSPSX_{24}X_{25}X_{26},$$
(SEQ ID NO: 235)

wherein
$X_1$ is Pro or absent;
$X_2$ is Pro or Leu;
$X_3$ is Asp or Glu;
$X_4$ is Val or Thr;
$X_5$ is Gly, Asp, Phe, Leu or Ser;
$X_7$ is Ser or Met;
$X_{10}$ is Leu or Phe;
$X_{11}$ is Ser or Gly;
$X_{12}$ is Met or Leu;
$X_{14}$ is absent or Thr;
$X_{16}$ is Pro, Leu, Arg, Glu, or Gly;
$X_{17}$ is Ser or Glu;
$X_{18}$ is Gln or Ala;
$X_{19}$ is Gly or Val;
$X_{24}$ is Tyr or Phe;
$X_{25}$ is Ala or Glu; and
$X_{26}$ is an aliphatic amino acid selected from Gly, Ala, Val, Leu, Ser, or Ile, optionally comprising up to 5 further amino acid substitutions.

Embodiment 2

The peptide according to embodiment 1, wherein the peptide of SEQ ID NO: 235 comprises up to 4 further amino acid substitutions.

Embodiment 3

The peptide according to any one of the preceding embodiments wherein the peptide of SEQ ID NO: 235 comprises up to 3 further amino acid substitutions.

Embodiment 4

The peptide according to any one of the preceding embodiments wherein the peptide of SEQ ID NO: 235 comprises up to 2 further amino acid substitutions.

Embodiment 5

The peptide according to any one of the preceding embodiments wherein the peptide of SEQ ID NO: 235 comprises up to 1 further amino acid substitutions.

Embodiment 6

The peptide according to any one of the preceding embodiments comprising the sequence wherein $$X_1X_2X_3X_4X_5SX_7DPX_{10}X_{11}X_{12}VX_{14}GX_{16}X_{17}X_{18}X_{19}RSPSX_{24}X_{25}X_{26},$$
(SEQ ID NO: 235)

wherein
$X_1$ is Pro or absent;
$X_2$ is Pro or Leu;
$X_3$ is Asp or Glu;
$X_4$ is Val or Thr;
$X_5$ is Gly, Asp, Phe, Leu or Ser;
$X_7$ is Ser or Met;
$X_{10}$ is Leu or Phe;
$X_{11}$ is Ser or Gly;
$X_{12}$ is Met or Leu;
$X_{14}$ is absent or Thr;
$X_{16}$ is Pro, Leu, or Arg;
$X_{17}$ is Ser or Glu;
$X_{18}$ is Gln or Ala;
$X_{19}$ is Gly or Val;
$X_{24}$ is Tyr or Phe;
$X_{25}$ is Ala or Glu; and
$X_{26}$ is an aliphatic amino acid selected from Gly, Ala, Val, Leu, Ser, or Ile.

Embodiment 7

The peptide according to any one of the preceding embodiments comprising the sequence $$X_1X_2X_3X_4X_5SX_7DPX_{10}X_{11}X_{12}VX_{14}GX_{16}X_{17}X_{18}X_{19}RSPSX_{24}X_{25}A,$$
(SEQ ID NO: 236)

wherein
$X_1$ is Pro or absent;
$X_2$ is Pro or Leu;
$X_3$ is Asp or Glu;
$X_4$ is Val or Thr;
$X_5$ is Gly, Asp, Phe, Leu or Ser;
$X_7$ is Ser or Met;
$X_{10}$ is Leu or Phe;
$X_{11}$ is Ser or Gly;
$X_{12}$ is Met or Leu;
$X_{14}$ is absent or Thr;
$X_{16}$ is Pro, Leu, or Arg;
$X_{17}$ is Ser or Glu;
$X_{18}$ is Gln or Ala;
$X_{19}$ is Gly or Val;
$X_{24}$ is Tyr or Phe; and
$X_{25}$ is Ala or Glu.

Embodiment 8

The peptide according to any one of the preceding embodiments wherein $X_1$ is Pro.

Embodiment 9

The peptide according to any one of the preceding embodiments wherein $X_1$ is absent.

Embodiment 10

The peptide according to any one of the preceding embodiments wherein $X_2$ is Pro.

Embodiment 11

The peptide according to any one of the preceding embodiments wherein $X_2$ is Leu.

Embodiment 12

The peptide according to any one of the preceding embodiments wherein $X_3$ is Asp.

Embodiment 13

The peptide according to any one of the preceding embodiments wherein $X_3$ is Glu.

Embodiment 14

The peptide according to any one of the preceding embodiments wherein $X_4$ is Val.

Embodiment 15

The peptide according to any one of the preceding embodiments wherein $X_4$ is Thr.

Embodiment 16

The peptide according to any one of the preceding embodiments wherein $X_5$ is Gly.

Embodiment 17

The peptide according to any one of the preceding embodiments wherein $X_5$ is Asp.

Embodiment 18

The peptide according to any one of the preceding embodiments wherein $X_5$ is Phe.

Embodiment 19

The peptide according to any one of the preceding embodiments wherein $X_5$ is Leu.

Embodiment 20

The peptide according to any one of the preceding embodiments wherein $X_5$ is Ser.

Embodiment 21

The peptide according to any one of the preceding embodiments wherein $X_7$ is Ser.

Embodiment 22

The peptide according to any one of the preceding embodiments wherein $X_7$ is Met.

Embodiment 23

The peptide according to any one of the preceding embodiments wherein $X_{10}$ is Leu.

Embodiment 24

The peptide according to any one of the preceding embodiments wherein $X_{10}$ is Phe.

Embodiment 25

The peptide according to any one of the preceding embodiments wherein $X_{11}$ is Ser.

Embodiment 26

The peptide according to any one of the preceding embodiments wherein $X_{11}$ is Gly.

Embodiment 27

The peptide according to any one of the preceding embodiments wherein $X_{12}$ is Met.

Embodiment 28

The peptide according to any one of the preceding embodiments wherein $X_{12}$ is Leu.

Embodiment 29

The peptide according to any one of the preceding embodiments wherein $X_{14}$ is absent.

Embodiment 30

The peptide according to any one of the preceding embodiments wherein $X_{14}$ is Thr.

Embodiment 31

The peptide according to any one of the preceding embodiments wherein $X_{16}$ is Pro.

Embodiment 32

The peptide according to any one of the preceding embodiments wherein $X_{16}$ is Leu.

Embodiment 33

The peptide according to any one of the preceding embodiments wherein $X_{16}$ is Arg.

Embodiment 34

The peptide according to any one of the preceding embodiments wherein $X_{16}$ is Glu.

Embodiment 35

The peptide according to any one of the preceding embodiments wherein $X_{16}$ is Gly.

Embodiment 36

The peptide according to any one of the preceding embodiments wherein $X_{17}$ is Ser.

Embodiment 37

The peptide according to any one of the preceding embodiments wherein $X_{17}$ is Glu.

Embodiment 38

The peptide according to any one of the preceding embodiments wherein $X_{18}$ is Gln.

Embodiment 39

The peptide according to any one of the preceding embodiments wherein $X_{18}$ is Ala.

Embodiment 40

The peptide according to any one of the preceding embodiments wherein $X_{19}$ is Gly.

Embodiment 41

The peptide according to any one of the preceding embodiments wherein $X_{19}$ is Val.

Embodiment 42

The peptide according to any one of the preceding embodiments wherein $X_{24}$ is Tyr.

Embodiment 43

The peptide according to any one of the preceding embodiments wherein $X_{24}$ is Phe.

Embodiment 44

The peptide according to any one of the preceding embodiments wherein $X_{25}$ is Ala.

Embodiment 45

The peptide according to any one of the preceding embodiments wherein $X_{25}$ is Glu.

Embodiment 46

The peptide according to any one of the preceding embodiments wherein $X_{26}$ is Gly.

Embodiment 47

The peptide according to any one of the preceding embodiments wherein $X_{26}$ is Ala.

Embodiment 48

The peptide according to any one of the preceding embodiments wherein $X_{26}$ is Val.

Embodiment 49

The peptide according to any one of the preceding embodiments wherein $X_{26}$ is Leu.

Embodiment 50

The peptide according to any one of the preceding embodiments wherein $X_{26}$ is Ser.

Embodiment 51

The peptide according to any one of the preceding embodiments wherein $X_{26}$ is Ile.

Embodiment 52

The peptide according to any one of the preceding embodiments wherein
$X_1$ is Pro or absent;
$X_2$ is Pro or Leu;
$X_3$ is Asp or Glu;
$X_4$ is Val or Thr;
$X_5$ is Gly or Asp;
$X_7$ is Ser or Met;
$X_{10}$ is Leu or Phe;
$X_{11}$ is Ser or Gly;
$X_{12}$ is Met or Leu;
$X_{14}$ is absent or Thr;
$X_{16}$ is Pro or Leu;
$X_{17}$ is Ser or Glu;
$X_{18}$ is Gln or Ala;
$X_{19}$ is Gly or Val;
$X_{24}$ is Tyr or Phe; and
$X_{25}$ is Ala or Glu.

Embodiment 53

The peptide according to any one of the preceding embodiments wherein
$X_1$ is Pro;
$X_2$ is Pro;
$X_3$ is Asp;
$X_4$ is Val;
$X_{10}$ is Phe;
$X_{11}$ is Gly;
$X_{12}$ is Leu;
$X_{14}$ is absent;
$X_{16}$ is Pro;
$X_{17}$ is Ser;
$X_{18}$ is Gln;
$X_{19}$ is Gly;
$X_{24}$ is Phe and
$X_{25}$ is Glu.

Embodiment 54

The peptide according to any one of the preceding embodiments comprising a sequence selected from the group consisting of

```
                                    (SEQ ID NO: 180)
PPDVGSMDPFGLVGPSQGRSPSFEA, (0470; SEQ ID NO: 237)
PPDVGSMDPFGLVGRSQGRSPSFEA, (0480; SEQ ID NO: 238)
PPDVFSMDPFGLVGPSQGRSPSFEA, (0481; SEQ ID NO: 239)
PPDVLSMDPFGLVGPSQGRSPSFEA, (0482; SEQ ID NO: 240)
PPDVSSMDPFGLVGPSQGRSPSFEA, (0486; SEQ ID NO: 241)
PPDVGSSDPFGLVGPSQGRSPSFEA, (FGF21 C25; SEQ ID NO: 191)
PPDVGSSDPLSMVGPSQGRSPSYAA, (FGF19 A25; SEQ ID NO: 178)
PLETDSMDPFGLVTGLEAVRSPSFEA, (SEQ ID NO: 179)
PLETDSMDPFGLVGPSQGRSPSFEA, (SEQ ID NO: 182)
PPDVGSMDPFGLVTGLEAVRSPSYAA, (0435; SEQ ID NO: 184)
PPDVGSSDPLSMVTGLEAVRSPSFEA,
and (SEQ ID NO: 188)
LETDSMDPFGLVTGLEAVRSPSFEA.
```

Embodiment 55

The peptide according to any one of the preceding embodiments comprising a sequence selected from the group consisting of

```
                          (SEQ ID NO: 180)
PPDVGSMDPFGLVGPSQGRSPSFEA, (0470; SEQ ID NO: 237)
PPDVGSMDPFGLVGRSQGRSPSFEA, (0480; SEQ ID NO: 238)
PPDVFSMDPFGLVGPSQGRSPSFEA, (0481; SEQ ID NO: 239)
PPDVLSMDPFGLVGPSQGRSPSFEA, (0482; SEQ ID NO: 240)
PPDVSSMDPFGLVGPSQGRSPSFEA,
and (0486; SEQ ID NO: 241)
PPDVGSSDPFGLVGPSQGRSPSFEA.
```

Embodiment 56

The peptide according to any one of the preceding embodiments comprising a sequence selected from the group consisting of

```
                  (FGF19 A25; SEQ ID NO: 178)
PLETDSMDPFGLVTGLEAVRSPSFEA, (SEQ ID NO: 179)
PLETDSMDPFGLVGPSQGRSPSFEA,
and (SEQ ID NO: 188)
LETDSMDPFGLVTGLEAVRSPSFEA.
```

Embodiment 57

The peptide according to any one of the preceding embodiments comprising the sequence

```
                               (SEQ ID NO: 180)
PPDVG SMDPF GLVGP SQGRS PSPEA.
```

Embodiment 58

The peptide according to any one of the preceding embodiments comprising the sequence

```
                     (0470; SEQ ID NO: 237)
PPDVG SMDPF GLVGR SQGRS PSFEA.
```

Embodiment 59

The peptide according to any one of the preceding embodiments comprising the sequence

```
                     (0480; SEQ ID NO: 238)
PPDVF SMDPF GLVGP SQGRS PSFEA.
```

Embodiment 60

The peptide according to any one of the preceding embodiments comprising the sequence

```
                     (0481; SEQ ID NO: 239)
PPDVL SMDPF GLVGP SQGRS PSFEA.
```

Embodiment 61

The peptide according to any one of the preceding embodiments comprising the sequence

```
                     (0482; SEQ ID NO: 240)
PPDVS SMDPF GLVGP SQGRS PSFEA.
```

Embodiment 62

The peptide according to any one of the preceding embodiments comprising the sequence

```
                     (0486; SEQ ID NO: 241)
PPDVG SSDPF GLVGP SQGRS PSFEA.
```

Embodiment 63

The peptide according to any one of the preceding embodiments comprising the sequence

```
                  (FGF21 C25; SEQ ID NO: 191)
PPDVG SSDPL SMVGP SQGRS PSYAA.
```

Embodiment 64

The peptide according to any one of the preceding embodiments comprising the sequence

```
                  (FGF19 A25; SEQ ID NO: 178)
PLETD SMDPF GLVTG LEAVR SPSFE A.
```

Embodiment 65

The peptide according to any one of the preceding embodiments comprising the sequence

```
                               (SEQ ID NO: 179)
PLETD SMDPF GLVGP SQGRS PSFEA.
```

Embodiment 66

The peptide according to any one of the preceding embodiments comprising the sequence

```
                               (SEQ ID NO: 182)
PPDVG SMDPF GLVTG LEAVR SPSYA A.
```

Embodiment 67

The peptide according to any one of the preceding embodiments comprising the sequence

```
                         (0435; SEQ ID NO: 184)
PPDVGSSDPLSMVTGLEAVRSPSFE A.
```

Embodiment 68

The peptide according to any one of the preceding embodiments comprising the sequence

```
                              (SEQ ID NO: 188)
LETDS MDPFG LVTGL EAVRS PSFEA.
```

Embodiment 69

An FGF21 peptide comprising the structure of A-B wherein A is a peptide according to SEQ ID NO: 195, optionally comprising up to 10 further amino acid modifications, and B is a peptide of any one of embodiments 1 to 68.

Embodiment 70

The FGF21 peptide according to embodiment 69 wherein A optionally comprises up to 9 further amino acid modifications.

Embodiment 71

The FGF21 peptide according to embodiment 69 wherein A optionally comprises up to 8 further amino acid modifications.

Embodiment 72

The FGF21 peptide according to embodiment 69 wherein A optionally comprises up to 7 further amino acid modifications.

Embodiment 73

The FGF21 peptide according to embodiment 69 wherein A optionally comprises up to 6 further amino acid modifications.

Embodiment 74

The FGF21 peptide according to embodiment 69 wherein A optionally comprises up to 5 further amino acid modifications.

Embodiment 75

The FGF21 peptide according to embodiment 69 wherein A optionally comprises up to 4 further amino acid modifications.

Embodiment 76

The FGF21 peptide according to embodiment 69 wherein A optionally comprises up to 3 further amino acid modifications.

Embodiment 77

The FGF21 peptide according to embodiment 69 wherein A optionally comprises up to 2 further amino acid modifications.

Embodiment 78

The FGF21 peptide according to embodiment 69 wherein A optionally comprises 1 further amino acid modification.

Embodiment 79

The FGF21 peptide according to any one of embodiments 69 to 78 wherein A is a peptide according to SEQ ID NO: 194.

Embodiment 80

The FGF21 peptide according to any one of embodiments 69 to 78 wherein A comprises one or more of amino acid modifications A31C, G43C, L98D, L100K, N121D, and/or D127K.

Embodiment 81

The FGF21 peptide according to any one of embodiments 69 to 78 wherein A comprises the amino acid modifications A31C, G43C, L98D, L100K, N121D, and D127K (SEQ ID NO: 196).

Embodiment 82

The FGF21 peptide according to any one of embodiments 69 to 78 wherein A is a peptide according to SEQ ID NO: 195.

Embodiment 83

The FGF21 peptide according to any one of embodiments 69 to 78 wherein A is a peptide according to SEQ ID NO: 195 and B is selected from the list consisting of

```
                                   (SEQ ID NO: 180)
    PPDVG SMDPF GLVGP SQGRS PSFEA (0470; SEQ ID NO: 237)
    PPDVG SMDPF GLVGR SQGRS PSFEA, (0480; SEQ ID NO: 238)
    PPDVF SMDPF GLVGP SQGRS PSFEA, (0481; SEQ ID NO: 239)
    PPDVL SMDPF GLVGP SQGRS PSFEA, (0482; SEQ ID NO: 240)
    PPDVS SMDPF GLVGP SQGRS PSFEA, (0486; SEQ ID NO: 241)
    PPDVG SSDPF GLVGP SQGRS PSFEA, (FGF21 C25; SEQ ID NO: 191)
    PPDVG SSDPL SMVGP SQGRS PSYAA, (FGF19 A25; SEQ ID NO: 178)
    PLETD SMDPF GLVTG LEAVR SPSFE A,
```

-continued

```
                            (SEQ ID NO: 179)
PLETD SMDPF GLVGP SQGRS PSFEA, (SEQ ID NO: 182)
PPDVG SMDPF GLVTG LEAVR SPSYA A, (0435; SEQ ID NO: 184)
PPDVG SSDPL SMVTG LEAVR SPSFE A,
and (SEQ ID NO: 188)
LETDS MDPFG LVTGL EAVRS PSFEA.
```

Embodiment 84

The FGF21 peptide according to any one of embodiments 69 to 78 wherein A is a peptide according to SEQ ID NO: 195 and B is selected from the group consisting of

```
                            (SEQ ID NO: 180)
PPDVG SMDPF GLVGP SQGRS PSFEA, (0470; SEQ ID NO: 237)
PPDVG SMDPF GLVGR SQGRS PSFEA, (0480; SEQ ID NO: 238)
PPDVF SMDPF GLVGP SQGRS PSFEA, (0481; SEQ ID NO: 239)
PPDVL SMDPF GLVGP SQGRS PSFEA, (0482; SEQ ID NO: 240)
PPDVS SMDPF GLVGP SQGRS PSFEA,
and (0486; SEQ ID NO: 241)
PPDVG SSDPF GLVGP SQGRS PSFEA.
```

Embodiment 85

The FGF21 peptide according to any one of embodiments 69 to 78 wherein
A is a peptide according to SEQ ID NO: 195 and
B is selected from the group consisting of

```
                      (FGF19 A25; SEQ ID NO: 178)
PLETD SMDPF GLVTG LEAVR SPSFE A (0430; SEQ ID NO: 179)
PLETDSMDPFGLVGPSQGRSPSFEA (SEQ ID NO: 188)
LETDS MDPFG LVTGL EAVRS PSFEA
```

Embodiment 86

The FGF21 peptide according to any one of embodiments 69 to 78 wherein
A is a peptide according to SEQ ID NO: 195 and
B is LETDS MDPFG LVTGL EAVRS PSFEA (SEQ ID NO: 188).

Embodiment 87

The FGF21 peptide according to any one of embodiments 69 to 78 wherein
A is a peptide according to SEQ ID NO: 196 and
B is selected from the list consisting of

```
                            (SEQ ID NO: 180)
PPDVG SMDPF GLVGP SQGRS PSFEA (0470; SEQ ID NO: 237)
PPDVG SMDPF GLVGR SQGRS PSFEA, (0480; SEQ ID NO: 238)
PPDVF SMDPF GLVGP SQGRS PSFEA, (0481; SEQ ID NO: 239)
PPDVL SMDPF GLVGP SQGRS PSFEA, (0482; SEQ ID NO: 240)
PPDVS SMDPF GLVGP SQGRS PSFEA, (0486; SEQ ID NO: 241)
PPDVG SSDPF GLVGP SQGRS PSFEA, (FGF21 C25; SEQ ID NO: 191)
PPDVG SSDPL SMVGP SQGRS PSYAA, (FGF19 A25; SEQ ID NO: 178)
PLETD SMDPF GLVTG LEAVR SPSFE A, (SEQ ID NO: 179)
PLETD SMDPF GLVGP SQGRS PSFEA, (SEQ ID NO: 182)
PPDVG SMDPF GLVTG LEAVR SPSYA A, (0435; SEQ ID NO: 184)
PPDVG SSDPL SMVTG LEAVR SPSFE A,
and (SEQ ID NO: 188)
LETDS MDPFG LVTGL EAVRS PSFEA
```

Embodiment 88

The FGF21 peptide according to any one of embodiments 69 to 78 wherein
A is a peptide according to SEQ ID NO: 196 and
B is selected from the group consisting of

```
                            (SEQ ID NO: 180)
PPDVG SMDPF GLVGP SQGRS PSFEA (0470; SEQ ID NO: 237)
PPDVG SMDPF GLVGR SQGRS PSFEA, (0480; SEQ ID NO: 238)
PPDVF SMDPF GLVGP SQGRS PSFEA, (0481; SEQ ID NO: 239)
PPDVL SMDPF GLVGP SQGRS PSFEA, (0482; SEQ ID NO: 240)
PPDVS SMDPF GLVGP SQGRS PSFEA,
and (0486; SEQ ID NO: 241)
PPDVG SSDPF GLVGP SQGRS PSFEA.
```

Embodiment 89

The FGF21 peptide according to any one of embodiments 69 to 78 wherein
A is a peptide according to SEQ ID NO: 196 and
B is selected from the group consisting of

```
                    (FGF19 A25; SEQ ID NO: 178)
PLETD SMDPF GLVTG LEAVR SPSFE A, (SEQ ID NO: 179)
PLETD SMDPF GLVGP SQGRS PSFEA,
and (SEQ ID NO: 188)
LETDS MDPFG LVTGL EAVRS PSFEA.
```

Embodiment 90

The FGF21 peptide according to any one of embodiments 69 to 78 wherein
A is a peptide according to SEQ ID NO: 196 and
B is LETDS MDPFG LVTGL EAVRS PSFEA (SEQ ID NO: 188).

Embodiment 91

The FGF21 peptide according to any one of embodiments 69 to 90 wherein the peptide consists of SEQ ID NO: 192.

Embodiment 92

The FGF21 peptide according to any one of embodiments 69 to 90 wherein the peptide consists of SEQ ID NO: 193.

Embodiment 93

The FGF21 peptide according to any one of embodiments 69 to 90 wherein the peptide consists of SEQ ID NO: 206.

Embodiment 94

The FGF21 peptide according to any one of embodiments 69 to 90 wherein the peptide consists of SEQ ID NO: 207.

Embodiment 95

The FGF21 peptide according to any one of embodiments 69 to 90 wherein the peptide consists of SEQ ID NO: 208.

Embodiment 96

The FGF21 peptide according to any one of embodiments 69 to 90 wherein the peptide consists of SEQ ID NO: 209.

Embodiment 97

The FGF21 peptide according to any one of embodiments 69 to 90 wherein the peptide consists of the sequence

```
                          (0470; SEQ ID NO: 242)
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLK
EDGYNVYQSEAHGLPLHLPGDKSPHRKPAPRGPARFLPLPGLPPALPEPP
GILAPQPPDVGSMDPFGLVGRSQGRSPSFEA.
```

Embodiment 98

The FGF21 peptide according to any one of embodiments 69 to 90 wherein the peptide consists of the sequence

```
                          (0480; SEQ ID NO: 243)
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLK
EDGYNVYQSEAHGLPLHLPGDKSPHRKPAPRGPARFLPLPGLPPALPEPP
GILAPQPPDVFSMDPFGLVGPSQGRSPSFEA.
```

Embodiment 99

The FGF21 peptide according to any one of embodiments 69 to 90 wherein the peptide consists of the sequence

```
                          (0481; SEQ ID NO: 244)
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLK
EDGYNVYQSEAHGLPLHLPGDKSPHRKPAPRGPARFLPLPGLPPALPEPP
GILAPQPPDVLSMDPFGLVGPSQGRSPSFEA.
```

Embodiment 100

The FGF21 peptide according to any one of embodiments 69 to 90 wherein the peptide consists of the sequence

```
                          (0482; SEQ ID NO: 245)
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLK
EDGYNVYQSEAHGLPLHLPGDKSPHRKPAPRGPARFLPLPGLPPALPEPP
GILAPQPPDVSSMDPFGLVGPSQGRSPSFEA.
```

Embodiment 101

The FGF21 peptide according to any one of embodiments 69 to 90 wherein the peptide consists of the sequence

```
                          (0486; SEQ ID NO: 246)
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLK
EDGYNVYQSEAHGLPLHLPGDKSPHRKPAPRGPARFLPLPGLPPALPEPP
GILAPQPPDVGSSDPFGLVGPSQGRSPSFEA.
```

Embodiment 102

A pharmaceutical composition comprising the FGF21 peptide according to any one of embodiments 69 to 101 and pharmaceutically acceptable excipient.

Embodiment 103

The FGF21 peptide according to any one of embodiments 69 to 101 for use as a medicament.

Embodiment 104

The FGF21 peptide according to any one of embodiments 69 to 101 for use in the treatment of diabetes.

Embodiment 105

The FGF21 peptide according to any one of embodiments 69 to 101 for use in the treatment of obesity.

Embodiment 106

The FGF21 peptide according to any one of embodiments 69 to 101 for use in reducing weight gain and inducing weight loss.

Example 1

Fibroblast growth factor-21 (FGF21) has been intensively studied as a metabolic hormone with a particular interest in its therapeutic potential. At the cellular level, FGF21 interacts with a complex of fibroblast growth factor receptor (FGFR) and a tissue specific co-receptor Klotho β (KLB). The N- and C-termini of FGF21 are vital for effective biochemical signaling. The deletion of the seventeen N-terminal residues of FGF21 (FGF21 18-181) inactivates the molecule to generate a competitive antagonist of the native hormone. Here, we have demonstrated that the C-terminal fragment of FGF21 as well as FGF19 are capable of fully antagonizing the native FGF21 in vitro signaling.

Materials & Methods
Protein Synthesis:

The human FGF21 or FGF19 gene sequence was inserted in modified expression pET21b vector containing yeast small ubiquitin-like modifier (SUMO) sequence after 6×His tag, using In-Fusion HD EcoDry Cloning Plus kit. For the generation of point mutant analogs, corresponding primers were obtained from Integrated DNA technologies and mutagenesis was performed by standard PCR method. E. coli OrigamiB(DE3) cells were transformed with modified pET vector containing the gene of interest fused to a $His_6$-sumo tag. FGF21 protein expression was induced overnight and the cells were harvested. The soluble whole cell lysate was applied to a nickel affinity chromatography column for enrichment of the desired protein. Subsequently, the tag was cleaved and pure protein was obtained by anion exchange chromatography.

Cell Culture:

Cells were cultured in 10% Fetal Bovine Serum containing DMEM High glucose GLUTAMAX® at 37 C, 95% humidity, 5% $CO_2$. For generating the cell line with stable expression, human KLB gene was synthesized by Genscript and subcloned into pcDNA3.1(+) with ZEOCIN® resistance vector (INVITROGEN®) by NheI and NotI restriction enzyme sites. HEK 293T cells were obtained from ATCC and were transiently transfected at 80% confluency using Lipofectamine 3000 (Invitrogen). Selection for KLB-expressing cells was initiated 48 hours post-transfection in the growth media containing 100 µg/ml of ZEOCIN® (Gibco) and continued for 4 weeks with fresh media added every third day. Human KLB expression in pooled cells was confirmed by Western blot and a functional FGF21 MAPK phosphorylation assay.

Erk1/2 Phosphorylation Assay:

293 HEK cells expressing hKLB were plated to 90% confluency in 96 well plates coated with poly-D-Lysine. Cells were serum starved for three hours in 0.1% BSA containing media prior to stimulation with protein and/or an antagonist peptide for ten minutes at 37° C. The cell lysate was used for the detection of phospho-Erk1/2 levels by AlphaSureFire kit using the prescribed protocol. The degree of biochemical activation was recorded and analyzed using Origin software by logistic curve fitting. Tests at each concentration were done in triplicates, and the standard deviation is as shown in the graphs. The calculation of maximal activities was done keeping the FGF21 157-181 or FGF19 169-194 peptide activity as standard. The difference between the Erk1/2 phosphorylation signal for the highest (10 µM) and the lowest (0 µM) tested dose for native peptide was considered as 100% and accordingly all the other values were assigned.

Peptide Synthesis:

Synthesis was achieved using a Chemmatrix Rink amide resin using an automated ABI433A or Symphony peptide synthesizer that employed Fmoc/HOBT/DIC coupling protocols. The peptides were cleaved from the solid-support using $TFA/TIS/H_2O$ (95:2.5:2.5) for two hours. Following ether precipitation the peptide was solubilized in 20% $CH_3CN$ and lyophilized. These peptides were purified by Waters Symmetry Preparative C8 column with a linear gradient from aqueous CAN in 0.1% TFA. The purity within the set of site-specific alanine mutated peptides was assessed by LCMS and concentrations were adjusted accordingly for the in vitro assay.

Circular Dichroism:

The CD properties of FGF-proteins were recorded using a Jasco J-715 instrument. The mean residue ellipticity was calculated and plotted as a function of wavelength using Origin software.

Results

Figure 2:
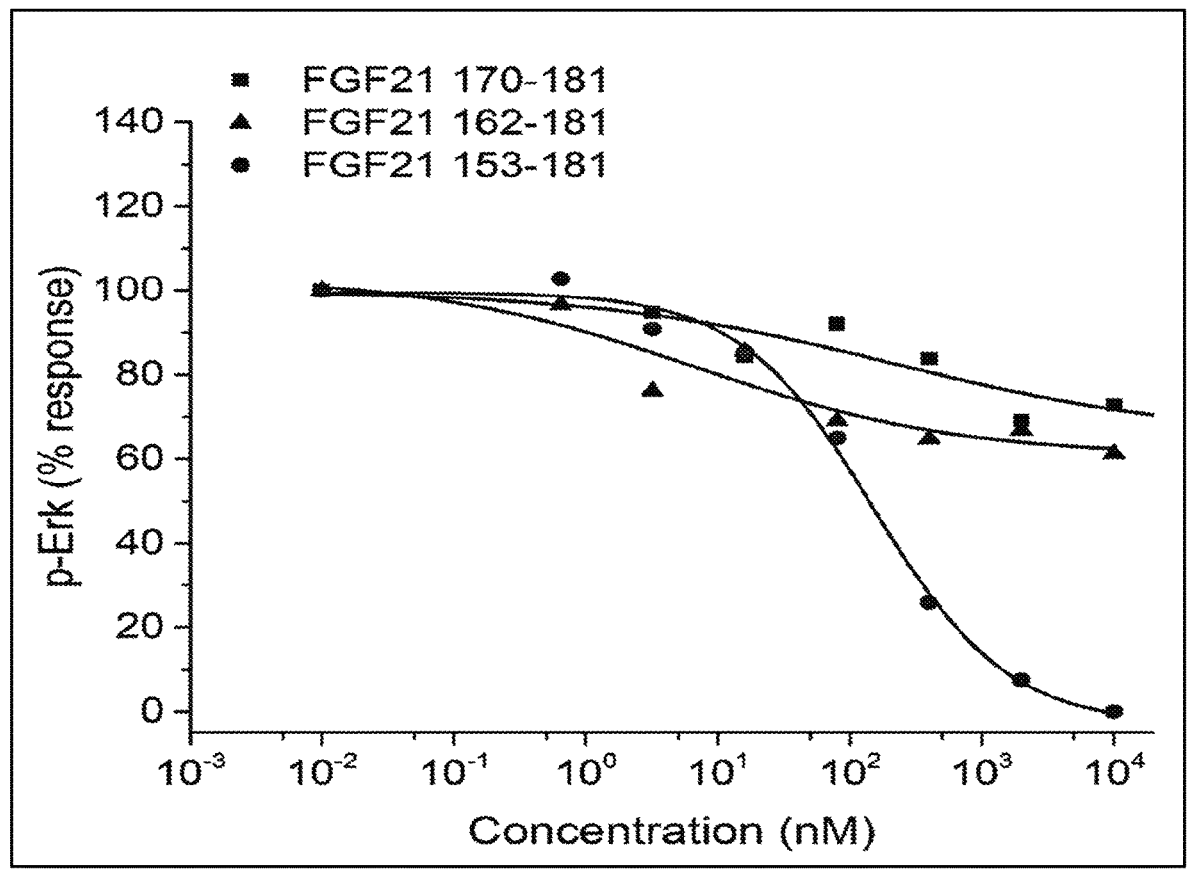
FIG. 2 is a graph comparing the ability of varying lengths of C-terminal peptides of FGF21 to antagonize to FGF21 activity (10 nM stimulation) in 293 HEK hKLB cells. The results demonstrate a terminal fragment of greater than 20 amino acids is required for antagonism of FGF21 activity.

We observed that the C-terminal portion of FGF 19 or 21 can antagonize native FGF21 signaling in similar fashion to the known, and much longer fragment 18-181. (see FIG. 1). The minimum effective length for FGF21 antagonism was determined to be 25 amino acids, representing residues 157-181 of the FGF21 protein (SEQ ID NO: 2), see the data presented in FIGS. 2 & 3A. The corresponding 26 residues of FGF19 (169-194) (FIG. 3B) were sufficient in replicating the effect that FGF21 18-181 elicits in vitro. Both FGF21 and FGF19 C-terminal peptides were equally effective antagonists of FGF21 activity, suggesting that these peptides interact with the receptor complex with same ability. Peptides shorter than 23 amino acids in length were found to be non-functional. A representative example of non-functional smaller fragments is demonstrated by the FGF21 162-181 peptide (FIG. 2). FGF21 159-181 peptide (23-amino acid) demonstrated weak antagonism and further extension by one residue to FGF21 160-181 peptide (24-amino acid) dramatically improved its antagonistic potential, attaining the optimal performance at 25-amino acid length. Peptides beyond the 25-mer were equally effective antagonists, not better, hence all further analyses were carried out with the 25-mer peptide as the standard. It was confirmed that the phenomenon was KLB-receptor complex specific, since these peptides could not antagonize FGF1 activity in a similar setup for FGF23 in KL-expressing cells.

Figure 3A:
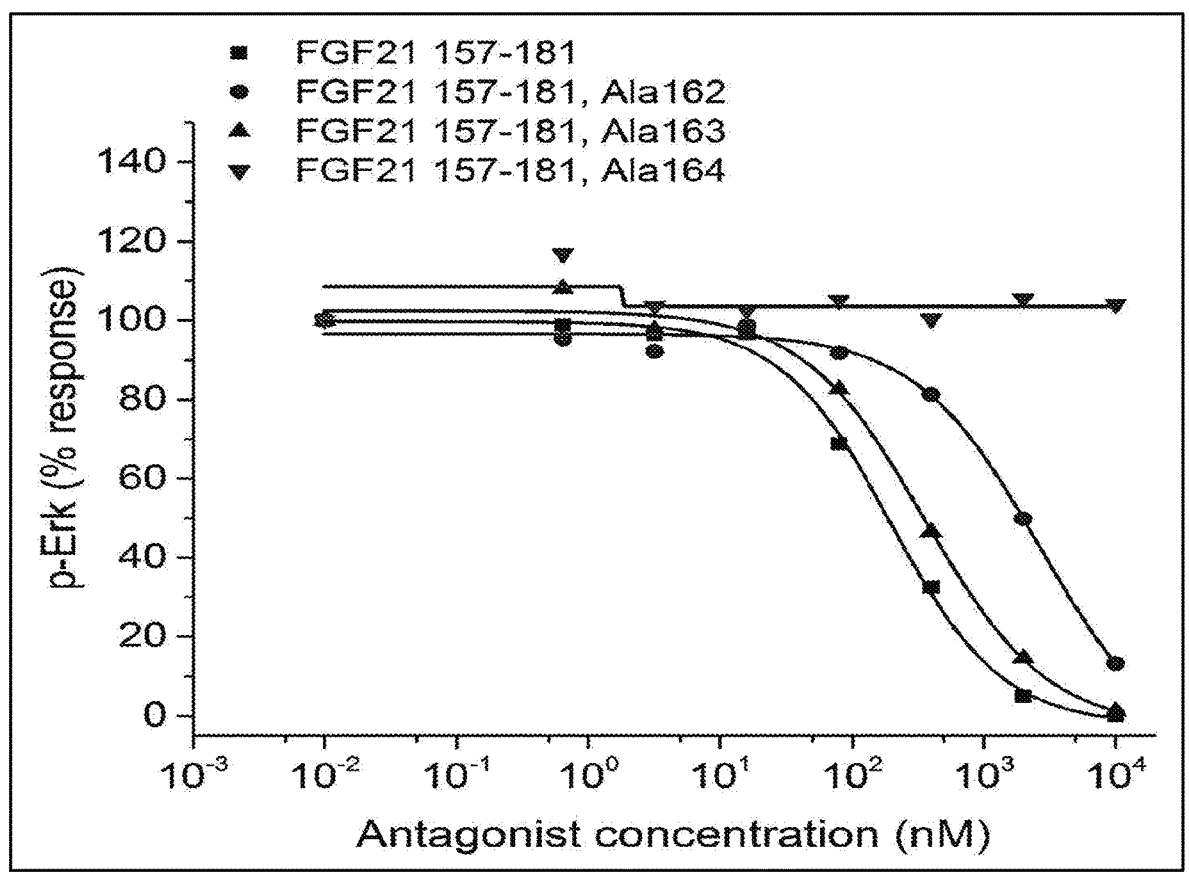
FIGS. 3A & 3B are graphs demonstrating that the C-terminal 25 amino acid fragment of FGF21 (FIG. 3A) or FGF19 (FIG. 3B) is sufficient for antagonism of FGF21 activity. Also provided is the activity of various alanine-mutated peptides of FGF21 157-181 as antagonists to FGF21 activity (FIG. 3A).
Figure 3B:
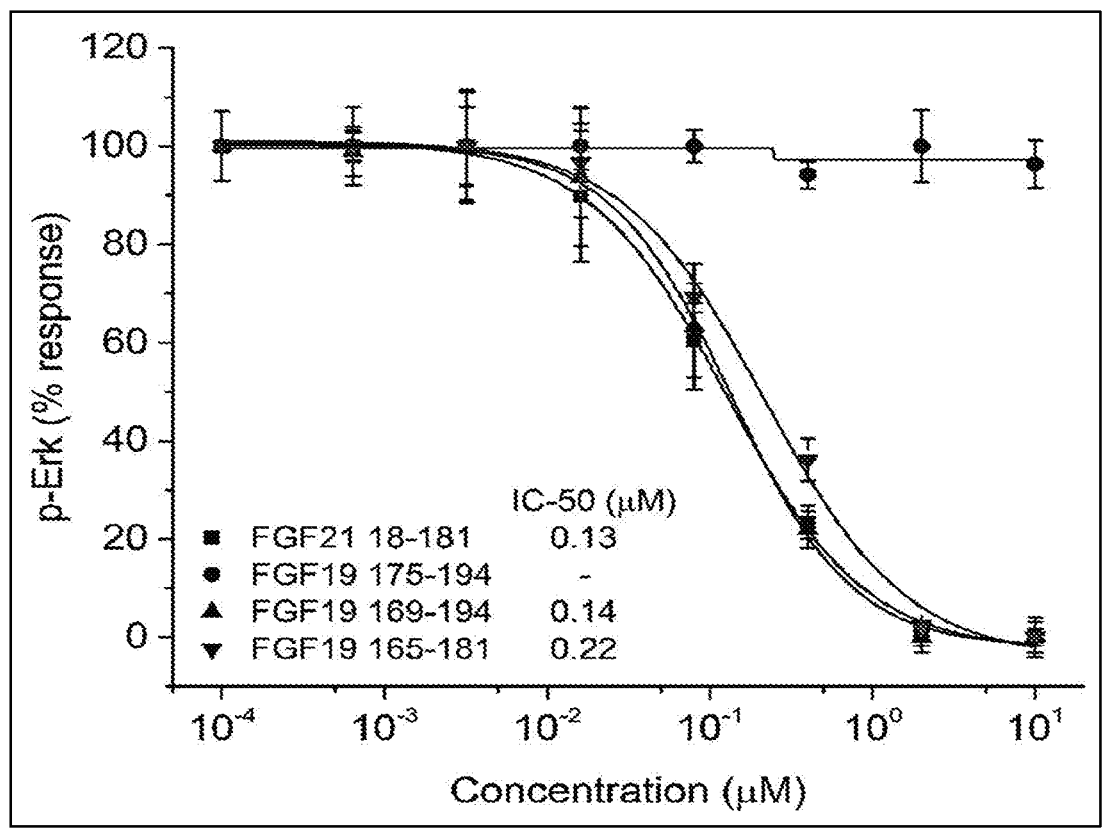
Figure 4:
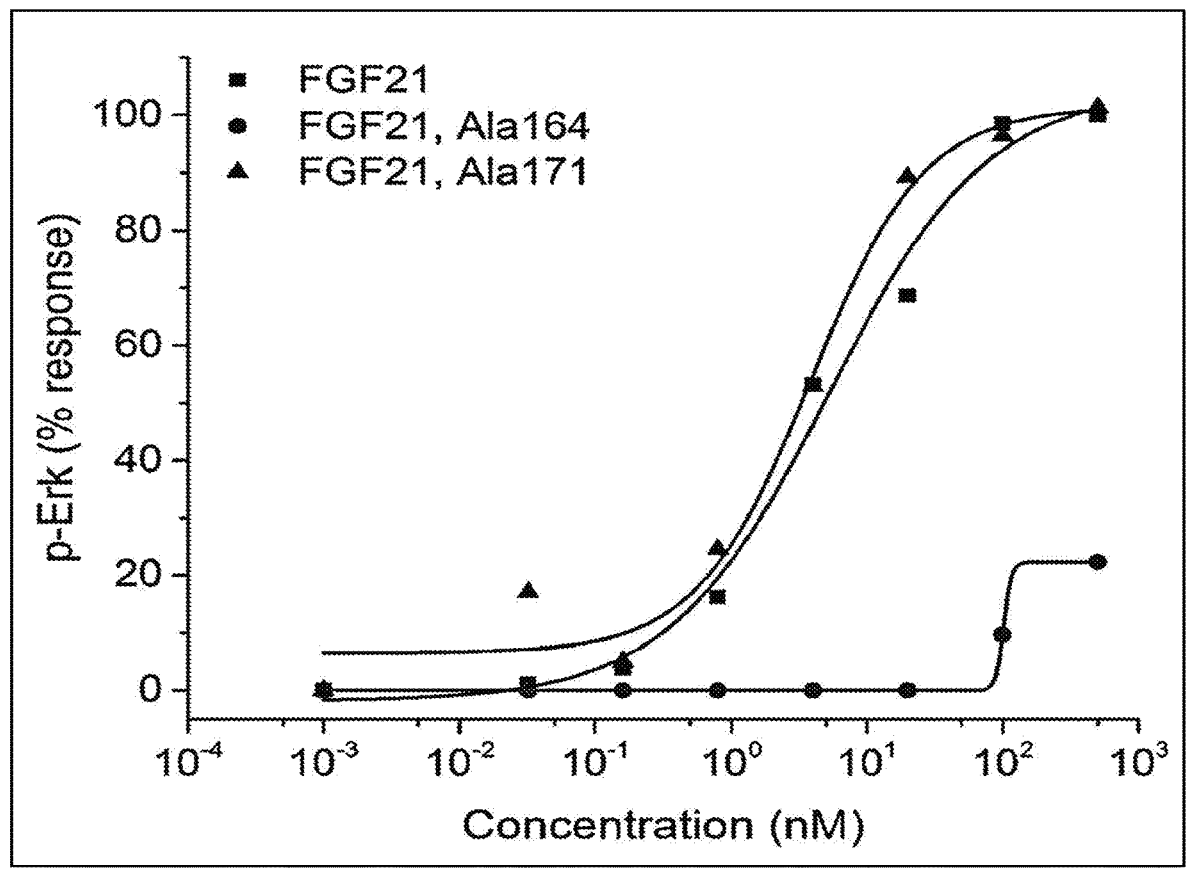
FIG. 4 is a graph presenting data for FGF21 analogs with alanine mutations at positions 164 and 171 compared to native FGF21 activity. Alanine substitution at position 164 was found to significantly impact FGF21 activity.

To gain more insight into the specific amino acid requirements for each peptide antagonist, we performed a complete alanine scan of the FGF21 157-181 peptide and identified several sites with significantly altered antagonistic activity (FIGS. 3A & 4). More particularly, Table 1 provides a summary of the complete alanine scan of FGF21 157-181 and FGF19 169-194 peptide sequences. Each peptide was tested for its ability to antagonize native FGF21 response by measuring the change in phosphorylation status of Erk1/2. The efficacy of each peptide is represented as % maximal activity, with native sequence attaining 100% response.

Table 2(A) lists a subset of peptides that achieve 95% or greater maximal activity. Table 2(B) lists a subset of peptides that were not able to achieve a full response shown with their corresponding % maximal activity. NC: Not calculated by the logistic curve fitting used. The peptides of Group A in Table 2(A) depicts the set of peptides that showed complete antagonism to the native FGF21 signaling and thus represent amino acids positions that were tolerant to the individual alanine substitutions, with some having marginally improved or worse potencies with one exception; FGF19 169-194 K194A. Group B in Table 2(B) represents the peptides had a profound deleterious impact on their antagonistic ability, such that they were unable to achieve full antagonist response to native FGF21. The listed peptides of Table 2(B) were significantly weaker antagonists or inactive (maximal activity <95% and/or TC-50 values >1 µM).

TABLE 1

Alanine Scan of FGF21 25mer

| Peptide | Modification | IC-50 (nM) | % max activity |
| --- | --- | --- | --- |
| PPDVG SSDPL SMVGP SQGRS PSYAS (SEQ ID NO: 191) | C25 | 168 ± 83 | 100.0 |
| APDVG SSDPL SMVGP SQGRS PSYAS (SEQ ID NO: 210) | A1 | 33.0 | 100 |
| PADVG SSDPL SMVGP SQGRS PSYAS (SEQ ID NO: 211) | A2 | 137.3 | 98.5 |
| PPAVG SSDPL SMVGP SQGRS PSYAS (SEQ ID NO: 212) | A3 | 2283.2 | 87.8 |
| PPDAG SSDPL SMVGP SQGRS PSYAS (SEQ ID NO: 213) | A4 | 5926.4 | 63.6 |
| PPDVA SSDPL SMVGP SQGRS PSYAS (SEQ ID NO: 214) | A5 | 90.1 | 102.5 |
| PPDVG ASDPL SMVGP SQGRS PSYAS (SEQ ID NO: 215) | A6 | 2647.4 | 89.2 |
| PPDVG SADPL SMVGP SQGRS PSYAS (SEQ ID NO: 216) | A7 | 359.2 | 94.5 |
| PPDVG SSAPL SMVGP SQGRS PSYAS (SEQ ID NO: 217) | A8 | — | — |
| PPDVG SSAPL SMVGP SQGRS PSYAS (SEQ ID NO: 218) | A9 | — | — |
| PPDVG SSDPA SMVGP SQGRS PSYAS (SEQ ID NO: 219) | A10 | 3315.9 | 76.0 |
| PPDVG SSDPL AMVGP SQGRS PSYAS (SEQ ID NO: 220) | A11 | 101.6 | 98.0 |
| PPDVG SSDPL SAVGP SQGRS PSYAS (SEQ ID NO: 221) | A12 | — | — |
| PPDVG SSDPL SMAGP SQGRS PSYAS (SEQ ID NO: 222) | A13 | 2106.1 | 87.9 |
| PPDVG SSDPL SMVAP SQGRS PSYAS (SEQ ID NO: 223) | A14 | 135.6 | 97.7 |
| PPDVG SSDPL SMVGA SQGRS PSYAS (SEQ ID NO: 224) | A15 | 134.3 | 93.9 |
| PPDVG SSDPL SMVGP AQGRS PSYAS (SEQ ID NO: 225) | A16 | 120.3 | 101.4 |
| PPDVG SSDPL SMVGP SAGRS PSYAS (SEQ ID NO: 226) | A17 | 138.9 | 99.7 |
| PPDVG SSDPL SMVGP SQARS PSYAS (SEQ ID NO: 227) | A18 | 139.0 | 102.9 |
| PPDVG SSDPL SMVGP SQGAS PSYAS (SEQ ID NO: 228) | A19 | 102.1 | 100.1 |
| PPDVG SSDPL SMVGP SQGRA PSYAS (SEQ ID NO: 229) | A20 | 3228.4 | 73.5 |
| PPDVG SSDPL SMVGP SQGRS ASYAS (SEQ ID NO: 230) | A21 | 2242.5 | 70.5 |
| PPDVG SSDPL SMVGP SQGRS PAYAS (SEQ ID NO: 231) | A22 | 752.1 | 78.5 |
| PPDVG SSDPL SMVGP SQGRS PSAAS (SEQ ID NO: 232) | A23 | 3984.2 | 73.6 |
| PPDVG SSDPL SMVGP SQGRS PSYAA (SEQ ID NO: 233) | A25 | 45.0 | 99.0 |

TABLE 2(A)

≥95% Maximal activity

| FGF21 | | FGF19 | |
|---|---|---|---|
| Position | IC-50 (μM) | Position | IC-50 (μM) |
| WT | 0.16 ± 0.05 | WT | 0.27 ± 0.09 |
| P157 | 0.39 | P169 | 0.21 |
| P158 | 0.62 | E171 | 0.12 |
| G161 | 0.09 | D173 | 0.46 |
| S163 | 0.36 | M175 | 0.15 |
| S167 | 0.15 | T182 | 0.52 |
| G170 | 0.13 | G183 | 0.40 |
| P171 | 0.12 | L184 | 0.20 |
| S172 | 0.11 | E185 | 0.43 |
| Q173 | 0.13 | V187 | 0.69 |
| G174 | 0.15 | R188 | 0.38 |
| R175 | 0.10 | E193 | 0.85 |
| S181 | 0.06 | K194 | 0.005 |

TABLE 2(B)

<95% Maximal activity

| FGF21 | | FGF19 | |
|---|---|---|---|
| Position | IC-50 (μM) | Position | IC-50 (μM) |
| D159 | 1.50 | L170 | 2.17 |
| V160 | 2.69 | T172 | 1.40 |
| S162 | 2.44 | S174 | 3.39 |
| D164 | NC | D176 | NC |
| P165 | NC | P177 | NC |
| L166 | 2.75 | F178 | NC |
| M168 | NC | G179 | 1.93 |
| V169 | 4.60 | L180 | NC |
| S176 | 2.21 | V181 | 1.81 |
| P177 | 2.57 | S189 | >2.00 |
| S178 | 0.67 | P190 | >2.00 |
| Y179 | 4.16 | S191 | >2.00 |
| | | F192 | 2.97 |

Figure 7A:
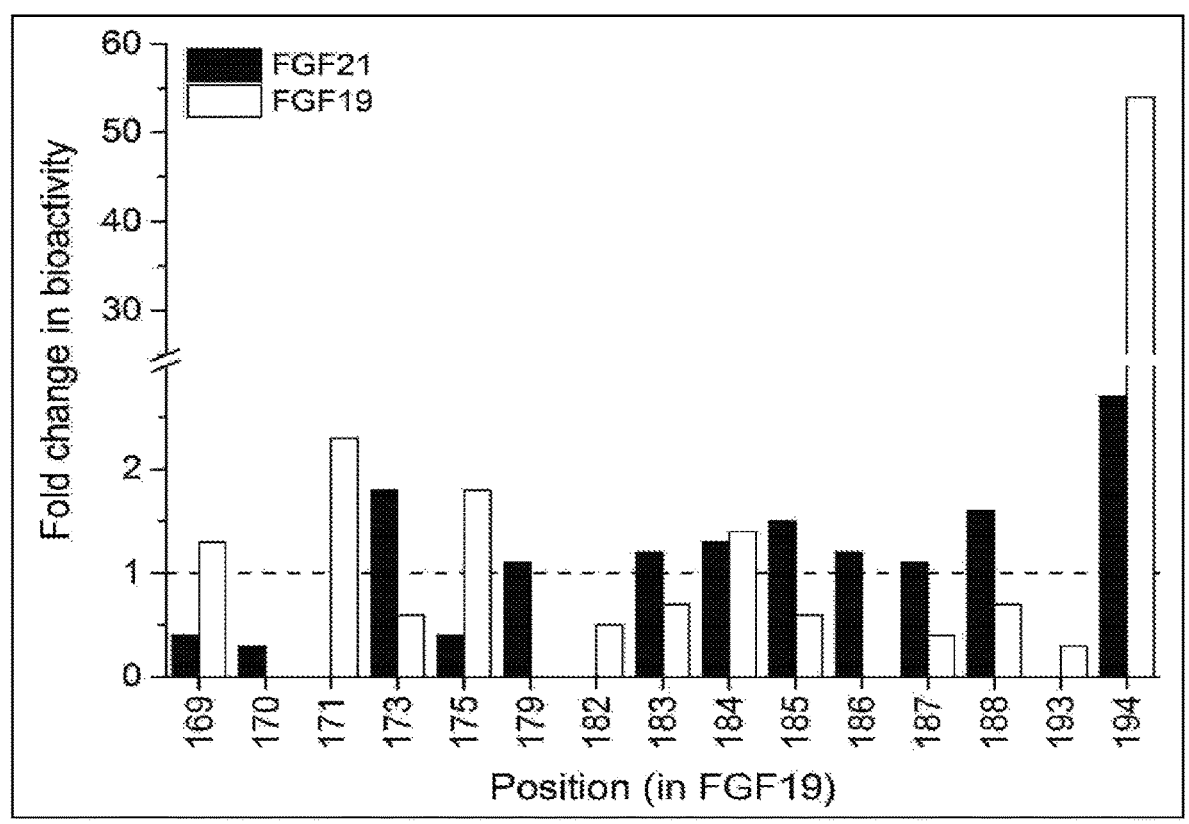
FIGS. 7A-7C provided data regarding the bioactivity of FGF21 157-181 or FGF19 169-194 alanine scan mutation analogs.
Figure 7B:
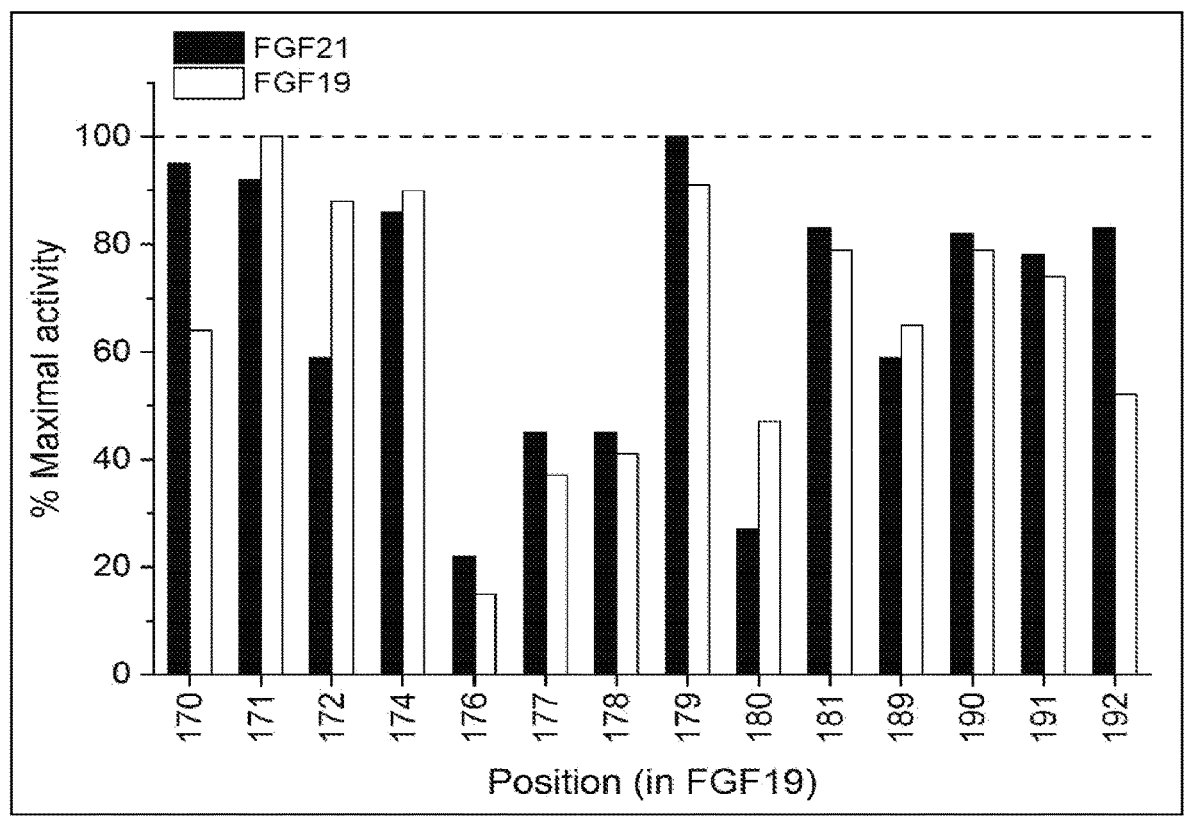
Figure 7C:
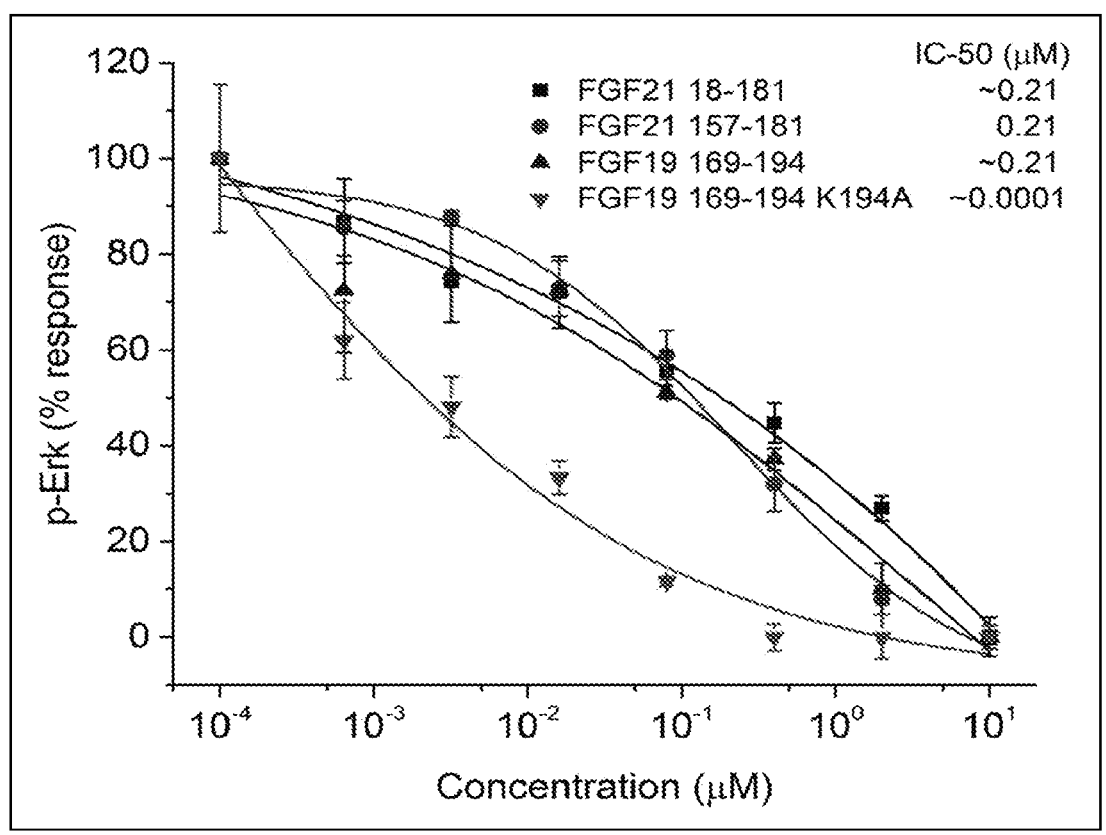
Figure 8A:
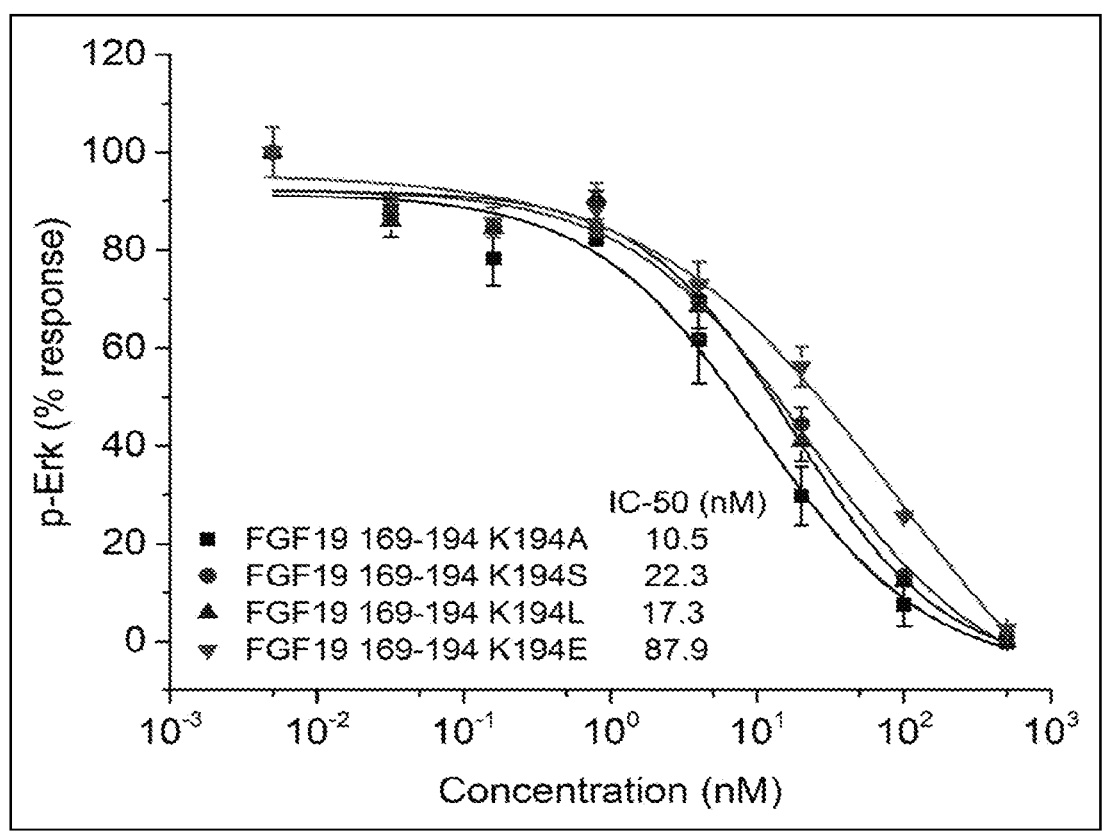
FIGS. 8A & 8B. are graphs representing the consequences of substitutions at the terminal position of the antagonist peptide.
Figure 8B:
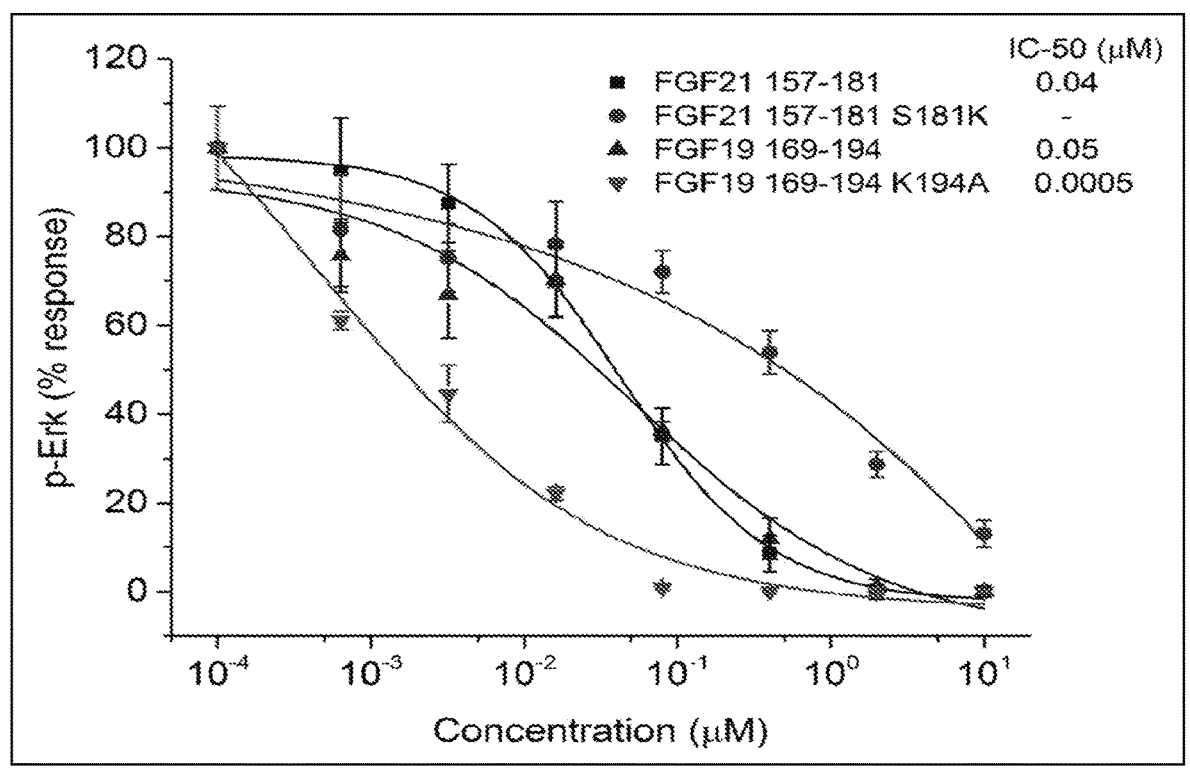
Figure 9A:
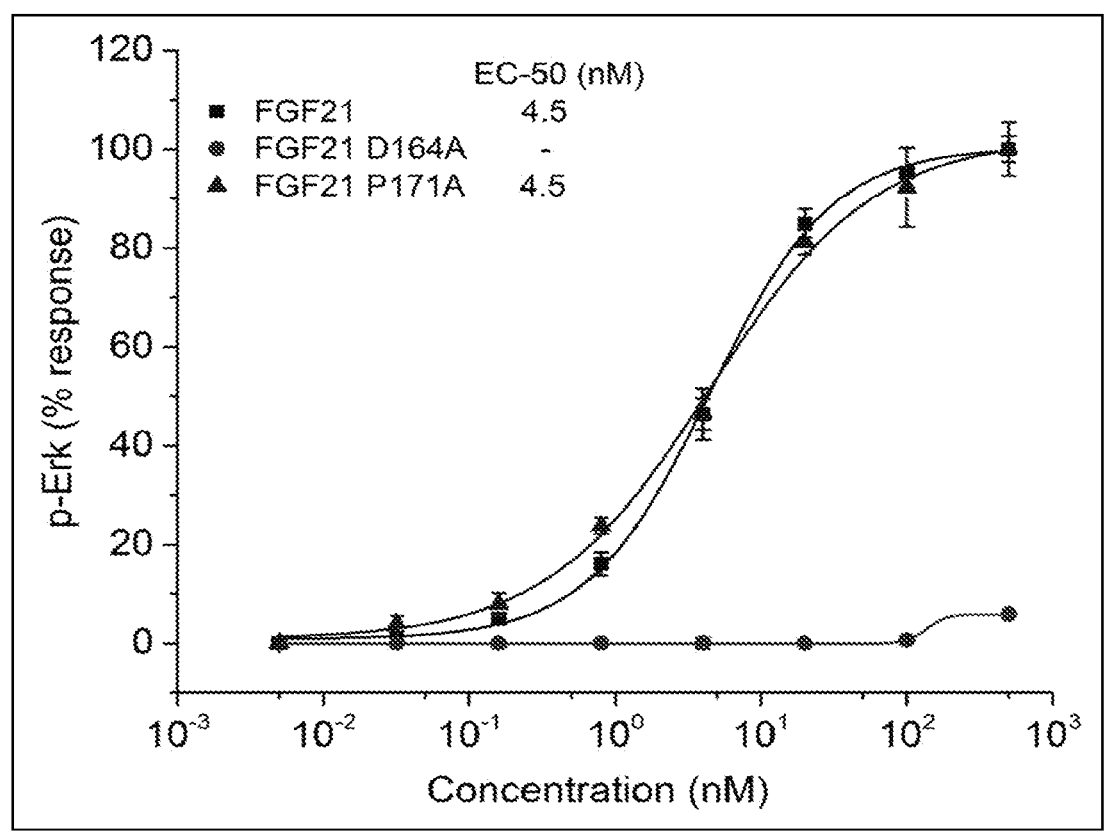
FIGS. 9A & 9B. are graphs demonstrating the translatability between the effects of alanine substitution seen in the antagonist peptides and their corresponding full length agonist analogs. Selected alanine mutations from the antagonist peptides were incorporated into their corresponding full length FGF21 or FGF19 protein sequences and tested for their ability to activate Erk1/2 phosphorylation in 293T HEK hKLB cells.
Figure 9B:
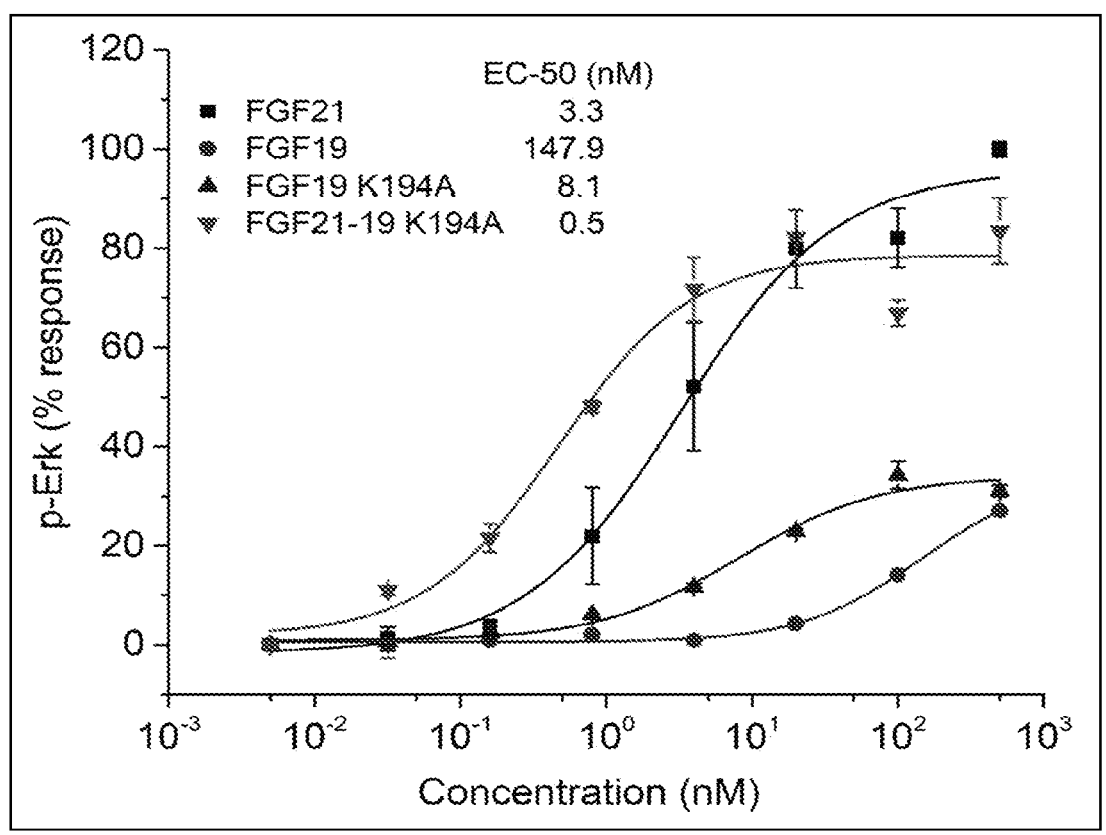
Figure 10A:
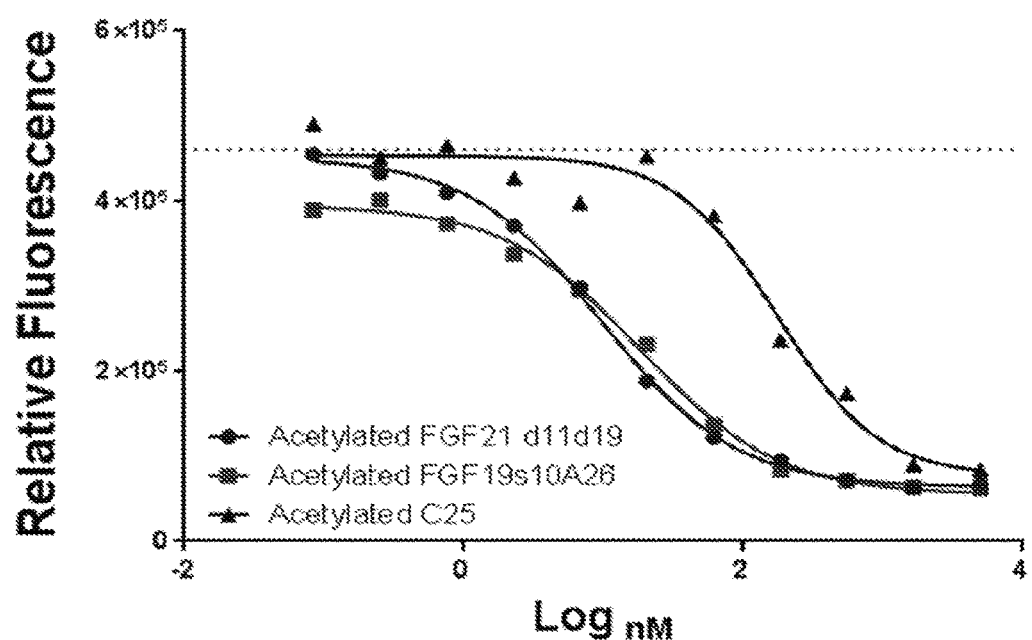
FIGS. 10A & 10B are graphs demonstrating the FGF21 and FGF19 peptides are functional in mouse as well as human cells. FGF21 and FGF19 peptides were acetylated at the N-terminus to help increase stability for use in vivo. Acetylated FGF21 and FGF19 peptides retain their antagonistic activity at both human (FIG. 10A) and mouse (FIG. 10B) cells that overexpressing human and mouse Klotho β (KLB), respectively.
Figure 10B:
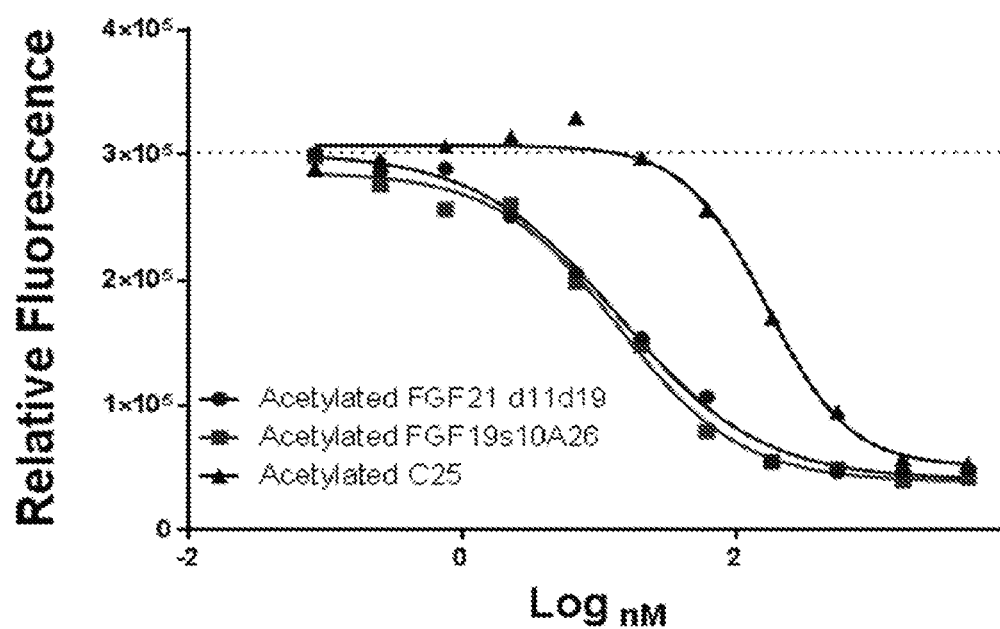

Additionally, we tested the ability of FGF19 169-194 K194A peptide to antagonize FGF21 activity in Hep3B cells, and found that this peptide was a superior antagonist compared to the native sequence as seen in the engineered 293T HEK hKLB cells (FIG. 7C). We tested the ability of FGF21/FGF19 C-terminal peptides to antagonize native FGF19 function Hep3B cells and found them to be effective antagonists, and again the FGF19 169-194 K194A peptide was observed to be a superior antagonist (FIG. 7C).

FGF21 analogs with site-specific alanine mutations predicted by the peptide antagonist screen were synthesized and assessed for agonist activity. We chose one mutation which debilitates the antagonism by substituting alanine at position 164, and another which preserves the antagonistic function at position 171. Both the site specific alanine FGF21 analogs were tested for their ability to induce Erk1/2 phosphorylation in comparison to the native FGF21. We found that the observed agonistic activity was indeed in complete agreement with the antagonist activity seen by the short peptides. The results validated the ability to translate from one molecular format to another.

Figure 5:
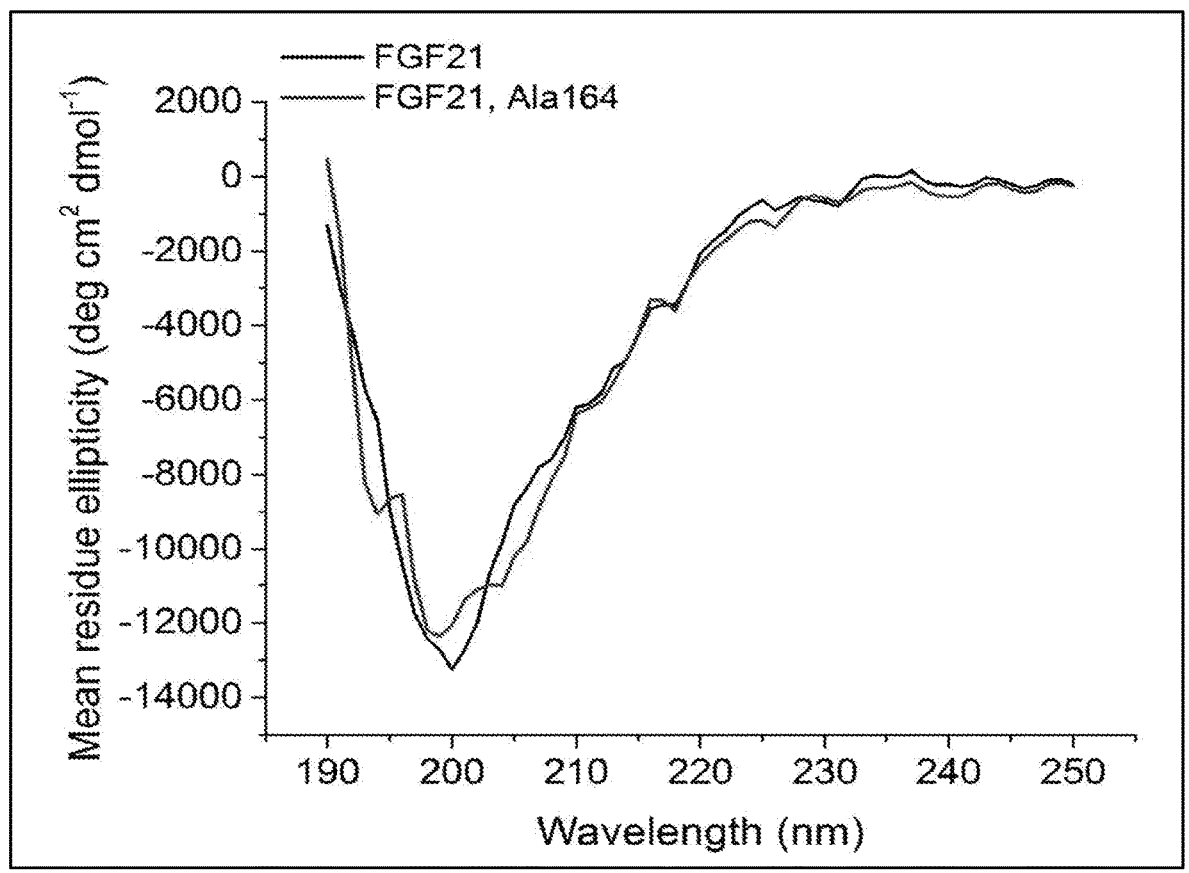
FIG. 5 provides the Far-UV CD spectra comparing native FGF21 and the Ala164 site-specific analog demonstrating the loss of antagonism with the Ala164 is not associated with changes in the secondary structure for the peptide.

To confirm that the FGF21 D164A analog was not compromised in its activity due to a substantial change in its secondary structure we recorded the CD spectra of the FGF21 D164A and compared it to the native FGF21 signature. The CD spectra of the Ala164 FGF21 is comparable to native FGF21, which implies that the inability to biochemically signal is a function of local and not systemic change to the protein structure. (FIG. 5). FGF19 & 21 share high identity in their C-terminal sequences (FIG. 6). This region based upon analogy with FGF23 is suspected to be of importance in binding to KLB. The results demonstrate that a peptide fragment representing as little as 15% of the full length protein is fully effective in antagonizing native FGF21 in vitro signaling at ~10× molar concentration. A complete alanine scan of the peptide revealed a number of sites that sharply differed in antagonistic effectiveness. The most debilitating alanine mutations occurred in residues that were identical among FGF19 and 21, and a specific example is positon 164 (FIG. 4). These results define the precise positions that constitute the high affinity interactions of FGF21 with its co-receptor KLB, and provide a basis for optimizing protein agonism through analysis of peptide-based antagonism (FIG. 6; Table 1).

Positions 8, 9 and 12 were found to be critical residues, whereas positions 3, 4, 6, 10, 13, 20, 21 and 23 were found to be positions impacting activity. The low activity associated with peptides comprising these specific amino acid substitutions (when mutated to alanine) identifies these amino acids as part of the putative binding domain for KLB. Eleven of the twenty-five residues within this C-terminal peptide demonstrated more than a 10× reduction in potency when mutated to alanine.

Example 2

Further modifications to the FGF19 and FGF21 C-terminal sequences.

The initial alanine scan of the FGF19 169-194 K194A peptide fragment revealed that substitution of the C-terminal amino acid with an alanine (K194A for FGF19 and S181A for FGF21) significantly enhanced the antagonist properties of the peptide (see Table 2(A)). Furthermore, the creation of a full length FGF19 analog comprising the FGF19 169-194 K194A fragment demonstrated that the FGF29 analog was indeed an improved analog in the engineered 293T HEK hKLB cells (FIG. 7C).

To assess the activity of the best antagonist peptide as its agonist counterpart, we generated a chimeric analog which had the core of FGF21 1-156 and an extension of the FGF19 169-194 K194A peptide, and evaluated its activity. We found this to be approximately 5-fold more potent than native FGF21 (FIG. 7C). This fortifies our previous observations that there is a firm correlation between the KLB-binding ability of the C-terminal peptides in isolation and their corresponding function as agonists.

Example 3

Further Mutational Analysis

The results of a D-amino acid scan of the FGF21 C-terminal 25 amino acid peptide (SEQ ID NO: 191) are presented in Table 3. The activity of each peptide (all having the primary sequence of SEQ ID NO: 191) was determined using the assay described in Example 1. Stepwise D-isomer mutations within the 25-terminal amino acids of FGF21 (SEQ ID NO: 191) largely mimicked the results of the alanine scan. Two mutations at S11 and R19, however significantly increased antagonistic potency of the peptide over the native terminus by 5- and 2-fold respectively.

TABLE 3

D11 and D19 increased the potency of C25 peptide.

| Sample ID | Sequences | IC50 (nM) | % Activity vs C25 |
|---|---|---|---|
| C25 | PPDVG SSDPL SMVGP SQGRS PSYAS (SEQ ID NO: 191) | 283.48 ± 135.61 | 100.000 |
| d1 | pPDVG SSDPL SMVGP SQGRS PSYAS | 876.53 ± 537.33 | 54.16 ± 24.05 |
| d2 | PpDVG SSDPL SMVGP SQGRS PSYAS | 4718.00 ± 2988.67 | 7.61 ± 1.78 |
| d3 | PPdVG SSDPL SMVGP SQGRS PSYAS | 6101.50 ± 6479.22 | 15.63 ± 20.51 |
| d4 | PPDvG SSDPL SMVGP SQGRS PSYAS | Ambiguous | Ambiguous |
| d6 | PPDVG sSDPL SMVGP SQGRS PSYAS | 1981.85 ± 2045.17 | 32.49 ± 42.20 |
| d7 | PPDVG SsDPL SMVGP SQGRS PSYAS | Ambiguous | Ambiguous |
| d8 | PPDVG SSdPL SMVGP SQGRS PSYAS | Ambiguous | Ambiguous |
| d9 | PPDVG SSDpL SMVGP SQGRS PSYAS | Ambiguous | Ambiguous |
| d10 | PPDVG SSDPl SMVGP SQGRS PSYAS | Ambiguous | Ambiguous |
| d11 | PPDVG SSDPL sMVGP SQGRS PSYAS | 57.32 ± 31.13 | 596.16 ± 211.38 |
| d12 | PPDVG SSDPL SmVGP SQGRS PSYAS | Ambiguous | Ambiguous |
| d13 | PPDVG SSDPL SMvGP SQGRS PSYAS | Ambiguous | Ambiguous |
| d15 | PPDVG SSDPL SMVGp SQGRS PSYAS | 374.95 ± 188.36 | 66.84 ± 34.79 |
| d16 | PPDVG SSDPL SMVGP sQGRS PSYAS | 530.58 ± 289.19 | 45.98 ± 16.23 |
| d17 | PPDVG SSDPL SMVGP SqGRS PSYAS | 262.48 ± 143.30 | 90.34 ± 24.24 |
| d19 | PPDVG SSDPL SMVGP SQGrS PSYAS | 151.78 ± 151.66 | 270.70 ± 136.83 |
| d20 | PPDVG SSDPL SMVGP SQGRs PSYAS | 33700.00 ± 44510.18 | 2.30 ± 1.83 |
| d21 | PPDVG SSDPL SMVGP SQGRS pSYAS | 7799.67 ± 1501.53 | 3.80 ± 0.87 |
| d22 | PPDVG SSDPL SMVGP SQGRS PsYAS | Ambiguous | Ambiguous |
| d23 | PPDVG SSDPL SMVGP SQGRS PSyAS | Ambiguous | Ambiguous |
| d24 | PPDVG SSDPL SMVGP SQGRS PSYaS | 1133.67 ± 435.35 | 32.29 ± 13.52 |
| d25 | PPDVG SSDPL SMVGP SQGRS PSYAs | 263.50 ± 120.11 | 118.62 ± 38.73 |

Combining the mutations that were identified by the alanine and D-isomer scan into a single peptide resulted in antagonists that had elevated potency compared to the native C-terminal peptides (see Table 4; lowercase letters identifying amino acids in D-isomer conformation).

TABLE 4

Double mutations of FGF21 and 19 have additive affects increasing potency ~10 fold over native peptide.

| Peptide | Sequence | IC50 (nM) |
|---|---|---|
| FGF21 D11 | PPDVG SSDPL sMVGP SQGRS PSYAS (SEQ ID NO: 185) | 19.9 ± 5.24 |
| FGF21 D19 | PPDVG SSDPL SMVGP SQGrS PSYAS (SEQ ID NO: 186) | 52.55 ± 10.82 |
| FGF21 D11D19 | PPDVG SSDPL sMVGP SQGrS PSYAS (SEQ ID NO: 187) | 14.13 ± 3.87 |

TABLE 4-continued

Double mutations of FGF21 and 19 have additive affects increasing potency ~10 fold over native peptide.

| Peptide | Sequence | IC50 (nM) |
|---|---|---|
| FGF19 A26 | LETDS MDPFG LVTGL EAVRS PSFEA (SEQ ID NO: 188) | 17.89 ± 4.57 |
| FGF19 S10 | LETDS MDPFs LVTGL EAVRS PSFES (SEQ ID NO: 189) | 194.34 ± 81.39 |
| FGF19 S10A26 | LETDS MDPFs LVTGL EAVRS PSFEA (SEQ ID NO: 190) | 10.92 ± 6.33 |
| FGF21 C25 | PPDVG SSDPL SMVGP SQGRS PSYAS (SEQ ID NO: 191) | 182.34 ± 56.35 |

Example 4

FGF19/FGF21 Chimeric Peptides

Chimeric peptides we prepared and tested for their ability to antagonize native FGF21 signaling using the method of Example 1. The results of these experiments are provided in Table 5. In summary, the results indicate that maximal activity is obtained in the 25mer C-terminal peptide that comprises FGF19 amino acids at positions 6-13 with a non-charged amino acid (e.g., alanine) at position 25. More particularly, FGF21 based C-terminal peptide fragments having a terminal alanine at position 25 and the amino acids 6-13 of FGF19 retained the enhanced potency of native FGF19 with the terminal alanine.

TABLE 5

| Peptide | Sequence | IC50 |
| --- | --- | --- |
| FGF21 C25 | PPDVGSSDPLSMVGPSQGRSPSYAS (SEQ ID NO: 177) | 115.9 ± 4 |
| FGF19 A25 | PLETDSMDPFGLVTGLEAVRSPSFEA (SEQ ID NO: 178) | 19.1 ± 1.5 |
| 0430 | PLETDSMDPFGLVGPSQGRSPSFEA (SEQ ID NO: 179) | 15.9 ± 1.1 |
| 0431 | PPDVGSMDPFGLVGPSQGRSPSFEA (SEQ ID NO: 180) | 4.1 ± 0.1 |
| 0432 | PLETDSSDPLSMVGPSQGRSPSFEA (SEQ ID NO: 181) | 119.8 ± 6.3 |
| 0433 | PPDVGSMDPFGLVTGLEAVRSPSYAA (SEQ ID NO: 182) | 10.7 ± 0.7 |
| 0434 | PLETDSSDPLSMVTGLEAVRSPSYAA (SEQ ID NO: 183) | 263.6 ± 78.8 |
| 0435 | PPDVGSSDPLSMVTGLEAVRSPSFEA (SEQ ID NO: SEQ ID NO: 184) | 65.1 ± 4.8 |

Figure 11A:
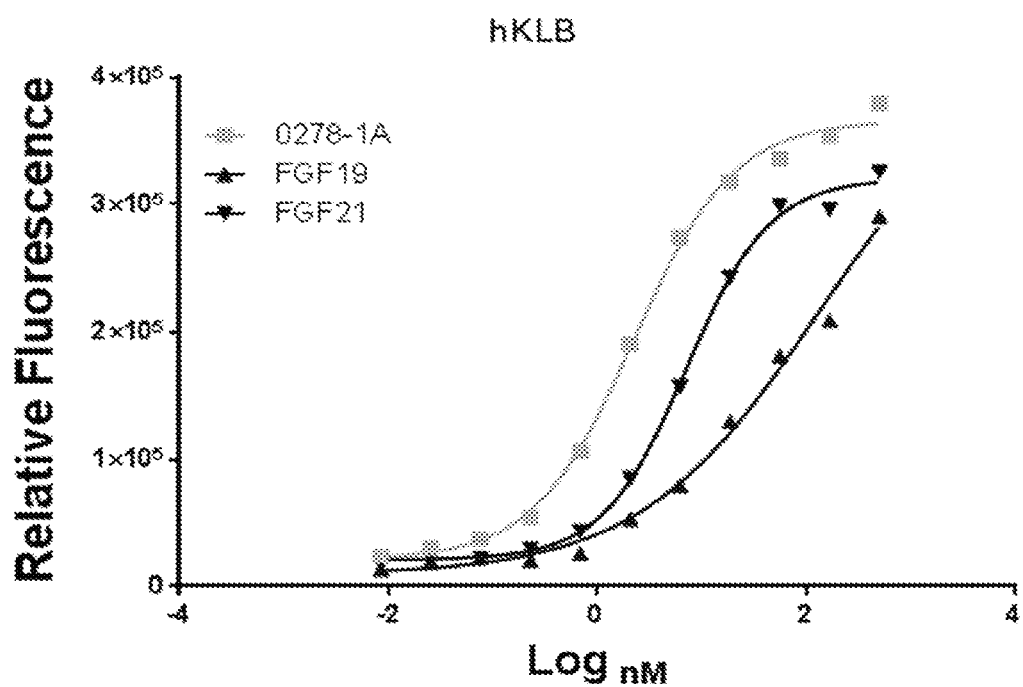
FIGS. 11A & 11B are graphs demonstrating that modification of FGF21 by replacing the native C-terminal 25 amino acids with the FGF19 A26 antagonistic peptide significantly increases agonism at both human (FIG. 11A) and mouse (FIG. 11B) KLB. This fusion, called 0278-1A, has enhanced potency (1.82±0.37 & 2.15±0.54) compared to both FGF21 (8.42±4.1 & 3.96±1.51) and FGF19 (65.78±58.19 & 25.67±21.32) in cells that overexpressed both human and mouse KLB.
Figure 11B:
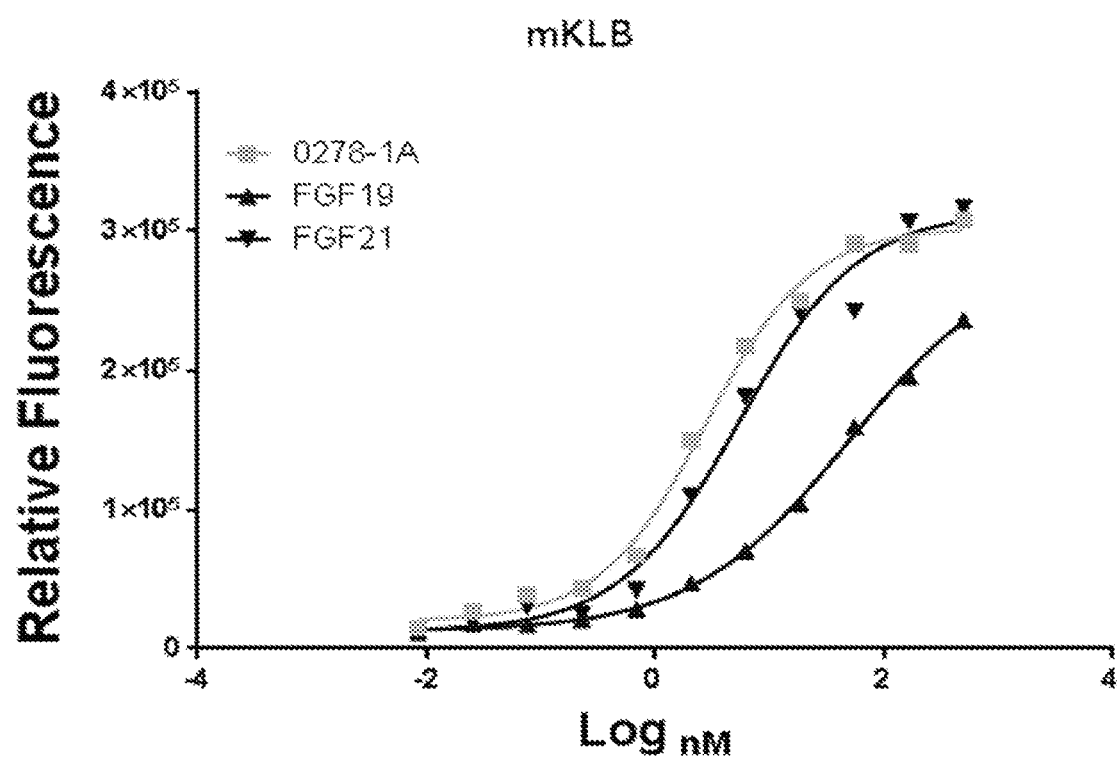
Figure 12:
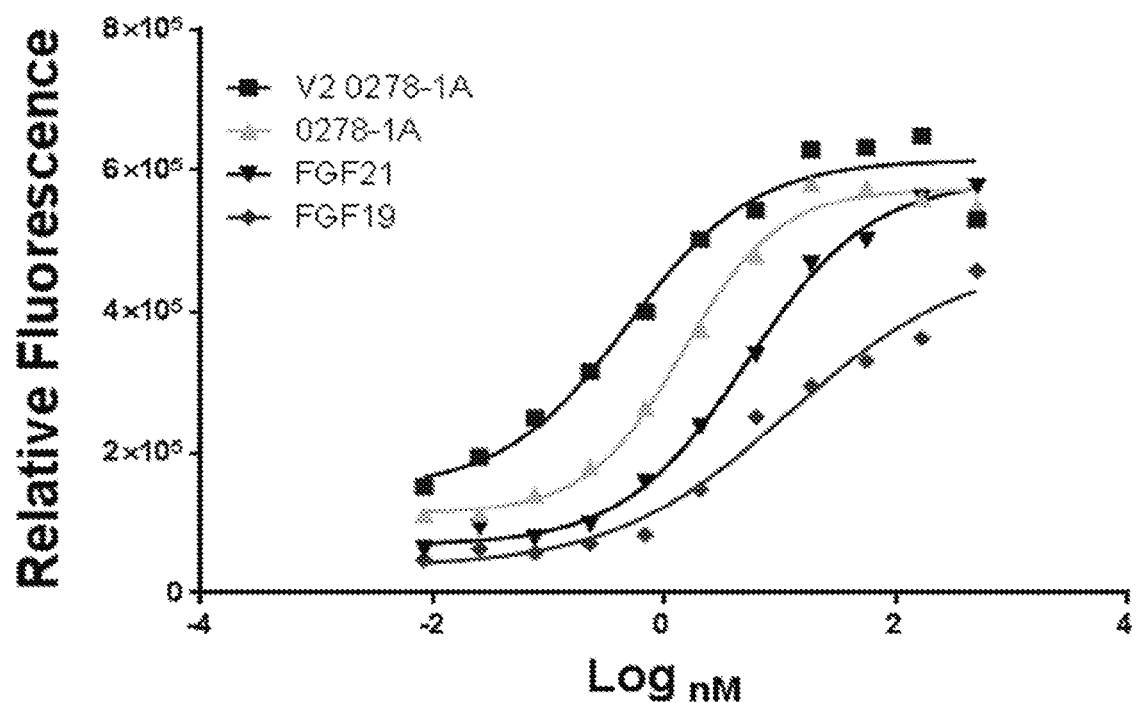
FIG. 12 is a graph demonstrating modification of the N-Terminus of FGF21 analog 0278-1A by amino acid substitutions A31C, G43C, L98D, L100K, N121D, and D127K (position numbering based on the native FGF21 sequence) to generate analog V2-0278-1A, increases potency relative to 0278-1A. V2-0278-1A displays ~2-3× higher potency (0.35±0.12 nM) versus 0278 (1.13±0.28) in cells overexpressing human KLB.

Modifying FGF21 by substituting the native C-terminal 25 amino acids of FGF21 with the potent FGF19 A26 antagonistic 25mer peptide significantly increases agonism at both human and mouse KLB (See FIGS. 11A and 11B). A fusion of the N-terminus of FGF21 and highly potent C-terminal peptide FGF19 A26 was synthesized (SEQ ID NO: 192). This fusion, called 0268-1A, was confirmed to have enhanced potency (1.82±0.37 & 2.15±0.54) compared to both FGF21 (8.42±4.1 &3.96±1.51) and 19 (65.78±58.19 & 25.67±21.32) in cells that overexpressed both human (FIG. 11A) and mouse (FIG. 11B) KLB. Further modification of 0278-1A, by adding six mutations based on published data (A31C, G43C, L98D, L100K, N121I, D127K), produced V2 0278-1A (SEQ ID NO: 193). The peptide of V20278-1A having the 6amino acid substitutions in the N-terminus 0278-IA exhibited increased potency relative to 0278-1A (See FIG. 12). V2-0278-1A displays ~2-3× higher potency (0.35±0.12 nM) versus 0278-1A (1.13±0.28) in cells overexpressing human KLB (B).

Additional peptides derived from SEQ ID NO: 180 were investigated for their activity as antagonists of FGF21 receptor activity. Table 6 provides the results of further derivatives of SEQ ID NO: 180 including amino acid substitutions at positions 5, 7 and 15. All tested peptides had similar activities as the peptide of SEQ ID NO: 180.

TABLE 6

| Peptide | Sequence | IC50 |
| --- | --- | --- |
| 0431 | PPDVGSMDPFGLVGPSQGRSPSFEA (SEQ ID NO: 180) | 7.1 ± 3 |
| 0470 | PPDVGSMDPFGLVGRSQGRSPSFEA (SEQ ID NO: 237) | 4.9 ± 1.1 |

TABLE 6-continued

| Peptide | Sequence | IC50 |
| --- | --- | --- |
| 0480 | PPDVFSMDPFGLVGPSQGRSPSFEA (SEQ ID NO: 238) | 2.6 ± 0.5 |
| 0481 | PPDVLSMDPFGLVGPSQGRSPSFEA (SEQ ID NO: 239) | 2.6 ± 0.8 |
| 0482 | PPDVSSMDPFGLVGPSQGRSPSFEA (SEQ ID NO: 240) | 3.0 ± 1.3 |
| 0486 | PPDVGSSDPFGLVGPSQGRSPSFEA (SEQ ID NO: 241) | 4.7 ± 1.6 |

A fusion of the N-terminus of FGF21 (modified to comprise the substitutions A31C, G43C, L98D, L100K, N121D, and D127K) and highly potent C-terminal peptides of Table 6 produced the following compounds:

("FGF21 431A"; SEQ ID NO: 247)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSPREDLK

EDGYNVYQSEAHGLPLHLPGDKSPHRKPAPRGPARFLPLPGLPPALPEPP

GILAPQPPDVGSMDPFGLVGPSQGRSPSFEA;

("FGF21 470A"; SEQ ID NO: 248)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSPREDLK

EDGYNVYQSEAHGLPLHLPGDKSPHRKPAPRGPARFLPLPGLPPALPEPP

GILAPQPPDVGSMDPFGLVGRSQGRSPSFEA;

("FGF21 480A"; SEQ ID NO: 249)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSFREDLK

EDGYNVYQSEAHGLPLHLPGDKSPHRKPAPRGPARFLPLPGLPPALPEPP

GILAPQPPDVFSMDPFGLVGPSQGRSPSFEA;

("FGF21 481A"; SEQ ID NO: 250)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSFREDLK

EDGYNVYQSEAHGLPLHLPGDKSPHRKPAPRGPARFLPLPGLPPALPEPP

GILAPQPPDVLSMDPFGLVGPSQGRSPSFEA;

("FGF21 482A"; SEQ ID NO: 251)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSFREDLK

EDGYNVYQSEAHGLPLHLPGDKSPHRKPAPRGPARFLPLPGLPPALPEPP

GILAPQPPDVSSMDPFGLVGPSQGRSPSFEA;
and ("FGF21 486A"; SEQ ID NO: 252)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSFREDLK

EDGYNVYQSEAHGLPLHLPGDKSPHRKPAPRGPARFLPLPGLPPALPEPP

GILAPQPPDVGSSDPFGLVGPSQGRSPSFEA.

Each of these FGF21 analogs were tested for activity at the FGF21 receptor using the cell based assay disclosed in Example 1. The polypeptides of SEQ ID NOs 247-252, along with analog of those peptides where the C-terminal alanine is replace with a lysine were tested along with the native FGF21 polypeptide for activity at the FGF21 receptor. Each compound was tested in triplicate and the average IC50 was determined. The results are indicated below:

| | |
|---|---|
| FGF21 | 5.11 ± 0.55 |
| FGF21 480K | 1.62 ± 0.54 |
| FGF21 480A | 0.43 ± 0.04 |
| FGF21 | 6.35 ± 3 |
| FGF21 470K | 6.14 ± 1.93 |
| FGF21 470A | 0.61 ± 0.06 |
| FGF21 | 5.39 ± 3.19 |
| FGF21 431K | 4.3 ± 0.07 |
| FGF21 431A | 0.51 ± 0.21 |
| FGF21 | 2.67 ± 0.9 |
| FGF21 481K | 0.56 ± 0.06 |
| FGF21 481A | 0.19 ± 0.08 |
| FGF21 | 4.24 ± 1.07 |
| FGF21 482K | 1.81 ± 0.18 |
| FGF21 482A | 0.22 ± 0.03 |
| FGF21 | 2.03 ± 0.86 |
| FGF21 486K | 3.16 ± 0.56 |
| FGF21 486A | 0.21 ± 0.03 |

Example 5

In Vivo Administration of FGF Analogs to Mice Animals.

C57Bl/6 mice were obtained from Jackson Laboratories and fed a diabetogenic diet from Research Diets: a high-sucrose diet with 58% kcal from fat. Mice were group-housed on a 12:12-h light-dark cycle at 22° C. with free access to food and water. All studies were approved by and performed according to the guidelines of the Institutional Animal Care and Use Committee of the University of Cincinnati. All mice were treated by daily subcutaneous injections delivered in physiologically buffered saline at a dose of 0.3 or 1 mg/kg. Animals were weighed and food consumption was measured each day.

Statistical Analyses.

Unless indicated otherwise, all statistical analyses were performed using GraphPad Prism. The analysis of the results obtained in the in vivo experiments was performed using one-way ANOVAs followed by Tukey post hoc tests. P values lower than 0.05 were considered significant. The results are presented as means±s.e.m. of 7-8 replicates per group. Receptor activation data is ±s.d.

Figure 13A:
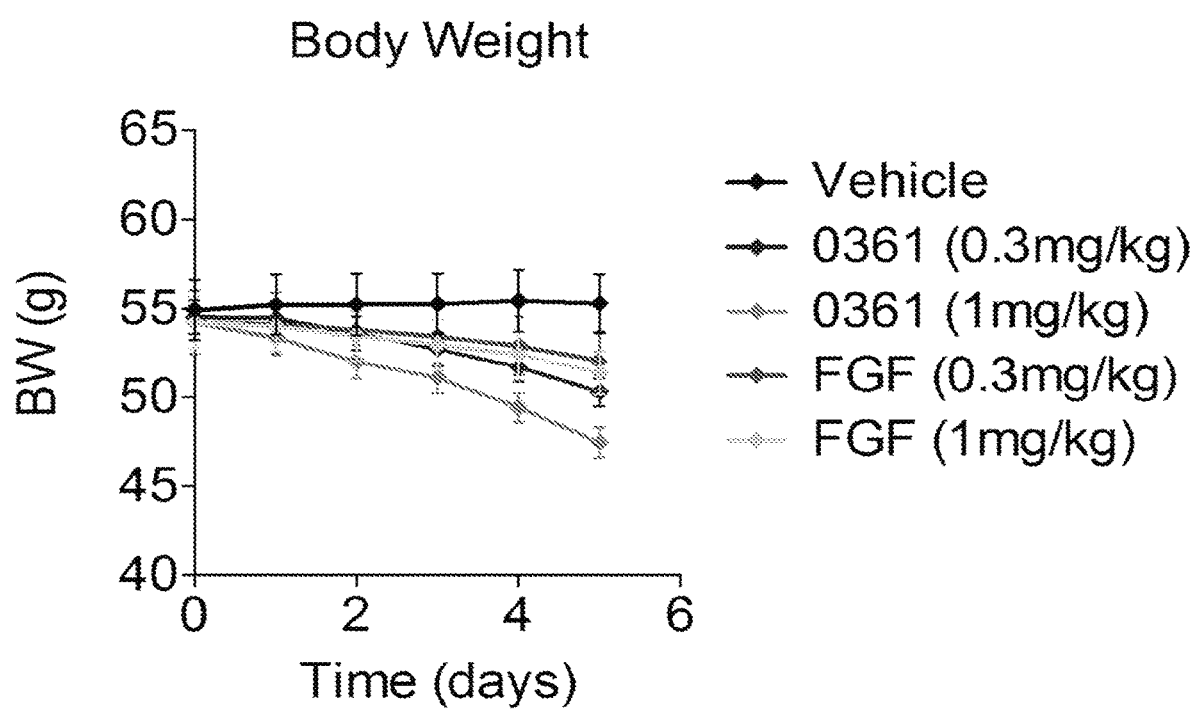
FIGS. 13A-13C provide data relating to the in vivo administration of the FGF21 analog of SEQ ID NO: 193 (analog 0361) administered at a dosage of 0.3 mg/kg or 1.0 mg/kg.
Figure 13B:
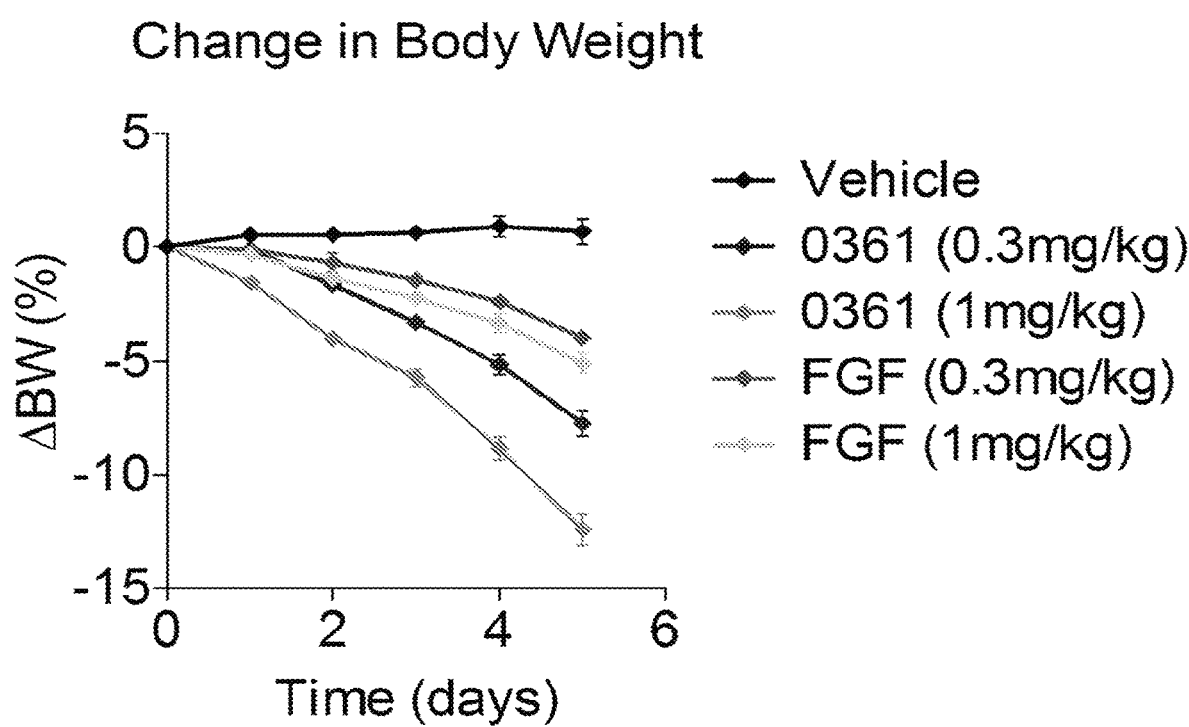
Figure 13C:
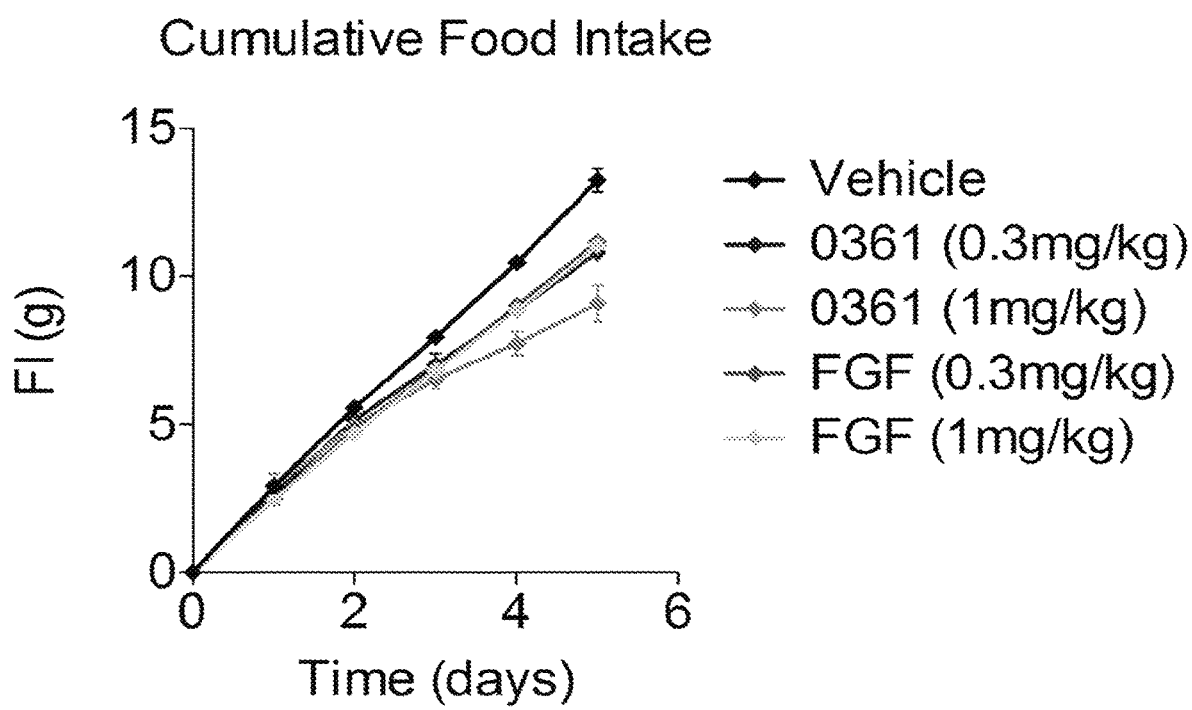

The effect of FGF analog V2-0278-1A on mice was investigated by administering either vehicle, FGF21 (at 0.3 mg/kg or 1.0 mg/kg) or V2-0278-1A (at 0.3 mg/kg or 1.0 mg/kg) and monitoring weight over the course of 6 days of treatment. FIGS. 13A and 13B demonstrate enhanced weight loss in mice receiving FGF analog V2-0278-1A relative to native FGF21. FIG. 13C demonstrates that mice receiving FGF analog V2-0278-1A had a reduced food intake relative to native FGF21.

The invention claimed is:

1. A peptide exhibiting antagonist activity against fibroblast growth factor 21 (FGF21) binding to Klotho β, wherein said peptide comprises a sequence selected from the group consisting of:

PPDVGSMDPFGLVGPSQGRSPSFEA, (SEQ ID NO: 180)

PPDVGSMDPFGLVGRSQGRSPSFEA, (SEQ ID NO: 237)

PPDVFSMDPFGLVGPSQGRSPSFEA, (SEQ ID NO: 238)

PPDVLSMDPFGLVGPSQGRSPSFEA, (SEQ ID NO: 239) and

PPDVSSMDPFGLVGPSQGRSPSFEA. (SEQ ID NO: 240)

2. The peptide of claim 1, wherein said peptide comprises a sequence selected from the group consisting of:

PPDVGSMDPFGLVGRSQGRSPSFEA, (SEQ ID NO: 237)

PPDVFSMDPFGLVGPSQGRSPSFEA, (SEQ ID NO: 238)

PPDVLSMDPFGLVGPSQGRSPSFEA, (SEQ ID NO: 239) and

PPDVSSMDPFGLVGPSQGRSPSFEA. (SEQ ID NO: 240)

3. The peptide of claim 1, wherein said peptide comprises the sequence of:

PPDVGSMDPFGLVGRSQGRSPSFEA (SEQ ID NO: 237).

4. A pharmaceutical composition comprising a peptide of claim 1 and a pharmaceutically acceptable carrier, diluent, or excipient.

5. A pharmaceutical composition comprising a peptide of claim 2 and a pharmaceutically acceptable carrier, diluent, or excipient.

6. A method of reducing weight gain or inducing weight loss in a patient in need thereof, comprising administering to said patient a pharmaceutical composition of claim 4 in an amount effective to reduce weight gain or induce weight loss.

7. A method of treating diabetes in a patient in need thereof, comprising administering to said patient a pharmaceutical composition of claim 4 in an amount effective to lower blood glucose level.

* * * * *